(12) United States Patent
Ratajczak et al.

(10) Patent No.: US 9,155,762 B2
(45) Date of Patent: Oct. 13, 2015

(54) USES AND ISOLATION OF STEM CELLS FROM BONE MARROW

(75) Inventors: Mariusz Ratajczak, Louisville, KY (US); Magdalena Kucia, Louisville, KY (US); Janina Ratajczak, Louisville, KY (US); Roberto Bolli, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 232 days.

(21) Appl. No.: 12/740,718

(22) PCT Filed: Oct. 30, 2008

(86) PCT No.: PCT/US2008/081832
§ 371 (c)(1),
(2), (4) Date: Mar. 11, 2011

(87) PCT Pub. No.: WO2009/059032
PCT Pub. Date: May 7, 2009

(65) Prior Publication Data
US 2011/0189136 A1    Aug. 4, 2011

Related U.S. Application Data

(63) Continuation-in-part of application No. 12/096,754, filed as application No. PCT/US2006/042780 on Nov. 2, 2006, now abandoned.

(60) Provisional application No. 61/000,954, filed on Oct. 30, 2007, provisional application No. 61/079,675, filed on Jul. 10, 2008, provisional application No. 60/748,685, filed on Dec. 8, 2005.

(51) Int. Cl.
| *A61K 35/12* | (2015.01) |
| *A61K 35/28* | (2015.01) |
| *A61K 38/18* | (2006.01) |
| *A61B 10/00* | (2006.01) |

(52) U.S. Cl.
CPC ............... *A61K 35/12* (2013.01); *A61K 35/28* (2013.01); *A61B 10/00* (2013.01); *A61K 38/18* (2013.01); *A61K 2035/124* (2013.01)

(58) Field of Classification Search
CPC .. A61K 35/12; A61K 35/28; A61K 2035/124
See application file for complete search history.

(56) References Cited

U.S. PATENT DOCUMENTS

| 5,589,369 A | 12/1996 | Seidman et al. |
| 5,650,550 A | 7/1997 | Korach et al. |
| 5,736,396 A | 4/1998 | Bruder et al. |
| 5,750,397 A | 5/1998 | Tsukamoto et al. |
| 5,777,195 A | 7/1998 | Fienberg et al. |
| 5,843,780 A | 12/1998 | Thomson |
| 6,007,993 A | 12/1999 | Wobus et al. |
| 6,090,622 A | 7/2000 | Gearhart et al. |
| 6,458,589 B1 | 10/2002 | Rambhatla et al. |
| 7,275,586 B2 | 10/2007 | Beck et al. |
| 7,422,736 B2 | 9/2008 | Hwang |
| 7,575,921 B2 | 8/2009 | Vacanti et al. |
| 7,816,140 B2 * | 10/2010 | Lau et al. ............ 435/455 |
| 2004/0018617 A1 | 1/2004 | Hwang |
| 2004/0265281 A1 | 12/2004 | Rodgerson et al. |
| 2005/0181502 A1 | 8/2005 | Furcht et al. |
| 2005/0255588 A1 | 11/2005 | Young et al. |
| 2006/0233768 A1 | 10/2006 | Hirose et al. |
| 2007/0243172 A1 | 10/2007 | Ra et al. |
| 2008/0038231 A1 | 2/2008 | Rodgerson et al. |
| 2009/0155225 A1 | 6/2009 | Ratajczak et al. |
| 2010/0055785 A1 | 3/2010 | Hantash |

FOREIGN PATENT DOCUMENTS

| EP | 1974018 A2 | 10/2008 |
| EP | 2032691 A2 | 3/2009 |
| WO | 0111011 A2 | 2/2001 |
| WO | 2004043990 A2 | 5/2004 |
| WO | 2004089439 A2 | 10/2004 |
| WO | 2005042723 A2 | 5/2005 |
| WO | 2007067280 A2 | 6/2007 |
| WO | 2007146432 A2 | 12/2007 |
| WO | 2009059032 A2 | 5/2009 |

OTHER PUBLICATIONS

Nguyen et al. Advanced Drug Delivery Reviews, 62: 1175-1186, 2010.*
Naldini. Nature Reviews: Genetics, 12: 301-315, 2011.*
Brunt et al. Can. J. Physiol. Pharmacol., 90: 327-335, 2012.*
Sylvester et al. Arch Surg 139:93-99, 2004.*
BD Pharm Lyse 555899—MSDS; BD Biosciences (online) 2006 [retrieved on Feb. 8, 2010]. Retrieved from the internet at URL: <http:www.bdbiosciences.com/external_files/pm/doc/msds/live/web_enabled/555899_MSDS_US_EN.03.pdf; see page 4, "ammonium chloride.", pp. 1-5.
Zuba-Surma E. K., et al., (2007), "Pluripotent bond marrow (BM)-Derived very small embryonic-like (VSEL) stem cells are mobilized after acute myocardial infarction in mice", Circulation, Lippincott Williams & Wilkins, col. 116, Nr. 16, Suppl. p. 260., XP009139499.
Dawn, B. et al., (2008) "Transplantation of bone marrow-derived very small embryonic-like stem cells attenuates left ventricular dysfunction and remodeling after myocardial infarction" Stem Cells, AlphaMed Press, 26(6):1646-1655, XP002604064.

(Continued)

*Primary Examiner* — Marcia S Noble
(74) *Attorney, Agent, or Firm* — Kenyon & Kenyon LLP

(57) ABSTRACT

The presently disclosed subject matter provides populations of stem cells that are purified from bone marrow, peripheral blood, and/or other sources. Also provided are methods of using the stem cells for treating tissue and/or organ damage in a subject.

15 Claims, 52 Drawing Sheets

(56) References Cited

OTHER PUBLICATIONS

Carrion, R. et al., (2003) "Progenitor Cell Mobilisation: A randomised study of 10 µg/kg/day (single dose) vs 2 × 5 µg/kg/day (split dose) G-CSF as stem cell mobitisation regimen in high-risk breast cancer patients", Bone Marrow Transplantation, 32(6):563-567.
Cottler-Fox, M. et al., (2003) "Stem Cell Mobilization" Hematology, 419-437.
European Search Report for EP12166007.0-2401 dated Oct. 10, 2012.
Examination Report in European Patent Application No. EP 078 09 600.5, dated May 11, 2009.
International Preliminary Report on Patentability in International Patent Application No. PCT/US06/042780, dated Mar. 24, 2009.
International Preliminary Report on Patentability in International Patent Application No. PCT/US07/014108, dated Dec. 16, 2008.
International Preliminary Report on Patentability in International Patent Application No. PCT/US2008/081832, dated May 4, 2010.
International Preliminary Report on Patentability in International Patent Application No. PCT/US2009/005414, dated Apr. 45, 2011.
Jiang, J et al., (2002) "Pluripotency of mesenchymal stem cells derived from adult marrow" Nature, 418(6893):41-49.
Kim, M.Y. et al., (2010) "Bone morphopenetic protein 4 stimulates attachment of neurospheres and astrogenesis of neural stem cells in neurospheres via phosphatidylinositol 3 kinase-mediated opregulation of N-cadherin", Neuroscience, vol. 170, Nr. 1, pp. 8-15, XP055031897.
Kogler et al , (2004) "A new human somatic stem cell from placetal cord blood with intrinsic pluripotent differentiation potential" Journal of Experimental Medicine, 200(2): 123-135.
Kucia, M. et al., (2005) "Bone marrow as a source of circulating CXCR4(+) tissue-committed stem cells", Biology of the Cell, 97(2). 133-146.
Kucia, M. et al., (2005) "Are bone marrow stem cells plastic or heterogenous—That is the question", Experimental Hematology, 33(6):1613-623.
Kucia, M. et al., (2005) "Bone marrow as a home of heteogenous populations of nonhematopoietic stem cells", Leukemia (BASINGSTOKE), 19(7):1118:1127.
Kucia, M. et al., (2007) "identification of very small embryonic like (VSEL) stem cells in hone marrow", Cell and Tissue Research, 331(1): 125-134.
Kucia M. et al,, (2006) "Physiological and pathological consequesnces of identification of very small embryonic like (VSEL) stem cells in adult bone marrow", Journal of Physiology and Pharmacology, vol. 57, Nr.: SUPPL 5, pp. 5-18, XP002604058.
Kucia, M. et al., (2007) "Morphological and molecular characterization of novel population of CXCR4+SSEA-4+,Oct-4+ very small embryonic-like cell purified from human cord blood—preliminary report", Leukemia vol. 21 pp. 297-303, XP003018776.
Kucia, M. et al., (2004) "Cells expressing early cardiac markers reside in the bone marrow and are mobilized into the peripheral blood after myocardial infarction", Circulation Research, vol. 95, Nr. 12, pp. 1191-1199, XP002592556.
Kucia, M. et al., (2006) "A population of very small embryonic-like (VSEL) CXCR4+SSEA-1-+Oct4+ stem cells identified in adult bone marrow" Leukemia, vol. 20 pp. 857-869, XP003013478.
Kucia, M. et al., (2006) "Cells enriched in markers of neural tissue-committed stem cells reside in the bone marrow and are mobilized into the peripheral blood following stroke", Leukemia, vol. 20, Nr.1, pp. 18-28, XP002604061.
Kucia, M. et al., (2006) "The migration of bone marrow-derived non-hemotopoietic tissue-committed stem cells is regulated in an SDF-1, HGF-, and LIF-dependent manner", Archivum Immunologiae et Therapiae Experimentalls, Birkhaeuser Verlag AG, vol. 54, Nr. 2, pp. 121-135, XP002604060.
Kucia, M. et al., (2008) "Evidence that very small embryonic-like cells are mobilized into peripheral blood"Stem Cells, Alphamed Press, vol. 26, Nr.8:2083-2092, Pub. Info. XP002604056.
Medicetty et al., (2009) "Evidence That Human Very Smalll Embryonic-Like Stem Cells (VSELs) Are Mobilized by G-CSF Into Periperhial Blood: A Novel Strategy to Obtain Human Pluripotent Stem Cells for Regenerative Medicine", Blood, vol. 114, Nr., 22, p. 594, XP009139590.
Tanaka, J. et al., (2002) "Effect of Continuous Subcutaneous Administration of a Low Dose of G-CSF on Stem Cell Mobilization in Healthy Donors: A Feasibility Study" International Journal of Hematology, 75(5): 489-492.
Supplementary Search Report in European Patent Application No. EP 068 27 358, dated Dec. 30, 2009.
Search Report and Written Opinion International Patent Application No. PCT/US08/81832, dated Mar. 25, 2009.
Search Report in International Patent Application No. PCT/US06/042780, dated Apr. 30, 2009.
Search Report and Written Opinion in International Patent Application No. PCT/US09/05414, dated Mar. 2, 2010.
Office Action for U.S. Appl. No. 12/096,754, mailed on Jul. 30, 2012.
Office Action for U.S. Appl. No. 12/096,754, mailed on Nov. 22, 2011.
Office Action for U.S. Appl. No. 13/121,913, mailed on Dec. 13, 2011.
Paczkowska, E. et al., (2009) "Clinical evidence that very small embryonic-like stem cells are mobilized into peripheral blood in patients after stroke", Stroke, vol. 40, Nr. 4, pp. 1237-1244, XP002084086.
Paczkowska, E. et al., (2005) "Human hematopoletic stem/progenitor-enriched CD34(+) cells are mobilized into peripheral blood during stress related to ischemic stroke or acute myocardial infarction", European Journal of Heamatology, vol. 75, Nr:6, pp. 461-467, XP002604059.
Pelacho, B. et al., (2007) "Mullipotent adult progenitor cell transplantation increases vascularity and improves left ventricular function after myocardial infarction"; Journal of Tissue Engineering and Regeneratice Medicine, vol. 1, Nr. 1, pp. 51-59., XP002604063.
Petit, I. et al., (2002) "G-CSF induces stem cell mobilization by decreasing bond marrow SDF-1 and up-regulating CXCR", Nature Immunology, 3(7): 687-694.
Prockop, D. (1997) "Marrow Stromal Cells as Stem Cells for Nonhematopoietic Tissues", Science, 276(5309): 71-74.
Ratajczak, M. Z. et al., (2008) "Very Small Embryonic-Like (VSEL) Stem Cells: Purification from Adult Organs, Characterization, and Biological Significance," Stem Cell Research, vol. 4, pp. 89-99.
Ratajczak, M. Z. et al, (2006) "The pleiotropic effects of the SDF-1-CXCR4 axis inorganigenesis, regeneration and tumorigenesis", Leukemia, vol. 20, No. 11, pp. 1915-1924, XP002604062.
Ratajczak, M. Z. et al., (2008) "Very small embryonic-like (VSEL) stem cells in adult organs and their potential role in rejuvenation of tissues and longevity", Experimental Geronotology, vol. 43, Nr. 11, Sp. lss. SI pp. 1009-1017, XP082604065.
Ratajczak, M. Z. et al., (2004), "Stem cell plasticity revisited: CXCR4-positive cells expressing mRNA for early muscle, liver and neutral cells 'hide out' in the bone marrow", Leukemia, vol. 18:1, 29-40, XP002604057.
Reynolds, B. A. et al., (2005) "Clonal and population analyses demonstrate that an EGF-responsive mammalian embryonic CNS precursor is a stem cell", Developmental Biology-CONF-64th Annual Meeting of the Society-for-Development-Biology, vol. 175, Nr. 1, pp. 113, XP008092745.
Chen, J. et al., Therapeutic Benefit of Intravenous Administration of Bone Marrow Stromal Cells After Cerebral Ischemia in Rats, Stoke, Journal of the Arrierican Heart Association; Apr. 2011, p. 1005-1011.
Mimura, Tatsuya, et al., Treatment of Rabbit Bullous Keratopathy with Precursors Derived from Cultured Human Corneal Endothilium, Investigative Ophthalmology and Visual Science, 2005, vol. 46, pp. 3637-3644.
Shin, Dong-Myung, et al., Novel Epigeneitc Mechanisms that Control Pluripotency and Quiescence of Adult Marrow-Derived Oct4+ Very Small Embryonic Like Stem Cells, Leukemia, 2009, vol. 23. pp. 2042-2051.

(56) References Cited

OTHER PUBLICATIONS

Miki, Toshio, et al., Stem Cell Characteristics of Amniotic Epithelial Cells, Stem Cells, 2005, 23:1549-59.

D'Ippolito, G. et al., (2004) "Marrow-isolated adult multilineage inducible (MIAMI) cells, a unique population of postnatal young and old human cells with extensive and differentiation potential" Journal of Cell Science, 117(14): 2971-2981.

Mason, David et al., (2001) "CD Antigens 2001." European Journal of Immunology, vol. 31, No. 10. Oct. 1, 2001, pp. 2841-2847.

* cited by examiner

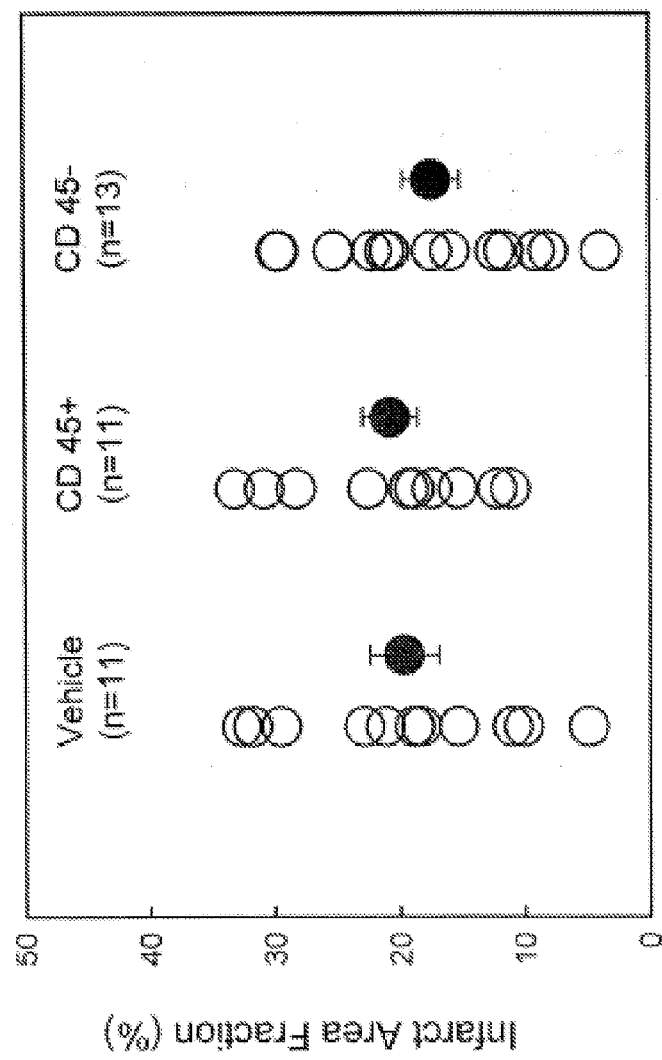

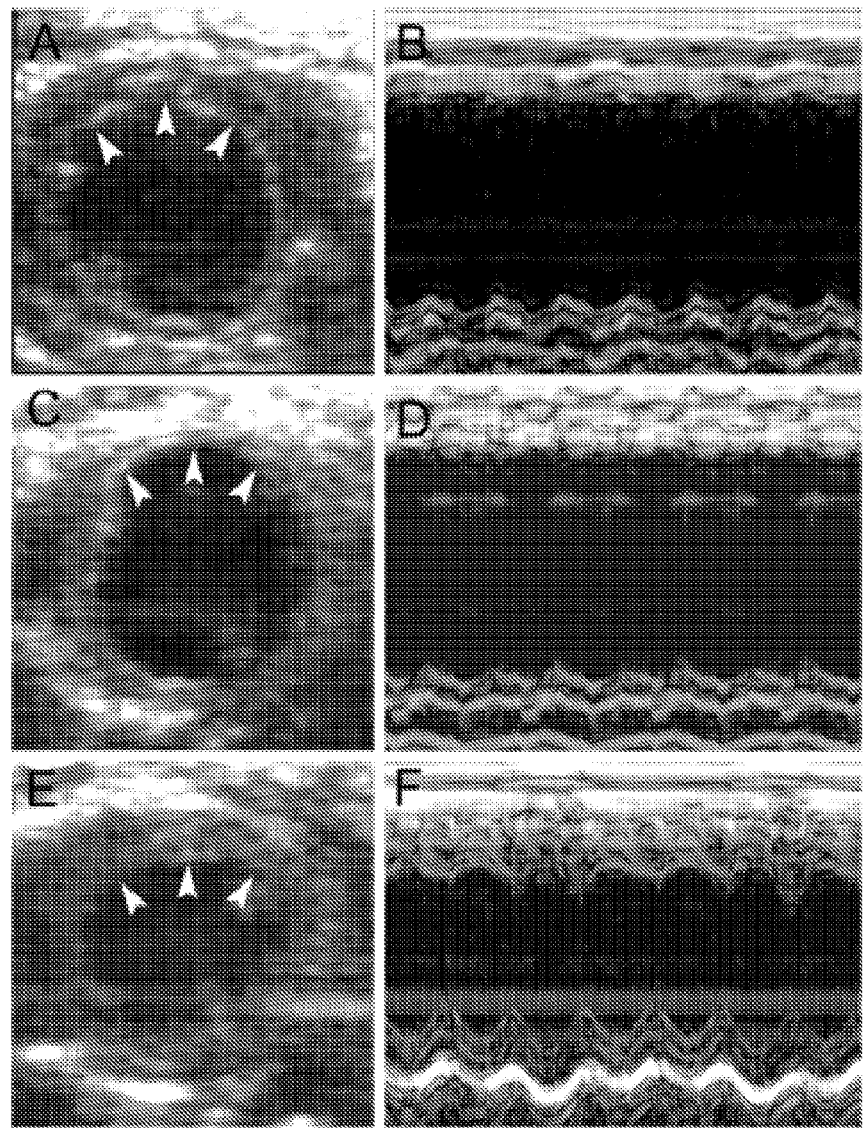
Figure 35 A-F

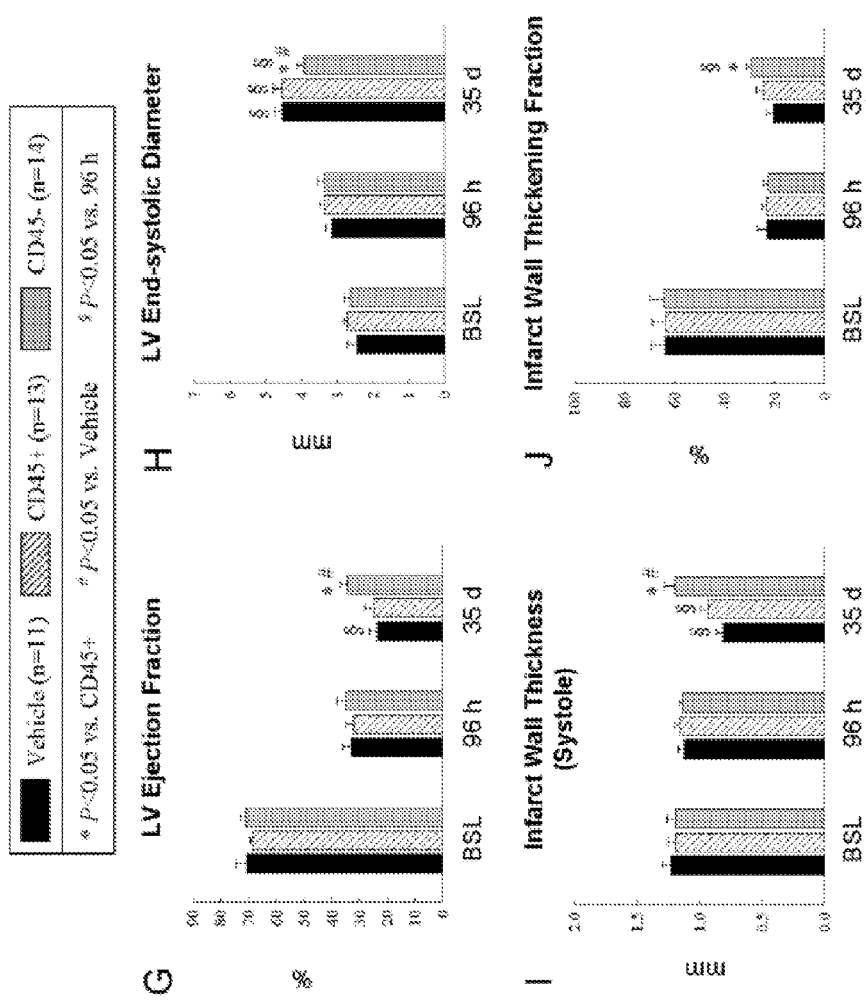
Figure 35 G-J

Figure 36 A-C

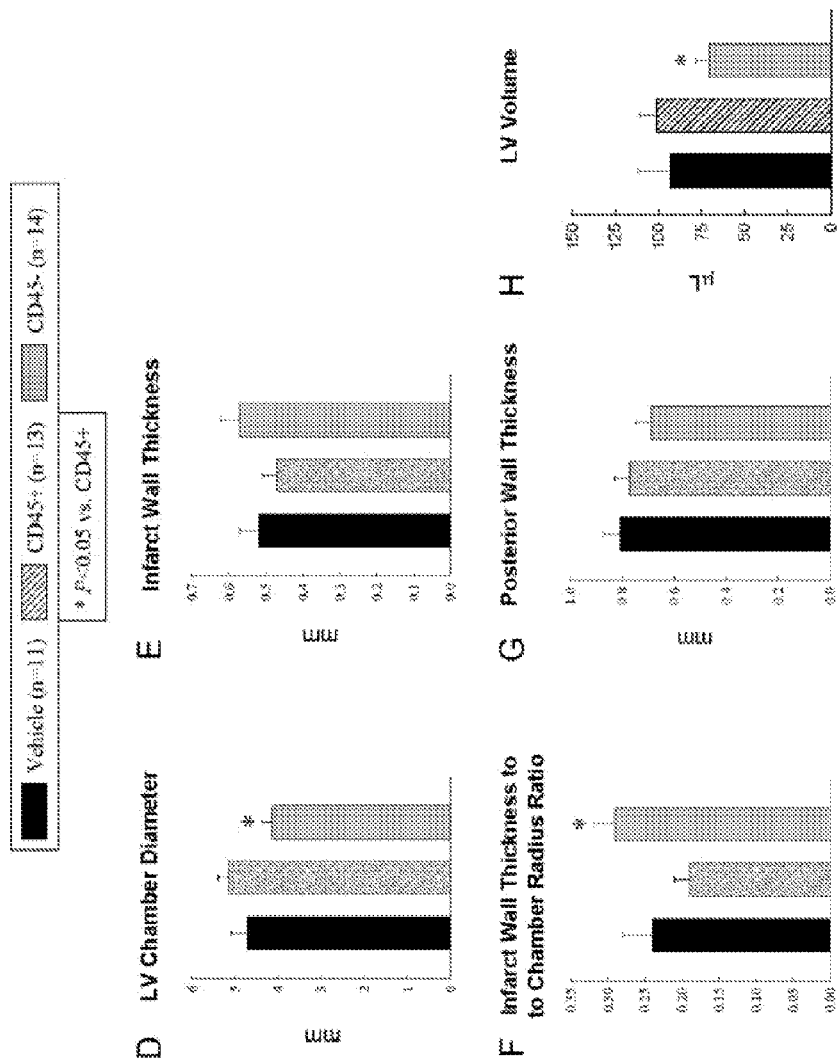
Figure 36 D-H

```
                             SEQUENCE LISTING

<160> NUMBER OF SEQ ID NOS: 80

<210> SEQ ID NO 1
<211> LENGTH: 22
<212> TYPE: DNA
<213> ORGANISM: Mus musculus

<400> SEQUENCE: 1
catacgcctg cagagttaag ca                                                22

<210> SEQ ID NO 2
<211> LENGTH: 24
<212> TYPE: DNA
<213> ORGANISM: Mus musculus

<400> SEQUENCE: 2
gatcacatgt ctcgatccca gtag                                              24

<210> SEQ ID NO 3
<211> LENGTH: 23
<212> TYPE: DNA
<213> ORGANISM: Mus musculus

<400> SEQUENCE: 3
accttcagga gatatgcaaa tcg                                               23

<210> SEQ ID NO 4
<211> LENGTH: 25
<212> TYPE: DNA
<213> ORGANISM: Mus musculus

<400> SEQUENCE: 4
ttctcaatgc tagttcgctt tctct                                             25

<210> SEQ ID NO 5
<211> LENGTH: 21
<212> TYPE: DNA
<213> ORGANISM: Mus musculus

<400> SEQUENCE: 5
cgttcccaga attcgatgct t                                                 21

<210> SEQ ID NO 6
<211> LENGTH: 22
<212> TYPE: DNA
<213> ORGANISM: Mus musculus

<400> SEQUENCE: 6
ttttcagaaa tcccttccct cg                                                22

<210> SEQ ID NO 7
<211> LENGTH: 21
<212> TYPE: DNA
<213> ORGANISM: Mus musculus

<400> SEQUENCE: 7
agatggcttc cctgacggat a                                                 21
```

```
<210> SEQ ID NO 8
<211> LENGTH: 22
<212> TYPE: DNA
<213> ORGANISM: Mus musculus

<400> SEQUENCE: 8
cctccaagct ttcgaaggat tt                                              22

<210> SEQ ID NO 9
<211> LENGTH: 20
<212> TYPE: DNA
<213> ORGANISM: Mus musculus

<400> SEQUENCE: 9
gcagtctacg gaaccgcatt                                                 20

<210> SEQ ID NO 10
<211> LENGTH: 21
<212> TYPE: DNA
<213> ORGANISM: Mus musculus

<400> SEQUENCE: 10
ttgaacttcc ctccggattt t                                               21

<210> SEQ ID NO 11
<211> LENGTH: 25
<212> TYPE: DNA
<213> ORGANISM: Mus musculus

<400> SEQUENCE: 11
gagctggatt cttttggatc agtaa                                           25

<210> SEQ ID NO 12
<211> LENGTH: 20
<212> TYPE: DNA
<213> ORGANISM: Mus musculus

<400> SEQUENCE: 12
gccaaaggtg accagacaca                                                 20

<210> SEQ ID NO 13
<211> LENGTH: 20
<212> TYPE: DNA
<213> ORGANISM: Mus musculus

<400> SEQUENCE: 13
ggagctcaat gaccgctttg                                                 20

<210> SEQ ID NO 14
<211> LENGTH: 20
<212> TYPE: DNA
<213> ORGANISM: Mus musculus

<400> SEQUENCE: 14
tccaggaagc gaaccttctc                                                 20

<210> SEQ ID NO 15
<211> LENGTH: 21
<212> TYPE: DNA
<213> ORGANISM: Mus musculus

<400> SEQUENCE: 15
ccctgatgat ccatcctcct t                                               21
```

```
<210> SEQ ID NO 16
<211> LENGTH: 30
<212> TYPE: DNA
<213> ORGANISM: Mus musculus

<400> SEQUENCE: 16
ctggaatatg ctagaaactc tagactcact                              30

<210> SEQ ID NO 17
<211> LENGTH: 19
<212> TYPE: DNA
<213> ORGANISM: Mus musculus

<400> SEQUENCE: 17
tccgttcgct caggtcctt                                          19

<210> SEQ ID NO 18
<211> LENGTH: 20
<212> TYPE: DNA
<213> ORGANISM: Mus musculus

<400> SEQUENCE: 18
cccagactga ccgaaaacga                                         20

<210> SEQ ID NO 19
<211> LENGTH: 20
<212> TYPE: DNA
<213> ORGANISM: Mus musculus

<400> SEQUENCE: 19
acgtcgtagc gcaggcttat                                         20

<210> SEQ ID NO 20
<211> LENGTH: 19
<212> TYPE: DNA
<213> ORGANISM: Mus musculus

<400> SEQUENCE: 20
cgcccaactc cgcttactt                                          19

<210> SEQ ID NO 21
<211> LENGTH: 18
<212> TYPE: DNA
<213> ORGANISM: Mus musculus

<400> SEQUENCE: 21
gggaggcgcc attgtaca                                           18

<210> SEQ ID NO 22
<211> LENGTH: 19
<212> TYPE: DNA
<213> ORGANISM: Mus musculus

<400> SEQUENCE: 22
gtgcaggcag gaagttcca                                          19

<210> SEQ ID NO 23
<211> LENGTH: 20
<212> TYPE: DNA
<213> ORGANISM: Mus musculus

<400> SEQUENCE: 23
ctaggagggc gtccttcatg                                         20
```

```
<210> SEQ ID NO 24
<211> LENGTH: 21
<212> TYPE: DNA
<213> ORGANISM: Mus musculus

<400> SEQUENCE: 24
cacgtattct gcccagcttt t                                              21

<210> SEQ ID NO 25
<211> LENGTH: 18
<212> TYPE: DNA
<213> ORGANISM: Mus musculus

<400> SEQUENCE: 25
ggacagccgg tgtgcatt                                                  18

<210> SEQ ID NO 26
<211> LENGTH: 19
<212> TYPE: DNA
<213> ORGANISM: Mus musculus

<400> SEQUENCE: 26
cactccggaa ccccaacag                                                 19

<210> SEQ ID NO 27
<211> LENGTH: 19
<212> TYPE: DNA
<213> ORGANISM: Mus musculus

<400> SEQUENCE: 27
ggagaagcgc aggctcaag                                                 19

<210> SEQ ID NO 28
<211> LENGTH: 20
<212> TYPE: DNA
<213> ORGANISM: Mus musculus

<400> SEQUENCE: 28
ttgagcaggg tgctcctctt                                                20

<210> SEQ ID NO 29
<211> LENGTH: 18
<212> TYPE: DNA
<213> ORGANISM: Mus musculus

<400> SEQUENCE: 29
cggatgtggc tcgtttgc                                                  18

<210> SEQ ID NO 30
<211> LENGTH: 18
<212> TYPE: DNA
<213> ORGANISM: Mus musculus

<400> SEQUENCE: 30
ttgggaccct cccgagat                                                  18

<210> SEQ ID NO 31
<211> LENGTH: 22
<212> TYPE: DNA
<213> ORGANISM: Mus musculus

<400> SEQUENCE: 31
```

```
tccagtgctg tctgctctaa gc                                             22
```

<210> SEQ ID NO 32
<211> LENGTH: 19
<212> TYPE: DNA
<213> ORGANISM: Mus musculus

<400> SEQUENCE: 32

```
tggcctgcga tgtctgagt                                                 19
```

<210> SEQ ID NO 33
<211> LENGTH: 18
<212> TYPE: DNA
<213> ORGANISM: Mus musculus

<400> SEQUENCE: 33

```
acccgcttcc ctcatcct                                                  18
```

<210> SEQ ID NO 34
<211> LENGTH: 22
<212> TYPE: DNA
<213> ORGANISM: Mus musculus

<400> SEQUENCE: 34

```
aaactcattt cgtgcaatgc tt                                             22
```

<210> SEQ ID NO 35
<211> LENGTH: 21
<212> TYPE: DNA
<213> ORGANISM: Mus musculus

<400> SEQUENCE: 35

```
catgcgaagc caatatgagg t                                              21
```

<210> SEQ ID NO 36
<211> LENGTH: 20
<212> TYPE: DNA
<213> ORGANISM: Mus musculus

<400> SEQUENCE: 36

```
tcagcatcct tccggttctg                                                20
```

<210> SEQ ID NO 37
<211> LENGTH: 22
<212> TYPE: DNA
<213> ORGANISM: Mus musculus

<400> SEQUENCE: 37

```
ggagccaaaa aagctgtcag tt                                             22
```

<210> SEQ ID NO 38
<211> LENGTH: 19
<212> TYPE: DNA
<213> ORGANISM: Mus musculus

<400> SEQUENCE: 38

```
cgtcctcgct cgtcctaca                                                 19
```

<210> SEQ ID NO 39
<211> LENGTH: 21
<212> TYPE: DNA
<213> ORGANISM: Mus musculus

<400> SEQUENCE: 39

```
acccttgcac tcactgcaaa g                                              21

<210> SEQ ID NO 40
<211> LENGTH: 21
<212> TYPE: DNA
<213> ORGANISM: Mus musculus

<400> SEQUENCE: 40
ggagaacatg aatcgcatcg t                                              21

<210> SEQ ID NO 41
<211> LENGTH: 19
<212> TYPE: DNA
<213> ORGANISM: Mus musculus

<400> SEQUENCE: 41
gcctgtaccc cccatcaag                                                 19

<210> SEQ ID NO 42
<211> LENGTH: 21
<212> TYPE: DNA
<213> ORGANISM: Mus musculus

<400> SEQUENCE: 42
acgtgggtct ggtgtgtttt c                                              21

<210> SEQ ID NO 43
<211> LENGTH: 20
<212> TYPE: DNA
<213> ORGANISM: Mus musculus

<400> SEQUENCE: 43
cggctgagca agctaaggtt                                                20

<210> SEQ ID NO 44
<211> LENGTH: 22
<212> TYPE: DNA
<213> ORGANISM: Mus musculus

<400> SEQUENCE: 44
ggaagaagcg ctctctttga aa                                             22

<210> SEQ ID NO 45
<211> LENGTH: 20
<212> TYPE: DNA
<213> ORGANISM: Mus musculus

<400> SEQUENCE: 45
ttcaagctgc cagaaaacca                                                20

<210> SEQ ID NO 46
<211> LENGTH: 21
<212> TYPE: DNA
<213> ORGANISM: Mus musculus

<400> SEQUENCE: 46
gagccttgtc agggtctttg g                                              21

<210> SEQ ID NO 47
<211> LENGTH: 20
<212> TYPE: DNA
<213> ORGANISM: Mus musculus
```

<400> SEQUENCE: 47
ccctctgaac ctgcaaatcg                                                    20

<210> SEQ ID NO 48
<211> LENGTH: 22
<212> TYPE: DNA
<213> ORGANISM: Mus musculus

<400> SEQUENCE: 48
tgatctgctc cctctcctca gt                                                 22

<210> SEQ ID NO 49
<211> LENGTH: 23
<212> TYPE: DNA
<213> ORGANISM: Mus musculus

<400> SEQUENCE: 49
aggaaccatg tctaccaaaa cca                                                23

<210> SEQ ID NO 50
<211> LENGTH: 19
<212> TYPE: DNA
<213> ORGANISM: Mus musculus

<400> SEQUENCE: 50
ctggctgagc tggcactgt                                                     19

<210> SEQ ID NO 51
<211> LENGTH: 21
<212> TYPE: DNA
<213> ORGANISM: Mus musculus

<400> SEQUENCE: 51
catgcacccc tttgagaacc t                                                  21

<210> SEQ ID NO 52
<211> LENGTH: 22
<212> TYPE: DNA
<213> ORGANISM: Mus musculus

<400> SEQUENCE: 52
atgtactgtt caggcagcga cc                                                 22

<210> SEQ ID NO 53
<211> LENGTH: 20
<212> TYPE: DNA
<213> ORGANISM: Mus musculus

<400> SEQUENCE: 53
cagtttcccc gagcttgcat                                                    20

<210> SEQ ID NO 54
<211> LENGTH: 17
<212> TYPE: DNA
<213> ORGANISM: Mus musculus

<400> SEQUENCE: 54
agaggcgggc agcattc                                                       17

<210> SEQ ID NO 55
<211> LENGTH: 20
<212> TYPE: DNA
<213> ORGANISM: Mus musculus

```
<400> SEQUENCE: 55
cgagcctgtg cctcctctaa                                              20

<210> SEQ ID NO 56
<211> LENGTH: 20
<212> TYPE: DNA
<213> ORGANISM: Mus musculus

<400> SEQUENCE: 56
gactcccatc acccatccat                                              20

<210> SEQ ID NO 57
<211> LENGTH: 24
<212> TYPE: DNA
<213> ORGANISM: Mus musculus

<400> SEQUENCE: 57
cctagctcag ttctctggac atga                                         24

<210> SEQ ID NO 58
<211> LENGTH: 24
<212> TYPE: DNA
<213> ORGANISM: Mus musculus

<400> SEQUENCE: 58
gcaggcctct aagatacgag aatt                                         24

<210> SEQ ID NO 59
<211> LENGTH: 20
<212> TYPE: DNA
<213> ORGANISM: Mus musculus

<400> SEQUENCE: 59
gacggacaag taccggctgc                                              20

<210> SEQ ID NO 60
<211> LENGTH: 20
<212> TYPE: DNA
<213> ORGANISM: Mus musculus

<400> SEQUENCE: 60
gacagcttag agatgatgat                                              20

<210> SEQ ID NO 61
<211> LENGTH: 19
<212> TYPE: DNA
<213> ORGANISM: Mus musculus

<400> SEQUENCE: 61
cgcgtcgact tattcatgg                                               19

<210> SEQ ID NO 62
<211> LENGTH: 20
<212> TYPE: DNA
<213> ORGANISM: Mus Musculus

<400> SEQUENCE: 62
cacacattga ttgtggcacc                                              20

<210> SEQ ID NO 63
<211> LENGTH: 23
<212> TYPE: DNA
```

```
<213> ORGANISM: Mus musculus

<400> SEQUENCE: 63
gagcatcctt tgctatcgga agc                                              23

<210> SEQ ID NO 64
<211> LENGTH: 23
<212> TYPE: DNA
<213> ORGANISM: Mus musculus

<400> SEQUENCE: 64
cgttatttcc tcctcgatga tgg                                              23

<210> SEQ ID NO 65
<211> LENGTH: 19
<212> TYPE: DNA
<213> ORGANISM: Homo sapiens

<400> SEQUENCE: 65
ttgccaagct cctgaagca                                                   19

<210> SEQ ID NO 66
<211> LENGTH: 21
<212> TYPE: DNA
<213> ORGANISM: Homo sapiens

<400> SEQUENCE: 66
cgtttggctg aataccttcc c                                                21

<210> SEQ ID NO 67
<211> LENGTH: 20
<212> TYPE: DNA
<213> ORGANISM: Homo sapiens

<400> SEQUENCE: 67
cccaaagctt gccttgcttt                                                  20

<210> SEQ ID NO 68
<211> LENGTH: 22
<212> TYPE: DNA
<213> ORGANISM: Homo sapiens

<400> SEQUENCE: 68
agacagtctc cgtgtgaggc at                                               22

<210> SEQ ID NO 69
<211> LENGTH: 22
<212> TYPE: DNA
<213> ORGANISM: Homo sapiens

<400> SEQUENCE: 69
gatgtggtcc gagtgtggtt ct                                               22

<210> SEQ ID NO 70
<211> LENGTH: 21
<212> TYPE: DNA
<213> ORGANISM: Homo sapiens

<400> SEQUENCE: 70
tgtgcatagt cgctgcttga t                                                21

<210> SEQ ID NO 71
<211> LENGTH: 20
```

```
<212> TYPE: DNA
<213> ORGANISM: Homo sapiens

<400> SEQUENCE: 71
gcagaaggcc tcagcaccta                                              20

<210> SEQ ID NO 72
<211> LENGTH: 19
<212> TYPE: DNA
<213> ORGANISM: Homo sapiens

<400> SEQUENCE: 72
aggttcccag tcgggttca                                               19

<210> SEQ ID NO 73
<211> LENGTH: 20
<212> TYPE: DNA
<213> ORGANISM: Homo sapiens

<400> SEQUENCE: 73
cccctggatt ttgcattcac                                              20

<210> SEQ ID NO 74
<211> LENGTH: 18
<212> TYPE: DNA
<213> ORGANISM: Homo sapiens

<400> SEQUENCE: 74
cgtgcgcaag aacaaacg                                                18

<210> SEQ ID NO 75
<211> LENGTH: 21
<212> TYPE: DNA
<213> ORGANISM: Homo sapiens

<400> SEQUENCE: 75
ccgacagttg taggccctgt t                                            21

<210> SEQ ID NO 76
<211> LENGTH: 20
<212> TYPE: DNA
<213> ORGANISM: Homo sapiens

<400> SEQUENCE: 76
ggcatcttcg ggttgatcct                                              20

<210> SEQ ID NO 77
<211> LENGTH: 24
<212> TYPE: DNA
<213> ORGANISM: Homo sapiens

<400> SEQUENCE: 77
gtgggcaggt gggagcttga ttct                                         24

<210> SEQ ID NO 78
<211> LENGTH: 21
<212> TYPE: DNA
<213> ORGANISM: Homo sapiens

<400> SEQUENCE: 78
ctggggcggc ctggtatgac a                                            21

<210> SEQ ID NO 79
```

```
<211> LENGTH: 20
<212> TYPE: DNA
<213> ORGANISM: Homo sapiens

<400> SEQUENCE: 79
aatgcggcat cttcaaacct                                            20

<210> SEQ ID NO 80
<211> LENGTH: 23
<212> TYPE: DNA
<213> ORGANISM: Homo sapiens

<400> SEQUENCE: 80
tgactttgtc acagcccaag ata                                        23
```

USES AND ISOLATION OF STEM CELLS FROM BONE MARROW

CROSS-REFERENCE TO RELATED APPLICATIONS

This application is a National Phase of International Application No. PCT/US2008/081832 filed Oct. 30, 2008, which claims the benefit of U.S. provisional Application Nos. 61/000,954, filed Oct. 30, 2007, and 61/079,675, filed Jul. 10, 2008. This application is also a continuation-in-part of U.S. application Ser. No. 12/096,754, filed Jun. 9, 2008, which is a National Phase of International Application No. PCT/US2006/042780, filed Nov. 2, 2006, which claims the benefit of U.S. provisional Application No. 60/748,685, filed Dec. 8, 2005. The contents of all of the above-identified applications are hereby incorporated by reference.

GOVERNMENT INTERESTS

This invention was made with Government support under Grant Nos. R01 HL072410, HL 055757, HL 068088 and HL 070897, awarded by the National Institutes of Health. The Government has certain rights to this invention.

FIELD OF THE DISCLOSURE

The presently disclosed subject matter relates, in general, to the identification, isolation, and use of a population of stem cells isolated from bone marrow, umbilical cord blood, and/or other sources and that are referred to herein as very small embryonic-like (VSEL) stem cells. More particularly, the presently disclosed subject matter relates to isolating said VSEL stem cells and employing the same, optionally after in vitro manipulation, to treat tissue and/or organ damage in a subject in need thereof.

BACKGROUND OF THE DISCLOSURE

The use of stem cells and stem cell derivatives has gained increased interest in medical research, particularly in the area of providing reagents for treating tissue damage either as a result of genetic defects, injuries, and/or disease processes. Ideally, cells that are capable of differentiating into the affected cell types could be transplanted into a subject in need thereof, where they would interact with the organ microenvironment and supply the necessary cell types to repair the injury.

Considerable effort has been expended to isolate stem cells from a number of different tissues for use in regenerative medicine. For example, U.S. Pat. No. 5,750,397 to Tsukamoto et al. discloses the isolation and growth of human hematopoietic stem cells that are reported to be capable of differentiating into lymphoid, erythroid, and myelomonocytic lineages. U.S. Pat. No. 5,736,396 to Bruder et al. discloses methods for lineage-directed differentiation of isolated human mesenchymal stem cells under the influence of appropriate growth and/or differentiation factors. The derived cells can then be introduced into a host for mesenchymal tissue regeneration or repair.

One area of intense interest relates to the use of embryonic stem (ES) cells, which have been shown in mice to have the potential to differentiate into 5 all the different cell types of the animal. Mouse ES cells are derived from cells of the inner cell mass of early mouse embryos at the blastocyst stage, and other pluripotent and/or totipotent cells have been isolated from germinal tissue (e.g., primordial germ cells; PGCs). The ability of these pluripotent and/or totipotent stem cells to proliferate in vitro in an undifferentiated state, retain a 10 normal karyotype, and retain the potential to differentiate to derivatives of all three embryonic germ layers (endoderm, mesoderm, and ectoderm) makes these cells attractive as potential sources of cells for use in regenerative therapies in post-natal subjects.

The development of human ES (hES) cells has not been as successful as the advances that have been made with mouse ES cells. Thomson et al. reported pluripotent stem cells from lower primates (U.S. Pat. No. 5,843,780; Thomson et al. (1995) 92 Proc Natl Acad Sci USA 7844-7848), and from humans (Thomson et al. (1998) 282 Science 1145-1 147). Gearhart et al. generated human embryonic germ (hEG) cell lines from fetal gonadal tissue (Shamblott et al. (1998) 95 Proc Natl Acad Sci USA 13726-1 3731; and U.S. Pat. No. 6,090,622). Both hES and hEG cells have the desirable characteristics of pluripotent stem cells in that they are capable of being propagated in vitro without differentiating, they generally maintain a normal karyotype, and they remain capable of differentiating into a number of different cell types. Clonally derived human embryonic stem cell lines maintain pluripotency and proliferative potential for prolonged periods in culture (Amit et al. (2000) 227 Dev Biol271-278).

One significant challenge to the use of ES cells or other pluripotent cells for regenerative therapy in a subject is to control the growth and differentiation of the cells into the particular cell type required for treatment of a subject. There have been several reports of the effect of growth factors on the differentiation of ES cells. For example, Schuldiner et al. report the effects of eight growth factors on the differentiation of cells into different cell types from hES cells (see Schuldiner et al. (2000) 97 Proc Natl Acad Sci USA 11307-11312). As disclosed therein, after initiating differentiation through embryoid body-like formation, the cells were cultured in the presence of bFGF, TGFPI, activin-A, BMP-4, HGF, EGF, PNGF, or retinoic acid. Each growth factor had a unique effect on the differentiation pathway, but none of the growth factors directed differentiation exclusively to one cell type.

Ideally, it would be beneficial to be able to isolate and purify stem and/or precursor cells from a subject that could be purified and/or manipulated in vitro before being reintroduced into the subject for treatment purposes. The use of a subject's own cells would obviate the need to employ adjunct immunosuppressive therapy, thereby maintaining the competency of the subject's immune system. However, the current strategies for isolating ES cell lines, particularly hES cell lines, preclude isolating the cells from a subject and reintroducing them into the same subject.

Thus, the search for other stem cell types from adult animals continues. For example, mesenchymal stem cells (MSCs) are one such cell type. MSCs have been shown to have the potential to differentiate into several lineages including bone (Haynesworth et al. (1992) 13 Bone 81-88), cartilage (Mackay et al. (1998) 4 Tissue Eng 41 5-28; Yoo et al. (1998) 80 J Bone Joint Surg Am 745-57), adipose tissue (Pittenger et al. (2000) 251 Curr Top Microbiol Immunol-11), tendon (Young et al. (1998) 16 J Orthop Res 406-13), muscle, and stroma (Caplan et al. (2001) 7 Trends Mol Med 259-64).

Another population of cells, multipotent adult progenitor cells (MAPCs), has also been purified from bone marrow (BM; Reyes et al. (2001) 98 Blood 25 261 5-2625; Reyes & Vetfaillie (2001) 938 Ann NY Acad Sci 231-235). These cells have been shown to be capable of expansion in vitro for more than 100 population doublings without telomere shortening or the development of karyotypic abnormalities. MAPCs have also been shown to be able to differentiate under defined culture conditions into various mesenchymal cell types (e.g., osteoblasts, chondroblasts, adipocytes, and skeletal myoblasts), endothelium, neuroectoderm cells, and more recently, into hepatocytes (Schwartz et al. (2000) 109 J Clin Invest 1291-1302).

Additionally, hematopoietic stem cells (HSCs) have been reported to be able to differentiate into numerous cell types. BM hematopoietic stem cells have been reported to be able to 'transdifferentiate' into cells that express early heart (Orlic et al. (2003) 7 Pediatr Transplant 86-88; Makino et al. (1999) 103 J Clin Invest 697-705), skeletal muscle (Labarge & Blau (2002) 111 Cell 589-601; Corti et al. (2002) 277 Exp Cell Res 74-85), neural (Sanchez-Ramos (2002) 69 Neurosci Res 880-893), liver (Petersen et al. (1999) 284 Science 1 168-1 170), or pancreatic cell (Lanus et al. (2003) 111 J Clin Invest 843-850; Lee & Stoffel (2003) 111 J Clin Invest 799-801) markers. In vivo experiments in humans also demonstrated that transplantation of CD34+ peripheral blood (PB) stem cells led to the appearance of donor-derived hepatocytes (Korbling et al. (2002) 346 N Engl J Med 738-746), epithelial cells (Korbling et al. (2002) 346 N Engl J Med 738-746), and neurons (Hao et al. (2003) 12 J Hematother Stem Cell Res 23-32). Additionally, human BM-derived cells have been shown to contribute to the regeneration of infarcted myocardium (Stamm et al., (2003) 361 Lancet 45-46).

These reports have been interpreted as evidence for the existence of the phenomenon of transdifferentiation or plasticity of adult stem cells. However, the concept of transdifferentiation of adult tissue-specific stem cells is currently a topic of extensive disagreement within the scientific and medical communities (see e.g., Lemischka (2002) 30 Exp Hematol 848-852; Holden & Vogel (2002) 296 Science 21 26-21 29). Studies attempting to reproduce results suggesting transdifferentiation with neural stem cells have been unsuccessful (Castro et al. (2002) 297 Science 1299). It has also been shown that the hematopoietic stem/progenitor cells (HSPC) found in muscle tissue originate in the BM (McKinney-Freeman et al. (2002) 99 Proc Natl Acad Sci USA 1341-1 346; Geiger et al. 100 Blood 721-723; Kawada & Ogawa (2001) 98 Blood 2008-2013). Additionally, studies with chimeric animals involving the transplantation of single HPCs into lethally irradiated mice demonstrated that transdifferentiation and/or plasticity of circulating HPSC and/or their progeny, if it occurs at all, is an extremely rare event (Wagers et al. (2002) 297 Science 2256-2259).

Thus, there continues to be a need for new approaches to generate populations of transplantable cells suitable for a variety of applications, including but not limited to treating injury and/or disease of various organs and/or tissues.

SUMMARY OF THE DISCLOSURE

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for forming an embryoid body-like sphere from a population of very small embryonic-like (VSEL) stem cells or derivatives thereof. In some embodiments, the methods comprise (a) providing a population of CD45− cells comprising VSEL stem cells or derivatives thereof; and (b) culturing the VSEL stem cells or derivatives thereof in a medium comprising one or more factors that induce embryoid body-like sphere formation of the VSEL stem cells or derivatives thereof for a time sufficient for an embryoid body-like sphere to form. In some embodiments, the VSEL stem cells or derivatives thereof comprise CD34+/lin−/CD45− or Sca-1+/lin−/CD45− very small embryonic-like (VSEL) stem cells. In some embodiments, the VSEL stem cells are about 3-4 μm in diameter, express at least one of SSEA-1, Oct-4, Rev-1, and Nanog, posses large nuclei surrounded by a narrow rim of cytoplasm, and have open-type chromatin (euchromatin). In some embodiments, the population of CD45− cells comprising VSEL stem cells or derivatives thereof is isolated from a human or from a mouse. In some embodiments, the population of CD45− cells comprising VSEL stem cells or derivatives thereof is isolated from a source in the human or the mouse selected from the group consisting of bone marrow, peripheral blood, spleen, cord blood, and combinations thereof. In some embodiments, the one or more growth factors that induce embryoid body-like sphere formation of the VSEL stem cells or derivatives thereof comprise epidermal growth factor (EGF), fibroblast growth factor-2, and combinations thereof. In some embodiments, the one or more factors are provided to the VSEL stem cells or derivatives thereof by co-culturing the VSEL stem cells or derivatives thereof with C2C12 cells.

In some embodiments, the presently disclosed methods further comprise isolating the population of CD45− cells comprising VSEL stem cells or derivatives thereof by a method comprising the steps of (a) providing an initial population of cells suspected of comprising CD45− stem cells; (b) contacting the initial population of cells with a first antibody that is specific for CD45 and a second antibody that is specific for CD34 or Sca-1 under conditions sufficient to allow binding of each antibody to its target, if present, on each cell of the initial population of cells; (c) selecting a first subpopulation of cells that are CD34+ or Sca-1+, and are also CD45−; (d) contacting the first subpopulation of cells with one or more antibodies that are specific for one or more cell surface markers selected from the group consisting of CD45R/B220, Gr-1, TCRαβ, TCRγδ, CD11b, and Ter-119 under conditions sufficient to allow binding of each antibody to its target, if present, on each cell of the population of cells; (e) removing from the first subpopulation of cells those cells that bind to at least one of the antibodies of step (d); and (f) collecting a second subpopulation of cells that are either CD34+/lin−/CD45− or Sca-1+/lin−/CD45−, whereby a subpopulation of CD45− stem cells is isolated. In some embodiments, each antibody comprises a detectable label. In some embodiments, the detectable label comprises a fluorescent label or a moiety that can be detected by a reagent comprising a fluorescent label. In some embodiments, the separating comprises FACS sorting. In some embodiments, the presently disclosed methods further comprise isolating those cells that are c-met+, c-kit+, and/or LIF-R+. In some embodiments, the presently disclosed methods further comprise isolating those cells that express one or more genes selected from the group consisting of SSEA-1, Oct-4, Rev-1, and Nanog. In some embodiments, the population of cells comprises a bone marrow sample, a cord blood sample, or a peripheral blood sample.

In some embodiments of the presently disclosed subject matter, the population of cells is isolated from peripheral blood of a subject subsequent to treating the subject with an amount of a mobilizing agent sufficient to mobilize the CD45⁻ stem cells comprising VSEL stem cells from bone marrow into the peripheral blood of the subject. In some embodiments, the mobilizing agent comprises at least one of granulocyte-colony stimulating factor (G-CSF) and a CXCR4 antagonist. In some embodiments, the CXCR4 antagonist is a T140 peptide. In some embodiments, the subject is a mouse.

In some embodiments, the presently disclosed methods further comprise contacting the subpopulation of stem cells with an antibody that binds to CXCR4 and isolating from the subpopulation of stem cells those cells that are CXCR4⁺.

In some embodiments, the presently disclosed methods further comprise isolating those cells that are CXCR4⁺ and/or AC133⁺.

In some embodiments, the presently disclosed methods further comprise selecting those cells that are HLA-DR⁻, MHC class I⁻, CD90⁻, CD29⁻, CD105⁻, or combinations thereof.

The presently disclosed subject matter also provides embryoid body-like spheres comprising a plurality of very small embryonic-like (VSEL) stem cells.

The presently disclosed subject matter also provides cell cultures comprising embryoid body-like spheres as disclosed herein. In some embodiments, the embryoid body-like spheres disclosed herein are provided in a medium comprising one or more factors that induce embryoid body-like sphere formation of the VSEL stem cells or derivatives thereof.

The presently disclosed subject matter also provides methods for differentiating a very small embryonic-like (VSEL) stem cell into a cell type of interest. In some embodiments, the method comprise (a) providing an embryoid body-like sphere comprising VSEL stem cells or derivatives thereof; and (b) culturing the embryoid body-like sphere in a culture medium comprising a differentiation-inducing amount of one or more factors that induce differentiation of the VSEL stem cells or derivatives thereof into the cell type of interest until the cell type of interest appears in the culture. In some embodiments, the cell type of interest is a neuronal cell or a derivative thereof. In some embodiments, the neuronal cell or derivative thereof is selected from the group consisting of an oligodendrocyte, an astrocyte, a glial cell, and a neuron. In some embodiments, the neuronal cell or derivative thereof expresses a marker selected from the group consisting of GFAP, nestin, β III tubulin, Olig1, and Olig2. In some embodiments, the culturing is for at least about 10 days. In some embodiments, the culture medium comprises about 10 ng/ml rhEGF, about 20 ng/ml FGF-2, and about 20 ng/ml NGF. In some embodiments, the cell type of interest is an endodermal cell or derivative thereof. In some embodiments, the culturing comprises culturing the embryoid body-like sphere in a first culture medium comprising Activin A; and thereafter culturing the embryoid body-like sphere in a second culture medium comprising N2 supplement-A, B27 supplement, and about 10 mM nicotinamide. In some embodiments, the culturing in the first culture medium is for about 48 hours. In some embodiments, the culturing in the second culture medium is for at least about 12 days. In some embodiments, the endodermal cell or derivative thereof expresses a marker selected from the group consisting of Nkx 6.1, Pdx 1, and C-peptide. In some embodiments, the cell type of interest is a cardiomyocyte or a derivative thereof. In some embodiments, the culturing is for at least about 15 days. In some embodiments, the culture medium comprises a combination of basic fibroblast growth factor, vascular endothelial growth factor, and transforming growth factor β1 in an amount sufficient to cause a subset of the embryoid body-like sphere cells to differentiate into cardiomyocytes. In some embodiments, the cardiomyocyte or derivative thereof expresses a marker selected from the group consisting of Nsx2.5/Csx and GATA-4.

In some embodiments of the presently disclosed methods, the embryoid body-like sphere is prepared by (a) providing a population of CD45⁻ cells comprising VSEL stem cells; and (b) culturing the VSEL stem cells in a culture medium comprising one or more factors that induce embryoid body-like sphere formation of the VSEL cells for a time sufficient for an embryoid body-like sphere to appear.

The presently disclosed subject matter also provides formulations comprising the differentiated very small embryonic-like (VSEL) stem cells disclosed herein in a pharmaceutically acceptable carrier or excipient. In some embodiments, the pharmaceutically acceptable carrier or excipient is acceptable for use in humans.

The presently disclosed subject matter also provides methods for treating an injury to a tissue in a subject. In some embodiments, the methods comprise administering to the subject a composition comprising a plurality of isolated CD45⁻ stem cells comprising VSEL stem cells in a pharmaceutically acceptable carrier, in an amount and via a route sufficient to allow at least a fraction of the population of CD45⁻ stem cells to engraft the tissue and differentiate therein, whereby the injury is treated. In some embodiments, the injury is selected from the group consisting of an ischemic injury, a myocardial infarction, and stroke. In some embodiments, the subject is a mammal. In some embodiments, the mammal is selected from the group consisting of a human and a mouse. In some embodiments, the isolated CD45⁻ stem cells comprising VSEL stem cells were isolated from a source selected from the group consisting of bone marrow, peripheral blood, spleen, cord blood, and combinations thereof.

In some embodiments, the presently disclosed methods further comprise differentiating the isolated CD45⁻ stem cells to produce a pre-determined cell type prior to administering the composition to the subject. In some embodiments, the pre-determined cell type is selected from the group consisting of a neural cell, an endoderm cell, a cardiomyocyte, and derivatives thereof.

The presently disclosed subject matter also provides methods for producing a chimeric animal. In some embodiments, the method comprise adding one or more of a population of CD45⁻ stem cells comprising VSEL stem cells to an embryo such that the one or more of the CD45⁻ stem cells develop into one or more cell types of the embryo. In some embodiments, the adding comprises injecting the one or more CD45⁻ stem cells into the blastocoel of a blastocyst stage embryo. In some embodiments, the adding comprises aggregating the one or more CD45⁻ stem cells comprising the VSEL stem cells with a morula stage embryo. In some embodiments, the presently disclosed methods further comprise gestating the embryo after adding the one or more CD45⁻ stem cells comprising the VSEL stem cells at least until birth to provide a chimeric animal.

The presently disclosed subject matter also provides methods for purifying a very small embryonic-like (VSEL) stem cell for a cell type of interest from a population of CD45⁻ stem cells. In some embodiments, the methods comprise (a) providing a population of CD45⁻ stem cells comprising VSEL stem cells; (b) identifying a subpopulation of the CD45⁻ stem cells that express a marker of VSEL stem cells; and (c) purifying the subpopulation. In some embodiments, the population and the subpopulation are both CD34⁺/CXCR4⁺/lin⁻ or Sca-1⁺/lin⁻ in addition to being CD45⁻. In some embodiments, the population of CD45⁻ stem cells comprising VSEL stem cells was isolated from a source selected from the group consisting of bone marrow, peripheral blood, spleen, cord blood, and combinations thereof. In some embodiments, the cell type of interest is selected from the group consisting of a skeletal muscle cell, an intestinal epithelium cell, a pancreas cell, an endothelial cell, an epidermis cell, a melanocyte, a neuronal cell, a myocardial cell, a chondrocyte, an adipocyte, a liver cell, a pancreas cell, an endothelial cell, an epithelial cell, a retinal pigment cell, and an endodermal cell. In some embodiments, the marker is selected from the group consisting of GFAP, Nestin, β III tubulin, Olig1, Olig2, Myf5, MyoD, Myogenin, Nsx2.5/Csx, GATA-4, α-Fetoprotein, CK19, Nkx 2-3, Tcf4, Nkx 6.1, Pdx 1, VE-cadherin, Krt 2-5, Krt 2-6a, BNC, DCT, TYR, and TRP. In some embodiments, the cell type of interest is a myocardial cell and the marker is selected from the group consisting of Nkx2.5/Csx, GATA-4, and MEF2C. In some embodiments, the cell type of interest is an endothelial cell and the marker is selected from the group consisting of VEGFR2, VE-cadherin, von Willebrand factor, and TIE2. In some embodiments, the cell type of interest is a skeletal muscle cell and the marker is selected from the group consisting of Myf5, MyoD, and myogenin. In some embodiments, the cell type of interest is a liver cell and the marker is selected from the group consisting of a-fetoprotein and CK19. In some embodiments, the cell type of interest is a neural cell and the marker is selected from the group consisting of β III tubulin, Olig1, Olig2, GFAP, and nestin. In some embodiments, the cell type of interest is a pancreas cell and the marker is selected from the group consisting of Nkx 6.1 and Pdx 1. In some embodiments, the cell type of interest is a melanocyte and the marker is selected from the group consisting of DCT, TYR, and TRP.

The presently disclosed subject matter also provides methods for identifying an inducer of embryoid body-like sphere formation. In some embodiments, the methods comprise (a) preparing a cDNA library comprising a plurality of cDNA clones from a cell known to comprise the inducer; (b) transforming a plurality of cells that do not comprise the inducer with the cDNA library; (c) culturing a plurality VSEL stem cells or derivatives thereof in the presence of the transformed plurality of cells under conditions sufficient to cause the VSEL stem cells or derivatives thereof to form an embryoid body-like sphere; (d) isolating the transformed cell comprising the inducer; (e) recovering a cDNA clone from the transformed cell; and (f) identifying a polypeptide encoded by the cDNA clone recovered, whereby an inducer of embryoid body-like sphere formation is identified. In some embodiments, the cell known to comprise the inducer is a C2C12 cell. In some embodiments, the plurality of cDNA clones comprise at least one primer binding site flanking at least one side of a cDNA cloning site in a cloning vector into which the cDNA clones are inserted. In some embodiments, the presently disclosed methods further comprise amplifying the cDNA clone present in the transformed cell using primers that hybridize to primer sites flanking both sides of the cDNA cloning site. In some embodiments, the identifying is by sequencing the cDNA clone.

The presently disclosed subject matter also provides methods for isolating a subpopulation of CD45$^-$ stem cells comprising VSEL stem cells from umbilical cord blood or a fraction thereof. In some embodiments, the methods comprise (a) contacting the umbilical cord blood or the fraction thereof with a first antibody—that is specific for CD45 and a second antibody that is specific for CD34 or Sca-1 under conditions sufficient to allow binding of each antibody to its target, if present, on each cell of the population of cells; (b) selecting a first subpopulation of cells that are CD34$^+$ or Sca-1$^+$, and are also CD45$^-$; (c) contacting the first subpopulation of cells with one or more antibodies that are specific for one or more cell surface markers selected from the group consisting of CD45R/B220, Gr-1, TCRαβ, TCRγδ, CD11b, and Ter-119 under conditions sufficient to allow binding of each antibody to its target, if present, on each cell of the population of cells; (d) removing from the first subpopulation of cells those cells that bind to at least one of the antibodies of step (d); and (e) collecting a second subpopulation of cells that are either CD34$^+$/lin$^-$/CD45$^-$ or Sca-1$^+$/lin$^-$/CD45$^-$, whereby a subpopulation of CD45$^-$ stem cells comprising VSEL stem cells is isolated. In some embodiments, the presently disclosed methods further comprise incubating the umbilical cord blood or the fraction thereof or any of the subpopulations in a hypotonic solution for a time sufficient to lyse essentially all erythrocytes that might be present. In some embodiments, the presently disclosed methods further comprise isolating those cells that are positive for at least one of CXCR4, c-met, c-kit, or LIF-R.

Accordingly, it is an object of the presently disclosed subject matter to provide new populations of stem cells, and methods of preparing and using the same. This object and other objects are achieved in whole or in part by the presently disclosed subject matter.

An object of the presently disclosed subject matter having been stated above, other objects will become evident as the description proceeds, when taken in connection with the Examples and Figures as described hereinbelow.

BRIEF DESCRIPTION OF THE DRAWINGS

FIG. 1A shows that Sca-1+/lin−/CD45− cells are small and measure 3-4 μm in diameter. They possess a relatively large nucleus surrounded by a narrow rim of cytoplasm. At the ultrastructural level, the narrow rim of cytoplasm possesses a few mitochondria, scattered ribosomes, small profiles of endoplasmic reticulum, and a few vesicles. The nucleus is contained within a nuclear envelope with nuclear pores. Chromatin is loosely packed and consists of euchromatin. FIG. 1B shows that in contrast, Sca-1+/lin−/CD45+ cells display heterogeneous morphology and are larger. They measure on average 8-10 μm in diameter and possess scattered chromatin and prominent nucleoli.

FIG. 3A depicts a photograph of a gel on which RT-PCR products have been separated and stained with ethidium bromide, and depict the results of expression of mRNA for CXCR4 (lane 1), c-Met (lane 3) and LIF-R (lane 5) in Sca-1+/lin−/CD45− is depicted. RT-PCR was run for 30 cycles. Negative RT-PCR reactions (DNA instead of cDNA: lanes 2, 4 and 6). Representative result from three independent sorts is shown. FIG. 3B depicts fluorescence micrographic images of Sca-1+/lin−/CD45− cells isolated by FACS and evaluated for expression of CXCR4, c-MET and LIF-R by immunohistochemical staining (the images were taken under Plan Apo 60XA11.40 oil objective (Nikon, Japan)). Negative staining controls are not shown. Representative result from four independent experiments is shown. FIG. 3C is a bar graph depicting the results of chemoattraction studies of Sca-1+/lin−/CD45− cells by MATRIGEL® drop containing SDF-1 or not (negative control). The number of chemoattracted Sca-1+/lin−/CD45− cells is shown per 100 µm of MATRIGEL® drop circumference. The data are pooled together from three independent experiments. *p<0.00001 as compared to control MATRIGEL®.

FIG. 4A are FACS dot-plots of cells sorted from BMMNC derived from 3 week old (upper panel) and 1 year old mice (lower panel). The left panels depict dot-plots of murine BMMNCs. Cells from the lymphoid gate that were Sca-1+/lin− (-middle panels) were sorted by FACS for CD45 expression (right panels). Three independent sorting experiments were performed (the BM of 8 mice was pooled for each sort). Representative sorts are shown. FIG. 4B is a bar graph depicting expression of mRNA for PSC and VSEL stem cell markers in Sca-1+/lin−/CD45− cells isolated by FACS from 3 week old and 1 year old mice was compared by RQ-PCR between the same number of sorted cells. Four independent sorting experiments were performed (the BM of 8 mice was pooled for each sort). Data are mean±SD. *p<0.01 vs. cells from old animals.

FIG. 6A is a dot-plot depicting FACS sorting of the SP of BMMNC. FIG. 6B is a bar graph depicting the expression of mRNA for PSC and VSEL stem cell markers in BMMNC, SP, SP Sca-1+/lin−/CD45−, SP Sca-1+/lin−/CD45+, Sca-1+/lin−/CD45−, Sca-1+/lin−/CD45+ cells isolated by FACS from 3 week old mice was compared by RQ-PCR between the same number of sorted cells. Three independent sorting experiments were performed (the BM of 8 mice was pooled for each sort). Data are presented as mean±SD. *p<0.01 vs. cells from old animals.

FIG. 9A depicts a micrographic image of an embryoid body (EB)-like spheres after co-culture of Sca-1+/lin−/CD45− BM cells with C2C12 cells under the conditions described in EXAMPLE 20. FIG. 9B is a fluorescence micrographic image depicting the expression of green fluorescent protein (GFP) in the Sca-1+/lin−/CD45− cells, indicating that these embryoid bodies are derived from purified Sca-1+/lin−/CD45− BM cells isolated from green immunofluorescence positive (GFP+) mice (C57BL/6-Tg(ACTB-EGFP)1Osb/J mice purchased from The Jackson Laboratory, Bar Harbor, Me., United States of America) and not the C2C12 cells.

FIG. 11A is a dot-plot of murine bone marrow MNC after hypotonic lysis. FIG. 11B is a dot-plot showing staining of cells from R1 gate for lineage markers expression and CD45 antigen. In this Figure, R2 indicates lineage minus and CD45 negative BM MNC. Cells from R1 and R2 were analyzed for expression of Sca-1 and co-expression of HLA-DR (see FIG. 11C), MHC class I (see FIG. 11D), CD29 (see FIG. 11E), CD90 (see FIG. 11F), and CD105 (see FIG. 11G) antigens.

FIGS. 22A-22C and 22D-22F depict images of culture plates in which Sca-1+/lin−/CD45− BMMNCs were grown. Numerous cells in plates with Sca-1+/lin−/CD45− cells were positive for cardiac-specific myosin heavy chain (FIGS. 22B, 22C, 22E1 and 22F; green fluorescence). Many of these cardiac-specific myosin heavy chain-positive cells were also positive for cardiac troponin I (FIGS. 22D and 22F [arrowheads]; red fluorescence). FIGS. 22G-22I are images of culture plates in which Sca-1+/lin−/CD45+ cells were grown. These cells were largely negative for the expression of the aforementioned cardiac-specific antigens (see FIG. 22H). Nuclei are identified in each of FIGS. 22A-22I by DAPI staining (blue fluorescence). Scale bar=20 μm.

FIG. 27A shows that human CB contained a population of lin−/CD45− MNC that express CXCR4 (0.037±0.02%, n=9), CD34 (0.118±0.028%, n=5), and CD133 (0.018±0.008%, n=5). FIG. 27B shows that these CXCR4+/CD133+/CD34+/lin−/CD45− cells are very small (about 3-5 μm; FIG. 27B, upper panel), whereas CB-derived lin−/CD45+ hematopoietic cells are larger (>6 μm; FIG. 27B, lower panel).

FIGS. 28A and 28B are bar graphs showing that CB-derived CXCR4+/CD133+/CD34+/lin−/CD45− cells sorted by FACS, as well as CXCR4+/lin−/CD45−, CD34+/lin−/CD45−, and CD133+/lin−/CD45−/cells are highly enriched for mRNA for transcriptions factors expressed by pluripotent embryonic cells such as Oct-4 and Nanog. FIG. 28C shows the results of RT-PCR that confirm the FACS analysis.

FIG. 34. Myocardial infarct size. Myocardial infarct area fraction ([infarct area/LV area]×100) assessed from Masson's trichrome-stained hearts in groups I-III, which were treated with vehicle, CD45+ hematopoietic stem cells, and VSELs, respectively. O, Individual mice; ●, mean±SEM.

FIG. 35. Echocardiographic assessment of LV function. Representative 2-dimensional (A,C,E) and M-mode (B,D,F) images from vehicle-treated (A,B), CD45+ cell-treated (C,D), and VSEL-treated (E,F) mice 35 d after coronary occlusion/reperfusion. The infarct wall is delineated by arrowheads (A,C,E). Compared with the vehicle-treated and CD45+ cell-treated hearts, the VSEL-treated heart exhibits a smaller LV cavity, a thicker infarct wall, and improved motion of the infarct wall. Panels G-J demonstrate that transplantation of VSEL improved echocardiographic measurements of LV systolic function 35 d after MI. Data are mean±SEM. n=11-14 mice/group. *P<0.05 vs. group II at 35 d; #P<0.05 vs. group I at 35 d; §P<0.05 vs. values at 96 h in respective groups.

FIG. 36. Morphometric assessment of LV remodeling. Representative Masson's trichrome-stained myocardial sections from vehicle-treated (A), CD45+ hematopoietic stem cell-treated (B), and VSEL-treated (C) hearts. Scar tissue and viable myocardium are identified in blue and red, respectively. Note that the LV cavity is smaller and the infarct wall thicker in the VSEL-treated heart. Panels D-H illustrate morphometric measurements of LV structural parameters. Data are mean±SEM. n=11-14 mice per group. *P<0.05 vs. group II.

BRIEF DESCRIPTION OF THE SEQUENCE LISTING

Figure 1:
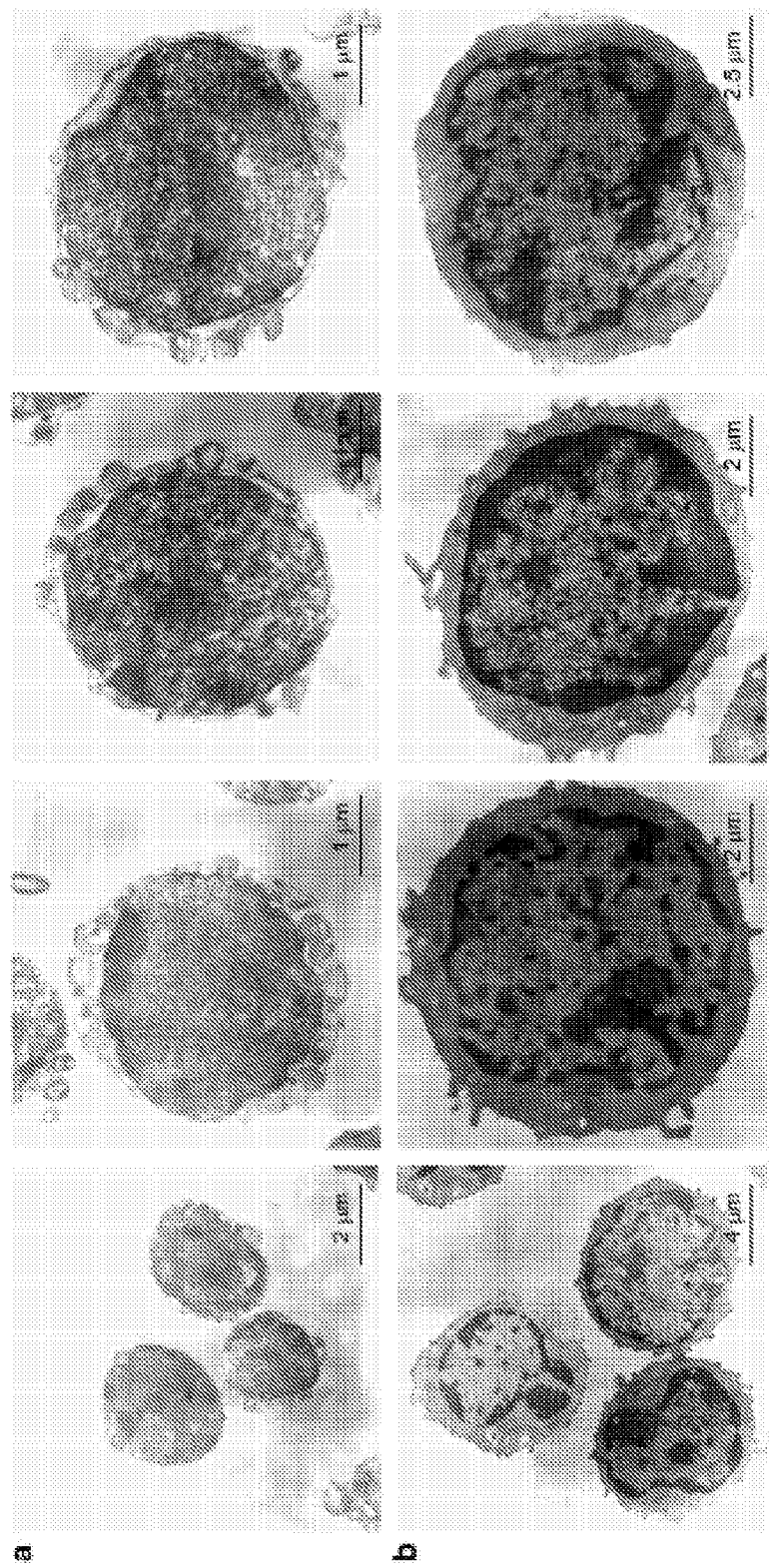
FIGS. 1A and 1B depict transmission electron microscopy (TEM) images of Sca-1+/lin−/CD45− and Sca-1+/lin−/CD45+ cells.

SEQ ID NOS: 1-64 are the nucleotide sequences of 32 primer pairs that can be used to amplify various murine nucleic acid sequences as summarized in Table 1.

TABLE 1

Sequences of Murine Primers Employed for Real Time RT-PCR

| Gene (GENBANK ® Accession No.) | Sequences (presented in 5' to 3' order |
|---|---|
| β2 microglobulin (NM_009735) | CATACGCCTGCAGAGTTAAGCA (SEQ ID NO: 1) |
| | GATCACATGTCTCGATCCCAGTAG (SEQ ID NO: 2) |
| Oct4 (X52437) | ACCTTCAGGAGATATGCAAATCG (SEQ ID NO: 3) |
| | TTCTCAATGCTAGTTCGCTTTCTCT (SEQ ID NO: 4) |
| Nanog (AY278951) | CGTTCCCAGAATTCGATGCTT (SEQ ID NO: 5) |
| | TTTTCAGAAATCCCTTCCCTCG (SEQ ID NO: 6) |
| Rex1 (M26382) | AGATGGCTTCCCTGACGGATA (SEQ ID NO: 7) |
| | CCTCCAAGCTTTCGAAGGATTT (SEQ ID NO: 8) |
| Dppa3 (NM_139218) | GCAGTCTACGGAACCGCATT (SEQ ID NO: 9) |
| | TTGAACTTCCCTCCGGATTTT (SEQ ID NO: 10) |
| Rif1 (NM_175238) | GAGCTGGATTCTTTTGGATCAGTAA (SEQ ID NO: 11) |
| | GCCAAAGGTGACCAGACACA (SEQ ID NO: 12) |
| GFAP (X02801) | GGAGCTCAATGACCGCTTTG (SEQ ID NO: 13) |
| | TCCAGGAAGCGAACCTTCTC (SEQ ID NO: 14) |
| Nestin (NM_016701) | CCCTGATGATCCATCCTCCTT (SEQ ID NO: 15) |
| | CTGGAATATGCTAGAAACTCTAGACTCACT (SEQ ID NO: 16) |
| β III tubulin (NM_023279) | TCCGTTCGCTCAGGTCCTT (SEQ ID NO: 17) |
| | CCCAGACTGACCGAAAACGA (SEQ ID NO: 18) |

TABLE 1-continued

Sequences of Murine Primers Employed for Real Time RT-PCR

| Gene (GENBANK ® Accession No.) | Sequences (presented in 5' to 3' order |
|---|---|
| Olig1 (NM_016968) | ACGTCGTAGCGCAGGCTTAT (SEQ ID NO: 19) |
| | CGCCCAACTCCGCTTACTT (SEQ ID NO: 20) |
| Olig2 (NM_016967) | GGGAGGCGCCATTGTACA (SEQ ID NO: 21) |
| | GTGCAGGCAGGAAGTTCCA (SEQ ID NO: 22) |
| Myf5 (NM_008656) | CTAGGAGGGCGTCCTTCATG (SEQ ID NO: 23) |
| | CACGTATTCTGCCCAGCTTTT (SEQ ID NO: 24) |
| MycD (NM_010868) | GGACAGGCGGTGTGCATT (SEQ ID NO: 25) |
| | CACTCCGGAACCCCAACAG (SEQ ID NO: 26) |
| Myogenin (X15784) | GGAGAAGCGCAGGCTCAAG (SEQ ID NO: 27) |
| | TTGAGCAGGGTGCTCCTCTT (SEQ ID NO: 28) |
| Nsx2.5/Csx (AF091351) | CGGATGTGGCTCGTTTGC (SEQ ID NO: 29) |
| | TTGGGACCCTCCCGAGAT (SEQ ID NO: 30) |
| GATA-4 (U85046) | TCCAGTGCTGTCTGCTCTAAGC (SEQ ID NO: 31) |
| | TGGCCTGCGATGTCTGAGT (SEQ ID NO: 32) |
| α-fetoprotein (NM_007423) | ACCCGCTTCCCTCATCCT (SEQ ID NO: 33) |
| | AAACTCATTTCGTGCAATGCTT (SEQ ID NO: 34) |
| CK19 (M28698) | CATGCGAAGCCAATATGAGGT (SEQ ID NO: 35) |
| | TCAGCATCCTTCCGGTTCTG (SEQ ID NO: 36) |
| Nkx2-3 (NM_008699) | GGAGCCAAAAAAGCTGTCAGTT (SEQ ID NO: 37) |
| | CGTCCTCGCTCGTCCTACA (SEQ ID NO: 38) |
| Tcf4 (NM_013685) | ACCCTTGCACTCACTGCAAAG (SEQ ID NO: 39) |
| | GGAGAACATGAATCGCATCGT (SEQ ID NO: 40) |
| Nkx6/1 (NM_144955) | GCCTGTACCCCCCATCAAG (SEQ ID NO: 41) |
| | ACGTGGGTCTGGTGTGTTTTC (SEQ ID NO: 42) |

TABLE 1-continued

Sequences of Murine Primers Employed for Real Time RT-PCR

| Gene (GENBANK® Accession No.) | Sequences (presented in 5' to 3' order |
|---|---|
| Pdx1 (NM_008814) | CGGCTGAGCAAGCTAAGGTT (SEQ ID NO: 43) |
| | GGAAGAAGCGCTCTCTTTGAAA (SEQ ID NO: 44) |
| VE-cadherin (X83930) | TTCAAGCTGCCAGAAAACCA (SEQ ID NO: 45) |
| | GAGCCTTGTCAGGGTCTTTGG (SEQ ID NO: 46) |
| Krt2-5 (NM_027011) | CCCTCTGAACCTGCAAATCG (SEQ ID NO: 47) |
| | TGATCTGCTCCCTCTCCTCAGT (SEQ ID NO: 48) |
| Krt2-6a (NM_008476) | AGGAACCATGTCTACCAAAACCA (SEQ ID NO: 49) |
| | CTGGCTGAGCTGGCACTGT (SEQ ID NO: 50) |
| BNC (NM_007562) | CATGCACCCCTTTGAGAACCT (SEQ ID NO: 51) |
| | ATGTACTGTTCAGGCAGCGACC (SEQ ID NO: 52) |
| DCT (NM_010024) | CAGTTTCCCCGAGCTTGCAT (SEQ ID NO: 53) |
| | AGAGGCGGGCAGCATTC (SEQ ID NO: 54) |
| TYR (NM_011661) | CGAGCCTGTGCCTCCTCTAA (SEQ ID NO: 55) |
| | GACTCCCATCACCCATCCAT (SEQ ID NO: 56) |
| TYRP1 (NM_031202) | CCTAGCTCAGTTCTCTGGACATGA (SEQ ID NO: 57) |
| | GCAGGCCTCTAAGATACGAGAATT (SEQ ID NO: 58) |
| CXCR4 (BC031665) | GACGGACAAGTACCGGCTGC (SEQ ID NO: 59) |
| | GACAGGCTTAGAGATGATGAT (SEQ ID NO: 60) |
| Met receptor (NM_008591) | CGCGTCGACTTATTCATGG (SEQ ID NO: 61) |
| | CACACATTGATTGTGGCACC (SEQ ID NO: 62) |
| LIF-R (NM_013584) | GAGCATCCTTTGCTATCGGAAGC (SEQ ID NO: 63) |
| | CGTTATTTCCTCCTCGATGATGG (SEQ ID NO: 64) |

SEQ ID NOS: 65-80 are the nucleotide sequences of 8 primer pairs that can be used to amplify various human nucleic acid sequences as summarized in Table 2.

TABLE 2

Sequences of Human Primers Employed for Real Time RT-PCR

| Gene (GENBANK® Accession No.) | Sequences (presented in 5' to 3' order) |
|---|---|
| Oct4 (DQ486513) | TTGCCAAGCTCCTGAAGCA (SEQ ID NO: 65) |
| | CGTTTGGCTGAATACCTTCCC (SEQ ID NO: 66) |
| Nanog (NM_024865) | CCCAAAGCTTGCCTTGCTTT (SEQ ID NO: 67) |
| | AGACAGTCTCCGTGTGAGGCAT (SEQ ID NO: 68) |
| Oct4 (DQ486513) | GATGTGGTCCGAGTGTGGTTCT (SEQ ID NO: 69) |
| | TGTGCATAGTCGCTGCTTGAT (SEQ ID NO: 70) |
| Nanog (NM_024865) | GCAGAAGGCCTCAGCACCTA (SEQ ID NO: 71) |
| | AGGTTCCCAGTCGGGTTCA (SEQ ID NO: 72) |
| Nkx2.5/Csx (NM_004387) | CCCCTGGATTTTGCATTCAC (SEQ ID NO: 73) |
| | CGTGCGCAAGAACAAACG (SEQ ID NO: 74) |
| VE-cadherin (AF240635) | CCGACAGTTGTAGGCCCTGTT (SEQ ID NO: 75) |
| | GGCATCTTCGGGTTGATCCT (SEQ ID NO: 76) |
| GFAP (NM_002055) | GTGGGCAGGTGGGAGCTTGATTCT (SEQ ID NO: 77) |
| | CTGGGGCGGCCTGGTATGACA (SEQ ID NO: 78) |
| β2 microglobulin (NM_004048) | AATGCGGCATCTTCAAACCT (SEQ ID NO: 79) |
| | TGACTTTGTCACAGCCCAAGATA (SEQ ID NO: 80) |

DETAILED DESCRIPTION

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. General Considerations

The concept that hematopoietic stem cells (HSC) isolated from relatively easily accessible sources such as bone marrow (BM), mobilized peripheral blood (mPB), or cord blood (CB) could be subsequently employed as precursors for other stem cells necessary for regeneration of various solid organs (e.g., heart, brain, liver or pancreas) created excitement in the scientific community. It had been postulated that HSC possess germlayer-unrestricted plasticity and can transdifferentiate into stem cells from all non-hematopoietic lineages. Unfortunately, the first promising reports showing a robust contribution of "HSC" to regeneration of different tissues were not reproduced by other investigators.

In response to this, the scientific community became polarized in its view on stem cell plasticity. Several alternative explanations of previously reported data have been proposed. The first concept that was rapidly accepted was explaining stem cell plasticity through the phenomenon of cell fusion. Data were presented that donor-derived HSC and/or monocytes might fuse with differentiated cells present in recipient tissues, leading to the creation of fused cells that have a double number of chromosomes in their nuclei and express cell surface and cytoplasmic markers that are derived from both "parental" cells.

Another explanation of stem cell plasticity is based on the appearance of epigenetic changes in cells exposed to external stimuli (e.g., organ damage, non-physiological culture conditions, and/or other stresses). Both cell fusion and epigenetic changes, however, are extremely rare, randomly occurring events that would not appear to fully account for the previously published positive "trans-dedifferentiation" data. Furthermore, fusion was excluded as a major contributor to the observed donor derived chimerism in several recently published studies.

The concept that BM might contain heterogeneous populations of stem cells was surprisingly not appreciated as a part of the discussion concerning stem cell plasticity. Disclosed herein is direct evidence that BM stem cells are heterogeneous and expected to be pluripotent. BM has been shown to contain endothelial-, bone-, skeletal muscle-, cardiac-, hepatic-, and neural-tissue committed stem cells.

However, these potential candidate cells had not been characterized well at the single cell level. As disclosed herein, murine bone marrow (BM) contains a population of rare (~0.02% of BMMNC) Sca-1+/lin−/CD45− cells that express markers of non-hematopoietic stem cells. More importantly, these rare cells were able to differentiate into cardiomyocytes, pancreatic cells, and grow neurospheres in in vitro cultures. These Sca-1+/lin−/CD45− cells have the morphology of, and express several markers of, undifferentiated embryonic-like stem cells.

Disclosed herein is the identification and purification from murine bone marrow (BM) of a subpopulation of rare CD34+/lin−/CD45− (human) or Sca-1+/lin−/CD45− (mouse) cells, referred to herein as "very small embryonic-like (VSEL) stem cells". In addition to being Sca-1+/lin−/CD45− or CD34+/lin−/CD45−, VSEL stem cells express markers of pluripotent stem cells (PSC) such as SSEA-1, Oct-4, Nanog, and Rex-1. The direct electron microscopic analysis revealed that VSEL stem cells are small (about 3-4 µm), possess large nuclei surrounded by a narrow rim of cytoplasm, and contain open-type chromatin (euchromatin) that is typical of embryonic stem cells. The number of VSEL stem cells is highest in BM from young (~1 month-old) mice, and decreases with age. It is also significantly diminished in short living DBA/2J mice as compared to long living C57BL/6 animals. VSEL stem cells respond strongly to SDF-1, HGF/SF, and LIF in vitro, and express CXCR4, c-met, and LIF-R. This population of VSEL stem cells expressing pluripotent- and tissue committed stem cells markers can be a source of pluripotent stem cells for tissue and/or organ regeneration.

II. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims. Thus, the phrase "a stem cell" refers to one or more stem cells, unless the context clearly indicates otherwise.

The terms "target tissue" and "target organ" as used herein refer to an intended site for accumulation of VSEL stem cells and/or an in vitro differentiated VSEL stem cell derivative following administration to a subject. For example, in some embodiments the methods of the presently disclosed subject matter involve a target tissue or a target organ that has been damaged, for example by ischemia or other injury.

The term "control tissue" as used herein refers to a site suspected to substantially lack accumulation of an administered cell. For example, in accordance with the methods of the presently disclosed subject matter, a tissue or organ that has not been injured or damaged is a representative control tissue, as is a tissue or organ other than the intended target tissue. For example, if the injury to be treated is a myocardial infarction, the intended target tissue would be the heart, and essentially all other tissues and organs in the subject can be considered control tissues.

The terms "targeting" and "homing", as used herein to describe the In vivo activity of a cell (for example, a VSEL stem cells and/or an in vitro differentiated VSEL stem cell derivative thereof) following administration to a subject, and refer to the preferential movement and/or accumulation of the cell in a target tissue as compared to a control tissue.

The terms "selective targeting" and "selective homing" as used herein refer to a preferential localization of a cell (for example, a VSEL stem cells and/or an in vitro differentiated VSEL stem cell derivative thereof) that results in an accumulation of the administered VSEL stem cells and/or an in vitro differentiated VSEL stem cell derivative thereof in a target tissue that is in some embodiments about 2-fold greater than accumulation of the administered VSEL stem cells and/or an in vitro differentiated VSEL stem cell derivative thereof in a control tissue, in some embodiments accumulation of the administered VSEL stem cells and/or an in vitro differentiated VSEL stem cell derivative thereof that is about 5-fold or greater, and in some embodiments an accumulation of the administered VSEL stem cells and/or an in vitro differentiated VSEL stem cell derivative thereof that is about 10-fold or greater than in an control tissue. The terms "selective targeting" and "selective homing" also refer to accumulation of a VSEL stem cells and/or an in vitro differentiated VSEL stem cell derivative thereof in a target tissue concomitant with an absence of accumulation in a control tissue, in some embodiments the absence of accumulation in all control tissues.

The term "absence of targeting" is used herein to describe substantially no binding or accumulation of a VSEL stem cells and/or an in vitro differentiated VSEL stem cell derivative thereof in one or more control tissues under conditions wherein accumulation would be detectable if present. The phrase also is intended to include minimal, background accumulation of a VSEL stem cells and/or an in vitro differentiated VSEL stem cell derivative thereof in one or more control tissues under such conditions.

The term "subject" as used herein refers to a member of any invertebrate or vertebrate species. Accordingly, the term "subject" is intended to encompass any member of the Kingdom Animalia including, but not limited to the phylum ChordaSa (i.e., members of Classes Osteichythyes (bony fish), Amphibia (amphibians), Reptilia (reptiles), Ayes (birds), and Mammalia (mammals)), and all Orders and Families encompassed therein.

Similarly, all genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes listed in Tables 1 and 2, which disclose GENBANK® Accession Nos. for the murine and human nucleic acid sequences, respectively, are intended to encompass homologous genes and gene products from other animals including, but not limited to other mammals, fish, amphibians, reptiles, and birds.

The methods of the presently disclosed subject matter are particularly useful for warm-blooded vertebrates. Thus, the presently disclosed subject matter concerns mammals and birds. More particularly contemplated is the isolation, manipulation, and use of VSEL stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of VSEL stem cells from livestock, including but not limited to domesticated swine (pigs and hogs), ruminants, horses, poultry, and the like.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods.

The term "isolated", as used in the context of a nucleic acid or polypeptide (including, for example, a peptide), indicates that the nucleic acid or polypeptide exists apart from its native environment. An isolated nucleic acid or polypeptide can exist in a purified form or can exist in a non-native environment.

The terms "nucleic acid molecule" and "nucleic acid" refer to deoxyribonucleotides, ribonucleotides, and polymers thereof, in single-stranded or double-stranded form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA, and "mRNA. Nucleic acids can be synthesized, or can be derived from any biological source, including any organism.

The term "isolated", as used in the context of a cell (including, for example, a VSEL stem cell), indicates that the cell exists apart from its native environment. An isolated cell can also exist in a purified form or can exist in a non-native environment.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

III. Isolation of Very Small Embryonic-Like (VSEL) Stem Cells

III.A. Generally

The presently disclosed subject matter provides methods of isolating a subpopulation of CD45– stem cells from a population of cells. In some embodiments, the method comprises (a) providing a population of cells suspected of comprising CD45– stem cells; (b) contacting the population of cells with a first antibody that is specific for CD45 and a second antibody that is specific for CD34 or Sca-1 under conditions sufficient to allow binding of each antibody to its target, if present, on each cell of the population of cells; (c) selecting a first subpopulation of cells that are CD34+ or Sca-1+, and are also CD45–; (d) contacting the first subpopulation of cells with one or more antibodies that are specific for one or more cell surface markers selected from the group including but not limited to CD45R/B220, Gr-1, TCRαβ, TCRγδ, CD11b, and Ter-119 under conditions sufficient to allow binding of each antibody to its target, if present, on each cell of the population of cells; (e) removing from the first subpopulation of cells those cells that bind to at least one of the antibodies of step (d); and (f) collecting a second subpopulation of cells that are either CD34+/lin–/CD45– or Sca-1+/lin–/CD45–, whereby a subpopulation of CD45– stem cells is isolated.

As used herein, the term "CD45" refers to a tyrosine phosphatase, also known as the leukocyte common antigen (LCA), and having the gene symbol PTPRC. This gene corresponds to GENBANK® Accession Nos. NP_002829 25 (human), NP_035340 (mouse), NP_612516 (rat), XP_002829 (dog), XP_599431 (cow) and AAR16420 (pig). The amino acid sequences of additional CD45 homologs are also present in the GENBANKB database, including those from several fish species and several non-human primates.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from humans (e.g., AAB25223), mice (NP_598415), rats (XP_223083), cats (NP_001009318), pigs (MP_999251), cows (NP_76434), and others.

In mice, some stem cells also express the stem cell antigen Sca-1 (GENBANK® Accession No. NP_034868), also referred to as Lymphocyte antigen Ly-6A.2.

Thus, the subpopulation of CD45− stem cells represents a subpopulation of all CD45− cells that are present in the population of cells prior to the separating step. In some embodiments, the subpopulation of CD45− stem cells are from a human, and are CD34+/CXCR4+/lin−/CD45−. In some embodiments, the subpopulation of CD45− stem cells are from a mouse, and are Sca-1+/lin−/CD45−.

The isolation of the disclosed subpopulations can be performed using any methodology that can separate cells based on expression or lack of expression of the one or more of the CD45, CXCR4, CD34, AC133, Sca-1, CD45R/B220, Gr-1, TCRαβ, TCRγδ, CD11b, and Ter-119 markers including, but not limited to fluorescence-activated cell sorting (FACS).

As used herein, lin− refers to a cell that does not express any of the following markers: CD45R/B220, Gr-1, TCRαβ, TCRγδ, CD11b, and Ter-119. These markers are found on cells of the B cell lineage from early Pro-B to mature B cells (CD45R/B220); cells of the myeloid lineage such as monocytes during development in the bone marrow, bone marrow granulocytes, and peripheral neutrophils (Gr-1); thymocytes, peripheral T cells, and intestinal intraepithelial lymphocytes (TCRαβ and TCRγδ); myeloid cells, NK cells, some activated lymphocytes, macrophages, granulocytes, B1 cells, and a subset of dendritic cells (CD11b); and mature erythrocytes and erythroid precursor cells (Ter-119).

The separation step can be performed in a stepwise manner as a series of steps or concurrently. For example, the presence or absence of each marker can be assessed individually, producing two subpopulations at each step based on whether the individual marker is present. Thereafter, the subpopulation of interest can be selected and further divided based on the presence or absence of the next marker.

Alternatively, the subpopulation can be generated by separating out only those cells that have a particular marker profile, wherein the phrase "marker profile" refers to a summary of the presence or absence of two or more markers. For example, a mixed population of cells can contain both CD34+ and CD34− cells. Similarly, the same mixed population of cells can contain both CD45+ and CD45− cells. Thus, certain of these cells will be CD34+/CD45+, others will be CD34+/CD45−, others will be CD34−/CD45+, and others will be CD34−/CD45−. Each of these individual combinations of markers represents a different marker profile. As additional markers are added, the profiles can become more complex and correspond to a smaller and smaller percentage of the original mixed population of cells. In some embodiments, the cells of the presently disclosed subject matter have a marker profile of CD34+/CXCR4+/lin−/CD45−, and in some embodiments, the cells of the presently disclosed subject matter have a marker profile of Sca-1+/lin−/CD45−.

In some embodiments of the presently disclosed subject matter, antibodies specific for markers expressed by a cell type of interest (e.g., polypeptides expressed on the surface of a CD34+/CXCR4+/lin−/CD45− or a Sca-1+/lin−/CD45− cell) are employed for isolation and/or purification of subpopulations of BM cells that have marker profiles of interest. It is understood that based on the marker profile of interest, the antibodies can be used to positively or negatively select fractions of a population, which in some embodiments are then further fractionated.

In some embodiments, a plurality of antibodies, antibody derivatives, and/or antibody fragments with different specificities is employed. In some embodiments, each antibody, or fragment or derivative thereof, is specific for a marker selected from the group including but not limited to Ly-6A/E (Sca-1), CD34, CXCR4, AC133, CD45, CD45R, B220, Gr-1, TCRαβ, TCRγδ, CD11b, Ter-119, c-met, LIF-R, SSEA-1, Oct-4, Rev-1, and Nanog. In some embodiments, cells that express one or more genes selected from the group including but not limited to SSEA-1, Oct-4, Rev-1, and Nanog are isolated and/or purified.

The presently disclosed subject matter relates to a population of cells that in some embodiments express the following antigens: CXCR4, AC133, CD34, SSEA-1 (mouse) or SSEA-4 (human), fetal alkaline phosphatase (AP), c-met, and the LIF-Receptor (LIF-R). In some embodiments, the cells of the presently disclosed subject matter do not express the following antigens: CD45, Lineage markers (i.e., the cells are lin−), HLA-DR, MHC class I, CD90, CD29, and CD105. Thus, in some embodiments the cells of the presently disclosed subject matter can be characterized as follows: CXCR4+/AC133+/CD34+/SSEA-1+ (mouse) or SSEA-4+ (human)/AP+/c-met+/LIF-R+/CD45−/lin−/HLA-DR−/MHC class I−/CD90-CD29−/CD105−.

In some embodiments, each antibody, or fragment or derivative thereof, comprises a detectable label. Different antibodies, or fragments or derivatives thereof, which bind to different markers can comprise different detectable labels or can employ the same detectable label.

A variety of detectable labels are known to the skilled artisan, as are methods for conjugating the detectable labels to biomolecules such as antibodies and fragments and/or derivatives thereof. As used herein, the phrase "detectable label" refers to any moiety that can be added to an antibody, or a fragment or derivative thereof, that allows for the detection of the antibody. Representative detectable moieties include, but are not limited to, covalently attached chromophores, fluorescent moieties, enzymes, antigens, groups with specific reactivity, chemiluminescent moieties, and electrochemically detectable moieties, etc. In some embodiments, the antibodies are biotinylated. In some embodiments, the biotinylated antibodies are detected using a secondary antibody that comprises an avidin or streptavidin group and is also conjugated to a fluorescent label including, but not limited to Cy3, Cy5, and Cy7. In some embodiments, the antibody, fragment, or derivative thereof is directly labeled with a fluorescent label such as Cy3, Cy5, or Cy7. In some embodiments, the antibodies comprise biotin-conjugated rat anti-mouse Ly-6A/E (Sca-1; clone E1 3-161.7), streptavidin-PE-Cy5 conjugate, anti-CD45-APCCy7 (clone 30-F11), anti-CD45R/B220-PE (clone RA3-6B2), anti-Gr-1-PE (clone RB6-8C5), anti-TCRαβ PE (clone H57-597), anti-TCRγδ PE (clone GL3), anti-CD11b PE (clone M 1/70) and anti-Ter-119 PE (clone TER-119). In some embodiments, the antibody, fragment, or derivative thereof is directly labeled with a fluorescent label and cells that bind to the antibody are separated by fluorescence-activated cell sorting. Additional detection strategies are known to the skilled artisan.

While FACS scanning is a convenient method for purifying subpopulations of cells, it is understood that other methods can also be employed. An exemplary method that can be used is to employ antibodies that specifically bind to one or more of CD45, CXCR4, CD34, AC133, Sca-1, CD45R/B220, Gr-1, TCRαβ, TCRγδ, CD11b, and Ter-119, with the antibodies comprising a moiety (e.g., biotin) for which a high affinity binding reagent is available (e.g., avidin or streptavidin). For example, a biotin moiety could be attached to antibodies for each marker for which the presence on the cell surface is desirable (e.g., CD34, Sca-1, CXCR4), and the cell population with bound antibodies could be contacted with an affinity reagent comprising an avidin or streptavidin moiety (e.g., a column comprising avidin or streptavidin). Those cells that bound to the column would be recovered and further fractionated as desired. Alternatively, the antibodies that bind to markers present on those cells in the population that are to be removed (e.g., CD45R/B220, Gr-1, TCRαβ, TCRγδ, CD11b, and Ter-119) can be labeled with biotin, and the cells that do not bind to the affinity reagent can be recovered and purified further.

It is also understood that different separation techniques (e.g., affinity purification and FACS) can be employed together at one or more steps of the purification process.

A population of cells containing the CD34+/CXCR4+/lin−/CD45− or Sca-1+/lin−/CD45− cells of the presently disclosed subject matter can be isolated from any subject or from any source within a subject that contains them. In some embodiments, the population of cells comprises a bone marrow sample, a cord blood sample, or a peripheral blood sample. In some embodiments, the population of cells is isolated from peripheral blood of a subject subsequent to treating the subject with an amount of a mobilizing agent sufficient to mobilize the CD45− stem cells from bone marrow into the peripheral blood of the subject. As used herein, the phrase "mobilizing agent" refers to a compound (e.g., a peptide, polypeptide, small molecule, or other agent) that when administered to a subject results in the mobilization of a VSEL stem cell or a derivative thereof from the bone marrow of the subject to the peripheral blood. Stated another way, administration of a mobilizing agent to a subject results in the presence in the subject's peripheral blood of an increased number of VSEL stem cells and/or VSEL stem cell derivatives than were present therein immediately prior to the administration of the mobilizing agent. It is understood, however, that the effect of the mobilizing agent need not be instantaneous, and typically involves a lag time during which the mobilizing agent acts on a tissue or cell type in the subject in order to produce its effect. In some embodiments, the mobilizing agent comprises at least one of granulocyte-colony stimulating factor (G-CSF) and a CXCR4 antagonist (e.g., a T140 peptide; Tamamura et al. (1998) 253 Biochem Biophys Res Comm 877-882).

In some embodiments, a VSEL stem cell or derivative thereof also expresses a marker selected from the group including but not limited to c-met, c-kit, LIF-R, and combinations thereof. In some embodiments, the disclosed isolation methods further comprise isolating those cells that are c-met+, c-kit+, and/or LIF-R+.

In some embodiments, the VSEL stem cell or derivative thereof also expresses SSEA-1, Oct-4, Rev-1, and Nanog, and in some embodiments, the disclosed isolation methods further comprise isolating those cells that express these genes.

The presently disclosed subject matter also provides a population of CD45− stem cells isolated by the presently disclosed methods.

III.B. Further Fractionation of the CD45− Stem Cell Population

Disclosed herein is the isolation and/or purification of subpopulations of CD34+/CXCR4+/lin−/CD45− or Sca-1+/lin−/CD45− cells. These cells comprise a heterogeneous population of cells comprising pluripotent and tissue-committed stem cells. Also disclosed herein are strategies that can be employed for purifying the disclosed subpopulations.

In some embodiments, the heterogeneous subpopulation is further fractionated to enrich for VSEL stem cells of certain lineages. As disclosed herein, the CD34+/CXCR4+/lin−/CD45− or Sca-1+/lin−/CD45− subpopulations comprise VSEL stem cells for various tissues including, but not limited to neural cells, skeletal muscle cells, cardiac cells, liver cells, intestinal epithelium cells, pancreas cells, endothelium cells, epidermis cells, and melanocytes. These cells can be further fractionated by purifying from the CD34+/CXCR4+/lin−/CD45− or Sca-1+/lin−/CD45− subpopulations those cells that express one or more markers associated with these lineages. For example, VSEL stem cells for neural tissue can be fractionated using reagents that detect the expression of glial fibrillary acidic protein (GFAP), nestin, β III tubulin, oligodendrocyte transcription factor 1 (Olig1), and/or oligodendrocyte transcription factor 2 (Olig2). Similarly, VSEL stem cells for skeletal muscle can be fractionated using reagents that detect the expression of Myf5, MyoD, and/or myogenin. Additional VSEL stem cell types and markers that can be employed include, but are not limited to cardiomyocyte VSEL stem cells (Nsx2.5/Csx, GATA-4), liver cell VSEL stem cells (α-Fetoprotein, CK19), intestinal epithelium VSEL stem cells (Nkx 2-3, Tcf4), pancreas cell TCSCs (Nkx 6.1, Pdx 1, C-peptide), endothelial cell VSEL stem cells (VE-cadherin), epidermal cell VSEL stem cells (Krt 2-5, Krt 2-6a, BNC), and melanocyte VSEL stem cells (DCT, TYR, TRP).

IV. Methods of Differentiating VSEL Stem Cells

IV.A. Generation of Embryoid Body-(EB) Like Spheres

The presently disclosed subject matter also provides a method of differentiating VSEL stem cells. In some embodiments, the methods comprise first generating an embryoid body-like sphere. As used herein, the phrases "embryoid body-like sphere" and "embryoid body-like" refer to an aggregate of cells that appears morphologically similar to an embryoid body formed by ES cells under appropriate in vitro culturing conditions. As used herein, the phrase is used interchangeably with "embryoid body" to refer to such aggregates when the cells that make up the embryoid body are CD34+/CXCR4+/lin−/CD45− or Sca-1+/lin−/CD45− cells isolated and/or purified using the presently disclosed techniques. Methods of generating EBs from ES cells are known in the art (see e.g., Martin & Evans (1975) in *Teratomas and Differentiation* (M. I. Sherman & D. Solter, Eds.), pp. 169-187, Academic Press, New York, N.Y., United States of America; Doetschman et al. (1985) 87 J Embryol Exp Morphol 27-45). Disclosed herein are methods to prepare EB-like spheres from other multipotent and pluripotent cells, including the CD34+/CXCR4+/lin−/CD45− or Sca-1+/lin−/CD45− cells.

In some embodiments, a method of forming an embryoid-like body from a population of very small embryonic-like (VSEL) stem cells or derivatives thereof comprises (a) providing a population of CD45− cells comprising VSEL stem cells or derivatives thereof; and (b) culturing the VSEL stem cells or derivatives thereof in vitro in a medium comprising one or more factors that induce embryoid-like body formation of the VSEL stem cells or derivatives thereof for a time sufficient for an embryoid-like body to appear.

As used herein, the term "one or more factors that induce embryoid-like body formation of the VSEL stem cells or derivatives thereof" refers to a biomolecule or plurality of biomolecules that when in contact with a plurality of VSEL stem cells or derivatives thereof induces the VSEL stem cells or derivatives thereof to form one or more embryoid body (EB-like)-like spheres. In some embodiments, the one or more factors that induce embryoid body-like formation of the VSEL stem cells or derivatives thereof comprise epidermal growth factor (EGF), fibroblast growth factor-2, and combinations thereof. In some embodiments, the one or more factors are provided to the VSEL stem cells or derivatives thereof by co-culturing the VSEL stem cells or derivatives thereof with C2C12 cells.

IV.B. Methods of Differentiating VSEL Stem Cells and Derivatives Thereof

Once EB-like spheres are generated, the cells therein can be differentiated in vitro by culturing the cells under appropriate conditions. In some embodiments, a method of differentiating a very small embryonic-like (VSEL) stem cell or derivative thereof into a cell type of interest in vitro comprises (a) providing an embryoid body-like comprising VSEL stem cells or derivatives thereof; and (b) culturing the embryoid body-like in a culture medium comprising a differentiation-inducing amount of one or more factors that induce differentiation of the VSEL stem cells or derivatives thereof into the cell type of interest until the cell type of interest appears in the in vitro culture.

As used herein, the phrase "differentiation-inducing amount" refers to an amount of a growth factor or other activator that when present within an in vitro differentiation medium, causes a VSEL stem cell or derivative thereof to differentiate into a cell type of interest. In some embodiments, the growth factor or other activator includes, but is not limited to epidermal growth factor (EGF), fibroblast growth factor-2 (FGF-2), nerve growth factor (NGF), basic fibroblast growth factor (bFGF), vascular endothelial growth factor (VEGF), transforming growth factor β1 (TGFβ1), and combinations thereof, and/or other supplements including, but not limited to N2 supplement-A, B27 supplement, and nicotinamide (available from Stem Cell Technologies Inc., Vancouver, British Columbia, Canada). See also Fraichard et al. (1995) 108 J Cell Sci 3181-3188.

The choice of growth factors and/or other supplements can depend on the cell type desired into which the EB-like spheres are to differentiate. In some embodiments, the EB-like spheres can be differentiated into neuronal derivatives including, but not limited to neurons, oligodendrocytes, astrocytes, and glial cells. As disclosed in EXAMPLE 22, EB-like spheres can be differentiated into neuronal derivatives by culturing them in medium comprising NEUROCULT® Basal Medium (Stem Cell Technologies Inc., Vancouver, British Columbia, Canada) supplemented with rhEGF, FGF-2, and NGF. EB-like spheres can be differentiated into endodermal derivatives by culturing them in medium comprising Activin A (see EXAMPLE 23). Also, EB-like spheres can be differentiated into cardiomyocytes by culturing them in medium comprising bFGF, VEGF, and TGFPI (see EXAMPLE 24).

Other cell types that can be generated in vitro from stem cells such as ES cells include, but are not limited to hepatocytes (Yamada et al. (2002) 20 Stem Cells 146-1 54), hematopoietic cells, and pancreatic cells.

V. Methods and Compositions for Treatment Using VSEL Stem Cells

V.A. Subjects

The presently disclosed subject matter also provides a method for treating an injury to a tissue or organ in a subject, the method comprising administering to the subject a pharmaceutical composition, wherein the pharmaceutical composition comprises a plurality of isolated CD45– stem cells comprising VSEL stem cells in a pharmaceutically acceptable carrier, in an amount and via a route sufficient to allow at least a fraction of the population of CD45– stem cells comprising VSEL stem cells to engraft the tissue and differentiate therein, whereby the injury is treated.

As used herein, the phrase "treating an injury to a tissue or organ in a subject" refers to both intervention designed to ameliorate the symptoms of causes of the injury in a subject (e.g., after initiation of the disease process) as well as to interventions that are designed to prevent the disease from occurring in the subject. Stated another way, the terms "treating" and grammatical variants thereof are intended to be interpreted broadly to encompass meanings that refer to reducing the severity of and/or to curing a disease, as well as meanings that refer to prophylaxis. In this latter respect, "treating" refers to "preventing" or otherwise enhancing the ability of the subject to resist the disease process.

V.B. Formulations

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and nonaqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

V.C. Administration

Suitable methods for administration the cells of the presently disclosed subject matter include, but are not limited to intravenous administration and delivery directly to the target tissue or organ. In some embodiments, the method of administration encompasses features for regionalized delivery or accumulation of the cells at the site in need of treatment. In some embodiments, the cells are delivered directly into the tissue or organ to be treated. In some embodiments, selective delivery of the presently disclosed cells is accomplished by intravenous injection of cells, where they home to the target tissue or organ and engraft therein. In some embodiments, the presently disclosed cells home to the target tissue or organ as a result of the production of an SDF-1 gradient produced by the target tissue or organ, which acts as a chemotactic attractant to the CXCR+ cells disclosed herein.

V.D. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

VI. Methods of Producing Chimeric Animals with VSEL Stem Cells

VSEL stem cells (e.g., the CD34+/CXCR4+/lin−/CD45− or Sca-1+/lin−/CD45− cells of the presently disclosed subject matter) and/or derivatives thereof can also be employed for producing chimeric animals using techniques known in the art applicable to ES cells (see e.g., Nagy et al. (2003) *Manipulating the Mouse Embryo. A Laboratory Manual, Third Edition*. Cold Spring Harbor Laboratory Press, Cold Spring Harbor, N.Y., United States of America; Robertson (1991) 44 Biol Reprod 238-45; Jaenisch (1988) 240 Science 1468-1474; Robertson et al. (1986) 323 Nature 445-447; Bradley et al. (1984) 309 Nature 255-258. See also U.S. Pat. Nos. 5,650,550; 5,777,195). For example, the cells can be injected into blastocysts or aggregated with morula stage embryos. In some embodiments, a chimera produced by introducing a VSEL stem cell or a derivative thereof into a recipient is a germline chimera that can transmit the genome of the VSEL stem cell to a subsequent generation.

VII. Other Applications

VII.A. Gene Expression Studies

The VSEL stem cells and derivatives thereof disclosed herein can also be employed for monitoring differentiation of cells in a target tissue (e.g., in a chimeric animal). For example, chimeric animals can be generated using purified subpopulations of VSEL stem cells (e.g., a purified subpopulation of cardiomyocyte VSEL stem cells), and the differentiation and/or development of derivatives of the VSEL stem cells can be examined in the chimera. In some embodiments, the VSEL stem cell comprises a detectable marker (e.g., a coding sequence encoding GFP operably linked to a promoter operable in the cells types to be monitored) to facilitate distinguishing VSEL stem cell derivatives from cells derived from the host animal into which the VSEL stem cells were introduced.

Additionally, the VSEL stem cells and derivatives thereof disclosed herein can also be employed for gene expression studies. For example, gene expression profiles can be determined for VSEL stem cells and derivatives thereof including, but not limited to purified subpopulations of VSEL stem cells, which can then be compared to other cell types including, but not limited to cell types that are either more or less differentiated than a VSEL stem cell. Stated another way, since a VSEL stem cell is more differentiated than a totipotent cell, yet less differentiated than a terminally differentiated cell, VSEL stem cells and derivatives thereof can be employed for producing and comparing gene expression profiles among various cell types along a differentiation pathway from a totipotent cell to a terminally differentiated cell, thereby identifying what genes are downregulated and upregulated as a cell differentiates from a totipotent cell to a VSEL stem cell to a terminally differentiated cell. Alternatively or in addition, gene expression profiles can be compared between VSEL stem cells and ES cells to identify genes the expression of which differ between these stem cell types.

VII.B. Methods of Identifying an Inducer of Embryoid Body-Like Sphere Formation The presently disclosed cells and methods can also be employed for identifying an inducer of embryoid body-like sphere formation. As used herein, the phrase "inducer of embryoid body-like sphere formation" refers to a molecule (e.g., a biomolecule including, but not limited to a polypeptide, a peptide, or a lipid) that cause a plurality of VSEL stem cells or derivatives thereof to form one or more embryoid body-like spheres under conditions wherein the VSEL stem cells or derivatives thereof do not otherwise form one or more embryoid body-like spheres. In some embodiments, such conditions include, but are not limited to culturing in a culture medium in which in the absence of the inducer, the VSEL stem cells or derivatives do not form one or more embryoid body-like spheres, but when the inducer is added to an identical culture medium, results in the VSEL stem cells or derivatives thereof forming one or more embryoid body-like spheres.

In some embodiments, the instant methods comprise (a) preparing a cDNA library comprising a plurality of cDNA clones from a cell known to comprise the inducer; (b) transforming a plurality of cells that do not comprise the inducer with the cDNA library; (c) culturing a plurality VSEL stem cells or derivatives thereof in the presence of the transformed plurality of cells under conditions sufficient to cause the VSEL stem cells or derivatives thereof to form an embryoid body-like sphere; (d) isolating the transformed cell comprising the inducer; (e) recovering a cDNA clone from the transformed cell; and (f) identifying a polypeptide encoded by the cDNA clone recovered, whereby an inducer of embryoid body-like formation is identified. In some embodiments, the plurality of cDNA clones are present within a cDNA cloning vector, and the vector comprises at least one nucleotide sequence flanking at least one side of the cloning site in the vector into which the cDNA clones are inserted that can bind a primer such as a sequencing primer. In some embodiments, both primer-binding nucleotide sequences are present flanking each side of the cloning site, allowing the cDNA insert to be amplified using the polymerase chain reaction (PCR). Accordingly, in some embodiments the instant methods further comprise amplifying the cDNA clone present in the transformed cell using primers that hybridize to primer sites flanking both sides of the cDNA cloning site, and in some embodiments the identifying step is performed by sequencing the cDNA clone directly or by sequencing the amplified PCR product.

It is understood, however, that other methods that are within the skill of the ordinary artisan can also be employed to identify an inducer. For example, in some embodiments the cell known to comprise the inducer is a C2C12 cell. C2C12-conditioned medium can be tested to determine whether the inducer present in C2C12 cultures is a diffusible molecule (e.g., a peptide, polypeptide, or bioactive lipid). If the inducer is a diffusible molecule, the C2C12-conditioned medium can be heat treated to determine whether the inducer is heat labile (such as a peptide or polypeptide) or not heat labile (such as a bioactive lipid). Fractionation studies including, but not limited to proteomic analysis and/or lipid chromatography can then be employed to identify putative inducer.

If C2C12-conditioned medium does not comprise an inducer, it implies that the inducer is present on C2C12 cells. Techniques that can be applied for identifying a membrane-bound inducer that is present on C2C12 cells include, but are not limited to the use of monoclonal antibodies and/or siRNAs. Alternatively or in addition, gene expression analysis can be employed, including, for example, the use of gene arrays, differential display, etc.

When a putative inducer is identified, its status as an inducer can be confirmed by transforming a cell line that does not contain the inducer with a nucleotide sequence encoding the inducer and confirming that the transformed cell line supports the formation of embryoid body-like spheres by VSEL stem cells or derivatives thereof.

Additionally, the VSEL stem cells and derivatives thereof can be employed for identifying other cells and cell lines that are capable of inducing formation of embryoid body-like spheres. Exemplary cell lines that can be examined include, but are not limited to murine fetal fibroblasts, and other murine and human malignant cell lines (e.g., teratomas and sarcomas).

Elective Collection and Banking of Autologous Peripheral VSELs

The present invention also provides for an elective healthcare insurance model using an individual's own VSELs for the individual's future healthcare uses, such as repair of myocardial infarction. An individual can elect to have his or her own VSELs collected, processed and preserved for future distribution for his or her healthcare needs. Preferably, the VSELs are collected while the donor is in healthy or "pre-disease" state. The process includes methods of collection, processing, and preservation of VSELs during non-diseased state. Such methods are disclosed in U.S. Patent Publication No. 2006/0233768 and U.S. Patent Publication No. 2008/0038231, each of which are herein incorporated by reference in their entirety.

According to one embodiment, there is provided a method of making VSELs available to a subject, comprising the steps of: the proactively collecting the VSELs from a subject with no immediate perceived health condition requiring treatment using his own collected VSELs; collecting VSELs from the subject; at the time of collection, earmarking the collected VSELs for use by the subject; preserving the collected VSELs in storage; and retrieving the stored VSELs if and when needed by the subject. In preferred embodiments, the subject is a human.

According to a preferred embodiment, the VSELs may be collected by an apheresis process. Accordingly, there is provided a method for collecting autologous VSELs from a pre-disease human subject; collecting VSELs from the peripheral blood of a pre-disease human subject using an apheresis process; at the time of collection, earmarking the collected cells for use by the human subject; and preserving the collected cells to maintain the cellular integrity of the cells.

According to another preferred embodiment, there is provided a method of collecting autologous VSELs from a pre-disease subject comprising the steps of administering to the pre-disease subject a stem cell stem cell potentiating agent; collecting VSELs from peripheral blood of a pre-disease subject using an apheresis process; at the time of collection, earmarking the collected cells for use by the subject; and preserving the collected cells to maintain the cellular integrity of the cells.

According to yet another preferred embodiment, there is provided a method of collecting autologous VSELs from a pre-disease subject comprising the steps of administering to the pre-disease subject a stem cell potentiating agent or mobilizing agent; collecting VSELs from peripheral blood pre-disease subject using an apheresis process; at the time of collection, earmarking the collected cells for use by the subject; and preserving the collected cells to maintain the cellular integrity of the cells; wherein the pre-disease subject is administered a stem cell potentiating agent on two consecutive days, with the subject receiving one dose per day, and wherein the apheresis process is performed on the third consecutive day. Preferably, the one or more stem cell potentiating agents is selected from the group consisting of G-CSF, GM-CSF, dexamethazone, a CXCR4 receptors inhibitor and a combination thereof. The CXCR4 receptor inhibitor may be selected from the group consisting of AMD3100, ALX40-4C, T22, T134, T140, and TAK-779.

According to another preferred embodiment, there is provided a method of collecting autologous VSELs from a pre-disease subject comprising the steps of: administering to the pre-disease subject at least two doses of G-CSF of about 1 µg/kg/day to 8 µg/kg/day; collecting VSELs from peripheral blood pre-disease subject using an apheresis process; at the time of collection, earmarking the collected cells for use by the subject; and preserving the collected cells to maintain the cellular integrity of the cells. The pre-disease subject may be administered at least two doses of G-CSF within a 2 to 6 day period. Preferably, at least two doses of G-CSF is administered on two consecutive days, with the subject receiving only one dose per day. More preferably, the subject receives two doses of G-CSF administered on consecutive days. In another preferred embodiment, the pre-disease subject is administered at least two doses of G-CSF within about 12 to about 36 hours of each other.

Accordingly to another preferred embodiment, the G-CSF is administered to a subject at a dose of about 4 to about 6 µg/kg/day or equivalent thereof.

Accordingly to another preferred embodiment, about 50 µg to about 800 µg per dose of G-CSF is administered subcutaneously to the subject.

Accordingly to another preferred embodiment, about 300 µg to about 500 µg per dose of G-CSF is administered subcutaneously to the subject.

Accordingly to another preferred embodiment, the subject is a human subject that has met at least one condition selected from the group consisting of between 10 and 200 kg in weight and between 2 to 80 years old.

The G-CSF may be administered subcutaneously. Preferably, about 480 µg per dose of G-CSF is administered subcutaneously to the pre-disease subject.

The collection of VSELs from peripheral blood using an apheresis process may be conducted the day after the second dose of G-CSF is administered. In a preferred embodiment, the collection of VSELs from peripheral blood using an apheresis process is conducted about 12 to about 36 hours after the second dose of G-CSF is administered. According to one embodiment, the collecting step is conducted when the subject is an adult or a non-neonate. According to another embodiment, the collecting step includes the step of collecting at least on the order of greater than $1 \times 10^{20}$ total nucleated cells, or at least on the order of $10^{19}$, or $10^{18}$, or $10^{17}$, or $10^{16}$, or $10^{15}$, or $10^{14}$, or $10^{13}$, or $10^{12}$, or $10^{11}$, or $10^{10}$, or $10^{9}$, or $10^8$, or $10^7$, or $10^6$, or $10^5$ total nucleated cells per subject in a single collection process. Preferably, the collecting step includes the step of collecting at least on the order of greater than $1\times10^{12}$ total nucleated cells per subject in a single collection process. Preferably, the collecting step includes the step of collecting at least on the order of greater than $1\times10^8$ CD34+ stem cells per subject in a single collection process. More preferably, the collecting step includes the step of collecting at least on the order of greater than $1\times10^9$ CD34+ stem cells per subject in a single collection process. Most preferably, the collecting step includes the step of collecting at least on the order of greater than $1\times10^{10}$ CD34+ stem cells per subject in a single collection process.

According to another embodiment, the collecting step is undertaken over multiple sessions.

According to yet another embodiment, the preserving step comprises storing the collected cells in a stem cell bank.

According to another embodiment, administration of the stem cell potentiating agent is performed for at least one week before the collecting step.

According to yet another embodiment, the health condition is selected from the group consisting of a neoplastic disorder, an immune disorder, and leucopenia.

According to preferred embodiments, the apheresis process is performed for at least one hour in the collecting step; at least two hours in the collecting step; at least three hours in the collecting step; at least four hours in the collecting step.

According to yet another embodiment, the preserving step preserves cells collected in the collecting step before substantial cell divisions.

According to yet another embodiment, the preserving step may also comprise the step of further processing the VSELs into multiple separate containers for storage. The processing step may also comprise the step of isolating one cell population enriched or depleted for a stem cell surface antigen. The stem cell surface antigen may be selected from the group consisting of CD34, lin, SSEA-1, Oct-4, Nanog, and Rex-1, KDR, CD45, and CD 133.

According to yet another embodiment, the preserving step may also comprise the step of determining from the collected population of cells at least a distinctive property associated with the person prior to storing in a the stem cell bank, so as to provide a means of secured identification to match the collected VSELs with the person at the time of use. The distinctive property may be a DNA or RNA sequence, or may be a proteome of a cell the one population of VSELs or the at least one population of non-VSELs. The determining step may further include providing an indicia with each population of cells representing information of the distinctive property The indicia may be embodied in at least one of a label, bar code, magnetic strip, and microchip, or may be embedded within the preserved collected populations of cells.

According to yet another embodiment, the preserving step may also comprise cryopreservation of the at least one population of VSELs and at least one population of non-VSELs. The at least one population of VSELs and at least one population of non-VSELs may cryopreserved in separate containers or may be cryopreserved in the same container.

According to other preferred embodiments, compositions and methods are provided for treating a patient in need thereof comprising administering to a subject an autologous, VSEL-enriched population of cells.

Preferably, the subject or person is in a non-disease or pre-disease state. It should be noted that the term "pre-disease" state (versus "post-disease" state) as used herein covers the absolute term of "healthy", "no disease" (versus "not healthy/diseased") and a relative term of a gradation in the disease progression ("healthier than" or "less diseased" than post-disease state). Since "pre-disease" can be defined by a time prior to a subject being diagnosed with a disease, the subject could be healthy in an absolute term or might already have the disease where the disease has not yet manifested itself, not yet been diagnosed, or not yet detected. Even in the latter scenario, for such a "pre-disease" state, it is possible that the disease may not be so widespread such that it has reached the cells collected; or even if the cells collected are diseased, they may be less aggressive or are of a healthier grade due to the early stage of their development, or the cells still retain some functioning necessary to combat the same disease and/or other diseases. Thus, the term "healthy" cells covers both the absolute term that the cells are healthy, and the term that, relatively speaking, these collected cells (from the subject before he becomes a patient) are healthier than what the patient (in his "post-disease" state) currently have in his body.

Specifically, "pre-disease" state could refer to prior diagnosis or knowledge of a specific targeted disease or diseases, or class or classes of diseases, of the subject (collectively "specific diseases"), such that stem cell can be collected from the subject at an opportune time in anticipation of the subject manifesting the specific diseases in the future. For example, in view of family health history, genetic history and/or profiling, a subject may be deemed to have a certain probability of contracting a certain specific disease (e.g., a certain cancer) during adult years.

Other definitions of "pre-disease" state may be adopted without departing from the scope and spirit of the present invention. For example, certain standards may be established to pre-diagnose the stem cell subject as being in a "pre-disease" state. This type of pre-diagnosis may be established as an optional screening process prior to collection of VSELs from the subject in the "pre-disease" state. Such "pre-disease" state standards may include one or more of the following considerations or references prior to collection, such as (a) pre-specific disease; (b) prior to actual knowledge by subject and/or health professionals of specific or general diseases; (c) prior to contraction and/or diagnosis of one or more classes of diseases; (d) prior to one or more threshold parameters of the subject relating to certain diseases, for example at a certain age, with respect to certain physical conditions and/or symptoms, with respect to certain specific diseases, with respect to certain prior treatment history and/or preventive treatment, etc.; (e) whether the subject fits into one or more established statistical and/or demographic models or profiles (e.g., statistically unlikely to acquire certain diseases); and (f) whether the subject is in a certain acceptable health condition as perceived based on prevailing medical practices.

The present invention provides an elective healthcare insurance model using an individual's own peripheral blood VSELs for the individual's future healthcare uses. More specifically, this invention provides a method in which an individual can elect to have his or her own VSELs collected, processed and preserved, while he or she is in healthy state, for future distribution for his or her healthcare needs. The invention also embodies methods of collection, processing, preservation, and distribution of adult (including pediatric) peripheral blood VSELs during non-diseased state. The VSELs collected will contain adequate dosage amounts, for one or more transplantations immediately when needed by the individual for future healthcare treatments.

Stem Cell Collection Process

The VSELs of the present invention may be collected from bone marrow, peripheral blood (preferably mobilized peripheral blood), spleen, cord blood, and combinations thereof.

The VSELs may be collected from the respective sources using any means known in the art. Generally, the method of collecting VSELs from a subject will include collecting a population of total nucleated cells and further enriching the population for VSELs.

According to another preferred embodiment, there is provided a method for collecting an adequate VSEL dosage from an individual donor during non-diseased state, processing the VSELs collected, cryogenically preserving them for future distribution for the donor's healthcare needs. In one embodiment of the current invention, VSELs and progenitor cells are collected during the non-disease or pre-disease phase by the process of apheresis from adult or pediatric peripheral blood, processed to optimize the quantity and quality of the collected VSELs, cryogenically preserved, and used for autologous therapeutic purposes when needed after they have been thawed. Autologous therapeutic purposes are those in which the cells collected from the donor are infused into that donor at a later time.

According to a preferred embodiment, the VSELs may be collected by an apheresis process, which typically utilizes an apheresis instrument.

According to a preferred embodiment, there is provided a method for collecting autologous VSELs from a pre-disease human subject; collecting VSELs from peripheral blood pre-disease human subject using an apheresis process; at the time of collection, earmarking the collected cells for use by the human subject; and preserving the collected cells to maintain the cellular integrity of the cells. The human subject may be an adult human or non-neonate child. Accordingly, the above processes may further include the collection of adult or non-neonate child peripheral blood VSELs where the cells are then aliquoted into defined dosage fractions before cryopreservation so that cells can be withdrawn from storage without the necessity of thawing all of the collected cells.

Collection may be performed on any person, including adult or a non-neonate child. Furthermore, collection may involve one or more collecting steps or collecting periods. For example, collection (e.g., using an apheresis process) may be performed at least two times, at least three times, or at least 5 times on a person. During each collecting step, the number of total nucleated cells collected per kilogram weight of the person may be one million ($1\times10^6$) or more (e.g., $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, $1\times10^{20}$). In preferred embodiments, the number of cells collected in a single collection session may be equal or greater than $1\times10^{15}$ total nucleated cells, or at least on the order of $10^{14}$, or $10^{13}$, or $10^{12}$, or $10^{11}$, or $10^{10}$, or $10^9$, or $10^8$, or $10^7$, or $10^6$, or $10^5$ total nucleated cells, depending on the weight and age of the donor.

Depending on the situation and the quantity and quality of VSELs to be collected from the donor, it may be preferable to collect the VSELs from donors when they are at an "adult" or a "matured" age (the term "adult" as used herein refers to and includes adult and non-neonate, unless otherwise used in a particular context to take a different meaning) and/or at a certain minimum weight. For example, VSELs are collected when the subject is within a range from 10 to 200 kg in accordance with one embodiment of the present invention, or any range within such range, such as 20 to 40 kg. In addition or in the alternative, it may be required that the subject be of a certain age, within a range from 2-80 years old (e.g., 2-10, 10-15, 12-18, 16-20, 20-26, 26-30, 30-35, 30-40, 40-45, 40-50, 55-60, 60-65, 60-70, and 70-80 years old) in accordance with one embodiment of the present invention.

Stem Cell Potentiating Agent

The amount of VSELs circulating in the peripheral blood cell may be increased with the infusion of cell growth factors prior to collection, such as, for example, granulocyte colony stimulating factor (G-CSF). The infusion of growth factors is routinely given to bone marrow and peripheral blood donors and has not been associated with any long lasting untoward effects. Adverse side effects are not common but include the possibility of pain in the long bones, sternum, and pelvis, mild headache, mild nausea and a transient elevation in temperature. The growth factor is given 1-6 days before peripheral blood VSELs are collected. 1-6 days after G-SCF is infused the peripheral blood VSELs are sterilely collected by an apheresis instrument.

In a preferred embodiment, there is provided a method of mobilizing a significant number of peripheral blood VSELs comprising the administration of a stem cell potentiating agent. The function of the stem cell potentiating agent is to increase the number or quality of the VSELs that can be collected from the person. These agents include, but are not limited to, G-CSF, GM-CSF, dexamethazone, a CXCR4 receptors inhibitor, Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin and growth related oncogene, as single agents or in combination. In a preferred embodiment, there is provided a method of mobilizing a significant number of peripheral blood VSELs comprising the administration of G-CSF to a predisease subject.

According to a preferred embodiment, the G-CSF is administered to a predisease subject over a 1 to 6 day course, which ends upon apheresis of the subjects peripheral blood. Preferably, the G-CSF is administered to a predisease subject at least twice over a 2 to 6 day period. For example, G-CSF may be administered on day 1 and day 3 or may be administered on day 1, day 3, and day 5 or, alternatively, day 1, day 2, and day 5. Most preferably, G-CSF is administered to a predisease subject twice for consecutive days over a 3 day course. Thus, according to the preferred embodiment, G-CSF is administered to a predisease subject on day 1 and day 2 followed by apheresis on day 3.

Additionally, according to preferred embodiments, a low dose G-CSF is administered to a subject. Thus, a subject may receive a dose of G-CSF of about 1 µg/kg/day to 8 µg/kg/day. Preferably, G-CSF is administered to a subject at a dose of about 2 to about 7 µg/kg/day or equivalent thereof. More preferably, G-CSF is administered to a subject at a dose of about 4 to about 6 µg/kg/day or equivalent thereof. For subcutaneous injections, the dose of G-CSF may be from about 50 µg to about 800 µg, preferably from about 100 µg to about 600 µg, more preferably from about 250 µg to 500 µg, and most preferably from about 300 µg to about 500 µg.

Accordingly to another preferred embodiment, antagonist or inhibitors of CXCR4 receptors may be used as a stem cell potentiating agents. Examples of CXCR4 inhibitors that have been found to increase the amount of VSELs in the peripheral blood include, but are not limited to, AMD3100, ALX40-4C, T22, T134, T140 and TAK-779. See also, U.S. Pat. No. 7,169,750, incorporated herein by reference in its entirety. These stem cell potentiating agents may be administered to the person before the collecting step. For example, the potentiating agent may be administered at least one day, at least three days, or at least one week before the collecting step. Preferably, the CXCR4 inhibitors are administered to a predisease subject at least twice over a 2 to 6 day period. For example, the CXCR4 inhibitors may be administered on day 1 and day 3 or may be administered on day 1, day 3, and day 5 or, alternatively, day 1, day 2, and day 5. Most preferably, the CXCR4 inhibitors are administered to a predisease subject twice for consecutive days over a 3 day course. Thus, according to the preferred embodiment, the CXCR4 inhibitors are administered to a predisease subject on day 1 and day 2 followed by apheresis on day 3.

The formulation and route of administration chosen will be tailored to the individual subject, the nature of the condition to be treated in the subject, and generally, the judgment of the attending practitioner. Suitable dosage ranges for CXCR4 inhibitors vary according to these considerations, but in general, the compounds are administered in the range of about 0.1 µg/kg to 5 mg/kg of body weight; preferably the range is about 1 µg/kg to 300 µg/kg of body weight; more preferably about 10 µg/kg to 100 µg/kg of body weight. For a typical 70-kg human subject, thus, the dosage range is from about 0.7 µg to 350 mg; preferably about 700 µg to 21 mg; most preferably about 700 µg to 7 mg. Dosages may be higher when the compounds are administered orally or transdermally as compared to, for example, i.v. administration.

Stem Cell Processing

In some embodiments of the invention, after collection, the VSELs are processed according to methods known in the art (see, for example, Lasky, L. C. and Warkentin, P. I.; Marrow and Stem Cell Processing for Transplantation; American Association of Blood Banks (2002)). In an embodiment of the invention, processing may include the following steps: preparation of containers (e.g., tubes) and labels, sampling and/or testing of the collected material, centrifugation, transfer of material from collection containers to storage containers, the addition of cryoprotectant, etc. In some embodiments, after processing, some of the processed VSELs can be made available for further testing.

The cells also may be processed, preferably before the preservation step is conducted. Processing may involve, for example, enrichment or depletion of cells with certain cell surface markers. Any cell surface marker, including the cell surface markers listed anywhere in this specification may be used as a criteria for enrichment or depletion. Furthermore, processing may involve analyzing at least one characteristic of one cell in the one population of VSELs or the at least one population of non-VSELs. The characteristic may be a DNA or RNA sequence. For example, the genomic DNA or RNA may be partially or completely sequenced (determined). Alternatively, specific regions of the DNA or RNA of a cell may be sequenced. For example, nucleic acids from a cell or a cell population may be extracted. Specific regions of these nucleic acid may be amplified using amplification probes in an amplification process. The amplification process may be, for example PCR or LCR. After amplification, the amplimers (products of amplification) may be sequenced. Furthermore, the DNA and RNA may be analyzed using gene chips, using hybridization or other technologies.

Specific uniqueness of this invention is that there will be no requirement for any kind of tissue typing since the collected VSELs will be used for autologous transplantation. However, tissue typing of specific kinds may be used for sample identification or for the use of these VSELs for possible allogeneic use. This type of information may include genotypic or phenotypic information. Phenotypic information may include any observable or measurable characteristic, either at a macroscopic or system level or microscopic, cellular or molecular level. Genotypic information may refer to a specific genetic composition of a specific individual organism, including one or more variations or mutations in the genetic composition of the individual's genome and the possible relationship of that genetic composition to disease. An example of this genotypic information is the genetic "fingerprint" and the Human Leukocyte Antigen (HLA) type of the donor. In some embodiments of the invention the VSELs will be processed in such a way that defined dosages for transplantation will be identified and aliquoted into appropriate containers.

In preferred embodiments, the number of cells in the VSEL-enriched population may be equal or greater than $2 \times 10^8$ total nucleated cells, or at least on the order of $10^7$, or $10^6$, or $10^5$, or $10^4$, depending on the weight and age of the donor. Aliquoting of these cells may be performed so that a quantity of cells sufficient for one transplant will be stored in one cryocyte bag or tube, while quantities of cells appropriate for micro-transplantation (supplemental stem cell infusion), will be stored in appropriate containers (cryocyte bags or cryotubes). Generally, at least one unit is collected at each collection session, and each unit collected is targeted at more than on the order of $10^3$, more preferably $10^4$, more preferably $10^5$, and most preferably $10^6$, in accordance with one embodiment of the present invention. This process constitutes a unique process for "unitized storage" enabling individuals to withdraw quantities of cells for autologous use without the necessity of thawing the total volume of cells in storage (further details discussed below). This may include processing the harvested VSELs to optimize the quantity of total nucleated cells to ensure sufficient number of cells for targeted diseases without or with little waste of cells (i.e., disease directed dosage). Fault tolerant and redundant computer systems will be used for data processing, to maintaining records relating to subject information and to ensure rapid and efficient retrieval VSELs from the storage repositories.

Stem Cell Enrichment or Sorting

The enrichment procedures preferably includes sorting the cells by size and/or cellular markers. For example, stem cells comprise approximately 0.1-1.0% of the total nucleated cells as measured by the surrogate CD34+ cells. Thus, stem cells may be sorted by their expression of CD34+. VSELs do not express CD45, and thus cells expressing CD45 may be sorted out of the desired VSEL-enriched population. VSEL stem cells express markers of pluripotent stem cells such as SSEA-1, Oct-4, Nanog, and Rex-1, and thus, similar strategies my be employed using these markers. VSEL enriched populations of stem cells may similarly be prepared by sorting TNC populations by size, either alone or in combination with other sorting strategies in order to prepare VSEL-enriched populations of cells.

In one aspect of the invention, the cells collected by the methods of the invention may be sorted into at least two subpopulations which may be cryopreserved separately or together (e.g., in the same vial). The at least two subpopulations of cells may be two subpopulation of VSELs. However, the at least two subpopulation of cells may be (1) a stem cell population or a population enriched for VSELs and (2) a non stem cell population or a population depleted for VSELs. Furthermore, it is also envisioned that the two subpopulations (i.e., (1) and (2) above) may be cryopreserved together.

VSELs may be sorted according to cell surface markers that are associated with VSELs. Since it is one embodiment of the invention to enrich for VSELs, useful markers for cell sorting need not be exclusively expressed in VSELs. A cell marker which is not exclusively expressed in stem cell will nevertheless have utility in enriching for VSELs. It should noted also that markers of differentiated cells are also useful in the methods of the invention because these markers may be used, for example, to selectively remove differentiated cells and thus enrich VSELs in the remaining cell population. Markers, cell surface or otherwise, which may be used in any of the processes of the invention include, at least, the following: Fetal liver kinase-1 (Flk1); Bone-specific alkaline phosphatase (BAP); Bone morphogenetic protein receptor (BMPR); CD34; CD34$^+$, Sca$^{1+}$, Lin$^-$ profile; CD38; c-Kit; Colony-forming unit (CFU); Fibroblast colony-forming unit (CFU-F); Hoechst dye; KDR; Leukocyte common antigen (CD45); Lineage surface antigen (Lin); Muc-18 (CD146); Stem cell antigen (Sca-1); Stro-1 antigen; Thy-1; CD14; Platelet Endothelial Cell Adhesion Molecule (PECAM-1 or CD31); CD73; Adipocyte lipid-binding protein (ALBP); Fatty acid transporter (FAT); Adipocyte lipid-binding protein (ALBP); B-1 integrin; CD133; Glial fibrillary acidic protein (GFAP); O4; CD166; Cytokeratin 19 (CK19); Nestin; Alkaline phosphatase; Alpha-fetoprotein (AFP); Bone morphogenetic protein-4; Brachyury; Cluster designation 30 (CD30); Cripto (TDGF-1); GATA-4 gene; GCTM-2; Genesis; Germ cell nuclear factor; Hepatocyte nuclear factor-4 (HNF-4); Nestin; Neuronal cell-adhesion molecule (N-CAM); Oct-4; Pax6; Stage-specific embryonic antigen-3 (SSEA-3); Stage-specific embryonic antigen-4 (SSEA-4); Stem cell factor (SCF or c-Kit ligand); Telomerase; TRA-1-60; TRA-1-81; Vimentin; MyoD and Pax7; Myogenin and MR4; CD36 (FAT); and CD29.

The pattern of markers express by VSELs may also be used to sort and categorize VSELs with greater accuracy. Any means of characterizing, including the detection of markers or array of markers, may be used to characterized and/or identify the cells obtained through the embodiments disclosed herein. For example, certain cell types are known to express a certain pattern of markers, and the cells collected by the processes described herein may be sorted on the basis of these known patterns. Multiparameter sorting may also be employed. The table that follows provides examples of the identifying pattern or array of markers that may be expressed by certain cell types.

| Cell Type | Markers |
| --- | --- |
| Hematopoietic stem cell | C34, CD45, CXCR4 |
| Endothelial Progenitors Cells | CD34, CD73, CD133, CXCR4, KDR, anti-M IgG |
| Very Small Embryonic Like Cell. (VSEL) | CD34, CD133, CXCR4, SSEA4, anti-M IgG |
| Mesenchymal VSELs | CD34, CD45, CD90, CD105, CD106, CD44 |

The size of the VSELs may also form a basis to devise a sorting strategy to prepare an enriched population of VSELs. A combination of cellular markers and size patterns may be used to sort and categorize VSELs with greater accuracy. Generally, an enriched population of VSELs is prepared by sorting for a size between 2-10 µm. In some embodiments, an enriched population of VSELs is prepared by sorting for a size between 2-8 µm. In some embodiments, an enriched population of VSELs is prepared by sorting for a size between 2-6 µm. In some embodiments, an enriched population of VSELs is prepared by sorting for a size between 2-5 µm. In some embodiments, an enriched population of VSELs is prepared by sorting for a size between 2-4 µm. In some embodiments, an enriched population of VSELs is prepared by sorting for a size between 3-5 µm. In some embodiments, an enriched population of VSELs is prepared by sorting for a size between 3-6 µm. In some embodiments, an enriched population of VSELs is prepared by sorting for a size between 3-8 µm.

Cellular Therapy

In one embodiment of the present invention, the VSELs are collected from the peripheral blood of a subject and introduced or transplanted back to the individual when the subject is in need of such cellular therapy.

VSELs and compositions comprising VSELs of the present invention can be used to repair, treat, or ameliorate various aesthetic or functional conditions (e.g. defects) through the augmentation of damage tissues. The VSELs of the present embodiments may provide an important resource for rebuilding or augmenting damaged tissues, and thus represent a new source of medically useful VSELs. In a preferred embodiment, the VSELs may be used in tissue engineering and regenerative medicine for the replacement of body parts that have been damaged by developmental defects, injury, disease, or the wear and tear of aging. The VSELs provide a unique system in which the cells can be differentiated to give rise to specific lineages of the same individual or genotypes. The VSELs therefore provide significant advantages for individualized stem cell therapy.

In addition, such VSELs and compositions thereof can be used for augmenting soft tissue not associated with injury by adding bulk to a soft tissue area, opening, depression, or void in the absence of disease or trauma, such as for "smoothing". Multiple and successive administrations of VSELs are also embraced by the present invention.

For stem cell-based treatments, a VSELs are preferably collected from an autologous or heterologous human or animal source. An autologous animal or human source is more preferred. Stem cell compositions are then prepared and isolated as described herein. To introduce or transplant the VSELs and/or compositions comprising the VSELs according to the present invention into a human or animal recipient, a suspension of mononucleated cells is prepared. Such suspensions contain concentrations of the VSELs of the invention in a physiologically-acceptable carrier, excipient, or diluent. Alternatively, stem cell suspensions may be in serum-free, sterile solutions, such as cryopreservation solutions. Enriched stem cell preparations may also be used. The stems suspensions may then be introduced e.g., via injection, into one or more sites of the donor tissue.

Concentrated or enriched cells may be administered as a pharmaceutically or physiologically acceptable preparation or composition containing a physiologically acceptable carrier, excipient, or diluent, and administered to the tissues of the recipient organism of interest, including humans and non-human animals. The stem cell-containing composition may be prepared by resuspending the cells in a suitable liquid or solution such as sterile physiological saline or other physiologically acceptable injectable aqueous liquids. The amounts of the components to be used in such compositions can be routinely determined by those having skill in the art.

The VSELs or compositions thereof may be administered by placement of the stem cell suspensions onto absorbent or adherent material, i.e., a collagen sponge matrix, and insertion of the stem cell-containing material into or onto the site of interest. Alternatively, the VSELs may be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the VSELs may be mediated by endoscopic surgery.

For injectable administration, the composition is in sterile solution or suspension or may be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

Consistent with the present invention, the VSELs may be administered to body tissues, including epithelial tissue (i.e., skin, lumen, etc.) muscle tissue (i.e. smooth muscle), blood, brain, and various organ tissues such as those organs that are associated with the urological system (i.e., bladder, urethra, ureter, kidneys, etc.).

According to another preferred embodiment, there is provided compositions and methods for enhancing engraftment of the peripheral blood VSELs. The cells collected from the peripheral blood of a subject may generally comprise a comprehensive mixture of cells. That is, there exist a mixture of VSELs, partially differentiated cells (e.g., progenitor cells or fibroblasts), and functional cells (i.e., terminally differentiated cells). The presence of progenitor cells, partially and possibly, terminally differentiated cells may have significant advantages with respect to a shorter time to reconstitution and other physiological benefits in the post-infusion period.

According to the general treatment method described herein, the cellular mixture, obtained through an apheresis process, may be administered to a subject, for example, by infusion into the blood stream of a subject through an intravenous (i.v.) catheter, like any other i.v. fluid. Alternatively, however, an individualized mixture of cells may be generated such as to provide a cellular therapy mixture specific for therapeutic needs of a subject. The comprehensive mixture of cells obtained such as through an apheresis process may be characterized, sorted, and segregated into distinct cell populations. Cell markers such as VSELs markers or tissue specific markers may be used to phenotypically characterize the populations of cells collected from the peripheral blood. Using these markers, it is possible to segregate and sort on the basis of cell type. The mixture of cells is thus transformed into populations of cells, which may be broadly classified into two portions: a stem cell portion and a non-stem cell portion. The non-stem cell portion may further be classified into a progenitor cell or fibroblast portion and a function cell or fully differentiated cell portion. Once the peripheral blood cellular mixture is sorted, the stem cell and non-stem cell portions may be cryopreserved and stored separately. In this manner, a library or repository of distinct cell populations from a subject may be created. Alternatively, stem cell and non-stem cell portions may the cryopreserved together and then sorted and separated prior to use.

The types of cell populations that may be generated in this manner include any population of a cell type that developed from a germ layer (i.e., endoderm, mesoderm, and ectoderm). These include, but are not limited to, peripheral blood VSELs, peripheral blood CD34+ cells, hematopoietic progenitor or differentiated cells, neural progenitor or differentiated cells, glial progenitor or differentiated cells, oligodendrocyte progenitor or differentiated cells, skin progenitor or differentiated cells, hepatic progenitor or differentiated cells, muscle progenitor or differentiated cells, bone progenitor or differentiated cells, mesenchymal stem or progenitor cells, pancreatic progenitor or differentiated cells, progenitor or differentiated chondrocytes, stromal progenitor or differentiated cells, cultured expanded stem or progenitor cells, cultured differentiated stem or progenitor cells, or combinations thereof. Of particular interest are hematopoietic cells, which may include any of the nucleated cells which may be involved with the erythroid, lymphoid or myelomonocytic lineages, as well as myoblasts and fibroblasts. Also of interest are progenitor cells, such as hematopoietic, neural, stromal, muscle (including smooth muscle), hepatic, pulmonary, gastrointestinal, and mesenchymal progenitor cells. Also of interest are differentiated cells, such as, osteoblasts, hepatocytes, granulocytes, chondrocytes, myocytes, adipocytes, neuronal cells, pancreatic, or combinations and mixtures thereof.

The cell populations of the various cells types may then be combined, recombined, or compounded into a cellular therapy mixture of cells appropriate for treating the disease of a subject and/or regenerating a specific tissue. A combination of VSELs, tissue specific progenitor cells, and optionally functional cells is thought to enhance the engraftment of the VSELs. Accordingly, in one embodiment, the present invention provides methods and products for using an autologous mixture of VSELs, progenitor cells, and optionally functional cells to enhance engraftment of stem or progenitor cells. This cellular therapy product may comprise: from about 10% to about 90% peripheral blood VSELs, about 10% to about 80% peripheral blood VSELs, about 10% to about 60% peripheral blood VSELs, or about 10% to about 40% peripheral blood VSELs; and from about 10% to about 90% non-VSELs, from about 20% to about 90% non-VSELs, from about 40% to about 90% non-VSELs, from about 60% to about 90% non-VSELs. The non-stem portion may optionally comprise from about 5% to about 50% functional cells, about 5% to about 40% functional cells, about 5% to about 30% functional cells, about 5% to about 20% functional cells, or about 5% to about 10% functional cells.

A suitable example of the cellular therapy product described above is the autologous mixture of PBSCs, hematopoietic progenitor cells, and optionally granulocytes or other functional cell of the hematopoietic system. Another example is a cellular therapy product comprising an autologous mixture of PBSCs, myocardial progenitor cells, and optionally myocardial cells.

According to another preferred embodiment, there is provided a method of treating a patient in need thereof comprising administering to a subject an autologous mixture of VSELs.

Stem Cell Banking

In another aspect of the present invention, the current invention provides a cell bank to support an elective healthcare insurance model to effectively protect members of the population from future diseases. An individual can elect to have his or her own VSELs collected, processed and preserved, while he or she is in healthy state, for future distribution for his or her healthcare needs.

Collected and processed VSELs are "banked" for future use, at a stem cell bank or depository or storage facility, or any place where VSELs are kept for safekeeping. The storage facility may be designed in such a way that the VSELs are kept safe in the event of a catastrophic event such as a nuclear attack. In some embodiments, the storage facility might be underground, in caves or in silos. In other embodiments, it may be on the side of a mountain or in outer space. The storage facility may be encased in a shielding material such as lead.

According to a preferred embodiment, there is provided a process of stem cell banking with four steps. Step A involves administrating one or more stem cell potentiating agents to a person to increase the amount of VSELs in the peripheral blood of the person. Step B involves collecting at least one population of VSELs and at least one population of non-VSELs from peripheral blood of said person using an apheresis process, wherein said person has no immediate perceived health condition requiring treatment using his own collected VSELs. Step C involves preserving the at least one population of VSELs and the at least one population of non-VSELs as a preserved populations of cells. Step D involves retrieving the preserved populations of cells for autologous transplantation of the VSELs into the person. Each aspect of this process is described in more detail below.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Bone Marrow Cells

Murine mononuclear cells (MNCs) were isolated from BM flushed from the femurs of pathogen-free, 3 week, 1 month, and 1 year old female C57BL/6 or DBA/2J mice obtained from the Jackson Laboratory, Bar Harbor, Me., United States of America. Erythrocytes were removed with a hypotonic solution (Lysing Buffer, BD Biosciences, San Jose, Calif., United States of America).

Alternatively, MNCs were isolated from murine BM flushed from the femurs of pathogen-free, 4- to 6-week-old female Balb/C mice (Jackson Laboratory) and subjected to Ficoll-Paque centrifugation to obtain light density MNCs. Sca-1+ cells were isolated by employing paramagnetic minibeads (Miltenyi Biotec, Auburn, Calif., United States of America) according to the manufacturer's protocol.

Light-density human BMMNCs were obtained from four cadaveric BM donors (age 52-65 years) and, if necessary, depleted of adherent cells and T lymphocytes (A-T-MNC) as described in Ratajczak et al. (2004a) 103 Blood 2071-2078 and Majka et al. (2001) 97 Blood 3075-3085. CD34+ cells were isolated by immunoaffinity selection with MINI-MACS™ paramagnetic beads (Miltenyi Biotec), according to the manufacturer's protocol and as described in Ratajczak et al. (2004a) 103 Blood 2071-2078 and Majka et al. (2001) 97 Blood 3075-3085. The purity of isolated CD34+ cells was determined to be >98% by FACS analysis.

Example 2

Sorting of Bone Marrow-Derived Cells

For murine BM cells, Sca-1+/lin−/CD45− and Sca-1+/lin−/CD45+ cells were isolated from a suspension of murine BMMNCs by multiparameter, live sterile cell sorting using a FACSVANTAGE™ SE (Becton Dickinson, Mountain View, Calif., United States of America). Briefly, BMMNCs (100× $10^6$ cells/ml) were resuspended in cell sort medium (CSM), containing 1×Hank's Balanced Salt Solution without phenol red (GIBCO, Grand Island, N.Y., United States of America), 2% heat-inactivated fetal calf serum (FCS; GIBCO), 10 mM HEPES buffer (GIBCO), and 30 U/ml of Gentamicin (GIBCO). The following monoclonal antibodies (mAbs) were employed to stain these cells: biotin-conjugated rat anti-mouse Ly-6A/E (Sca-1; clone E 13-161.7) streptavidin-PE-Cy5 conjugate, anti-CD45-APCCy7 (clone 30-F11), anti-CD45R/B220-PE (clone RA3-6B2), anti-Gr-1-PE (clone RB6-8C5), anti-TCRαβ PE (clone H57-597), anti-TCRγδ PE (clone GL3), anti-CD11b PE (clone M1/70) and anti-Ter-119 PE (clone TER-119). All mAbs were added at saturating concentrations and the cells were incubated for 30 minutes on ice and washed twice, then resuspended for sort in CSM at a concentration of 5×$10^6$ cells/ml.

Figure 11:
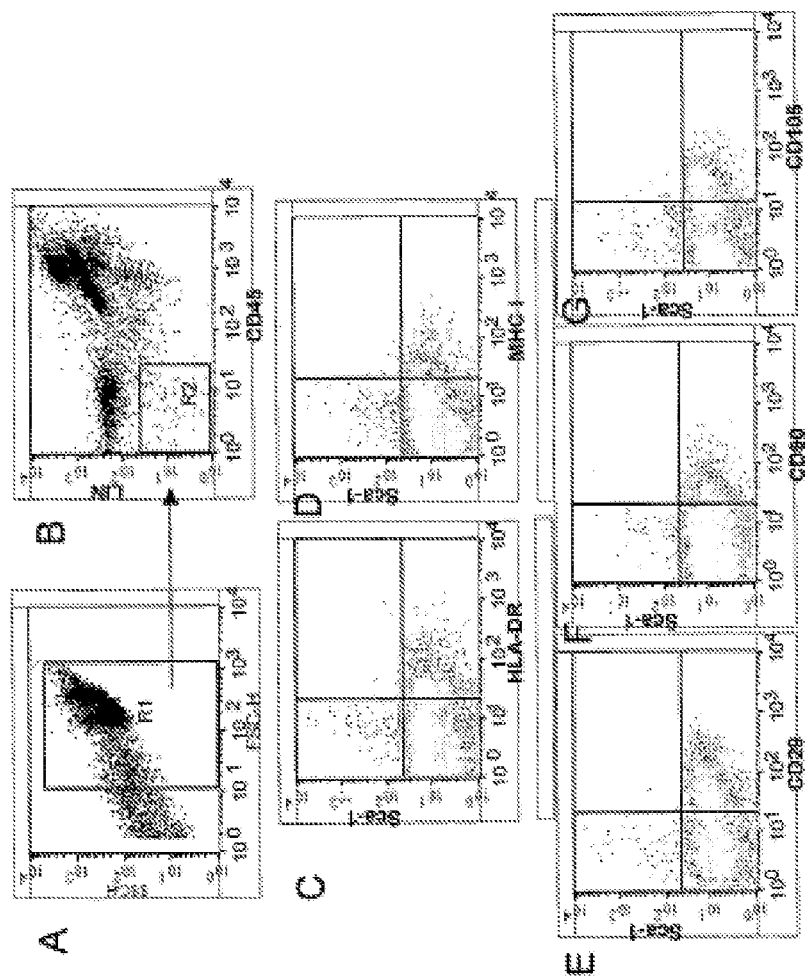
FIGS. 11A-11G are a series of dot-plots of FACS analysis of murine bone marrow cells.

Alternatively, whole murine BM was lysed in BD lysing buffer (BD Biosciences, San Jose, Calif., United States of America) for 15 minutes at room temperature and washed twice in PBS. A single cell suspension was stained for lineage markers (CD45R/B220 (clone RA3-6B2), Gr-1 (clone RB6-8C5), TCRαβ (clone H57-597), TCRγδ (clone GL3), CD11b (clone M1/70), Ter-119 (clone TER-119) conjugated with PE, CD45 (clone 30-F11) conjugated with PE-Cy5, biotin-conjugated rat anti-mouse Ly-6A/E (Sca-1) (clone E13-161.7), streptavidin-APC and MHC class I (clone CTDb), HLA-DR (clone YE2/36HLK) CD105/Endoglin, CD29 and CD90 (Thy 1) conjugated with FITC, for 30 minutes on ice. After washing they were analyzed by FACS (BD Biosciences, San Jose, Calif.). At least $10^6$ events were acquired and analyzed by using Cell Quest software. A series of dot-plots representing an exemplary series of sorts is presented in FIG. 11.

For human BM cells, CXCR4+/CD45+, CXCR4+/CD45−, CXCR4−/CD45+, and CXCR4−/CD45− BMMNCs were isolated by employing FITC-labeled anti-CD45 and PE-labeled anti-CXCR4 monoclonal antibodies from BD Biosciences Pharmingen (Palo Alto, Calif., United States of America) and a MOFLO™ cell sorter (DakoCytomation California Inc., Carpinteria, Calif., United States of America) as described in Ratajczak et al. (2004b) 18 Leukemia 29-80. Briefly, cells were stained for 30 minutes at 4° C., washed twice, sorted, and spun down immediately after sorting to isolate RNA using the Qiagen RNA isolation kit (Qiagen, Inc., Valencia, Calif., United States of America) according to the manufacturer's protocol.

Example 3

Side Population (SP) Cell Isolation

SP cells were isolated from the bone marrow according to the method of Goodell et al. (2005) Methods Mol Biol 343-352. Briefly, BMMNC were resuspended at $10^6$ cells/ml in pre-warmed DMEM/2% FBS and pre-incubated at 37° C. for 30 minutes. The cells were then labeled with 5 µg/ml Hoechst 33342 (Sigma Aldrich, St. Louis, Mo., United States of America) in DMEM/2% FBS and incubated at 37° C. for 90 minutes. After staining, the cells were pelleted, resuspended in ice-cold cell sort medium, and then maintained on ice until their sorting. Analysis and sorting were performed using a FACSVANTAGE™ (Becton Dickinson, Mountain View, Calif., United States of America). The Hoechst dye was excited at 350 nm and its fluorescence emission was collected with a 424/44 band pass (BP) filter (Hoechst blue) and a 675/20 BP filter (Hoechst red). All of the parameters were collected using linear amplification in list mode and displayed in a Hoechst blue versus Hoechst red dotplot to visualize the SP. Then, Sca-1+/lin−/CD45− and Sca-1+/lin−/CD45+ cells were isolated from a suspension of SP using biotin-conjugated rat anti-mouse Ly-6A/E (Sca-1; clone E13-161.7), streptavidin-PE-Cy5 conjugate, anti-CD45-APC-Cy7 (clone 30-F11), anti-CD45R/B220-PE (clone RA3-6B2), anti-Gr-1-PE (clone RB6-8C5), anti-TCRαβ PE (clone H57-597), anti-TCRγδ PE (clone GL3), anti-CD11b PE (clone M1/70), and anti-Ter-119 PE (clone TER-119) antibodies.

Example 4

Chemotactic Isolation

After the isolation of murine BM-, PB-, and spleen-derived MNCs, cells were re-suspended in serum-free medium and equilibrated for 10 minutes at 37° C. The lower chambers of Costar Transwell 24-well plates, 6.5-mm diameter, 5 µM pore filter (Costar Corning, Cambridge, Mass., United States of America) were filled with 650 J-11 of kerum-free medium and 0.5% BSA containing SDF-I (200 ng/ml), HGF (10 ng/ml), or LIF (50 ng/ml), or with medium alone (control) as described in Ratajczak et al. (2004b) 18 Leukemia 29-40 and Kucia et al. (2004a) 32 Blood Cells Mol Dis 52-57.

In certain experiments related to the myocardial infarction model (see EXAMPLE 25), supernatants from tissue homogenates of infarcted (LV anterior wall) or control (LV posterior wall) myocardium were employed. Cell suspensions (100 µl) were added to the upper chambers. The plates were incubated at 37° C., 95% humidity, 5% C02 for 5 hours and evaluated under an inverted microscope. Cells from the lower chambers were collected and their numbers counted by FACS analysis (FACSCAN™ Becton Dickinson) as described in Ratajczak et al. (2004a) 103 Blood 2071-2078 and Majka et al. (2001) 97 Blood 3075-3085.

Example 5

Transmission Electron Microscopy (TEM) Analysis

For transmission electron microscopy, the Sca-1+/lin−/CD45− and Sca-1+/lin−/CD45+ cells were fixed in 3% glutaraldehyde in 0.1 M cacodylate buffer pH 7.4 for 10 hours at 4° C., post-fixed in osmium tetride, and dehydrated. Fixed cells were subsequently embedded in LX112 and sectioned at 800A, stained with uranyl acetate and lead citrate and viewed on a Philips CMIO electron microscope operating at 60 kV.

Example 6

Reverse Transcription-Polymerase Chain Reaction (RT-PCR)

Total RNA was isolated using RNEASY® Mini Kit (Qiagen Inc., Valencia, Calif., United States of America). mRNA (10 ng) was reverse-transcribed with One Step RT-PCR (Qiagen Inc.) according to the instructions of the manufacturer. The resulting cDNA fragments were amplified using HOTSTARTAQ® DNA Polymerase (Qiagen Inc., Valencia, Calif., United States of America). The primers employed were for CXCR4 (GENBANK® Accession No. BC031665), forward primer 5'-GACGGACAAGTACCGGCTGC-3' (SEQ ID NO: 59) and reverse primer 5'-GACAGCTTA-GAGATGATGAT-3' (SEQ ID NO: 60); for Met receptor (GENBANK® Accession No. NM-008591), 25 forward primer 5'-CGCGTCGACTTATTCATGG-3' (SEQ ID NO: 61) and reverse primer 5'-CACACATTGATTGTGGCACC-3' (SEQ ID NO: 62); and for LIF-R (GENBANK® Accession No. NM-013584)' forward primer 5'-GAGCATCCTTTGC-TATCGGAAGC-3' (SEQ ID NO: 63) and reverse primer 5'-CGTTATTTCCTCCTCGATGATGG-3' (SEQ ID NO: 64). The correct sizes of the PCR products obtained were confirmed by separation on agarose gel.

Example 7

Real Time Quantitative RT-PCR (RQ-PCR)

For analysis of Oct4, Nanog, Rex1, Dppa3, Rif1, Myf5, MyoD, Myogenin, GFAP, nestin, β III tubulin, Olig1, Olig2, α-fetoprotein, CK19, Nsx2.5/Csx, GATA-4, VE-cad herin, DCT, TYR, TRP, Nkx 2-3, Tcf4, Krt 2-5, Krt 2-6a, BNC, Nkx 6.1 and Pdx1 mRNA levels, total mRNA was isolated from cells with the RNEASY® Mini Kit (Qiagen Inc., Valencia, Calif., United States of America). mRNA was reverse-transcribed with TAQMAN® Reverse Transcription Reagents (Applied Biosystems, Foster City, Calif., United 10 States of America). Detection of Oct4, Nanog, Rex1, Dppa3, Rif1, Myf5, MyoD, Myogenin, GFAP, nestin, β III tubulin, Olig1, Olig2, α-fetoprotein, CK19, Nsx2.5/Csx, GATA-4, VE-cad-herin, DCT, TYR, TRP, Nkx 2-3, Tcf4, Krt 2-5, Krt 2-6a, BNC, Nkx 6.1 and Pdx1 and R2-microglobulin mRNA levels was performed by real-time RT-PCR using an ABI PRISM® 7000 Sequence Detection System (ABI, Foster City, Calif., United States of America) employing the primers disclosed in Table I. A 25 µl reaction mixture contains 12.5 µl SYBR® Green PCR Master Mix, 10 ng of cDNA template, and forward and reverse primers. Primers were designed with PRIMER EXPRESS® software (Applied Biosystems, Foster City, Calif., United States of America) and are listed in Table 1.

The threshold cycle (Ct), i.e., the cycle number at which the amount of amplified gene of interest reached a fixed threshold, was determined subsequently. Relative quantitation of Oct4, Nanog, Rex1, Dppa3, Rif1, Myf5, MyoD, Myogenin, GFAP, nestin, β III tubulin, Olig1, Olig2, α-fetoprotein, CK19, Nsx2.5/Csx1 GATA-4, VE-cadherin, DCT, TYR, TRP, Nkx 2-3, Tcf4, Krt 2-5, Krt 2-6a, BNC, Nkx 6.1 and Pdx1 mRNA expression was calculated with the comparative Ct method. The relative quantitation value of target, normalized to an endogenous control β2-microglobulin gene and relative to a calibrator, is expressed as $2^{-\Delta\Delta Ct}$ (fold difference), where ΔCt=Ct of target genes (Myf5 of 30 Oct4, Nanog, Rex1, Dppa3, Rif1, Myf5, MyoD, Myogenin, GFAP, nestin, β III tubulin, Olig1, Olig2, a-fetoprotein, CK19, Nsx2.5/Csx, GATA-4, VE-cadherin, DCT, TYR, TRP, Nkx 2-3, Tcf4, Krt 2-5, Krt 2-6a, BNC, Nkx 6.1, Pdx1)-Ct of endogenous control gene (β2-microglobulin), and ΔΔCt=ΔCt of samples for target gene-ΔCt of calibrator for the target gene.

To avoid the possibility of amplifying contaminating DNA i) all the primers for real time RTR-PCR were designed with an intron sequence inside cDNA to be amplified, ii) reactions were performed with appropriate negative controls (template-free controls), iii) a uniform amplification of the products was rechecked by analyzing the melting curves of the amplified products (dissociation graphs), iv) the melting temperature (Tm) was 57-60° C., the probe Tm, was at least 10° C. higher than primer Tm, and finally, v) gel electrophoresis was performed to confirm the correct size of the amplification and the absence of unspecific bands.

The results of representative analyses are presented in Tables 3 and 4.

TABLE 3

RQ-PCR Analysis of VSEL Stem Cell Markers*

| | VSEL Stem Cell Markers | Sca-1+/lin−/ CD45+ | Sca-1+/lin−/ CD45− |
|---|---|---|---|
| neural | GFAP | 0.64 ± 0.03 | 243.41 ± 31.03* |
| | Nestin | 0.39 ± 0.06 | 128.31 ± 18.74* |
| | β III tubulin | 0.95 ± 0.09 | 201.36 ± 36.38* |
| | Olig1 | 1.02 ± 0.42 | 36.17 ± 7.14* |
| | Olig2 | 1.14 ± 0.47 | 15.20 ± 2.13* |
| skeletal muscle | Myf5 | 1.41 ± 0.29 | 179.76 ± 16.78* |
| | MyoD | 0.77 ± 0.50 | 151.78 ± 15.56* |
| | Myogenin | 0.76 ± 0.45 | 76.73 ± 3.21* |
| cardiac | Nsx2.5/Csx | 2.05 ± 0.12 | 98.63 ± 7.93* |
| | GATA-4 | 2.74 ± 0.41 | 268.63 ± 31.42* |
| liver | α-Fetoprotein | 0.57 ± 0.02 | 45.93 ± 3.82* |
| | CK19 | 1.12 ± 0.75 | 80.08 ± 9.01* |
| intestinal | Nkx 2-3 | 0.30 ± 0.01 | 0.26 ± 0.02 |
| epithelium | Tcf4 | 130.08 ± 10.27* | 33.74 ± 4.27* |
| pancreas | Nkx 6.1 | 0.68 ± 0.08 | 0.76 ± 0.08 |
| | Pdx 1 | 13.71 ± 2.65* | 8.41 ± 1.90* |
| endothelium | VE-cadherin | 1.05 ± 0.38 | 142.36 ± 12.49* |
| epidermis | Krt 2-5 | 1.25 ± 0.05 | 62.31 ± 6.81* |
| | Krt 2-6a | 0.69 ± 0.11 | 33.24 ± 3.24* |
| | BNC | 1.49 ± 0.41 | 57.53 ± 2.29* |
| melanocyte | DCT | 0.42 ± 0.02 | 6.49 ± 1.94* |
| | TYR | 0.38 ± 0.01 | 8.04 ± 1.08* |
| | TRP | 1.08 ± 0.20 | 13.95 ± 2.18* |

*Data are expressed as fold increase in expression (mean +/− SD) as compared to expression in input BMMNC. (n = 3 independent sorts, BM from 12 donors pooled for each sort).
*p < 0.00001.

TABLE 4

RQ-PCR Analysis of PSC Markers*

| PSC markers | Sca-1+/lin−/CD45+ | Sca-1+/lin−/CD45− |
|---|---|---|
| Oct4 | 0.85 ± 0.01 | 174.49 ± 12.43* |
| Nanog | 0.51 ± 0.02 | 145.14 ± 29.36* |
| Rex1 | 0.96 ± 0.07 | 140.91 ± 16.68* |
| Dppa3 | 0.24 ± 0.03 | 39.25 ± 4.49* |
| Rif1 | 15.17 ± 0.45 | 66.04 ± 7.83* |

*Data are expressed as fold increase in expression (mean +/− SD) as compared to expression in input BMMNC. (n = 3 independent sorts, BM from 12 donors pooled for each sort).
*p < 0.00001.

Example 8

Fluorescence Staining of the Sorted Cells

The expression of each antigen was examined in cells from four independent sorts. The Sca-1+/lin−/CD45− cells were fixed in 3.5% paraformaldehyde for 20 min, permeabilized by 0.1% Triton X100, washed in PBS, pre-blocked with 2% BSA and subsequently stained with antibodies to CXCR4 (1:100, rabbit polyclonal IgG; Santa Cruz Biotechnology, Santa Cruz, Calif., United States of America), Met (1:100, rabbit polyclonal IgG; Santa Cruz Biotechnology, Santa Cruz, Calif., United States of America), LIF Receptor gp190 (1:200, mouse monoclonal IgG; BD Biosciences), Oct4 (1:200, mouse monoclonal IgG; Chemicon Int., Temecula, Calif., United States of America), SSEA-1 (1:200, mouse monoclonal IgM; Chemicon Intl., Temecula, Calif., United States of America), and Nanog (1:200, goat polyclonal IgG; Santa Cruz Biotechnology, Santa Cruz, Calif., United States of America). Appropriate secondary Alexa Fluor 488 goat anti-rabbit IgG, Alexa Fluor 594 goat anti-mouse IgG, Alexa Fluor 594 goat anti-mouse IgG, Alexa Fluor 488 goat anti-mouse IgM and Alexa Fluor 594 rabbit anti-goat IgG were used 10 (1:400; Molecular Probes, Eugene, Oreg., United States of America).

In control experiments, cells were stained with secondary antibodies only. The nuclei were labeled with DAPI (Molecular Probes, Eugene, Oreg., United States of America). The fluorescence images were collected with the TE-FM Epi-Fluorescence system attached to a Nikon Inverted Microscope Eclipse TE300 and captured by a COOLSNAP™ HQ digital B/W CCD (Roper Scientific, Tucson, Ariz., United States of America) camera.

Example 9

Hematopoietic Assays

For cell proliferation assays, murine or human sorted BMMNCs were plated in serum-free methylcellulose cultures in the presence of granulocyte macrophage colony stimulating factor (GM-CSF)+interleukin (IL)-3 for colony-forming unit-granulocyte macrophage (CFU-GM) colonies, erythropoietin (EPO)+stem cell factor (SCF) for burst forming unit-erythroid (BFU-E) colonies, and thrombopoietin (TPO) for CFU-megakaryocytic colonies as described in Ratajczak et al. (2004a) 103 Blood 2071-2078 and Majka et al. (2001) 97 Blood 3075-3085. Using an inverted microscope, murine hematopoietic colonies were scored on day 7 and human hematopoietic colonies on day 12.

For the CFU-S assays, female Balb/C mice (4-6 weeks old) were 30 irradiated with a lethal dose of γ-irradiation (900 cGy). After 24 hours, the mice were transplanted with $1 \times 10^4$ sorted BMMNCs obtained from syngeneic mice via tail-vein injection. On day 12, spleens were removed and fixed in Tellysyniczky's fixative and CFU-Spleen colonies were counted on the surface of the spleen using a magnifying glass as described in Ratajczak et al. (2004a) 103 Blood 2071-2078.

For long term repopulation assays, C57BL/6 (Ly 5.2) mice were irradiated with a lethal dose of γ-irradiation (900 cGy). After 24 hours, the mice were transplanted (by tail vein injection) with $10^6$ of BMMNC isolated from C57BL/6 (Ly5.2) along with $2 \times 10^4$ of Sca-1+/lin−/CD45− cells or $2 \times 10^4$ of Sca-1+/lin−/CD45+ from C57BL/6 (Ly5.1) mice. Transplanted mice were bled at various intervals from the retro-orbital plexus to obtain samples for Ly5 phenotyping. Final analysis of donor-derived chimerism was evaluated 8-10 months after transplantation.

Example 10

Chimerism Assay

Samples of PBMNC and BMMNC were analyzed on a FACSVANTAGE™ (Becton Dickinson, Mountain View, Calif., United States of America). Cells were stained with FITC-conjugated anti-CD45.2 (clone 104) and PE-conjugated anti-CD45.1 (clone A20). The percentage of donor engraftment was calculated from two separate measurements (Ly5.1-positive and Ly5.2-negative) after subtraction of background.

Example 11

In Vitro Migration Assay to "MATRIGEL® Drop"

To investigate cell migration, briefly the SDF-1 at the concentration of 200 ng/ml or HGF/SF (1 0 ng/ml) or LIF (100 ng/ml) were dissolved in a Growth Factor Reduced MATRIGEL® Matrix (BD Bioscience, Bedford, Mass., United States of America) at 4° C. As a control the Growth Factor Reduced MATRIGEL® Matrix without chemoattractant was used. The drop of MATRIGEL® was transferred onto a glass bottom well (Willco Wells BV, Amsterdam, The Netherlands) and incubated at 37° C. for 30 minutes to polymerize. Subsequently, the Sca-1+/lin−/CD45− cells were resuspended in DMEM with 0.5% BSA were added at a density of $2 \times 10^3$ per well.

The plates were incubated at 37° C., 95% humidity, 5% $CO_2$ for 12 hours. Then Sca-1+/lin−/CD45− cells were stained with a Hoechst 33342 (Sigma Aldrich, St. Louis, Mo., United States of America) and the number of cells migrating to an SDF-1 gradient was quantified by counting the number of cells visible/100 μm of MATRIGEL® drop circumference using a TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Example 12

Statistical Analysis

Arithmetic means and standard deviations of our FACS data were calculated on a Macintosh computer PowerBase 180, using Instat 1.14 (Graphpad, San Diego, Calif., United States of America) software. Data were analyzed using the Student t-test for unpaired samples or ANOVA for multiple comparisons. Statistical significance was defined as $p<0.05$.

Example 13

Bone Marrow-Derived Sca-1+/lin−/CD45− Cells Resemble Undifferentiated Embryonic Stem Cells The instant co-inventors demonstrated previously that BM contains a population of hematopoietic Sca-1+/lin−/CD45+ and a population of nonhematopoietic Sca-1+/lin−/CD45− stem cells (Kucia et al. (2005b) 19 Leukemia 1118-1127), and that the latter cells are highly enriched in mRNA for markers of early VSEL stem cells. See Kucia et al. (2005b) 33 Exp Hematol 61 3-623 and Kucia et al. (2004b) Circ Res 1191-1199. Disclosed herein is an evaluation of the morphology of these rare cells by employing transmission electron microscopy (TEM).

As shown in FIGS. 1A and 1B, Sca-1+/lin−/CD45− (FIG. 1A) cells as compared to Sca-1+/lin−/CD45+ (FIG. 1B) cells are smaller in size (3-4 μm vs. 8-10 μm), contain relatively large nuclei, and have a narrow rim of cytoplasm. Additionally, DNA in the nuclei of these small Sca-1+/lin−/CD45− cells contain open-type euchromatin that is characteristic of pluripotent embryonic stem cells (see FIG. 1A). Thus, disclosed herein for the first time is morphological evidence for the presence of embryonic-like cells in adult BM.

Example 14

Bone Marrow-Derived Sca-1+/lin−/CD45− Cells Express Several Pluripotent Stem Cell (PSC) Markers Sca-1+/lin−/CD45− cells express mRNA typical for VSEL stem cells. As disclosed herein, an expanded panel of genes for several markers of VSEL stem cells for neural tissue, skeletal and heart muscle, liver, pancreas, epidermis, melanocytes and intestinal epithelium (see Table 3) was evaluated.

Figure 2:
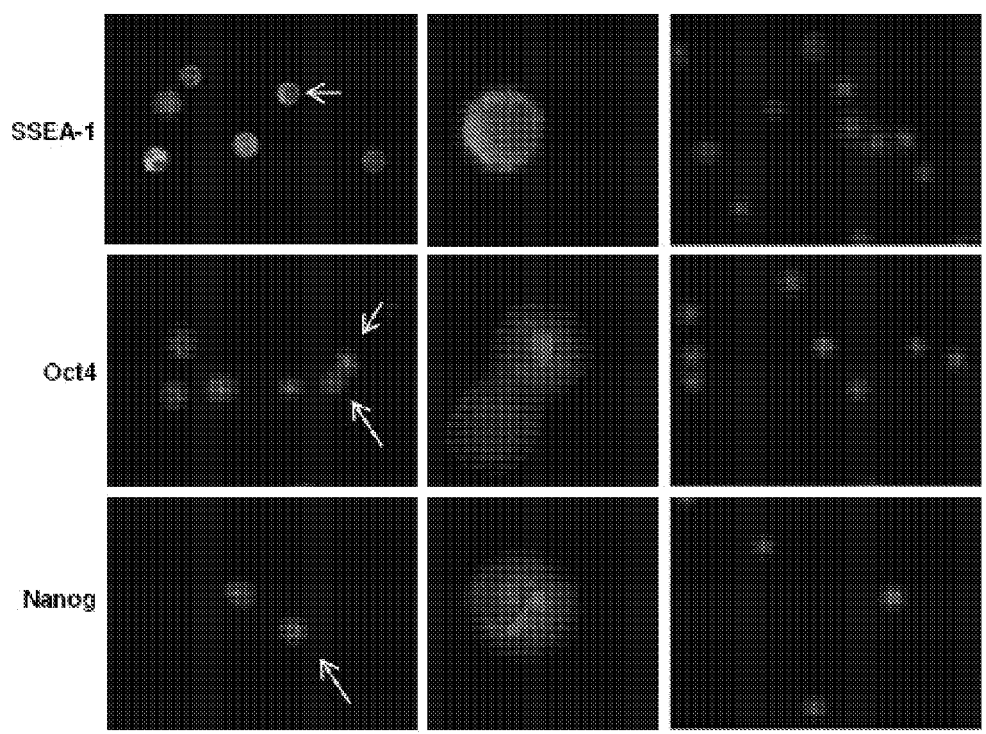
FIG. 2 depict fluorescence micrographic images depicting the results of expression studies on Sca-1+/lin−/CD45− cells and showing that Sca-1+/lin−/CD45− cells are SSEA-1+ and express Oct-4 and Nanog. As shown on the left panels, Sca-1+/lin−/CD45− cells isolated by FACS were evaluated for expression of SSEA-1, Oct-4, and Nanog. All images were taken under Plan Apo 60XA/1.40 oil objective (Nikon, Japan). The right panels show 10× enlarged images of representative cells (arrows) performed in ADOBE® PHOTOSHOP® CS software (Adobe System Incorporated, San Jose, Calif., United States of America). Negative staining controls are not shown. Staining was performed on cells isolated from four independent sorts. Representative data are shown.

Interestingly it was determined that these cells also express mRNA typically associated with PSC, including Oct-4, Nanog, Rex1, and Dppa3, and are enriched in mRNA for telomerase protein Rif1 (see Table 4). Additionally, the instant disclosure provides evidence that purified Sca-1+/lin−/CD45− cells express several embryonic stem cell markers, including SSEA-1, Oct-4, and Nanog, at the protein level (see FIG. 2). As depicted therein, SSEA-1, Oct-4, and Nanog were detectable on 57±7%, 43±6%, and 28±4% of Sca-1+/lin−/CD45− cells, respectively, demonstrating that PSC proteins are expressed in a freshly isolated defined population of cells from the BM.

Example 15

Bone Marrow-Derived Sca-1+/lin−/CD45− Express CXCR4, c-met, and LIF-R

Figure 3:
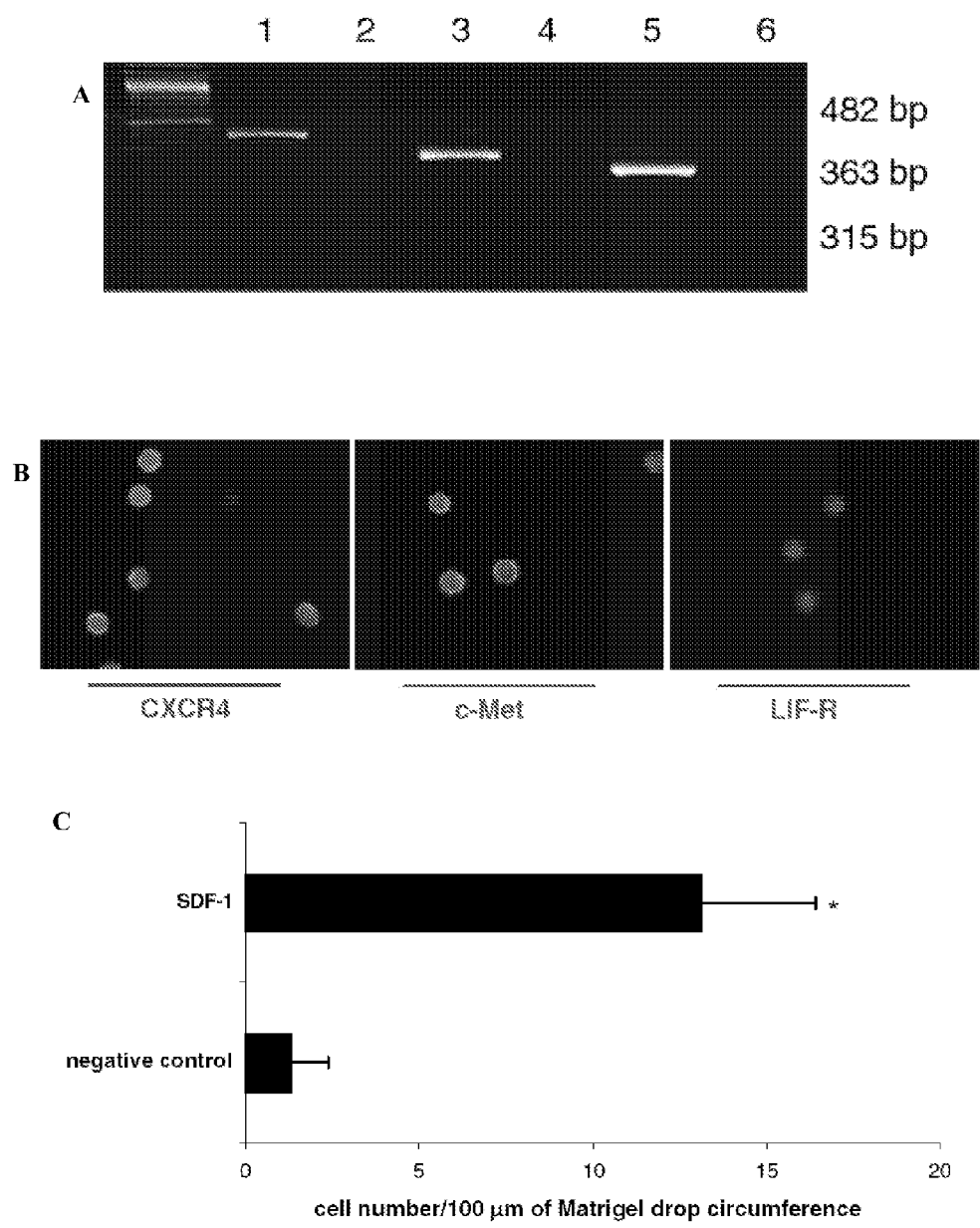
FIGS. 3A-3C depict the results of expression studies of Sca-1+/lin−/CD45− for CXCR4, c-met, and LIF-R.

Previous studies have demonstrated that BM-derived cells that express markers of VSEL stem cells could be isolated from a suspension of BMMNC by employing chemotaxis to stromal derived factor-1 (SDF-1), hepatocyte growth factor/scatter factor, (HGFISF) or leukemia inhibitory factor (LIF) gradients (Ratajczak et al. (2004b) 18 Leukemia 29-40). As disclosed herein, the corresponding population of Sca-1+/lin−/CD45− cells purified by FACS were examined for expression of the corresponding receptors (CXCR4, c-met, and LIF-R). FIG. 3A shows that Sca-1+/lin−/CD45− cells sorted by FACS express mRNA for all of these receptors. Additionally, as shown in FIG. 3B, expression of these receptors was also confirmed by immunostaining. These receptors were present on 82±6% (CXCR4), 61±8% (c-met), and 43±5% (LIF-R) of purified Sca-1+/lin−/CD45− cells. Furthermore, in direct chemotactic studies, it was determined that these highly purified cells respond robustly to SDF-1 (see FIG. 3C), HGF/SF, and LIF gradients.

Example 16

Sca-1+/lin−/CD45− Cells are Enriched in BM from Young Mice

Figure 4:
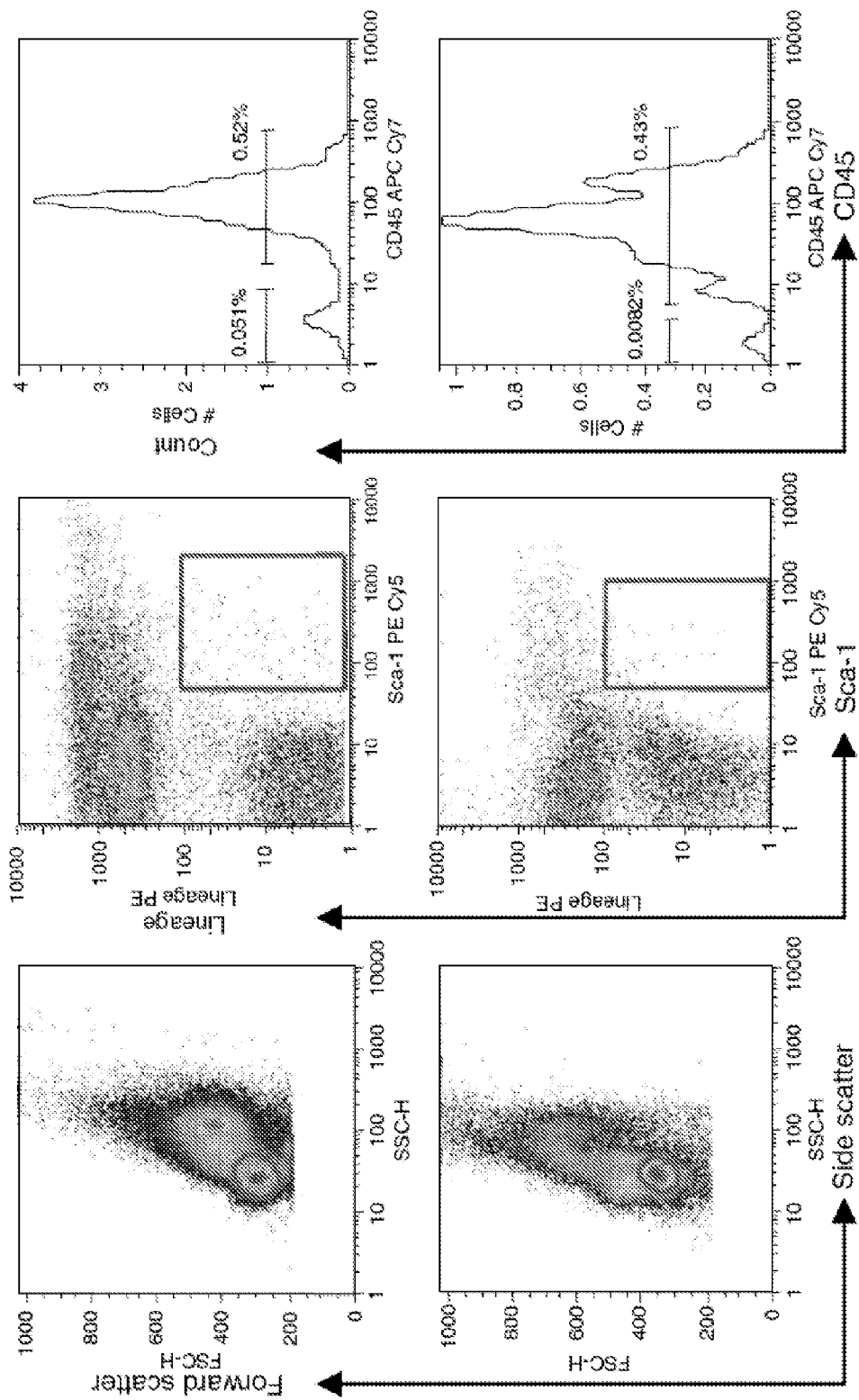
FIGS. 4A and 4B depict the results of FACS sorting Sca-1+/lin−/CD45− cells isolated from animals of different ages.
Figure 4:
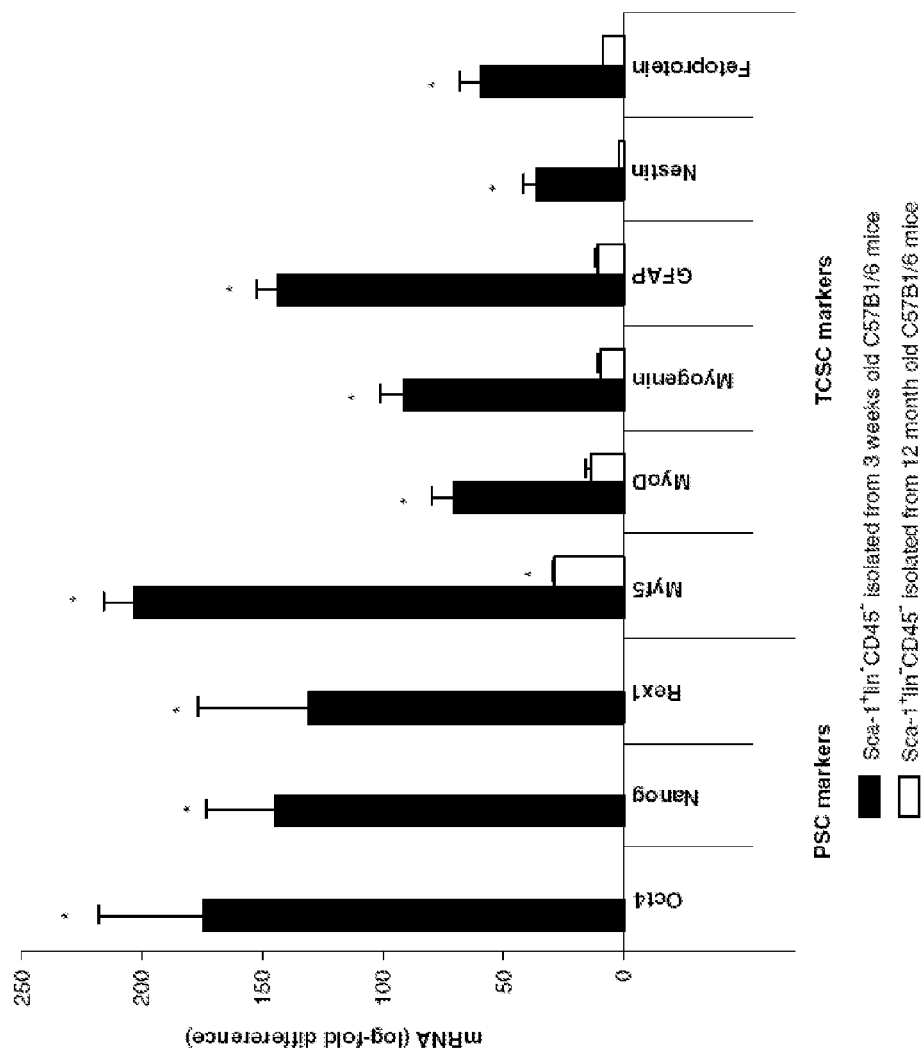

Previous RQ-PCR data generated by the co-inventors suggested that BM from young mice contains more PSC and/or VSEL stem cells than does BM 5 from older mice (Kucia et al. (2005b) Leukemia 1118-1127). As shown in FIG. 4, by employing FACS analysis of BMMNC derived from 1 month old and 1 year old mice, it has been determined that the number of Sca-1+/lin−/CD45− cells is reduced by about 6-10 times in BM from older animals (FIG. 4A, lower panel). Furthermore, the FACS analysis disclosed herein 10 corresponded with a significant decrease of mRNA expression for PSC and VSEL stem cell markers in BMMNC isolated from older animals as evaluated by RQ-PCR (FIG. 4B).

Example 17

Sca-1+/lin−/CD45− Cells are Decreased in Short Living DBA/2J Mice

Figure 5:
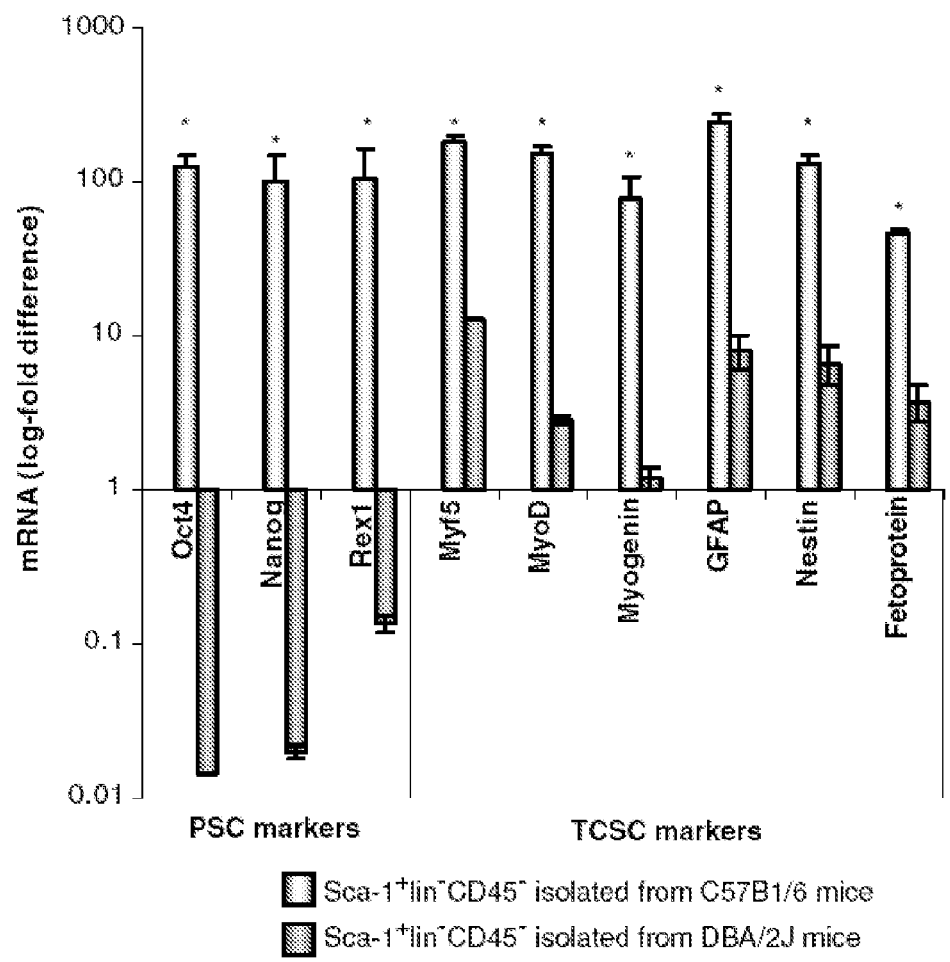
FIG. 5 is a bar graph depicting the results of comparing cell numbers from a mouse strain with a relatively long lifespan (C57BL/6) to that of a mouse strain with a relatively short lifespan (DBA/2J). The Figure shows the reduced number of Sca-1+/lin−/CD45− cells in the DBA/2J mice as compared to the C57Bl/6 mice. The expression of mRNA for PSC and VSEL stem cell markers in Sca-1+/lin−/CD45− cells isolated by FACS from three week old DBA/2J and C57Bl6 mice was compared by RQ-PCR between the same number of sorted cells. Three independent sorting experiments were performed (the BM of 6 mice was pooled for each sort). Data are mean±SD. *p<0.01 vs. cells from old DBA/2J mice.

Also disclosed herein is the discovery that the number of Sca-1+/lin−/CD45− cells varies with murine strain. In particular, it is shown that the number of these cells is reduced in short living DBA/2J mice as compared to long living C57BL/6 mice. The data presented in FIG. 5 demonstrated that in fact mRNA for several PSC/VSEL stem cells is significantly lower in mRNA isolated from BMMNC from 3 weeks old DBA/2J mice.

Example 18

Sca-1+/lin−/CD45− Cells are Present in the Side Population of BM Cells

It is known that the side population (SP) of BMMNC is highly enriched in stem cells (see e.g., Goodell et al. (1996) 183 J Exp Med 1797-1 806; Jackson et al. (2001) 107 J Clin Invest 1395-1 402; Macpherson et al. 118 J Cell Sci 2441-2450). To address whether the embryonic-like stem cells identified by the techniques disclosed herein are present in SP of BMMNC, a side population of BMMNC was isolated from BM (see FIG. 6A). For comparison, Sca-1+/lin−/CD45− cells were isolated from the same marrow samples (see FIG. 4A).

Figure 6:
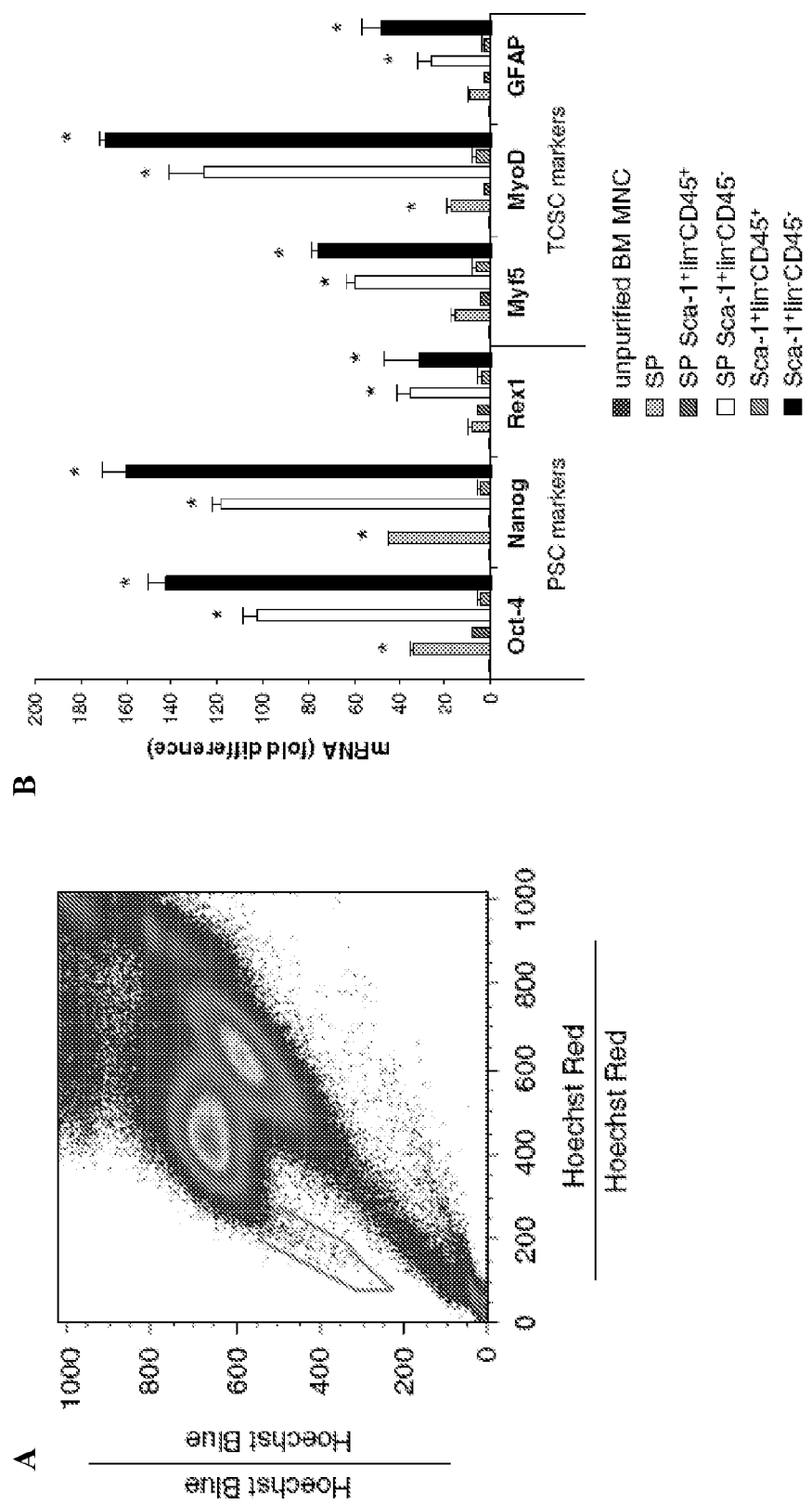
FIGS. 6A and 6B depict the sorting of a side population (SP) of bone marrow mononuclear cells (BMMNC).

Subsequently, both Sca-1+/lin−/CD45+ (SP Sca-1+/lin−/CD45+) and Sca-1+/lin−/CD45− (SP Sca-1+/lin−/CD45−) cells were isolated from SP BMMNC. All of these populations of cells were compared along with unpurified BMMNC for expression of mRNA for early PSC/VSEL stem cells. As shown in FIG. 6B, SP is highly enriched in mRNA for markers of PSC/VSEL stem cells. However, calculations of the total yield of Sca-1+/lin−/CD45− cells isolated from the same number of BMMNC revealed that the number of Sca-1+/lin−/CD45− cells resorted from SP was about two orders of magnitude lower when compared to direct sorting of these cells from the lymph gate of BMMNC. Additionally, SP cells depleted from a population of Sca-1+/lin−/CD45− did not express mRNA for PSC/VSEL stem cells, which suggests that the SP Sca-1+/lin−/CD45− cells probably account for the pluripotency of SP cells.

Example 19

Sca-1+/lin−/CD45− Cells in Contrast to Sca-1+/lin−/CD45+ Cells are Not Hematopoietic Several assays were employed to evaluate if embryonic like-cells isolated from BM possess hematopoietic potential. First, it was determined if these cells are able to grow in vitro hematopoietic colonies, but no clonogenic activity of these cells was detected. Next, Sca-1+/lin−/CD45− in contrast to Sca-1+/lin−/CD45+ cell did not radioprotect lethally irradiated mice or form CFU-S colonies in lethally irradiated syngeneic recipients.

Figure 7:
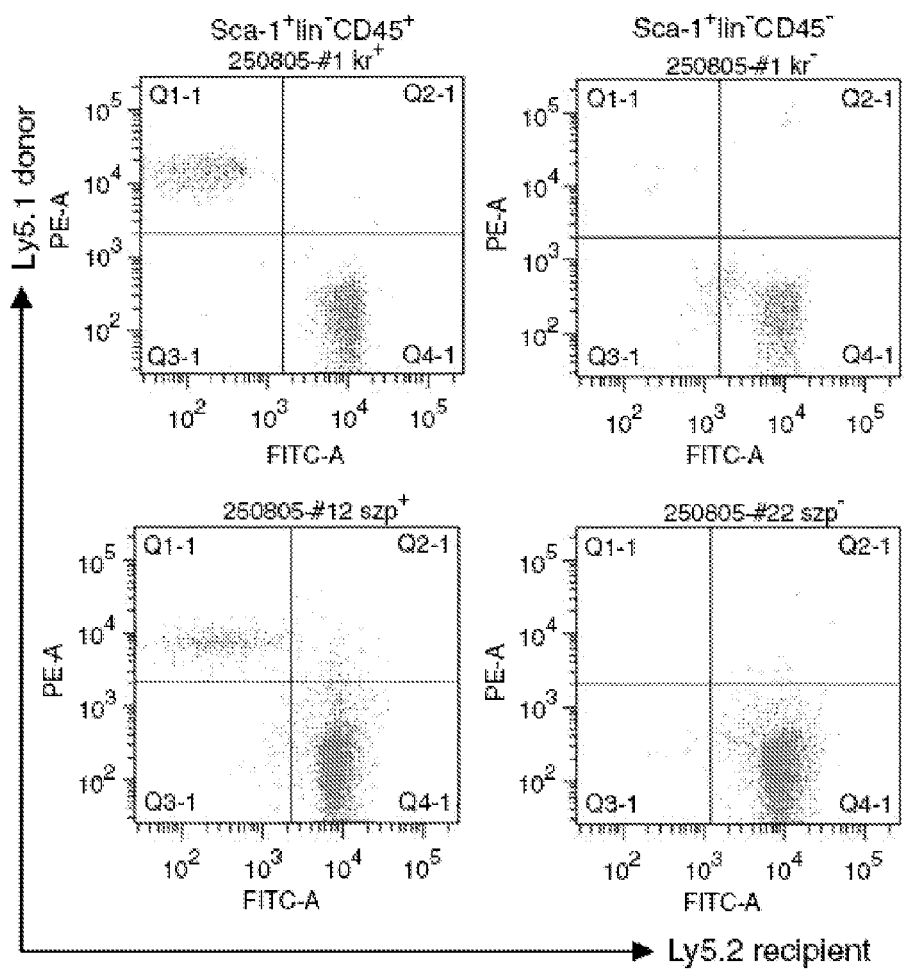
FIG. 7 is four dot-plots depicting the results of transplantation of various subpopulations of cells and the contribution of these cells to long-term hematopoiesis. Sca-1+/lin−/CD45− cells do not contribute to long-term hematopoiesis. Ly5.2 mice were transplanted with $10^4$ Sca-1+/lin−/CD45+ or $2×10^4$ Sca-1+/lin−/CD45− cells from Ly5.1 mice along with $10^6$ BMMNC Ly5.2 cells into Ly5.2 recipient mice and evaluated 8 months after transplantation for the presence of Ly5.1 cells by FACS. The upper panels depict analysis of MNC from the peripheral blood. The lower panels depict analysis of MNC from the bone marrow. Representative results are shown.

To address if these cells were be enriched for some long term hematopoietic repopulating stem cells, the contribution of these cells to long term repopulation of the hematopoietic system after transplantation to lethally irradiated mice was studied by employing donor/recipient animals congenic at the Ly.5 locus. Transplantation of $10^4$ Sca-1+/lin−/CD45+ cells from Ly5.1 mice along with $10^6$ BMMNC of Ly5.2 cells into Ly5.2 recipient mice resulted in about 17±3% chimerism of mice (n=6) as evaluated 8 months after transplantation. No contribution of donor cells to hematopoiesis was observed in similar experiments after transplantation of $2 \times 10^4$ Sca-1+/lin−/CD45− cells co-transplanted with $10^6$ BMMNC (see FIG. 7). Similar results were obtained in similar experiments after transplantation of green immunofluorescence positive (GFP+) Sca-1+/lin−/CD45− and Sca-1+/lin−/CD45+ cells into lethally irradiated syngeneic recipients.

Discussion of Examples 1-19

Contribution of BM-derived cells to organ regeneration has been explained by some investigators to involve the phenomenon of trans-dedifferentiation of HSC. However, the co-inventors have determined that BM contains a population of rare Sca-1+/lin−/CD45− cells that express several markers of non-hematopoietic stem cells and are able to differentiate in vitro cultures into mesoderm-derived cardiomyocytes and ectoderm-derived neural cells. These cells have been referred to as very small embryonic-like (VSEL) stem cells. It is possible that VSEL stem cells circulate during organogenesis and rapid body growth/expansion. Since VSEL stem cells respond to an SDF-1 gradient, the SDF-1-CXCR4 axis alone or in combination with other chemoattractants might play a crucial role in accumulation of these cells in young BM.

Disclosed herein is that these highly purified BM-derived Sca-1+/lin−/CD45− cells (~0.02% of BMMNC) express both at the mRNA and protein level several embryonic stem cell markers, such as surface marker SSEA-1 and transcription factors Oct-4, Nanog, and Rex-1. In direct TEM studies it was observed that these cells are very small (3-4 μm) and show a very immature morphology (e.g., they posses relatively large nuclei and contain immature open-type euchromatin). The open type of chromatin in these cells correlates with the presence of mRNA not only for embryonic stem cells but also mRNA for several VSEL stem cells, such as those that are competent to differentiate into skeletal muscle, heart muscle, neural, liver, intestinal epithelium, skin epidermis, melanocytes, and endocrine pancreas. Thus, disclosed herein for the first time is the identification at the morphological level a population of embryonic-like cells in adult BM.

Additionally, some of these cells express early developmental markers for neural, cardiac, or skeletal muscles at the protein level, suggesting that despite their similar homogenous morphology these cells show some degree of tissue commitment and are heterogeneous. It is interesting to note that the expression of several potential chemoattractants of stem cells (e.g., SDF-1, HGF/SF, and LIF) are upregulated in damaged organs, and hypoxia regulated/induced transcription factor (HIF-1) plays an important role in their expression (Ceradini et al. (2004) 10 Nat Med 858-864; Pennacchietti et al. (2003) 3 Cancer Cell 347-361). To support this notion, promoters of SDF-1, HGF/SF, and LIF, contain several functional HIF-1 binding sites. Thus the SDF-1-CXCR4, HGF/SF-c-met, and LIF-LIF-R axes might direct trafficking of stem cells.

To support this notion, disclosed herein is the demonstration that highly purified Sca-1+/lin−/CD45− cells express CXCR4, c-met, and LIF-R at the protein level, and respond robustly by chemotaxis to SDF-1, LIF, and HGF/SF gradients, respectively. This observation is in agreement with the fact that murine embryonic stem cells also express functional CXCR4, c-met, and LIF-R on their surfaces, and SDF-1, HGF/SF, and LIF affect the motility of these cells (Kucia et al. (2005c) 3 Stem Cells 879-894; Guo et al. (2005) 23 Stem Cells 1324-1332).

One might also expect that if a population of Sca-1+/lin−/CD45− BMMNC is enriched in embryonic-like PSC, these cells should be also able to differentiate along the hematopoietic lineage. However, neither protected lethally irradiated mice nor contributed to long-term hematopoiesis after transplantation into lethally irradiated recipients. Thus, the population of CD45− cells appears to be restricted to heterogeneous non-hematopoietic VSEL stem cell only. However, it is also possible that in the standard assays disclosed herein the potential pluripotency of Sca-1+/lin−/CD45− BMMNC was not detected and the final answer on their hematopoietic potential is obtained after injection into a developing blastocyst.

The number of embryonic-like stem cells identified is higher in BM in young animals, and their number decreases with age. Furthermore, Sca-1+/lin−/CD45− cells are barely detectable in 1 year old mice which corresponds to a 50 year old human. This age dependent content of VSEL stem cells in BM might explain why regeneration processes are more efficient in younger individuals. Differences were also noticed in the content of Sca-1+/lin−/CD45− cells among BMMNC between long and short living mouse strains. The concentration of these cells is much higher in BM of long living (e.g., C57BL/6) as compared to relatively short living (DBA/2J) mice.

Finally, VSEL stem cells were highly mobile and responded to an SDF-1 gradient and adhered to BM-derived fibroblasts. Time-lapse studies revealed that these cells attach rapidly to, migrate beneath, and/or undergo emperipolesis in these cells. Interaction of VSEL stem cells with BM-derived fibroblasts was efficiently inhibited after their preincubation with CXCR4 antagonist, T140. Since fibroblasts secrete SDF-1 and other chemottractants, they might create a homing environment for these cells. Their robust interaction with BM-derived fibroblasts has an important implication—suggesting that isolated BM stromal cells might be "contaminated" by these small embryonic-like PSC/VSEL stem cells.

It appears that the Sca-1+/lin−/CD45− cells disclosed herein represent a new subpopulation of BM-derived stem cells. For example, mesenchymal stem cells (MSC) have a morphology similar to that of fibroblastic cells. Hematopoietic cells are CD45+. MSC are also CXCR4− and CD34−, and have never been identified at the single cell level. Similarly, putative multipotent adult progenitor cells (MAPC) have not been definitively identified at the single cells level, nor have USSC cells or MIAMI cells. The existences of these cells have only been postulated based on observed in vitro differentiation of cord blood or marrow cells to different tissues.

Furthermore, the fact that Sca-1+/lin−/CD45− PSC/VSEL stem cells are very small should be considered, especially in protocols based on gradient or velocity centrifugation employed to isolate stem cells from BM, mPB, and CB. It is very likely that the majority of PSC/VSEL stem cells could be lost during those isolation procedures because of their very small size.

Example 20

Formation of Embryoid Body-Like Spheres

GFP+ Sca-1+/lin−/CD45− (55×10$^4$/35 mm glass bottom plate) isolated from BMMNC of C57BL/6-Tg(ACTB-EGFP) 10sb/J mice (available from The Jackson Laboratory, Bar Harbor, Me., United States of America) were cultured along with C2C12 cells (1.5×10$^6$/35 mm glass bottom plate), which is a subclone of the mouse myoblast cell line commercially available from the American Type Culture Collection (ATCC; Manassas, Va., United States of America) in Dulbecco's Modified Eagle's Medium with 4 mM L-glutamine, 4.5 g/l glucose, 5% heat-inactivated FBS, 10 ng/ml rhEGF, 10 ng/ml FGF-2. The growth factors were added to the cultures daily. The medium was exchanged every 72 hours. The embryoid body-like spheres started appearing about 5-7 days after starting the co-cultures.

Figure 12:
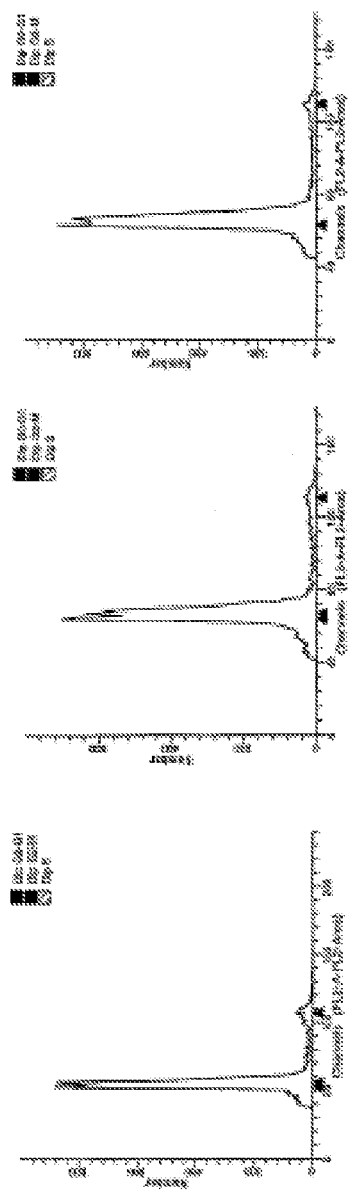
FIG. 12 is a series of dot-plots of propidium iodide-stained cells from VSEL stem cell-derived spheres (VSEL-DS). Three independent representative examples are shown.

Cells from VSEL stem cell-derived spheres (VSEL-DS) were stained with propidium iodide and subjected to FACS analysis to assess ploidy of the cells. Three independent examples are shown in FIG. 12.

Figure 8:
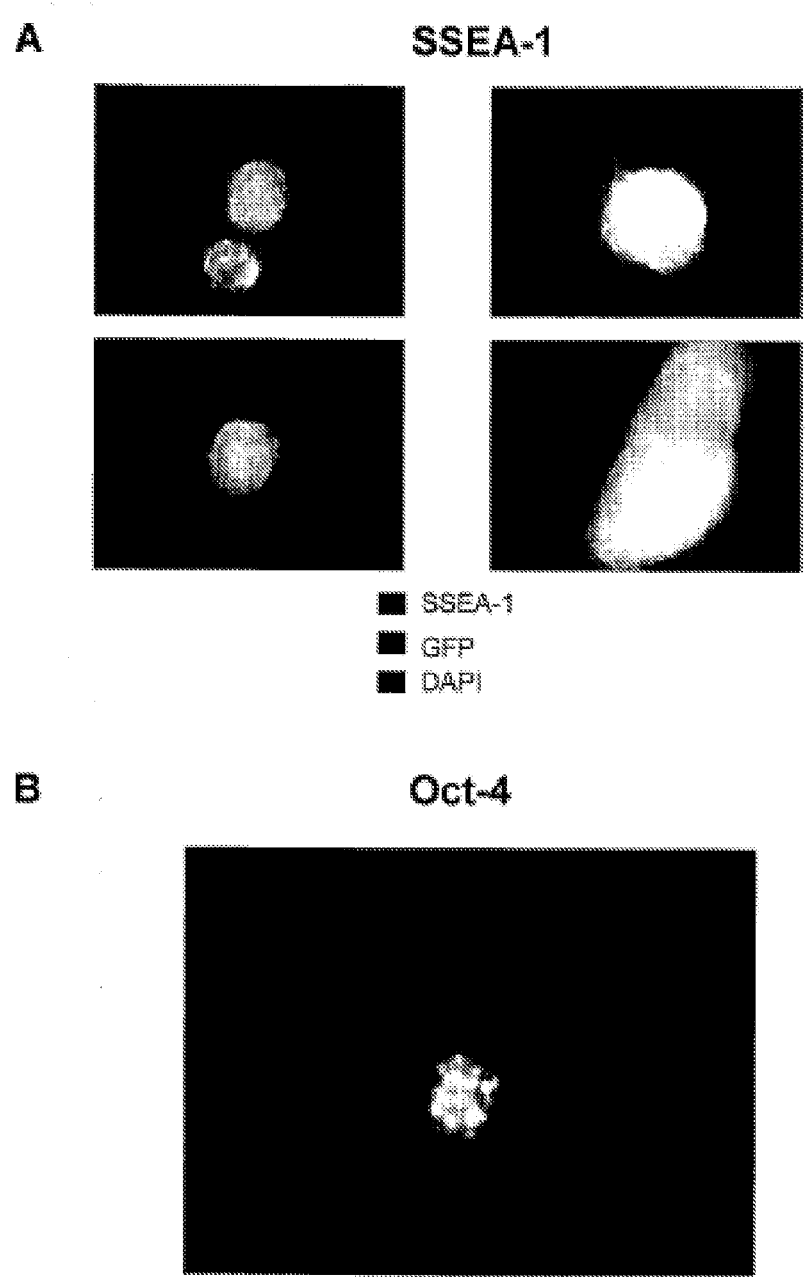
FIGS. 8A and 8B depict fluorescence micrographic images depicting staining of ES-like spheres of Sca-1+/lin−/CD45− BM cells with antibodies specific for SSEA-1 (FIG. 8A; 4 panels) or Oct-4 (FIG. 8B).
Figure 9:
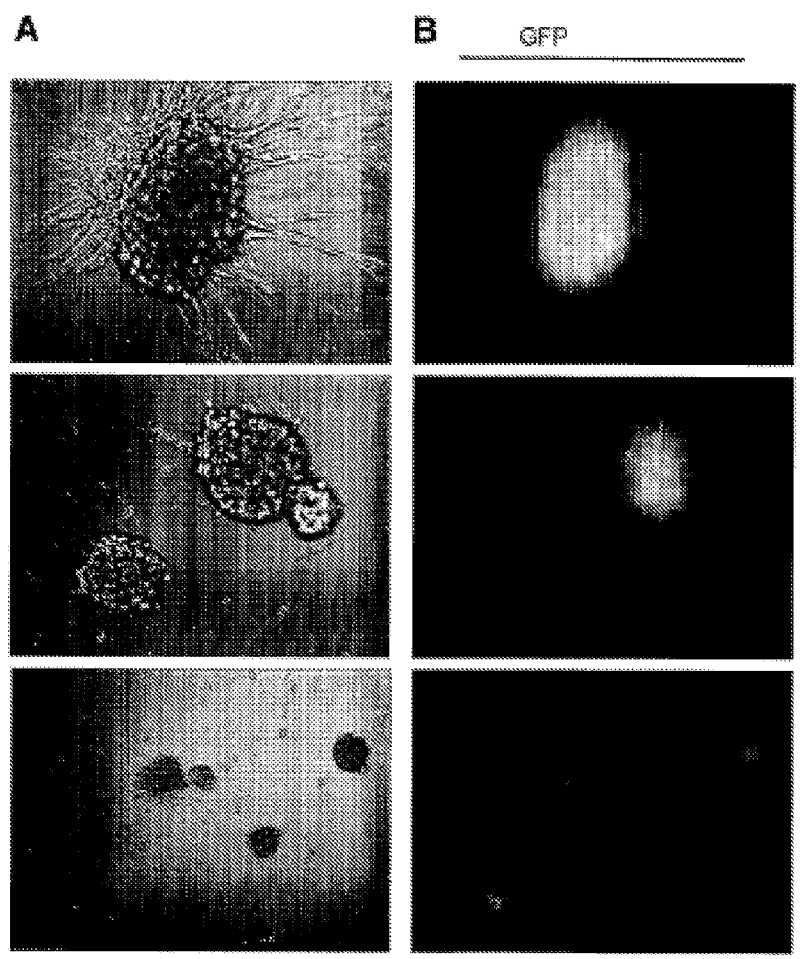
FIGS. 9A and 9B depict the formation of embryoid body-like spheres of GFP+ Sca-1+/lin−/CD45− BM cells on C2C12 cells.

The embryonic bodies were fixed in 3.5% paraformaldehyde for 20 minutes, permeabilized by 0.1% Triton X100, washed in PBS, pre-blocked with 2% BSA and subsequently stained with antibodies to SSEA-1 (1:200, mouse monoclonal IgM; Chemicon Intl., Temecula, Calif., United States of America; see FIG. 8A), or Oct-4 (1:200, mouse monoclonal IgG; Chemicon Intl.; see FIG. 8B). Appropriate secondary Alexa Fluor 594 anti-mouse IgM and Alexa Fluor 594 goat anti-mouse IgG were used (1:400; Molecular Probes, Eugene, Oreg., United States of America). In control experiments, cells were stained with secondary antibodies only. The nuclei were labeled with DAPI (Molecular Probes, Eugene, Oreg., United States of America). The Green Fluorescent Protein was visualized by anti-green fluorescent protein Alexa Fluor 488 conjugate (1:400; Molecular Probes, Eugene, Oreg., United States of America; see FIGS. 9A and 9B). The fluorescence images were collected with the TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Example 21

Plating of VSEL Stem Cells on C2C12 Cells

Murine C2C12 cells are a primitive myoblastic cells line is employed as a model for myogeneic differentiation. In order to differentiate/expand VSEL stem cells into myogenic lineage, purified by FACS BM-derived Sca-1+/lin−/CD45− VSEL stem cells were plated over C2C12 cells. 5-10% of plated VSEL stem cells began proliferate and form slightly attached/floating embryoid body-like spheres containing round cells.

In order to rule out the possibility that these embryoid body-like spheres were formed from the C2C12 cells, VSEL stem cells were isolated from GFP+ mice and embryoid body-like spheres were formed as in EXAMPLE 20. It was determined that the embryoid body-like spheres were formed by the GFP+ VSEL stem cells.

Figure 10:
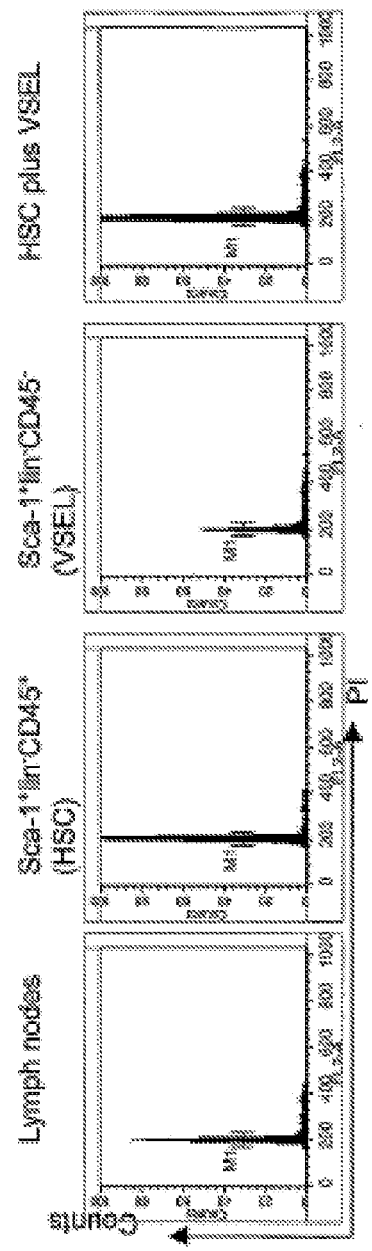
FIG. 10 is a series of dot-plots of propidium iodide-stained cells isolated from murine lymph nodes, HSCs (hematopoietic stem cells; Sca-1+/lin−/CD45+) or VSEL stem cells (Sca-1+/lin−/CD45−).

The possibility of fusion between C2C12 cells and VSEL stem cells was excluded by DNA ploidy analysis. Briefly, cells isolated from murine lymph nodes, HSCs (hematopoietic stem cells; Sca-1+/lin−/CD45+) or VSEL stem cells (Sca-1+/lin−/CD45−) were stained with propidium iodide and subjected to FACS analysis. DNA contents per cell were determined by staining cells with propidium iodide and subsequent FACS analysis (see FIG. 10).

Figure 13:
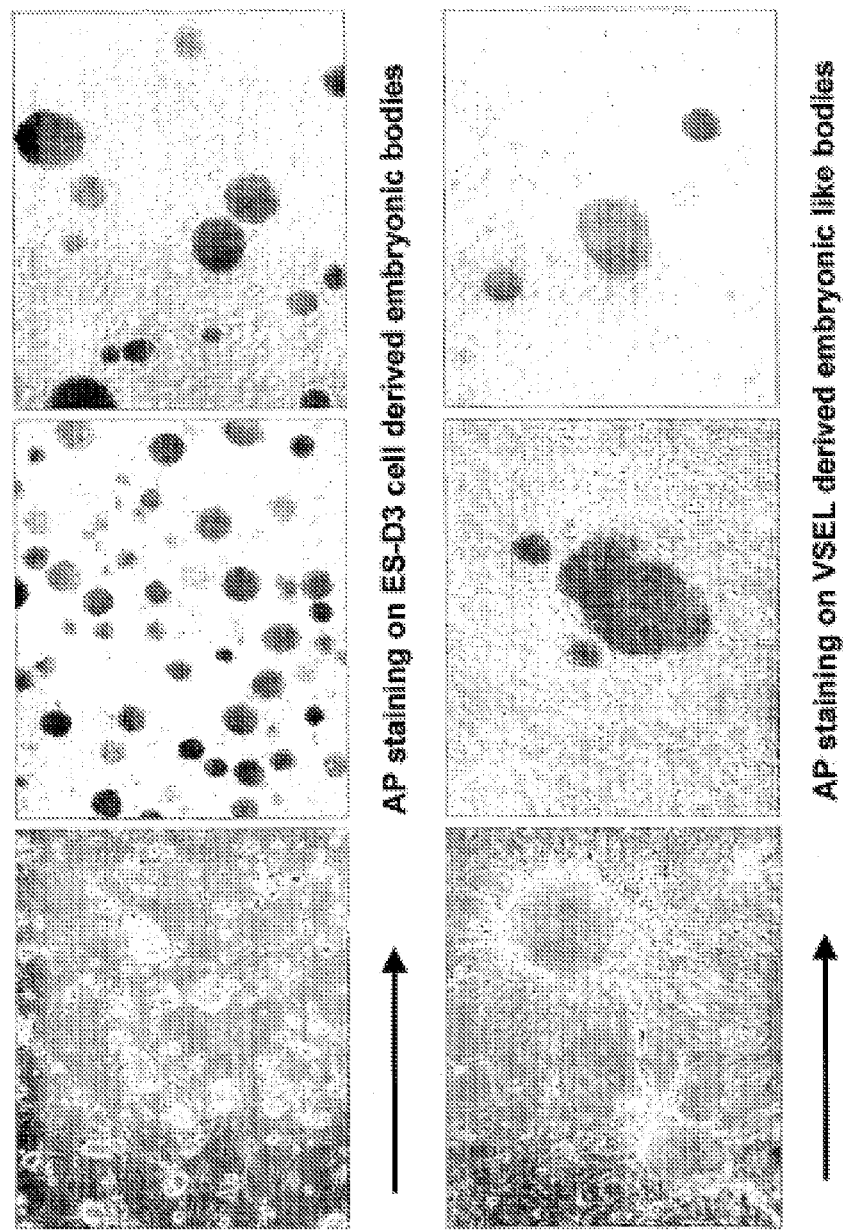
FIG. 13 depicts photographs of alpkaline phosphatase (AP) staining on embryoid bodies formed from D3 embryonic stem cells (ED-D3; top panel) and on embryoid body-like spheres formed from VSEL stem cells (bottom panel).

Interestingly, the embryoid body-like spheres expressed embryonic stem cell-specific alkaline phosphatase (see FIG. 13).

Figure 14:
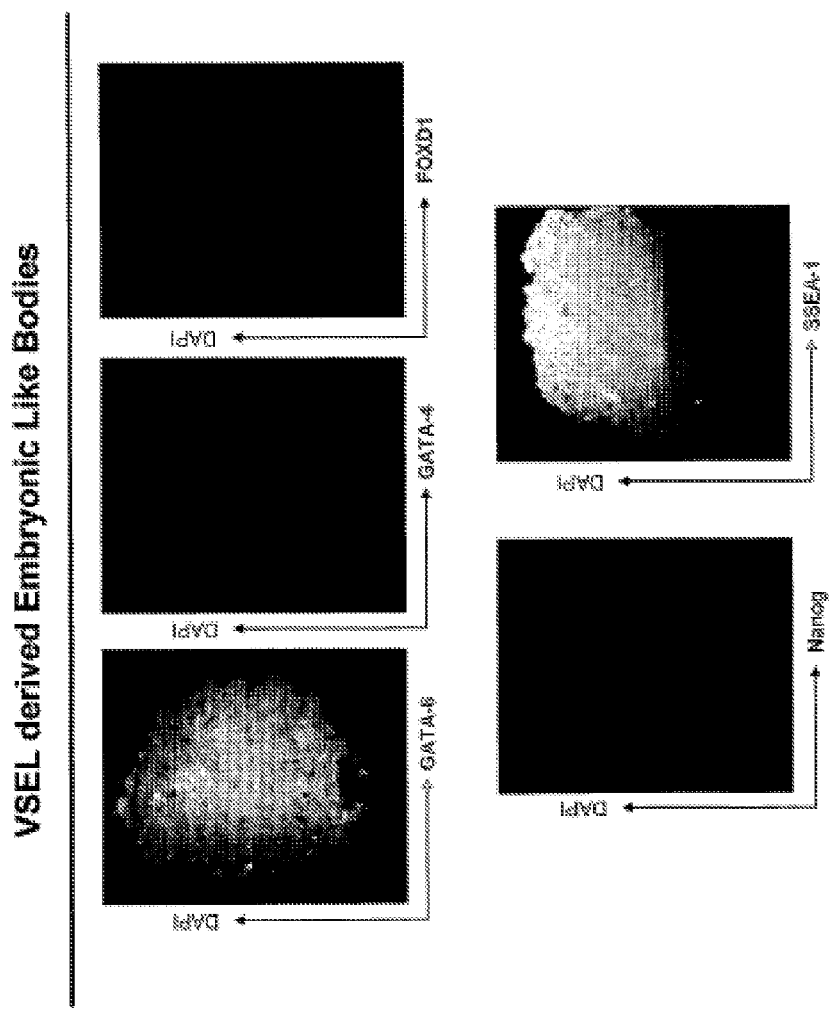
FIG. 14 depicts fluorescence micrographic images demonstrating that VSEL stem cell-derived embryonic body-like spheres express early embryonic developmental markers such as SSEA-1, GATA-6, GATA-4, FOXD1, and Nanog.

Further characterization of the embryoid body-like spheres revealed that they expressed early embryonic developmental markers such as SSEA-1, GATA-6, GATA-4, FOXD1, and Nanog (see FIG. 14). Transmission electron microscopy revealed that the cells that were present in the VSEL stem cell-derived embryoid body-like spheres were larger in size than the original VSEL stem cells from which they were derived (FIG. 15, upper panel), but still possessed very primitive nuclei containing euchromatin.

Figure 15:
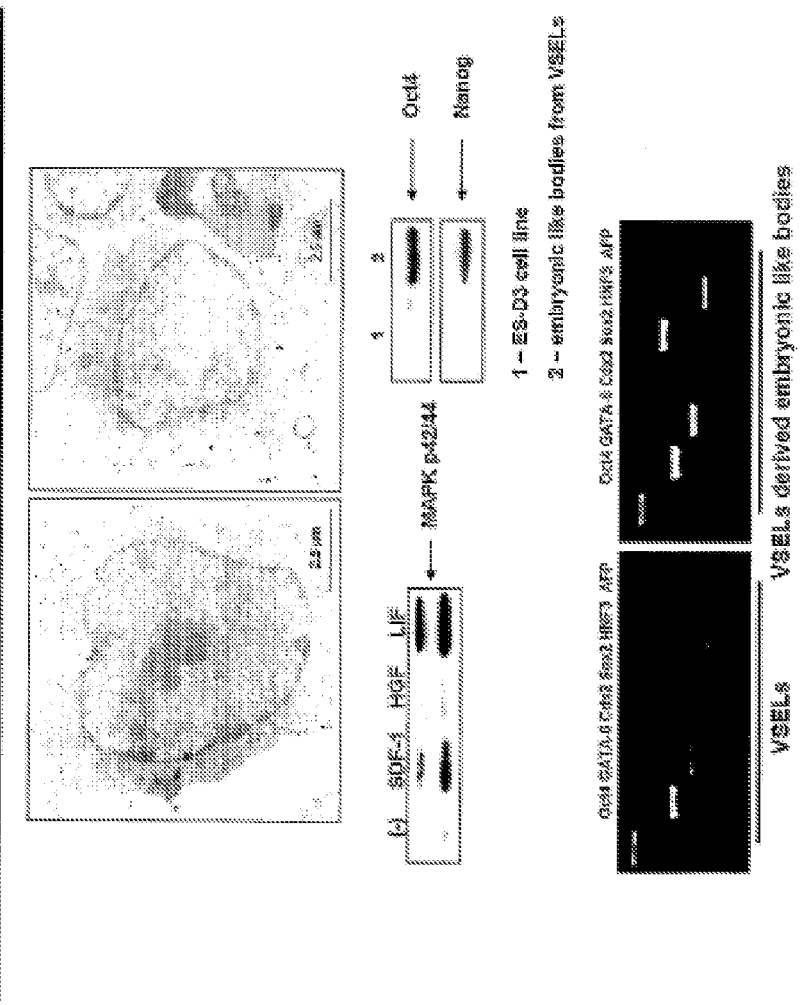
FIG. 15 depicts transmission electron microscopy of the cells that were present in the VSEL stem cell-derived embryoid body-like spheres showing that these cells were larger in size than the original VSEL stem cells from which they were derived (FIG. 15, upper panel), but still possessed very primitive nuclei containing euchromatin. The middle panel of FIG. 15 depicts the results of studies of phosphorylation of MAPKp42/44 after stimulation of cells isolated from VSEL stem cell-derived embryoid body-like spheres with SDF-1, HGF/SF, and LIF, indicating that the corresponding receptors (CXCR4, c-met, and LIF-R, respectively) are expressed on the surfaces of these cells. And finally, the lower panel of FIG. 15 depicts the results of RT-PCR analysis of cells isolated from consecutive passages of cells from VSEL stem cell-derived embryoid body-like spheres, which revealed an increase in expression of mRNA for genes regulating gastrulation of embryonic bodies such as GATA-6, Cdx2, Sox2, HNF3, and AFP.
Figure 16:
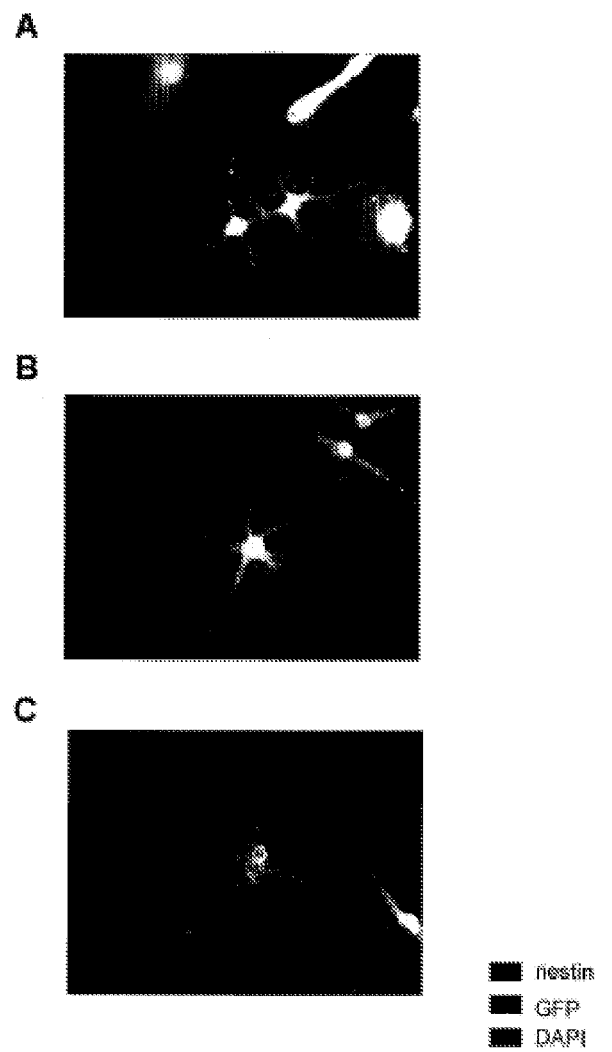
FIGS. 16A-16C and 17A-17D depict fluorescence micrographic images depicting the differentiation of ES like spheres into oligodendrocytes (FIGS. 16A-16C) or neurons (FIGS. 17A-17D). Cells were stained with antibodies directed to nestin, which were detecting using an Alexa Fluor 594-labeled goat anti-mouse IgG secondary antibody, which imparts a red fluorescence. GFP present in the cells was detected with an anti-green fluorescent protein Alexa Fluor 488 conjugate (green fluorescence), and nuclei were stained with DAPI (blue fluorescence).
Figure 17:
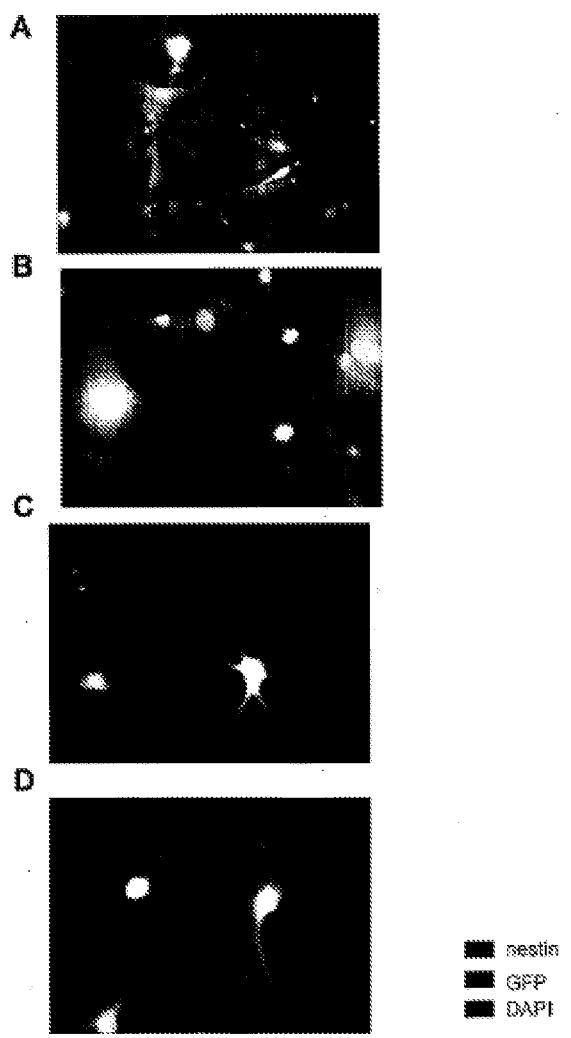

Developmental migration of VSEL stem cells can be orchestrated by SDF-1, HGF/SF, and LIF. It was further determined that cells isolated from VSEL stem cell-derived embryoid body-like spheres responded to stimulation by these factors by robust phosphorylation of MAPKp42/44, which suggested that these factors might play a role in their development and migration. It was further determined that the corresponding receptors (CXCR4, c-met, and LIF-R, respectively) were expressed on the surface of the VSEL stem cell-derived embryoid body-like spheres (FIG. 15, middle panel).

Furthermore, cells from VSEL stem cell-derived embryoid body-like spheres (VSEL-DS), after replating over C2C12 cells, can again grow new embryoid body-like spheres (up to at least 5-7 additional passages). However, the number and size of these embryoid body-like spheres became smaller with each passage. RT-PCR analysis of cells isolated from the embryoid body-like spheres from consecutive passages revealed an increase in expression of mRNA for genes regulating gastrulation of embryonic bodies, such as GATA-6, Cdx2, Sox2, HNF3, AFP (FIG. 15, lower panel).

Example 22

Neuronal Differentiation of Embryoid Body-Like Spheres

To generate neuronal derivatives (neurons, oligodendrocytes, glial cells), 10-50 embryoid body-like spheres/35 mm glass bottom plate were plated in NeuroCult Basal Medium (Stem Cell Technologies, Vancouver, British Columbia, Canada) supplemented with 10 ng/ml rhEGF, 20 ng/ml FGF-2, and 20 ng/ml NGF. Cells were cultured for 10-15 days. Growth factors were added every 24 hours and medium was replaced every 2-3 days.

At day 15 of differentiation, the cells were fixed in 3.5% paraformaldehyde for 20 minutes, permeabilized by 0.1% Triton X100, washed in PBS, pre-blocked with 2% BSA, and subsequently stained with antibodies to β III tubulin (1:100, rabbit polyclonal IgG; Santa Cruz Biotechnology, Santa Cruz, Calif., United States of America), nestin (1:200, mouse monoclonal IgGI; Chemicon Intl., Temecula, Calif., United States of America), or O4 (1:200, oligodendrocyte marker 4, mouse monoclonal IgM; Chemicon Intl.). Appropriate secondary Alexa Fluor 594 goat anti-rabbit IgG, Alexa Fluor 594 goat anti-mouse IgG, and Alexa Fluor 594 goat anti-mouse IgM were used (1:400, Molecular Probes, Eugene, Oreg., United States of America). In control experiments, cells were stained with secondary antibodies only.

FIGS. 16A-16C and 17A-17D summarize the staining of oligodendrocytes (FIGS. 16A-16C) and neurons (FIGS. 17A-17D) derived from VSEL stem cells. In FIGS. 16 and 17, the blue color is indicative of DAPI staining of nuclei (Molecular Probes; blue color), nestin staining appears red, and Green Fluorescent Protein (GFP) was visualized by anti-green fluorescent protein Alexa Fluor 488 conjugate (1:400; Molecular Probes, Eugene, Oreg., United States of America). The GFP is present in the isolated cells, which were isolated from GFP+ mice (C57BL/6-Tg(ACTbEGFP)1 Osb/J mice purchased from The Jackson Laboratory, Bar Harbor, Me., United States of America). The fluorescence images were collected with the TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Example 23

Endodermal Differentiation of Embryoid Body-Like Spheres

Before initiating differentiation, embryoid body-like spheres were given a brief wash in PBS. 10-50 embryoid body-like spheres per 35 mm glass bottom plate were plated in DMEM/F12 Medium with 4 mM L-glutamine, 4.5 g/l glucose, 1% heat-inactivated FBS, and 50 ng/ml of recombinant human Activin A. After 48 hours, medium was exchanged and differentiation was carried out in DMEM/F12 Medium with 4 mM L-glutamine, 4.5 g/l glucose, and 5% heat-inactivated FBS in the presence of N2 supplement-A, B27 supplement, and 10 mM nicotinamide (purchased from Stem Cell Technologies Inc., Vancouver, British Columbia, United States of America). Medium was changed every second day. Islet-like clusters appeared after 12-17 days of culture.

After 17 days of differentiation, cells were fixed in 3.5% paraformaldehyde for 20 minutes, permeabilized by 0.1% Triton X100, washed in PBS, pre-blocked with 2% BSA, and subsequently stained with antibodies to pancreatic C-peptide (1:100; guinea pig IgG, Linco Research, Inc., St. Charles, Mo., United States of America). Appropriate secondary Alexa Fluor 594 anti-guinea pig IgG were used (1:400; Molecular Probes, Eugene, Oreg., United States of America). In control experiments, cells were stained with secondary antibodies only.

Figure 18:
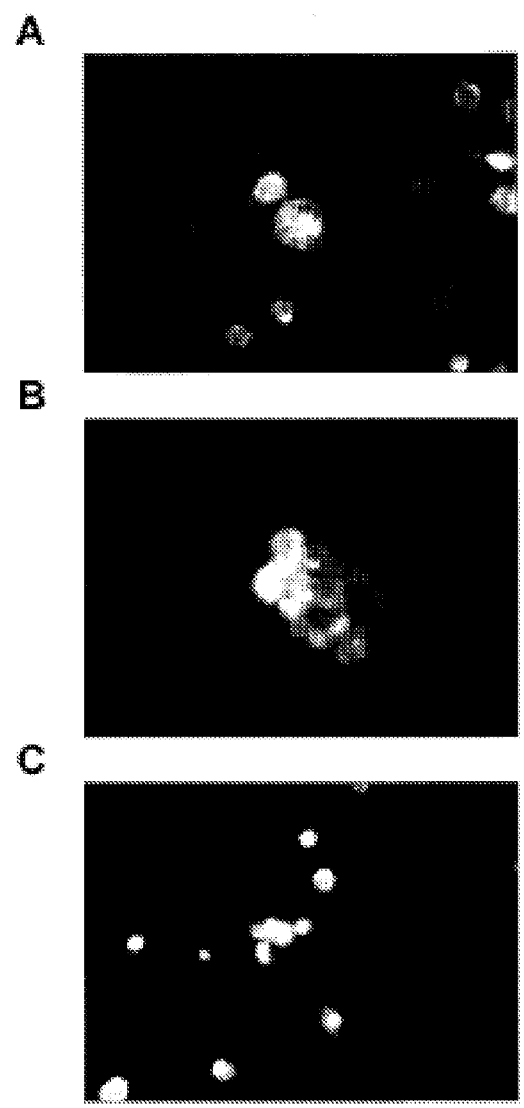
FIGS. 18A-18C depict fluorescence micrographic images depicting the differentiation of ES-like spheres into endodermal cells expressing a marker for pancreatic cells (C-peptide).

FIGS. 18A-18C summarize the staining of endodermal cells derived from VSEL stem cells. In FIGS. 18A-18C, the blue color is indicative of DAPI staining of nuclei (Molecular Probes, Eugene, Oreg., United States of America; blue color), C-peptide staining appears red, and Green Fluorescent Protein (GFP) was visualized by anti-green fluorescent protein Alexa Fluor 488 conjugate (1:400; Molecular Probes, Eugene, Oreg., United States of America). The GFP is present in the isolated cells, which were isolated from GFP+ mice (C57BL/6-Tg(ACTB-EGFP)1 Osb/J mice purchased from The Jackson Laboratory, Bar Harbor, Me., United States of America). The fluorescence images were collected with the TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Example 24

Cardiomyocyte Differentiation of Embryoid Body-Like Spheres 10-50 embryoid body-like spheres/35 mm glass bottom plate were plated in DMEM with 4 mM L-glutamine, 4.5 g/l glucose, 10% heat-inactivated FBS, and 10 ng/ml bFGF, 10 ng/ml VEGF, and 10 ng/ml TGFβL Growth factors were added every 24 hours and medium was replaced every 2-3 days. Cardiomyocytes differentiated after about 15-17 days of differentiation.

At day 17 of differentiation, cells were fixed in 3.5% paraformaldehyde for 20 minutes, permeabilized by 0.1% Triton X100, washed in PBS, pre-blocked with 2% BSA, and subsequently stained with antibodies to Troponin I (1:200; mouse monoclonal IgG2b, Chemicon Intl., Temecula, Calif., United States of America), and α-sarcomeric actinin (1:100; mouse monoclonal IgM, Abeam, Inc., Cambridge, Mass., United States of America). Appropriate secondary Alexa Fluor 594 goat anti-mouse IgG, and Alexa Fluor 594 anti-mouse IgM were used (1:400; Molecular Probes, Eugene, Oreg., United States of America). In control experiments, cells were stained with secondary antibodies only.

Figure 19:
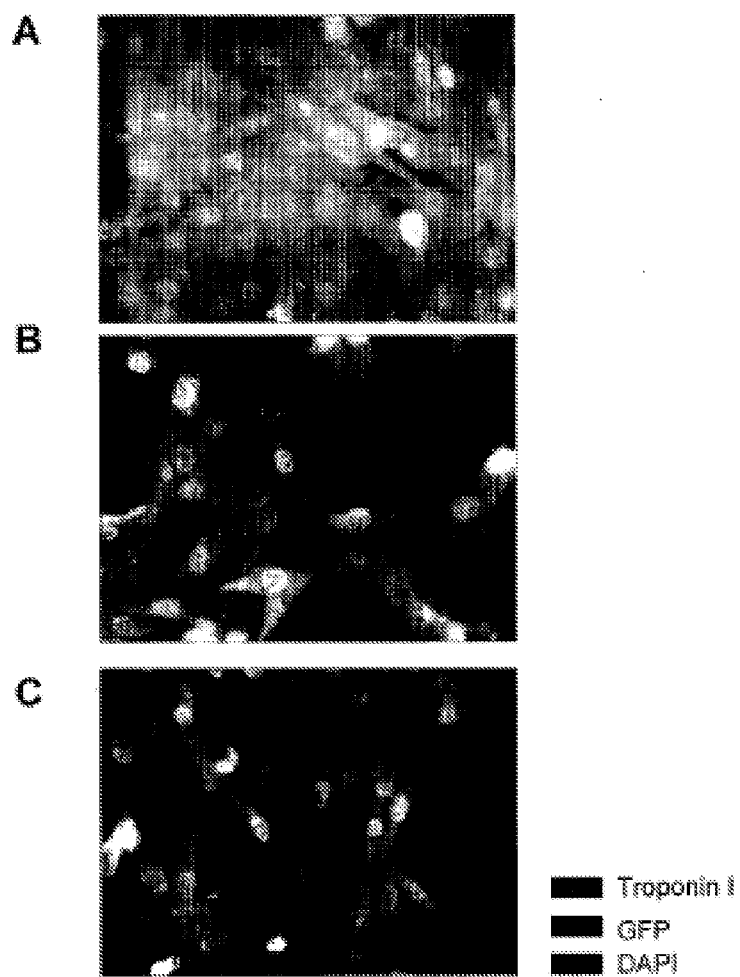
FIGS. 19A-19C and 20A-20D depict fluorescence micrographic images depicting the differentiation of ES-like spheres into cardiomyocytes. These cells express green fluorescent protein (GFP), indicating that the cardiomyocytes are derived from embryoid bodies formed by GFP+ Sca-1+/lin−/CD45− BM cells. Cells were stained with antibodies directed to troponin I or α sarcomeric actinin (FIGS. 19 and 20, respectively), which were detecting using an Alexa Fluor 594-conjugated secondary antibody, which imparts a red fluorescence. GFP present in the cells was detected with an anti-green fluorescent protein Alexa Fluor 488 conjugate (green fluorescence), and nuclei were stained with DAPI (blue fluorescence).
Figure 20:
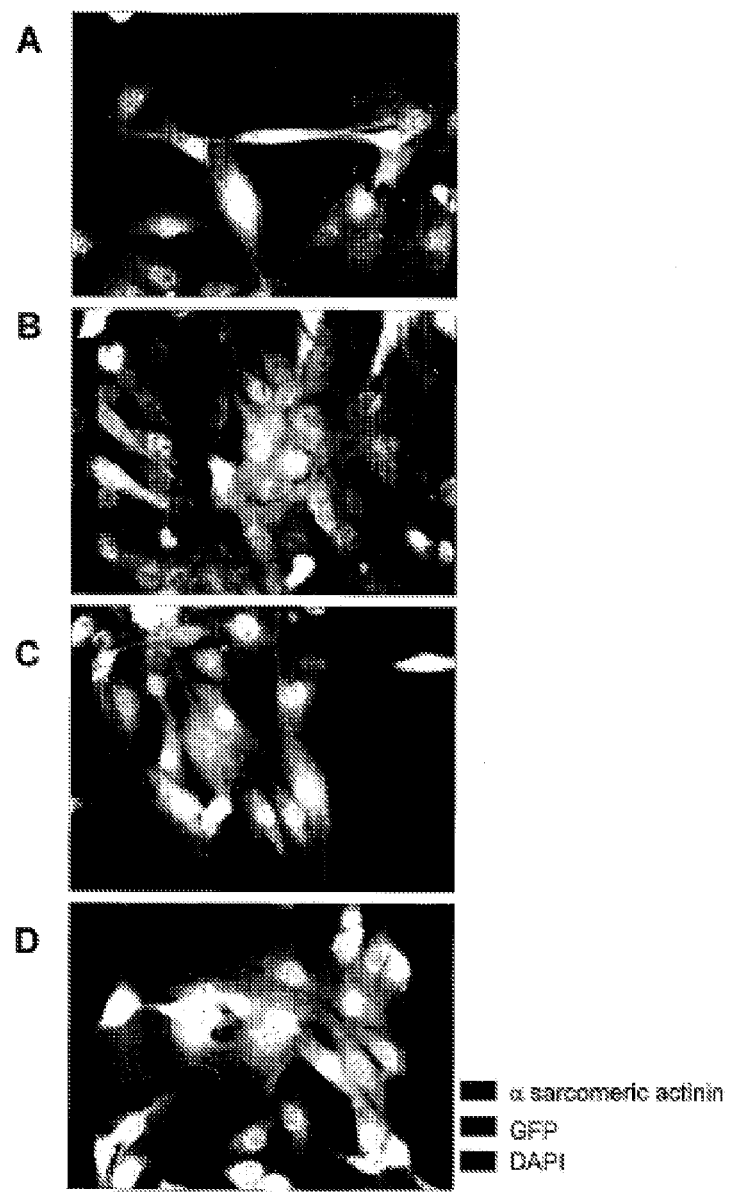

FIGS. 19A-19C and 20A-20D summarize the staining of cardiomyocytes derived from VSEL stem cells. In FIGS. 19A-19C, the blue color is indicative of DAPI staining of nuclei (Molecular Probes, Eugene, Oreg., United States of America; blue color), troponin I staining appears red, and Green Fluorescent Protein (GFP) was visualized by anti-green fluorescent protein Alexa Fluor 488 conjugate (1:400; Molecular Probes, Eugene, Oreg., United States of America). In FIGS. 20A-20D, the red color corresponds to staining of a sarcomeric actinin. The GFP is present in the isolated cells, which were isolated from GFP+ mice (C57BL/6-Tg(ACTB-EGFP)1Osb/J mice purchased from The Jackson Laboratory, Bar Harbor, Me., United States of America). The fluorescence images were collected with the TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Discussion of Examples 21-24

Figure 21:
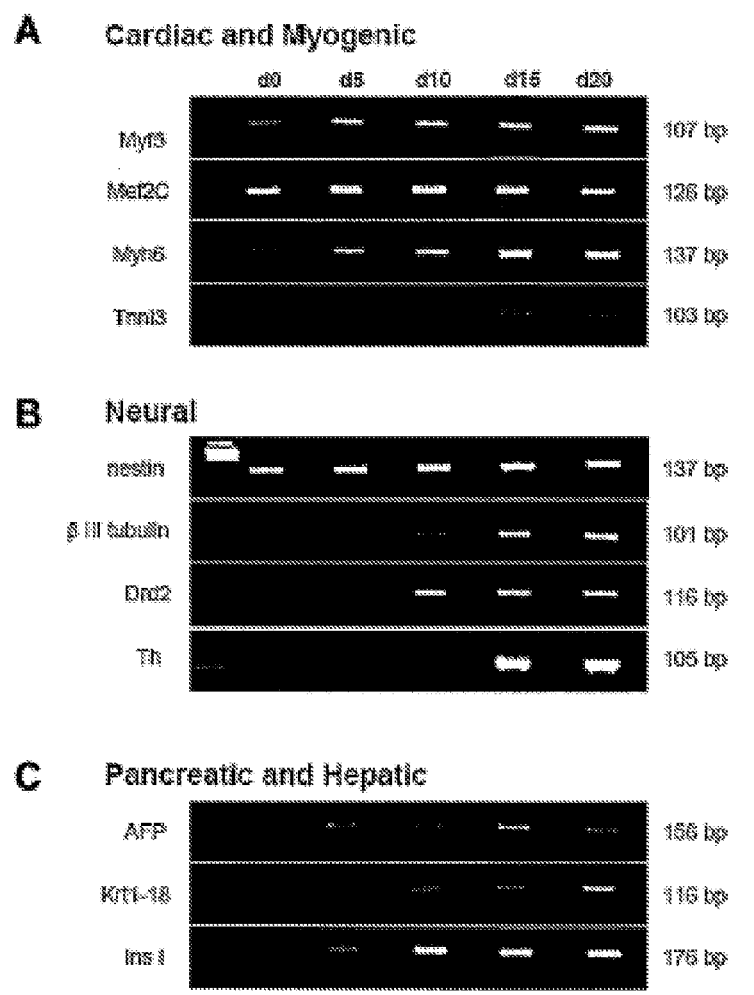
FIGS. 21A-21C depict the results of RT-PCR on cells from single VSEL stem cell-derived spheres, which indicated that these cells can differentiate into cardiomyocytes (mesoderm; see FIG. 21A), neural cells and oligodendrocytes (ectoderm; see FIG. 21B), and pancreatic or hepatic cells (endoderm; see FIG. 21C).

To support the hypothesis that cells present in embryoid body-like spheres growing from single VSEL stem cells are able to differentiate into all three germ layers, cells from single VSEL-DS were plated in differentiating media that support grow of cardiac myocytes, neuronal cells, and pancreatic cells. Both histochemical staining as well as RT-PCR analysis (FIGS. 21A-21C) revealed that cells from single VSEL stem cell-derived spheres differentiate into cardiomyocytes (mesoderm), neural cells and oligodendrocytes (ectoderm), and pancreatic β-islets (endoderm) insulin-producing cells. These changes in cell morphology and expression of lineage-specific proteins were paralleled by upregulation of tissue-specific genes (see FIG. 21).

Example 25

Studies of Myocardial Infarction

Two groups (n=24/group) of wild-type mice (C57BL/6, 129 strain, body wt. 25-35 g, age 12-16 weeks) purchased from Jackson Laboratory were used.

The experimental preparation has been described in Guo et al. (1998) 275 Am J Physiol H1375-1387 and Guo et al. (1999) 96 Proc Natl Acad Sci. USA 11507-11512. Mice were anesthetized with pentobarbital sodium (50 mg/kg i.p.), intubated, and ventilated using a small rodent ventilator. Body temperature, heart rate, and arterial pH were carefully maintained within the physiological range throughout the experiments. Using a sterile technique, the chest was opened through a midline sternotomy. An 8-0 nylon suture was passed with a tapered needle under the left anterior descending coronary artery 2-3 mm from the tip of the left auricle, and a non-traumatic balloon occluder was applied on the artery. Coronary occlusion was induced by inflating the balloon occluder. Mice in group I underwent a 30 minute coronary occlusion followed by reperfusion while mice in group II underwent a sham operation (1 hour open-chest state). See Guo et al. (1998) 275 Am J Physiol H1375-1387 and Guo et al. (1999) 96 Proc Natl Acad ScL USA 11507-11512. Mice (n=6 mice in each group at each time-point) were sacrificed at 6 hours, 24 hours, 48 hours, or 96 hours after the onset of reperfusion.

Following euthanasia, blood samples (1.0-1.5 ml from each mouse) were collected in heparin-rinsed syringes for the isolation of peripheral blood mononuclear cells (PBMNCs). Myocardial tissue samples were harvested from the ischemic and non-ischemic regions and frozen immediately in liquid nitrogen for mRNA extraction.

Example 26

In Vitro Expression of Cardiac Markers

The ability of the bone marrow-derived Sca-1+/lin−/CD45− MNCs to differentiate into a cardiomyocyte phenotype in culture was tested. Due to the inability of the Sca-1+/lin−/CD45− cells to survive when cultured alone, Sca-1+/lin−/CD45− and Sca-1+/lin−/CD45+ BMMNCs were cultured in separate plates along with unpurified bone marrow cells that provide a conducive milieu for cell survival. Twenty-one days later, these cells were immunostained to examine the expression of cardiac-specific myosin heavy chain and cardiac troponin I. Cultured cells in plates to which the Sca-1+/lin−/CD45− BMMNCs were added (FIGS. 22A-22C and 22D-22F) exhibited a different phenotype compared with the plates to which the Sca-1+/lin−/CD45+ cells were added. Numerous cells in plates with Sca-1+/lin−/CD45− cells were positive for cardiac-specific myosin heavy chain (FIGS. 22B, 22C, 22E, and 22F; green fluorescence). Many of these cardiac-specific myosin heavy chain-positive cells were also positive for cardiac troponin I (FIGS. 22D and 22F [arrowheads]; red fluorescence).

Figure 22:
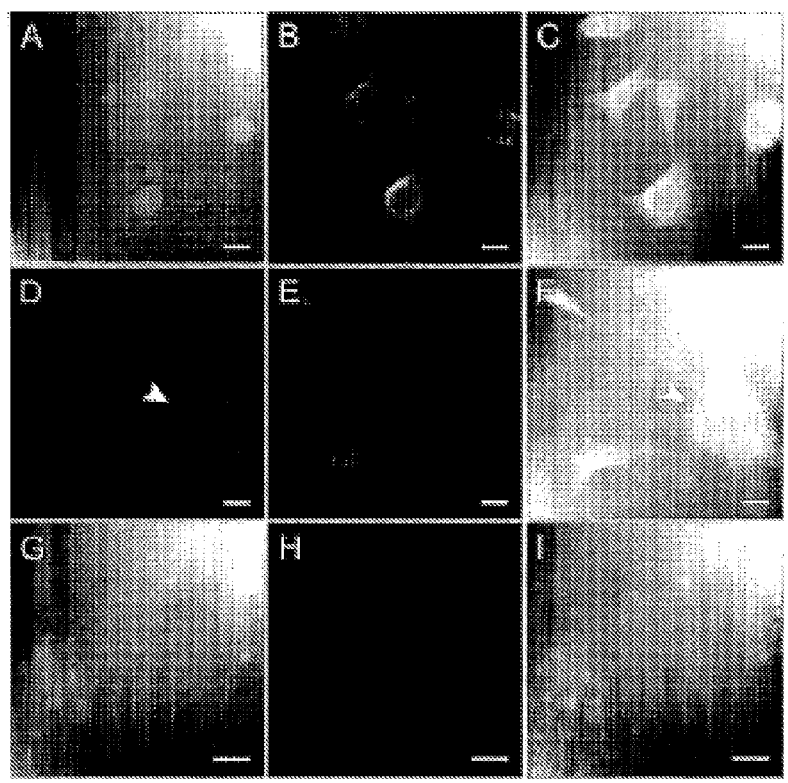
FIGS. 22A-22I depict immunofluorescent and transmission confocal microscopic images documenting the expression of cardiac-specific antigens in cultured cells.

In contrast, cultured cells in plates to which the Sca-1+/lin−/CD45+ cells were added (FIGS. 22G-22I) were largely negative for the expression of these cardiac-specific antigens (FIG. 22H). In FIGS. 22A-22I, the nuclei are identified by DAPI (blue fluorescence). These results indicate that Sca-1+/lin−/CD45− cells are capable of differentiating into a cardiomyocyte phenotype in culture.

Example 27

Immunohistochemistry

The expression of cardiac-specific markers (GATA-4 and Nkx2.5/Csx) in PSC/VSEL stem cells was verified by immunocytochemistry. Murine control (unpurified) BMMNCs and BMMNCs chemoattracted to SDF-1, HGF, and LIF, or Sca-1+/lin−/CD45− and Sca-1+/lin−/CD45+ BM-derived cells sorted by FACS were fixed in 1% paraformaldehyde for 30 minutes, permeabilized with 0.5% Triton X-100, and incubated overnight at 4° C. with rabbit polyclonal anti-GATA-4 (Santa Cruz) and rabbit polyclonal anti-Nkx2.5/Csx (Santa Cruz Biotechnology, Santa Cruz, Calif., United States of America) primary antibodies. FITC- and TRITC-labeled secondary antibodies were used for the detection of GATA-4 and Nkx2.5/Csx, respectively. Cells positive for cardiac markers were counted using a confocal microscope (Zeiss LSM 510, Carl Zeiss, Thornwood, N.Y., United States of America) and expressed as a percentage of total MNCs.

Example 28

Functional Pluripotent VSEL Stem Cell Numbers Decrease with Age

Figure 23:
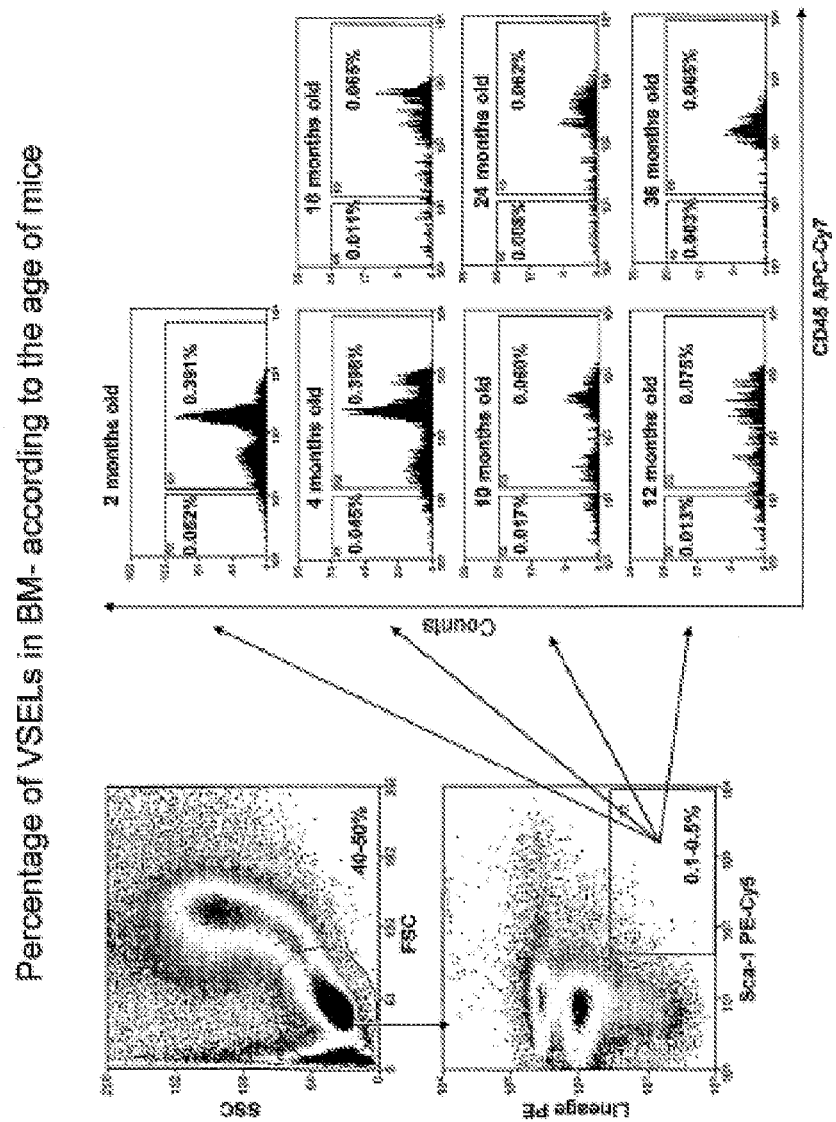
FIG. 23 depicts the results of FACS sorting of Sca-1+/lin−/CD45− cells showing that the yield of these cells that could be sorted decreased with age of the donor animal.
Figure 24:
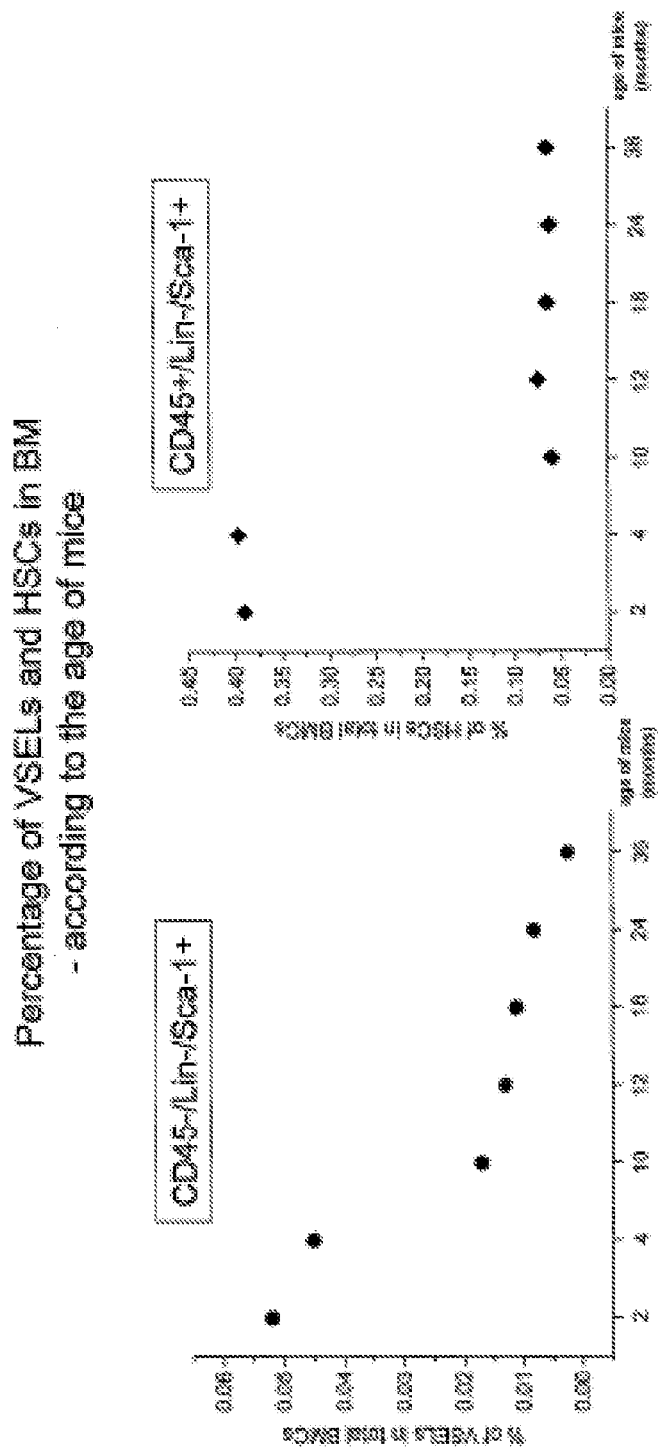
FIG. 24 is two graphs depicting the percentages of VSEL stem cells (left panel) and HSCs (right panel) present in the bone marrow of mice as a function of age.
Figure 25:
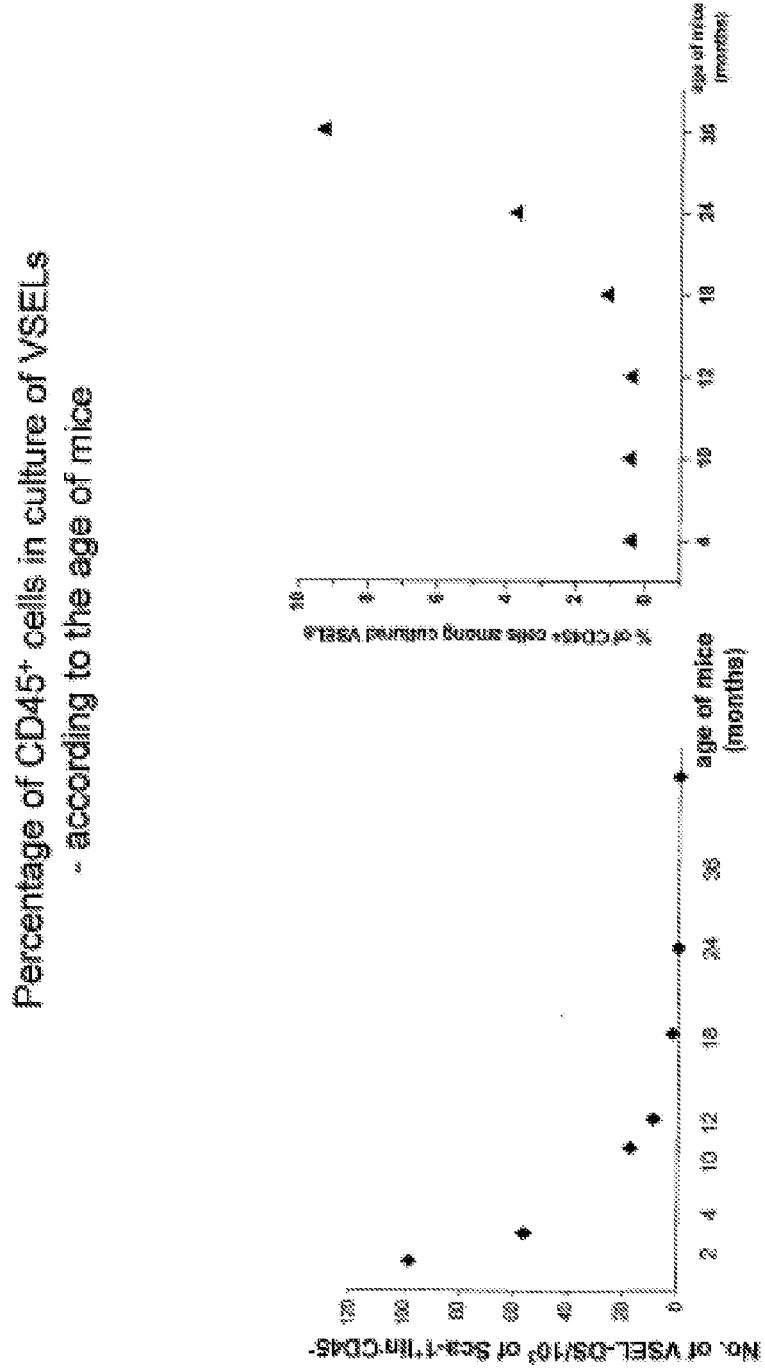
FIG. 25 is two graphs depicting the decline in the ability of VSEL stem cells isolated from older mice to form embryoid body-like spheres (left panel) and the increased percentage of CD45+ cells in cultures of VSEL stem cells according to the age of the mice from which the cells were isolated (right panel).
Figure 26:
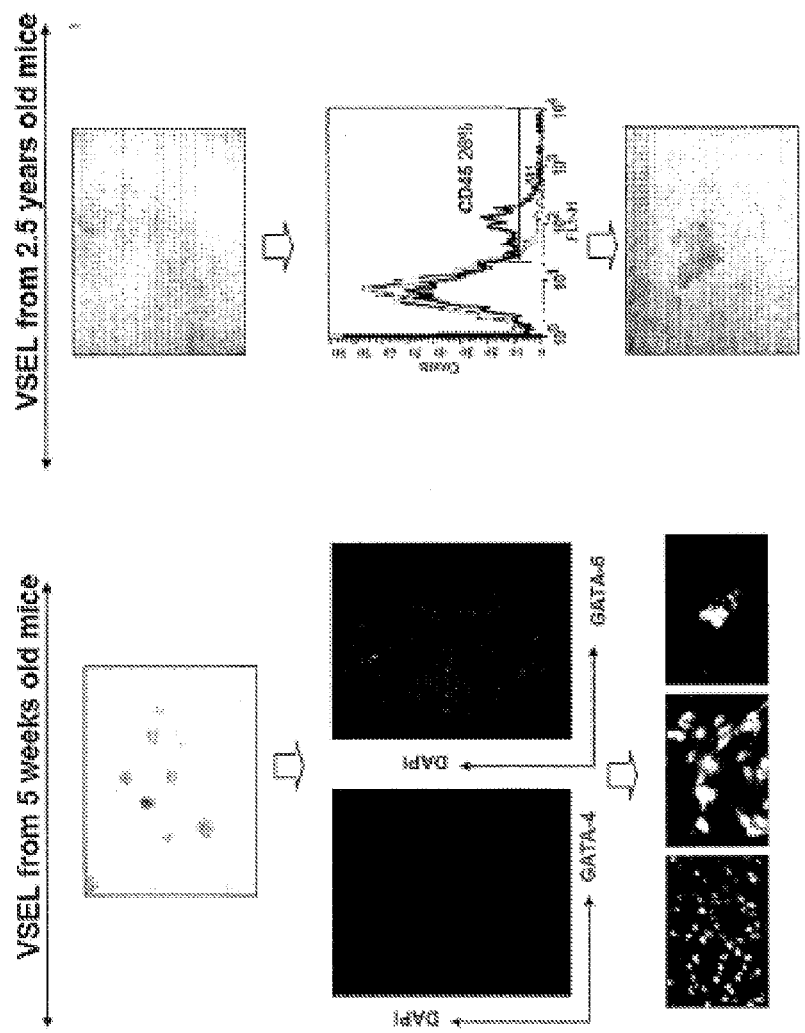
FIG. 26 different expression patterns for VSEL stem cells isolated from 5 week old mice (left panel) versus 2.5 year old mice (right panel). In the left panel are shown immunofluorescent and transmission confocal microscopic images documenting the expression of different hematopoietic antigens in cultured cells from 5 week old mice. In the right panel is shown that in VSEL stem cells isolated from 2.5 year old mice, CD45 is expressed and the cells were able to grow hematopoietic colonies in secondary cultures in methylcellulose cultures.

The number of VSEL stem cells in young versus old mice was also investigated. The yield of Sca-1+/lin−/CD45− cells that could be sorted by FACS was observed to decrease with age (FIGS. 23 and 24). It was further determined that VSEL-DS could be formed in co-cultures with C2C12 cells only by VSEL stem cells that were isolated from young mice (FIG. 25). Interestingly, VSEL stem cells from 2.5-year old animals formed cells clusters of round cells when co-cultured with C2C12. These round cells expressed the CD45 antigen and were able to grow hematopoietic colonies in secondary cultures in methyllocelulose (FIG. 26).

Example 29

Isolation of VSEL Stem Cells from Cord Blood

Staining and isolation of Cord Blood (CB) derived VSEL stem cells. Whole human umbilical CB was lysed in BD lysing buffer (BD Biosciences, San Jose, Calif., United States of America) for 15 minutes at room temperature and washed twice in PBS. A single cell suspension was stained for various lineage markers (CD2 clone RPA-2.10; CD3 clone UCHT1; CD14 clone M5E2; CD66b clone G10F5; CD24 clone ML5; CD56 clone NCAM16.2; CD16 clone 3G8; CD19 clone HIB19; and CD235a clone GA-R2) conjugated with FITC, CD45 (clone HI30) conjugated with PE, and combination of CXCR4 (clone 12G5), CD34 (clone 581) or CD133 (CD133/1) conjugated with APC, for 30 minutes on ice. After washing, cells were analyzed by FACS (BD Biosciences, San Jose, Calif., United States of America). At least $10^6$ events were acquired and analyzed by using Cell Quest software.

CXCR4+/lin−/CD45−, CD34+/lin−/CD45−, or CD133+/lin−/CD45− cells were sorted from a suspension of CB MNC by multiparameter, live sterile cell sorting (MOFLO™, Dako A/S, Fort Collins, Colo., United States of America, or BD FACSARIA™ Cell-Sorting System, BD Biosciences, San Jose, Calif., United States of America).

Transmission electron microscopy (TEM) analysis. For transmission electron microscopy, the CXCR4+/lin−/CD45− cells were fixed in 3% glutaraldehyde in 0.1 M cacodylate buffer pH 7.4 for 10 hours at 4° C., post-fixed in osmium tetride, and dehydrated. Fixed cells were subsequently embedded in LX112 resin (Ladd Research Industries, Inc., Burlington, Vt., United States of America) and sectioned at 800A, stained with uranyl acetate and lead citrate, and viewed on a Philips CM10 electron microscope (Philips, Eindhoven, the Netherlands) operating at 60 kV.

RT-PCR. Total RNA was isolated using the RNEASY® Mini Kit (Qiagen Inc., Valencia, Calif., United States of America). mRNA (10 ng) was reverse-transcribed with One Step RT-PCR (Qiagen Inc., Valencia, Calif., United States of America) according to the instructions of the manufacturer. The resulting cDNA fragments were amplified using HOT-STARTAQ® DNA Polymerase (Qiagen Inc., Valencia, Calif., United States of America). Primer sequences for Oct4 were forward primer: 5'-TTG CCA AGC TCC TGA AGC A-3' (SEQ ID NO: 65) and reverse primer: 5'-CGT TTG GCT GAA TAC CTT CCC-3' (SEQ ID NO: 66), for Nanog were forward primer: 5'-CCC AAA GCT TGC CTT GCT TT-3' (SEQ ID NO: 67) and reverse primer: 5'-AGA CAG TCT CCG TGT GAG CCA T-3' (SEQ ID NO: 68). The correct size of PCR products was confirmed by separation on agarose gel.

Real time RT-PCR (RQ-PCR). For analysis of Oct4, Nanog, Nkx2.5/Csx, VE-cadherin, and GFAP mRNA levels, total mRNA was isolated from cells with the RNEASY® Mini Kit (Qiagen Inc., Valencia, Calif., United States of America). mRNA was reverse-transcribed with TAQMAN® Reverse Transcription Reagents (Applied Biosystems, Foster City, Calif., United States of America). Detection of Oct4, Nanog, Nkx2.5/Csx, VE-cadherin, GFAP, and β2-microglobulin mRNA levels was performed by real-time RT-PCR using an ABI PRISM® 7000 Sequence Detection System (Applied Biosystems, Foster City, Calif., United States of America). A 25 µl reaction mixture contains 12.5 µl SYBR Green PCR Master Mix, 10 ng of cDNA template, 5'-GAT GTG GTC CGA GTG TGG TTC T-3' (SEQ ID NO: 69) forward and 5'-TGT GCA TAG TCG CTG CTT GAT-3' (SEQ ID NO: 70) reverse primers for Oct4; 5'-GCA GAA GGC CTC AGC ACC TA-3' (SEQ ID NO: 71) forward and 5'-AGG TTC CCA GTC GGG TTC A-3' (SEQ ID NO: 72) reverse primers for Nanog; 5'-CCC CTG GAT TTT GCA TTC AC-3' (SEQ ID NO: 73) forward and 5'-CGT GCG CAA GAA CAA ACG-3' (SEQ ID NO: 74) reverse primers for Nkx2.5/Csx; 5'-CCG ACA GTT GTA GGC CCT GTT-3' (SEQ ID NO: 75) forward and 5'-GGC ATC TTC GGG TTG ATC CT-3' (SEQ ID NO: 76) reverse primers for VE-cadherin; 5'-GTG GGC AGG TGG GAG CTT GAT TCT-3' (SEQ ID NO: 77) forward and 5'-CTG GGG CGG CCT GGT ATG ACA-3' (SEQ ID NO: 78) reverse primers for GFAP; 5'-AAT GCG GCA TCT TCA AAC CT-3' (SEQ ID NO: 79) forward and 5'-TGA CTT TGT CAC AGC CCA AGA TA-3' (SEQ ID NO: 80) reverse primers for 2 microglobulin. Primers were designed with PRIMER EXPRESS® software (Applied Biosystems, Foster City, Calif., United States of America).

The threshold cycle (Ct; i.e., the cycle number at which the amount of amplified gene of interest reached a fixed threshold) was determined subsequently. Relative quantitation of Oct4 and Nanog mRNA expression was calculated with the comparative Ct method. The relative quantization value of target, normalized to an endogenous control β2-microglobulin gene and relative to a calibrator, is expressed as $2^{-\Delta\Delta Ct}$ (fold difference), where ΔCt=Ct of target genes (Oct4, Nanog, Nkx2.5/Csx, VE-cadherin, GFAP)−Ct of endogenous control gene (β2-microglobulin), and ΔΔCt=ΔCt of samples for target gene-ΔCt of calibrator for the target gene.

To avoid the possibility of amplifying contaminating DNA, all the primers for real time RT-PCR were designed with an intron sequence inside the cDNA to be amplified, reactions were performed with appropriate negative controls (template-free controls), a uniform amplification of the products was rechecked by analyzing the melting curves of the amplified products (dissociation graphs), the melting temperature (Tm) was 57-60° C., the product Tm was at least 10° C. higher than primer Tm, and gel electrophoresis was performed to confirm the correct size of the amplification product and the absence of unspecific bands.

Fluorescent staining of CB-derived VSEL stem cells. The expression of each antigen was examined in cells from four independent experiments. CXCR4+/lin−/CD45− cells were fixed in 3.5% paraformaldehyde for 20 minutes, permeabilized by 0.1% Triton X100, washed in PBS, pre-blocked with 2% BSA, and subsequently stained with antibodies to SSEA-4 (clone MC-813-70; 1:100; mouse monoclonal IgG, Chemicon Intl., Temecula, Calif., United States of America), Oct-4 (clone 9E3; 1:100; mouse monoclonal IgG, Chemicon Intl., Temecula, Calif., United States of America), and Nanog (1:200; goat polyclonal IgG, Santa Cruz Biotechnology, Inc., Santa Cruz, Calif., United States of America). Appropriate secondary Alexa Fluor 488 goat anti-mouse IgG, Alexa Fluor 594 goat anti-mouse IgG, and Alexa Fluor 594 rabbit anti-goat were used (1:400; Molecular Probes, Eugene, Oreg., United States of America).

In control experiments, cells were stained with secondary antibodies only. The nuclei were labeled with DAPI (Molecular Probes, Eugene, Oreg., United States of America). The fluorescence images were collected with the TE-FM Epi-Fluorescence system attached to a Nikon Inverted Microscope Eclipse TE300 and captured by a cool snap HQ digital B/W CCD (Roper Scientific, Tucson, Ariz., United States of America) camera.

Statistical Analysis. Arithmetic means and standard deviations of FACS data were calculated on a Macintosh computer PowerBase 180, using Instat 1.14 (GraphPad, San Diego, Calif., United States of America) software. Data were analyzed using the Student t-test for unpaired samples or ANOVA for multiple comparisons. Statistical significance was defined as $p<0.05$.

VSEL stem cells were also isolated from human cord blood using the general FACS procedure outlined in EXAMPLE 2. For human cells, antibodies directed against CXCR4 (labeled with allophycocyanin (APC)), CD45 (labeled with phycoerythrin (PE)), CD19, CD16, CD2, CD14, CD3, CD24, CD56, CD66b, and CD235a were employed. Antibodies against the lineage markers were labeled with fluorescein isothiocyanate (FITC). The isolated VSEL stem cells were CXCR4+/lin−/CD45− under TEM looked like murine VSEL stem cells (i.e., were about 3-4 μm in diameter, posses large nuclei surrounded by a narrow rim of cytoplasm, and contain open-type chromatin (euchromatin)), and were enriched in markers of pluripotent stem cells by real time RT-PCR (see EXAMPLE 7).

Figure 32:
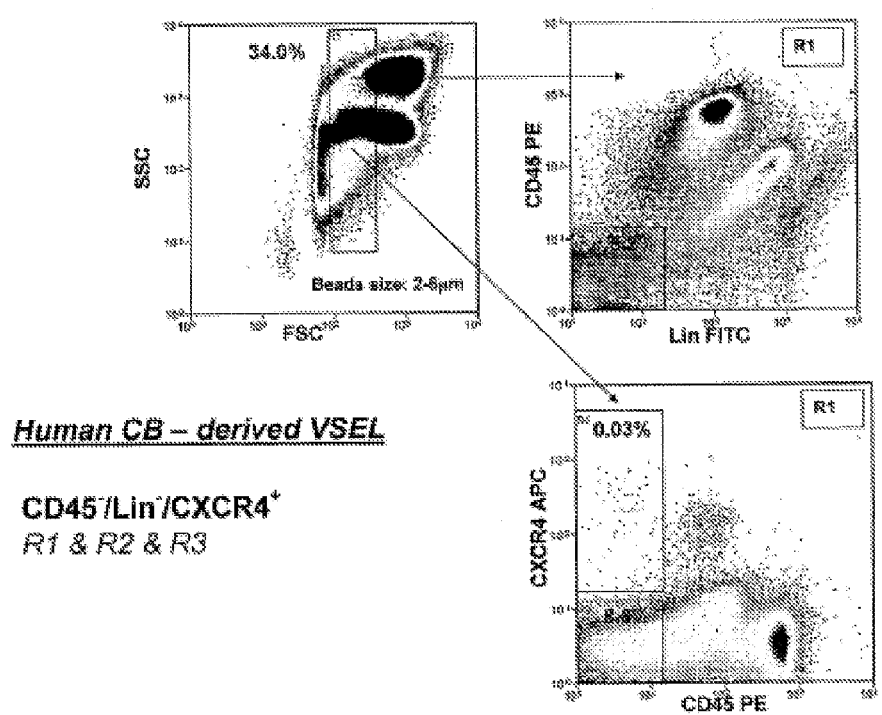
FIG. 32 is an outline of a FACS-based strategy for isolating VSEL stem cells from human cord blood.

Discussion of Example 29: A population of CD34+ CD133+ CXCR4+/lin−/CD45− Cells is Present in CB Multiparameter analysis (outlined in FIG. 32) was performed to determine if human CB mononuclear cells (CB MNC) contained a population of cells that resemble VSEL stem cells. In order to separate MNC from CB, Ficoll-Paque centrifugation was not employed, and erythrocytes were removed by hypotonic lysis. Additionally, it was hypothesized that CB-VSEL stem cells, like their counterparts in adult murine BM, would be small and lin−/CD45−.

Thus, a population of small (<5 μm) lin−/CD45− CB MNC was investigated. That these cells might express CXCR4 as do their murine BM-derived counterparts was also investigated. In addition, the cells were tested for expression of other human stem cell antigens such as CD133 and CD34.

Figure 27:
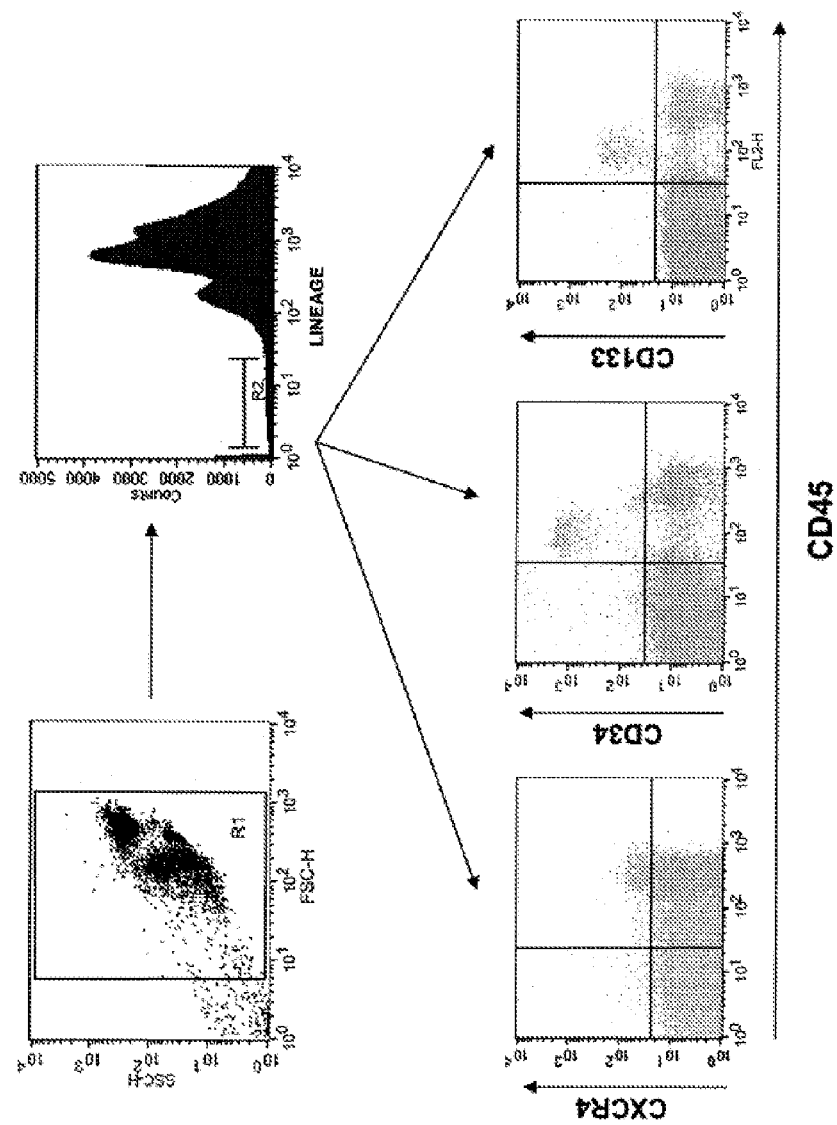
FIGS. 27A-27B depict the results of FACS sorting of human cord blood.
Figure 27:
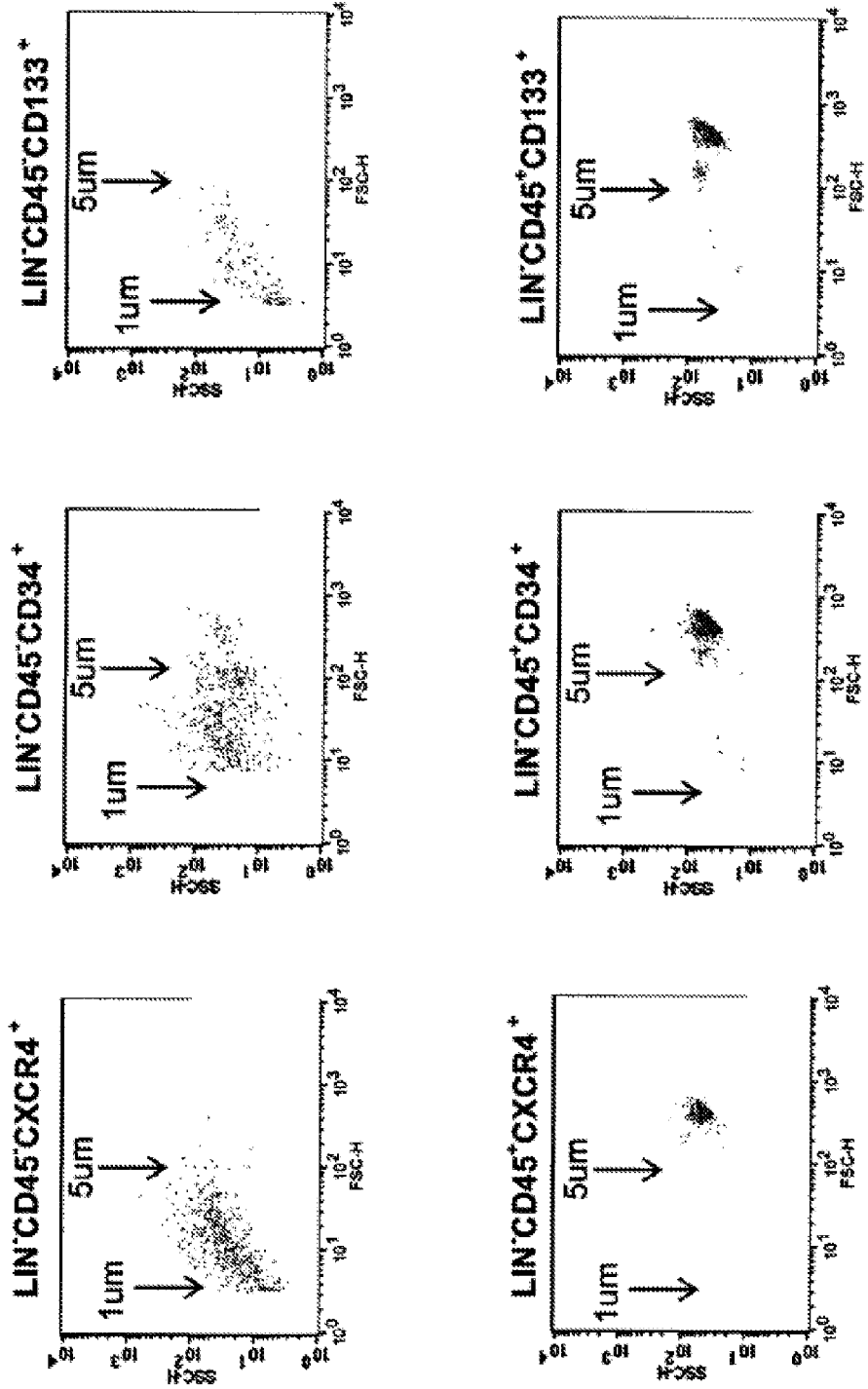

FIG. 27A shows that human CB contained a population of lin−/CD45− MNC that express CXCR4 (0.037±0.02%, n=9), CD34 (0.118±0.028%, n=5), and CD133 (0.018±0.008%, n=5). These CXCR4+/CD133+/CD34+/lin−/CD45− cells were sorted by FACS in a manner similar to VSEL stem cells, did not grow hematopoietic colonies in vitro, and also similar to murine VSEL stem cells are very small (about 3-5 μm; FIG. 27B, upper panel). In contrast, CB-derived lin−/CD45+ hematopoietic cells are larger (>6 μm; FIG. 27B, lower panel). Furthermore, a significant overlap in co-expression of CXCR4, CD34, and CD133 antigens was observed among CB-derived small lin−/CD45− cells, and it was determined that 0.015±0.005% of lin−/CD45− cells were CXCR4+/CD133+/CD34+.

Figure 28:
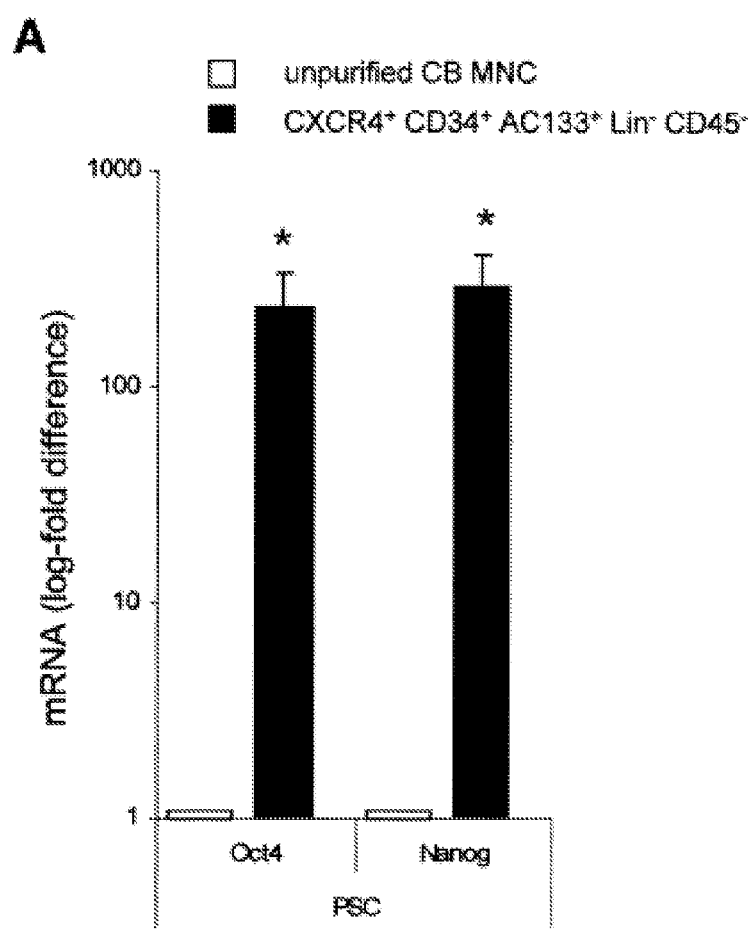
FIGS. 28A-28C depict the results of gene expression studies on sorted cells from human cord blood.
Figure 28:
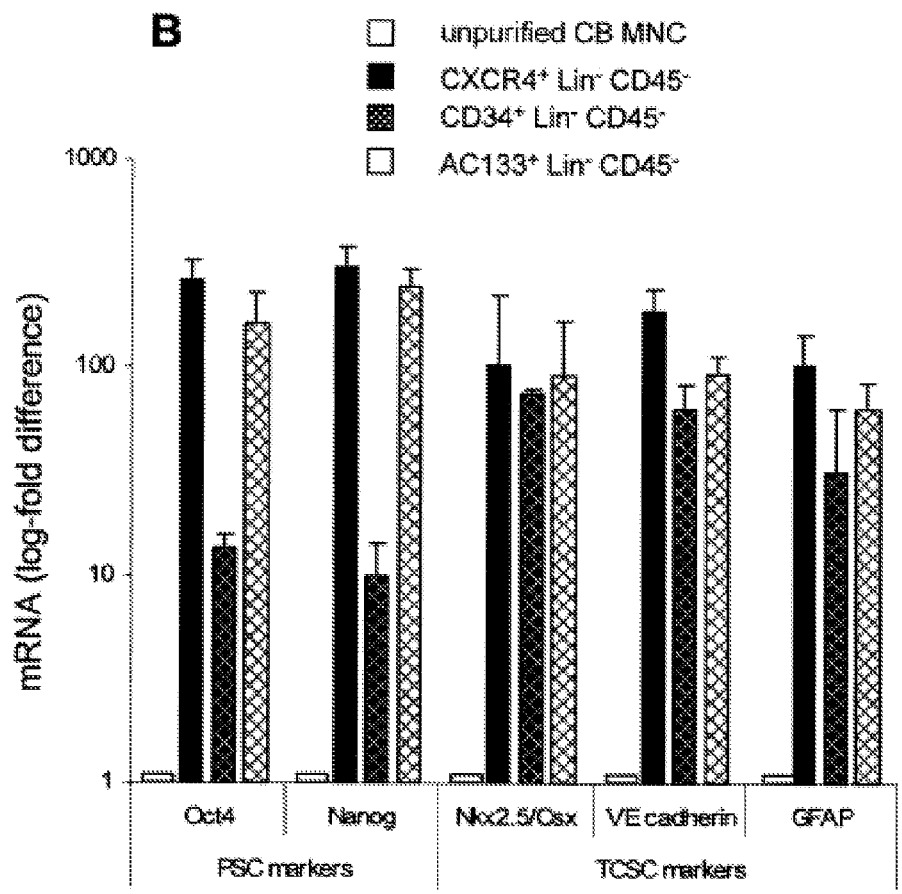
Figure 28:
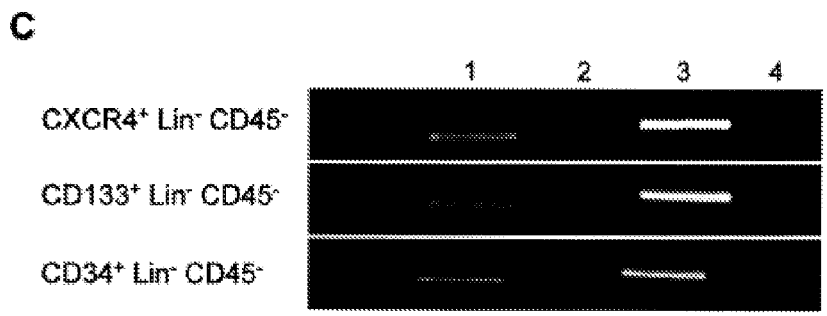

CB-derived CXCR4+/CD133+/CD34+/lin−/CD45− cells sorted by FACS, as well as CXCR4+/lin−/CD45−, CD34+/lin−/CD45−, and CD133+/lin−/CD45−/cells are highly enriched for mRNA for transcriptions factors expressed by pluripotent embryonic cells such as Oct-4 and Nanog (FIGS. 28A and 28B). Expression of these markers was subsequently confirmed by regular RT-PCR (FIG. 28C). Furthermore, these cells, as is disclosed herein for BM-derived VSEL stem cells, are also enriched in mRNA for several developmental genes for different organs/tissues such as Nkx2.5/Csx, VE-cadherin, and GFAP, which are markers for cardiac-, endothelial- and neural tissue committed stem cells (TCSC), respectively.

Figure 29:
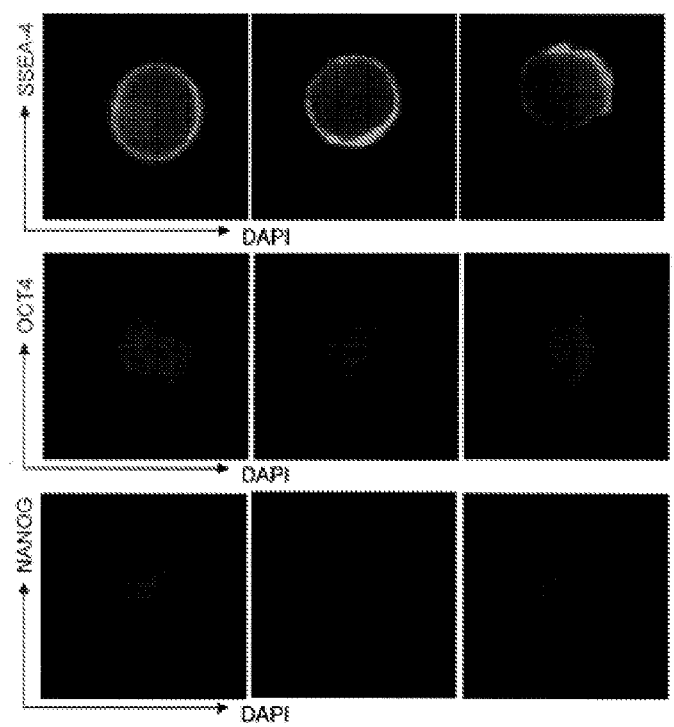
FIG. 29 depicts the results of immunofluorescence staining of CB-VSEL stem cells showing that highly purified CB-derived CXCR4+/lin−/CD45− cells expressed SSEA-4 on their surface and Oct-4 and Nanog transcription factors in nuclei.

CB-derived CXCR4+/lin−/CD45− cells express SSEA-4, Oct-4, and Nanog at the protein level. Murine BM-derived VSEL stem cells express SSEA-1, Oct-4, and Nanog at the protein level. Thus, immunofluorescence staining was performed to evaluate if CB-VSEL stem cells also expressed similar embryonic stem cell markers. FIG. 29 shows an example of staining showing that highly purified CB-derived CXCR4+/lin−/CD45− cells expressed SSEA-4 on their surface and Oct-4 and Nanog transcription factors in nuclei.

Figure 30:
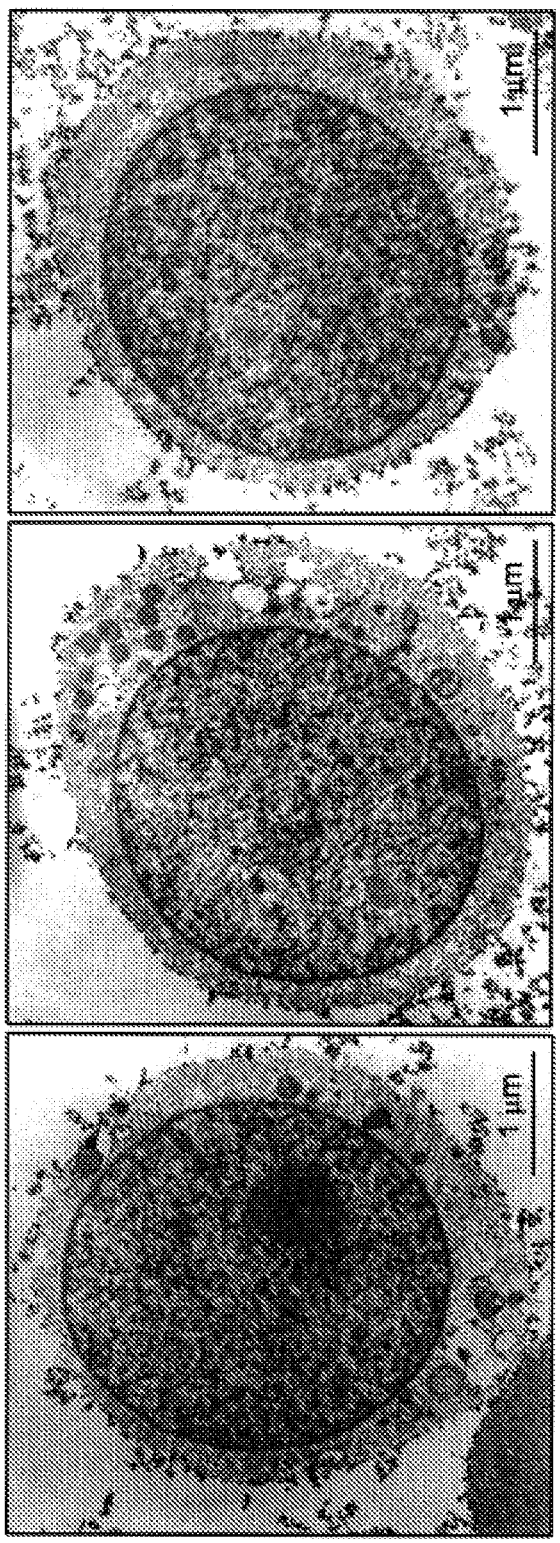
FIG. 30 depicts photomicroscopic images of three different CB-VSEL stem cells demonstrating that these cells were very small ~3-5 μm and contained relatively large nuclei and a narrow rim of cytoplasm with numerous mitochondria. DNA in the nuclei of these cells contained open-type euchromatin that is characteristic for pluripotent embryonic stem cells.

Transmission electron-microscopy analysis of CB-derived CXCR4+/lin−/CD45−/cells. CXCR4+/CD34+/CD133+/lin−/CD45− cells were analyzed by transmission electron microscopy (TEM). FIG. 30 shows that CB-VSEL stem cells were very small ~3-5 μm and contained relatively large nuclei and a narrow rim of cytoplasm with numerous mitochondria. DNA in the nuclei of these cells contained open-type euchromatin that is characteristic for pluripotent embryonic stem cells. Thus, the presently disclosed subject matter provides for the first time morphological evidence for the presence of a distinct population of very small embryonic-like (VSEL) stem cells in adult CB.

Example 30

VSEL-DS can Differentiate into Hematopoietic Cells

Figure 31:
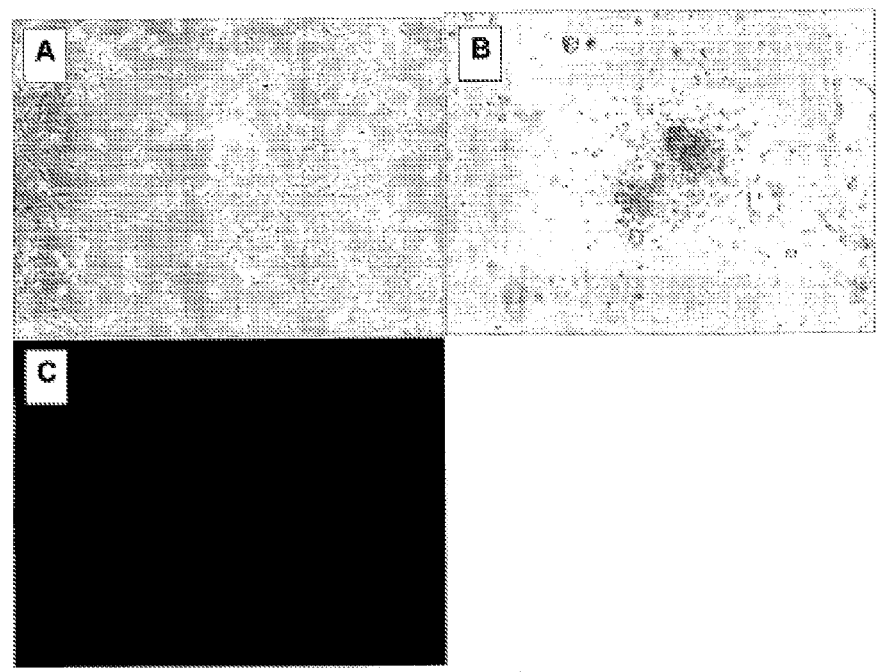
FIGS. 31A-31C depict photomicroscopic images showing that VSEL stem cell-DS derived from GFP+ mice can form small secondary spheres if plated in methylcellulose cultures supplemented with IL-3+GM-CSF (FIGS. 31A and 31B). The single cell suspension prepared from these secondary spheres recovered by methylcellulose solubilization from the primary methylcellulose cultures, if plated again in methylcellulose cultures (FIG. 31B) or plasma clot (FIG. 31C) and stimulated by IL-3 and GM-CSF formed hematopoietic colonies. Evidence that these were hematopoietic colonies was obtained by FACS analysis of CD45 expression of cells derived from solubilized colonies growing in methylcellulose or by immunofluorescence staining cells from colonies growing in plasma clot cultures for CD45.

It was observed that cells isolated from VSEL-DS derived from GFP+ mice formed small secondary spheres if plated in methylcellulose cultures supplemented with IL-3+GM-CSF (FIGS. 31A and 31B). The single cell suspension prepared from these secondary spheres recovered by methylcellulose solubilization from the primary methylcellulose cultures, if plated again in methylcellulose cultures (middle panel) or plasma clot (right panel) and stimulated by IL-3 and GM-CSF formed hematopoietic colonies. Evidence that these were hematopoietic colonies was obtained by FACS analysis of CD45 expression of cells derived from solubilized colonies growing in methylcellulose or by immunofluorescence staining cells from colonies growing in plasma clot cultures for CD45 (FIG. 31C).

In parallel, cells isolated from the colonies growing in methylcellulose were analyzed for expression of hematopoietic genes by employing real time RT-PCR. Upregulation of mRNA for hematopoietic transcription factors such as c-myb, PU-1, and SCL was observed by normal RT-PCR and by RQ-PCR during expansion in the presence of IL-3+GM-CSF. Thus, VSEL stem cells might be a source of the most primitive HSC in BM.

Example 31

Ex Vivo Differentiation of VSEL-DS into Hematopoietic Cells

VSEL-DS are trypsinized and plated in methylcellulose-based medium (StemCell Technologies Inc., Vancouver, British Columbia, Canada). At day 5 of culture in methylcellulose medium, cells proliferate and form small spheres. These spheres are recovered from methylcellulose cultures by aspiration, are washed and trypsinized to obtain a single cell suspension, and re-plated in methylcellulose-based medium that contains a selected combination of cytokines and growth factors for hematopoietic colony formation.

For CFU-GM colony growth, murine interleukin-3 (mIL-3)+murine granulocyte-macrophage colony stimulating factor m(GM-CSF) is added. At the same time, an aliquot of these cells is plated in plasma clot cultures. The reason for this is that these cultures are suitable for analysis by immunofluorescence and immunohistochemical staining. At day 4-6 hematopoietic colonies are formed both in methylcellulose and plasma clot conditions. Cells from the colonies growing in methylcellulose are recovered for mRNA isolation or FACS analysis.

Example 32

Transplantation of Bone Marrow-Derived Very Small Embryonic-Like Stem Cells (VSELs) Attenuates Left Ventricular Dysfunction and Remodeling After Myocardial Infarction Adult bone marrow (BM) contains Sca-1+/Lin−/CD45− very small embryonic-like stem cells (VSELs) that express markers of several lineages, including cardiac markers, and differentiate into cardiomyocytes in vitro. We examined whether BM-derived VSELs promote myocardial repair after a reperfused myocardial infarction (MI). Mice underwent a 30-min coronary occlusion followed by reperfusion and received intramyocardial injection of vehicle (n=11), $1\times10^4$ Sca-1+/Lin−/CD45+ EGFP-labeled hematopoietic stem cells (n=13 [cell control group]), or $1\times10^5$ Sca-1+/Lin−/CD45− EGFP-labeled cells (n=14 [VSEL-treated group]) at 48 h after MI. At 35 d after MI, VSEL-treated mice exhibited improved global and regional left ventricular (LV) systolic function (echocardiography) and attenuated myocyte hypertrophy in surviving tissue (histology and echocardiography) compared with vehicle-treated controls. In contrast, transplantation of Sca-1+/Lin−/CD45+ cells failed to confer any functional or structural benefits. Scattered EGFP+ myocytes and capillaries were present in the infarct region in VSEL-treated mice, but their numbers were very small. Transplantation of a relatively small number of CD45− VSELs is sufficient to improve LV function and alleviate myocyte hypertrophy after MI, whereas a 10-fold greater number of CD45+ hematopoietic stem cells is ineffective. These results support the potential therapeutic utility of VSEL transplantation for cardiac repair.

Numerous studies in animals have documented improvement in left ventricular (LV) function and anatomy following bone marrow (BM) cell (BMC) therapy after myocardial infarction (MI)[1]. The initial results of clinical trials also suggest improvement in LV function and reduction in scar size with BMC therapy in patients with acute MI as well as ischemic cardiomyopathy [2]. However, several different BMC types, numbers, and routes of administration have been used in studies in animals and humans.

Adult BM contain a population of small CXCR4+ cells that are nonhematopoietic and express markers of lineage commitment for several different tissues, thereby exhibiting the potential to differentiate into various unrelated lineages [3-5]. These very small embryonic-like stem cells (VSELs) are Sca-1+/Lin−/CD45−; they express (among other lineage markers) cardiac markers, including Nkx2.5/Csx, GATA-4, and MEF2C, and acquire a cardiomyocytic phenotype in vitro under specific culture conditions [5]. VSELs may account, at least in part, for the beneficial effects observed with BMC therapy in MI. Thus, selective administration of VSELs should be sufficient in itself to produce a functional and structural improvement in experimental MI, despite the absence of all of the other cell types present in the BM.

Accordingly, the goals of the present study were: (i) to determine whether direct intramyocardial transplantation of VSELs results in improvement in LV function and postinfarct remodeling, and (ii) to investigate the potential mechanisms underlying the effects of VSEL therapy. TQ separate cell-specific from nonspecific actions, Sca-1+/Lin−/CD45− VSELs were directly compared with Sca-1+/Lin−/CD45+ cells, which are highly enriched in hematopoietic stem cells and differ from VSELs only with respect to CD45 expression. The results show that administration of small numbers of VSELs after a reperfused MI is sufficient to improve LV function and dimensions and to attenuate cardiomyocyte hypertrophy. In contrast, transplantation of much larger numbers of Sca-1+/Lin−/CD45+ cells had no beneficial effect. The ability of VSELs to alleviate postinfarction LV remodeling warrants further investigation of the therapeutic utility of these cells and may have significant implications for the design of future studies of BMC mediated cardiac repair both in animals and in humans.

The present study was performed in accordance with the guidelines of the Animal Care and Use Committee of the University of Louisville School of Medicine and with the Guide for the Care and Use of Laboratory Animals (Department of Health and Human Services, Publication No. [NIH] 86-23).

Figure 45:
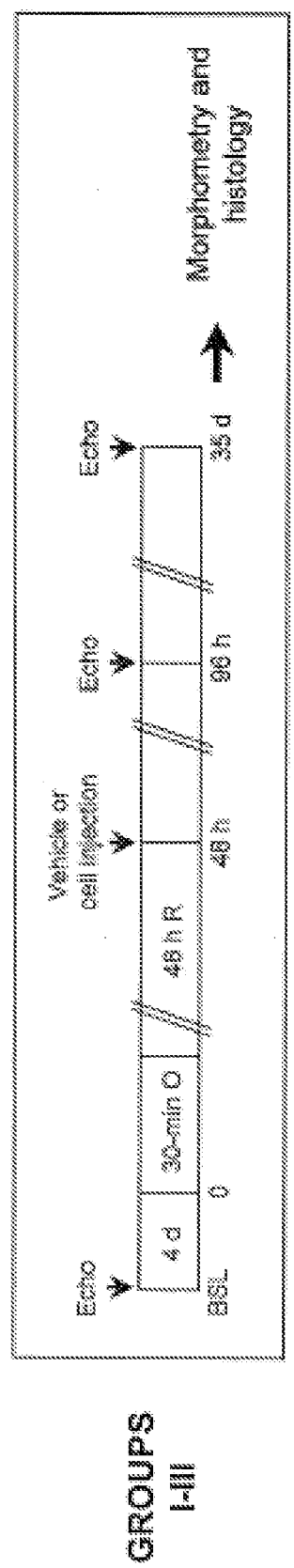
FIG. 45. Experimental protocol. Three groups of WT mice were used (groups I-III, n=11-14/group). Four days after a baseline echocardiogram, mice underwent a 30-min coronary occlusion followed by reperfusion. Forty-eight hours after MI, mice received intramyocardial injection of vehicle (group I), Sca-1+/Lin-/CD45+ hematopoietic stem cells (group II), or Sca-1+/Lin-/CD45- VSELs (group III). Echocardiograms were repeated at 48 h after cell transplantation and at 35 d after MI. At 35 d after MI, mice were sacrificed for morphometric and histologic studies.

Experimental protocol. This study was performed in a well-established murine model of MI [6,7]. The experimental protocol is summarized in FIG. 45. All mice (groups I-III) underwent a 30-min coronary occlusion followed by 35 d of reperfusion. At 48 h after reperfusion, mice received an intramyocardial injection of vehicle (group I), CD45+ hematopoietic stem cells (group II), or VSELs (group III). Echocardiographic studies were performed 4 d prior to coronary occlusion/reperfusion, 48 h after cell injection (i.e., 96 h after MI), and 35 d after MI (prior to sacrifice).

Figure 33:
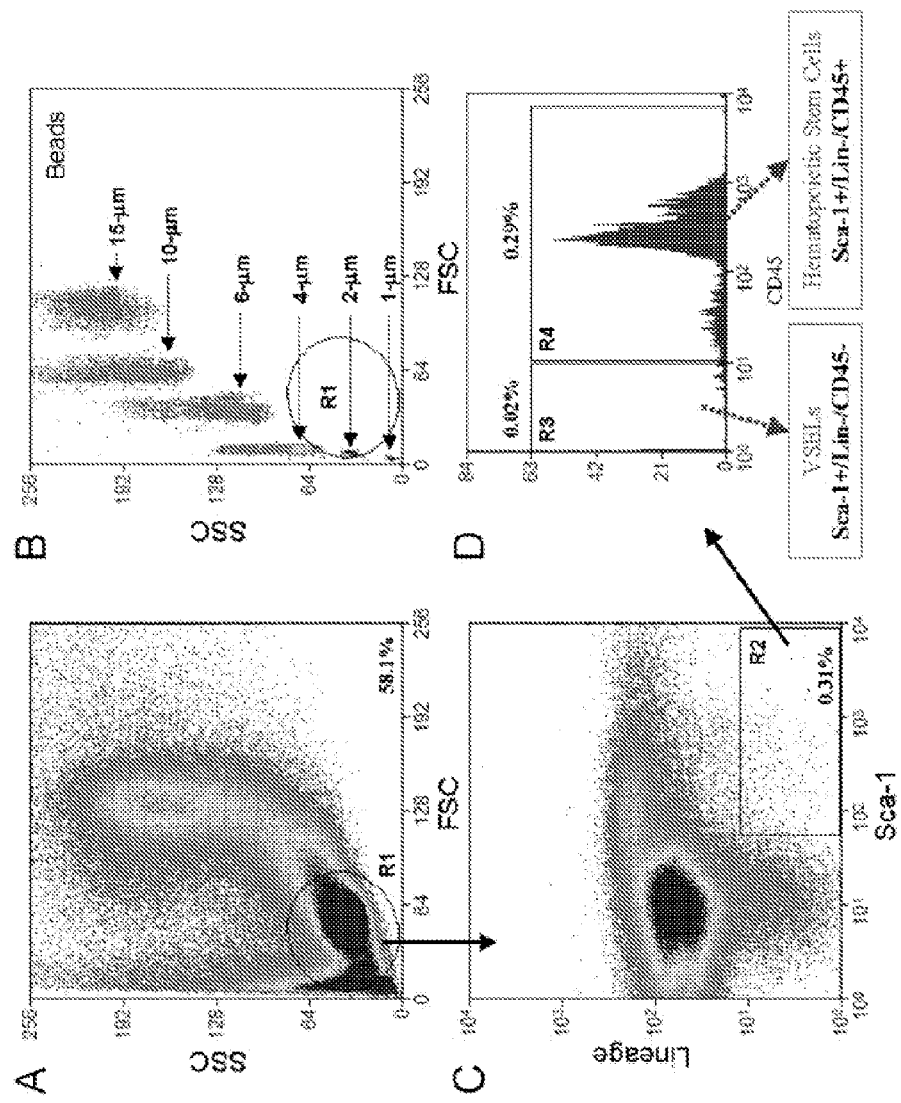
FIG. 33. Flow cytometric isolation of BM-derived Sca-1+/Lin−/CD45+ hematopoietic stem cells and Sca-1+/Lin−/CD45− VSELs. Representative dot-plots show sorting of small cells from the lymphoid gate (A) based on expression of Sca-1 (FITC) and lineage markers (PE) (C), and CD45 (APC). Panel D shows that region 3 (R3) contains Sca-1+/Lin−/CD45− VSELs while region 4 (R4) contains Sca-1+/lin−/CD45+ cells. By comparing the sorting of BMCs with the sorting of beads with known diameter, the FSC axis in panel B confirms the very small size (2-10μ) of the cells in the region of interest in panel A. As shown here (R3), only 0.02% of total BMCs are VSELs. FSC, forward scatter characteristics; SSC, side scatter characteristics.

Isolation of VSELs and Sca-1+/Lin−/CD45+ hematopoietic stem cells. VSELs and CD45+ cells were isolated as previously described [5]. Briefly, BMCs were obtained from the femur and tibia of 4-6-wk-old male EGFP transgenic mice and red blood cells were lyzed with a 0.9% solution of NH4Cl. Freshly isolated BMCs were resuspended in PBS containing 1% fetal bovine serum (FBS, HyClone, Logan, Utah). The following primary antibodies were added simultaneously: biotin-conjugated monoclonal rat anti-mouse Ly-6A/E (Sca-1) (clone E13-161.7), APC-Cy7-conjugated monoclonal rat anti-mouse CD45 (clone 30-F11), and PE-conjugated monoclonal rat anti-mouse lineage markers (anti-CD45R/B220 [PE; clone RA3-6B2], anti-Gr-1 [PE; clone RB6-8C5], anti-TCRαβ[PE; clone H57-597], anti-TCRγδ [PE; clone GL3], anti-CD11b [PE; clone M1/70], anti-Ter119 [PE; clone TER-119]). Secondary staining was performed using PE-Cy5-conjugated streptavidin. All reagents were purchased from BD Pharmingen (San Jose, Calif.). Staining was performed at 4° C. for 20 min, and cells were washed with PBS supplemented with 1% FBS after staining. Flow cytometric cell sorting was performed using a MoFlo machine (Dako, Carpinteria, Calif.) according to the scheme presented in FIG. 33. Bulk-sorted cells were collected into 2 ml DMEM with 10% FBS. The purity was assessed by reanalyzing isolated cells immediately following sorting. The viability of sorted cells always exceeded 90%. Sorted cells were pelleted via centrifugation at 1000 g for 10 min and resuspended in DMEM with 10% FBS in a smaller volume proportional to cell number. Cells were aliquoted in a 50-µl volume for intramyocardial injection (total dose, 100,000 cells for group II and 10,000 cells for group III).

Myocardial infarction and cell transplantation. Three groups of wild-type (WT) mice (C57/BL6 strain, body wt. 20-25 g, age 10-12 wk, Jackson Laboratories) were used. The experimental preparation has been described in detail [6, 7]. Mice were anesthetized with pentobarbital sodium (50 mg/kg i.p.), intubated, and ventilated using a small rodent ventilator. Body temperature, heart rate, and arterial pH were carefully maintained within the physiological range throughout the experiments. Using a sterile technique, the chest was opened through a midline sternotomy. An 8-0 nylon suture was passed with a tapered needle under the left anterior descending coronary artery 2 mm from the tip of the left auricle, and a nontraumatic balloon occluder was applied on the artery. Coronary occlusion was induced by inflating the balloon occluder. Successful performance of coronary occlusion and reperfusion was verified by visual inspection (i.e., by noting the development of a pale color in the distal myocardium upon inflation of the balloon and the return of a bright red color due to hyperemia after deflation) and by observing S-T segment elevation and widening of the QRS on the ECG during ischemia and their resolution after reperfusion [6, 7]. The chest was then closed in layers, and a small catheter was left in the thorax for 10-20 min to evacuate air and fluids. The mice were removed from the ventilator, kept warm with heat lamps, given fluids (1.0-1.5 ml of 5% dextrose in water intraperitoneally), and allowed 100% oxygen via nasal cone. Forty-eight hours later, mice were reanesthetized and ventilated and the chest reopened via aseptic technique. Vehicle (50 μl, group I), Sca-1+/Lin−/CD45+ hematopoietic stem cells (100,000 cells in 50 μl, group II), or Sca-1+/Lin−/CD45− VSELs (10,000 cells in 50 μl, group III) were injected intramyocardially using a 30-gauge needle. A total of five injections were made in the periinfarct region in a circular pattern, at the border between infarcted and noninfarcted myocardium. The chest was closed in layers and the mice allowed to recover as described above.

Echocardiographic studies. Echocardiograms were obtained using an HDI 5000 SonoCT echocardiography machine (Philips Medical Systems) equipped with a 15-7 MHz linear broadband and a 12-5 MHz phased array transducers [8]. The mice were anesthetized with pentobarbital (25 mg/kg i.p.). The anterior chest was shaved and the mice were placed in the left lateral decubitus position. Using a rectal temperature probe, body temperature was carefully maintained close to 37.0° C. with a heating pad throughout the study. Modified parasternal long-axis and parasternal short-axis views were used to obtain two-dimensional (2-D), M-mode, and spectral Doppler images [8]. Systolic and diastolic anatomic parameters were obtained from M-mode tracings at the mid-papillary level. LV volume was estimated by the Teichholz formula. LV mass was estimated by the area-length method. Images were analyzed off-line using the Prosolv data analysis software (version 2.5, Problem Solving Concepts, Inc., Indianapolis, Ind.) by an investigator who was blind to the treatment allocation.

Morphometric analyses. At the end of the study, the thorax was opened, the abdominal aorta was cannulated, and the heart was arrested in diastole with KCl and $CdCl_2$, excised, and perfused retrogradely through the aorta with 10% neutral-buffered formalin. The right atrium was cut to allow drainage. The perfusion pressure was adjusted to match the mean arterial pressure. The LV chamber was filled with fixative from a pressure reservoir set at a height equivalent to the in vivo measured LV end-diastolic pressure [8-10]. The LV was sectioned serially into four rings perpendicular to its longitudinal axis, processed, and embedded in paraffin. The infarct area fraction was calculated by computerized planimetry (Image-Pro Plus, Media-Cybernetics, Carlsbad, Calif.) of digital images of three Masson's trichrome-stained serial LV sections taken at 0.5-1.0 mm intervals along the longitudinal axis [8, 9]. The mid-section was used to measure LV diameter. The thickness of the infarct wall, septal wall, and posterior wall was calculated in serial sections and averaged 18, 91. An average sarcomere length of 2.1 pm was utilized in all cases to correct the raw measurements of LV anatomical parameters [10].

For the assessment of cardiomyocyte cross-sectional area, digital images were acquired from trichrome-stained myocardial sections. Cardiomyocyte cross-sectional area was measured in transversely sectioned myocytes with a circular profile and a central nucleus [11, 12]. On average, a total of 100 myocytes were measured in each heart. All morphometric analyses were performed by investigators who were blind to the treatment allocation.

Immunohistochemistry. Immunohistochemistry was performed in formalin-fixed 4-μm thick histological sections. Cardiomyocytes were recognized by the presence of α-sarcomeric actin (Sigma) and troponin T (Santa Cruz); endothelial cells by PECAM-1 (Santa Cruz) and von Willebrand factor (Sigma); and smooth muscle cells by α-smooth muscle actin (Sigma) [8, 13]. Colocalization of cell-specific markers with EGFP was used to identify cells that originated from BMCs [8, 14]. Nuclei were identified with DAPI.

For the assessment of capillary density [11, 12], sections were stained with an anti-CD31 (Santa Cruz) primary antibody followed by the addition of a TRITC-conjugated secondary antibody [13]. CD31-positive capillary profiles were counted at 100× magnification in contiguous fields in the infarct zone, border zone, and nonischemic zone. On average, a total of 40-50 fields were counted in each heart.

Statistical analysis. Data are reported as mean±SEM. Morphometric and histologic data were analyzed with a one-way ANOVA whereas serial echocardiographic parameters were analyzed with a two-way (time and group) ANOVA followed by Student's t-tests with the Bonferroni correction as appropriate [15]. All statistical analyses were performed using the SPSS software (version 8, SPSS, Inc., Chicago, Ill.).

Results

Exclusions. A total of 233 mice (73 VVT and 160 EGFP transgenic) were used. Sixty-six WT mice were assigned to the myocardial infarction studies (groups I-III), 160 EGFP transgenic mice were used as BM donors for cell isolation, and 7 mice were used for the determination of myocyte area. Sixteen mice died in the early postinfarction period and 9 mice died within 72 h after intramyocardial injection. Three mice were excluded from the study due to failure of the coronary occluder, leaving a total of 11, 13, and 14 mice in groups I, II, and III, respectively.

Myocardial infarct size. The average infarct area fraction did not differ significantly among the three groups (FIG. 34). The infarct area fraction measures the average area of scarred tissue, expressed as a percent of the LV area in three LV sections 0.5-1.0 mm apart [8, 9, 12].

Transplantation of VSELs attenuates LV systolic dysfunction. Before coronary occlusion (baseline), all parameters of LV function, measured by echocardiography, were similar in groups I, II, and III (FIG. 35). At 48 h after cell transplantation (96 h after. reperfusion), the degree of LV systolic functional impairment was also similar among the groups (FIG. 35), indicating that both the injury sustained during ischemia/reperfusion and that associated with intramyocardial injection were comparable. In vehicle-treated (group I) and CD45+ cell-treated (group II) mice, there was further functional deterioration between 96 h and 35 d after reperfusion (FIG. 35G-J). In contrast, in VSEL-treated mice (group III) neither global (FIG. 35G) nor regional (FIG. 35I,J) LV systolic function was impaired at 35 d as compared with 96 h. As a result, at 35 d mice in group III exhibited significantly greater LV ejection fraction (FIG. 35A-F,G) and smaller LV end-systolic diameter (FIG. 35A-F,H) compared with vehicle-treated (group I) and CD45+ cell-treated (group II) mice. In group III there was also enhanced regional myocardial function in the infarct region, as evidenced by a 48% (P<0.05) and 29% (P<0.05) greater systolic infarct wall thickness (FIG. 3I) and a 44% (P<0.05) and 21% greater systolic wall thickening fraction compared with groups I and II, respectively (FIG. 3A-F,J).

Figure 46:
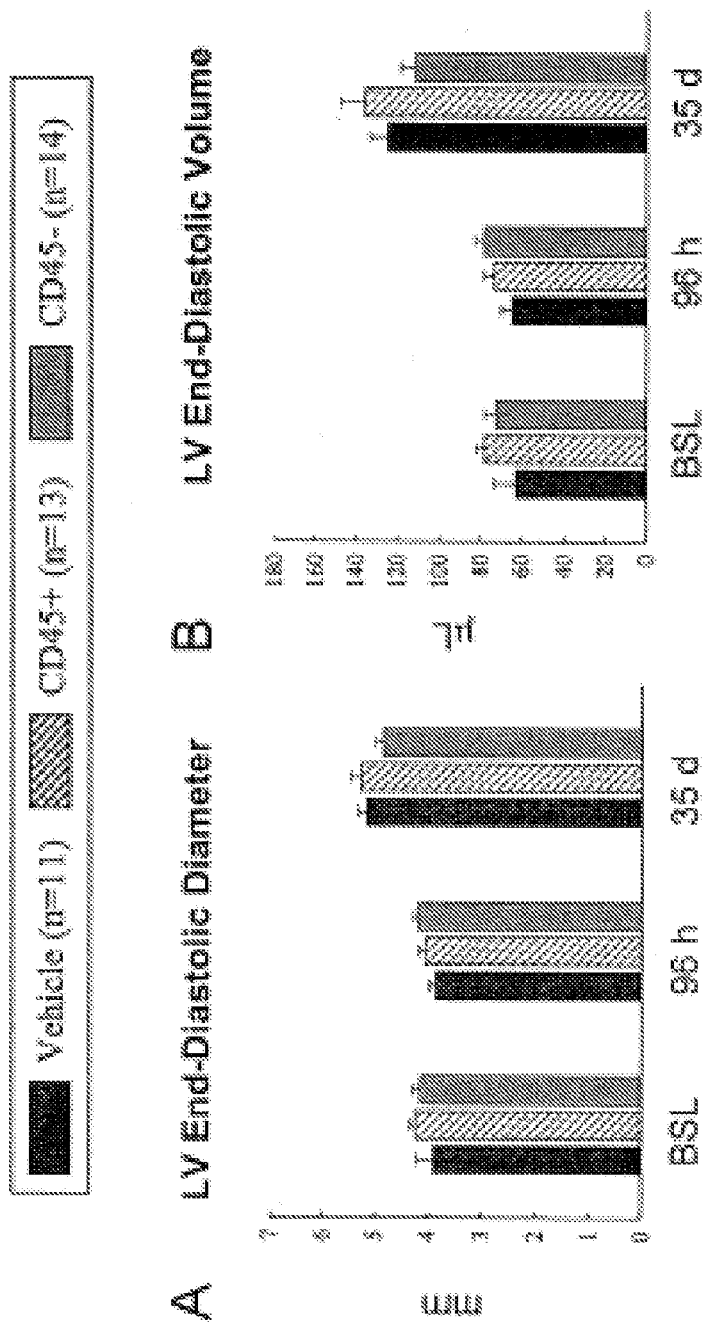
FIG. 46. Echocardiographic assessment of LV remodeling. Panels A and B illustrate echocardiographic measurements of LV dimensions. Data are mean±SEM. n=11-14 mice per group.

Transplantation of VSELs halts LV remodeling. The extent of LV remodeling at 35 d after infarction was assessed both morphometrically (FIG. 36) and echocardiographically (FIG. 46). Morphometry was performed on trichrome-stained LV sections obtained at the mid-papillary level (FIG. 4A-C). By morphometry, the average LV chamber diameter was 12% and 20% smaller in group III as compared with groups I and II, respectively (P=NS vs. group I; P<0.05 vs. group II) (FIG. 36D). The infarct wall thickness and the posterior LV wall thickness did not differ significantly among the three groups (FIG. 36E,G). The infarct wall thickness-to-chamber radius ratio was increased significantly in group III compared with group II (P<0.05) (FIG. 36F). On average, the morphometrically estimated LV volume was 24% and 30% smaller in group III vs. groups I and II, respectively (P=NS vs. group I; P<0.05 vs. group II) (FIG. 36H). The echocardiographic measurements of LV diameter and volume at 35 d mirrored the trends observed by morphometry (FIG. 46). In summary, both by morphometry and by echocardiography, there was a trend toward improvement in LV remodeling in VSEL-treated mice as compared with vehicle-treated mice, but the differences were not statistically significant. No such trend was observed in CD45+ cell treated mice (group II).

Figure 37:
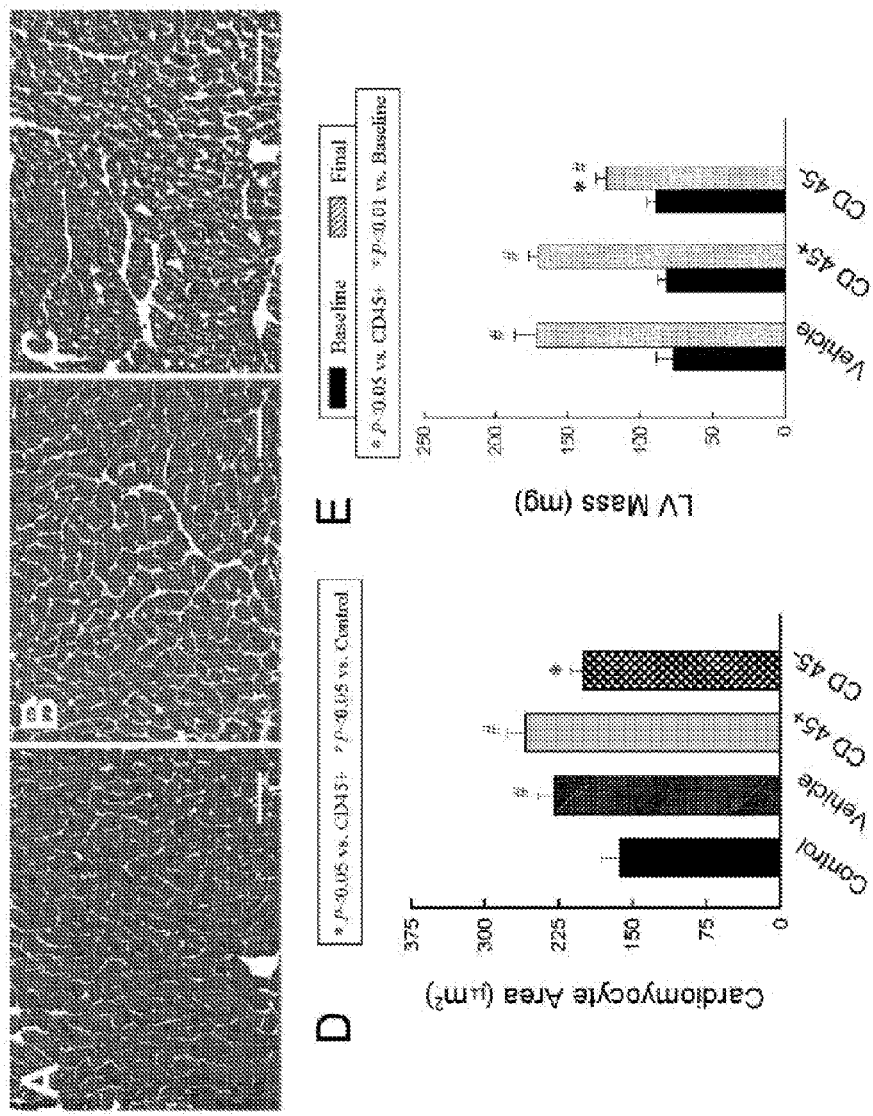
FIG. 37. Assessment of cardiomyocyte and left ventricular hypertrophy. Panels A-C show representative images of cardiomyocytes in the viable myocardium from Masson's trichrome-stained vehicle-treated (A), CD45+ hematopoietic stem cell-treated (B), and VSEL-treated hearts (C). Scale bar=50 pm. In contrast to CD45+ hematopoietic stem cell-treated hearts, VSEL-treated hearts did not exhibit increased myocyte cross-sectional area as compared with noninfarcted control hearts (D). Echocardiographically estimated LV mass was significantly less in VSEL-treated hearts (E). Data are mean±SEM. n=11-14 mice/group. D: *P<0.05 vs. group II; #P<0.05 vs. Control; E: *P<0.05 vs. group II and III (final); #P<0.05 vs respective baseline values.

Transplantation of VSELs attenuates LV hypertrophy. Since postinfarct LV remodeling is associated with myocyte hypertrophy and increased LV mass, we investigated the effects of cell therapy on these parameters. To this end, we compared the three infarcted groups (groups I-III) with a separate control group of noninfarcted mice that were of similar age (10-12 wks) and did not undergo surgery. Compared with noninfarcted control mice, the cross-sectional myocyte area was significantly increased both in vehicle-treated and in CD45+ cell-treated mice (228±16 $\mu m^2$ [+41%] and 258±17 $\mu m^2$ [+59%] in groups I and II, respectively, vs. 162±20 $\mu m^2$ in noninfarcted controls; P<0.05 for both) (FIG. 37). In contrast, in VSEL-treated mice (group III) the myocyte area did not differ from noninfarcted mice (FIG. 37). The myocyte area in group III was 15% (P=NS) and 30% (P<0.05) smaller, respectively, than in groups I and II (FIG. 37). These results were corroborated by the echocardiographic estimates of LV mass. Although at 35 d after MI the echocardiographically-estimated LV mass was significantly increased in all groups compared with baseline values, in VSEL-treated mice the LV mass was 28% smaller than in groups I and II (123±7 mg vs. 172±14 and 170±6 mg, respectively; P<0.05 for both) (FIG. 37). Taken together, these data indicate that transplantation of VSELs is associated with attenuation of myocyte hypertrophy in surviving tissue.

Figure 38:
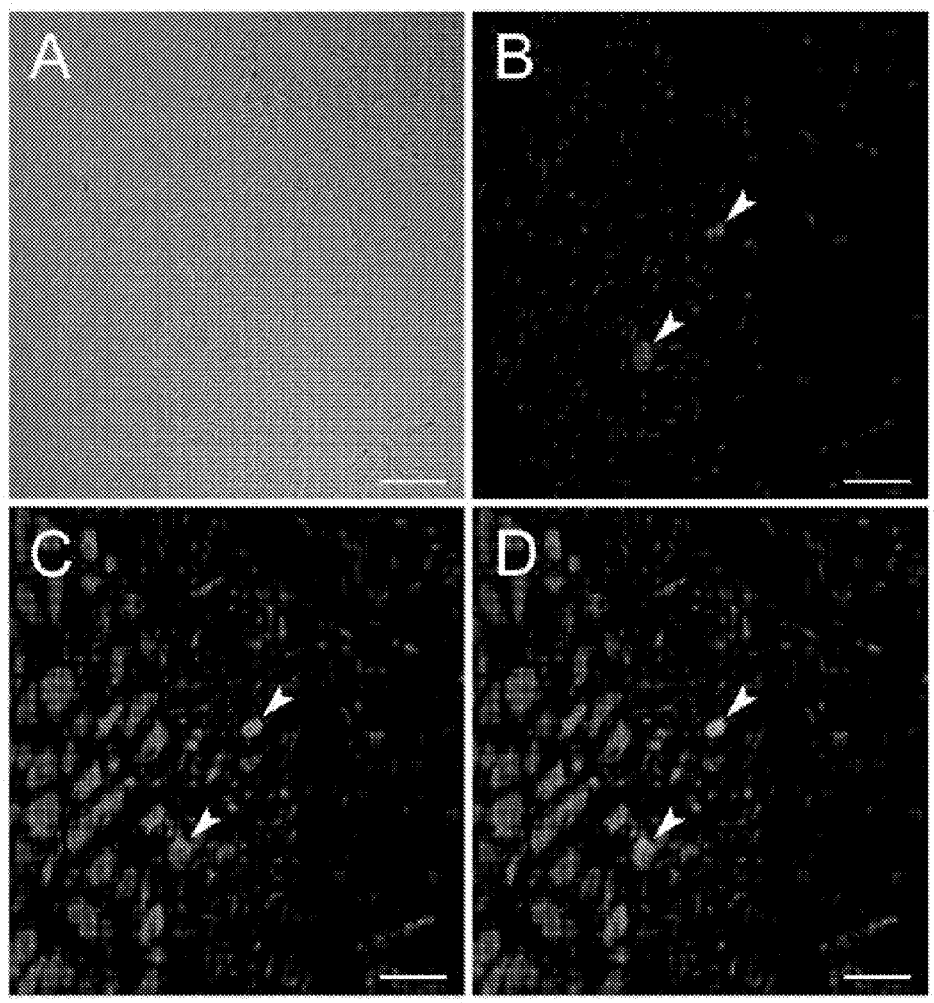
FIG. 38. VSEL transplantation and cardiomyocyte regeneration. VSELs and myocytes are identified by EGFP (B,D, green) and α-sarcomeric actin (C,D, red), respectively; panel D shows the merged image. Two myocytes are shown that are positive for both EGFP (arrowheads, B, green) and α-sarcomeric actin (arrowheads, C, red). Nuclei are stained with DAPI (A,D, blue). Scale bar=40 μm.
Figure 39:
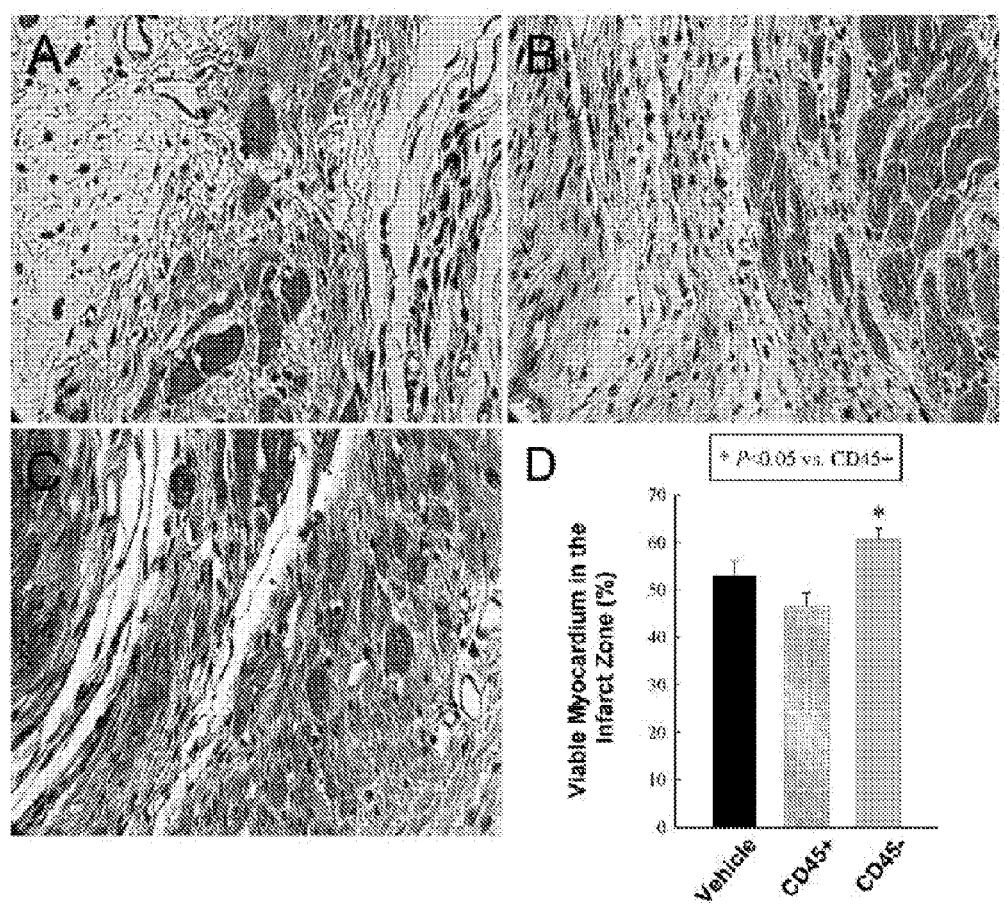
FIG. 39. Assessment of myocyte area fraction in the infarct area. Panels A-C illustrate representative examples of scar in Masson's trichrome stained vehicle-treated (A), CD45+ hematopoietic stem cell-treated (B), and VSEL-treated (C) hearts. Magnification ×600. Quantitative data are presented in panel D. Data are mean±SEM. n=11-14 mice/group. *P<0.05 vs. group II.

Impact of VSEL therapy on viable myocardium in the scar. Cardiomyocytes derived from transplanted cells were identified by concomilant positivity for α-sarcomeric actin and EGFP [8, 14]. Scattered EGFP+ cardiomyocytes were identified in the infarct zone in group III (FIG. 38) whereas none was observed in group II; the number of EGFP+ myocytes, however, was extremely small. To assess the effect of cell therapy on infarct repair, the area occupied by myocytes in the infarct zone was measured and expressed as a percentage of the total infarct area. (The infarct area was defined as the entire segment of LV that contained scar in myocardial sections stained with Masson's trichrome). Myocytes constituted 52.9±3.3%, 46.5±2.9% and 603±2.3% of the infarct zone in groups I, II, and III, respectively (FIG. 39); therefore, the amount of viable myocardium in the infarct zone was, on average, 15% and 30% greater in VSEL-treated mice compared with vehicle-treated and CD45+ cell treated mice, respectively (P=NS vs. vehicle; P<0.05 vs. CD45+ cells).

Figure 47:
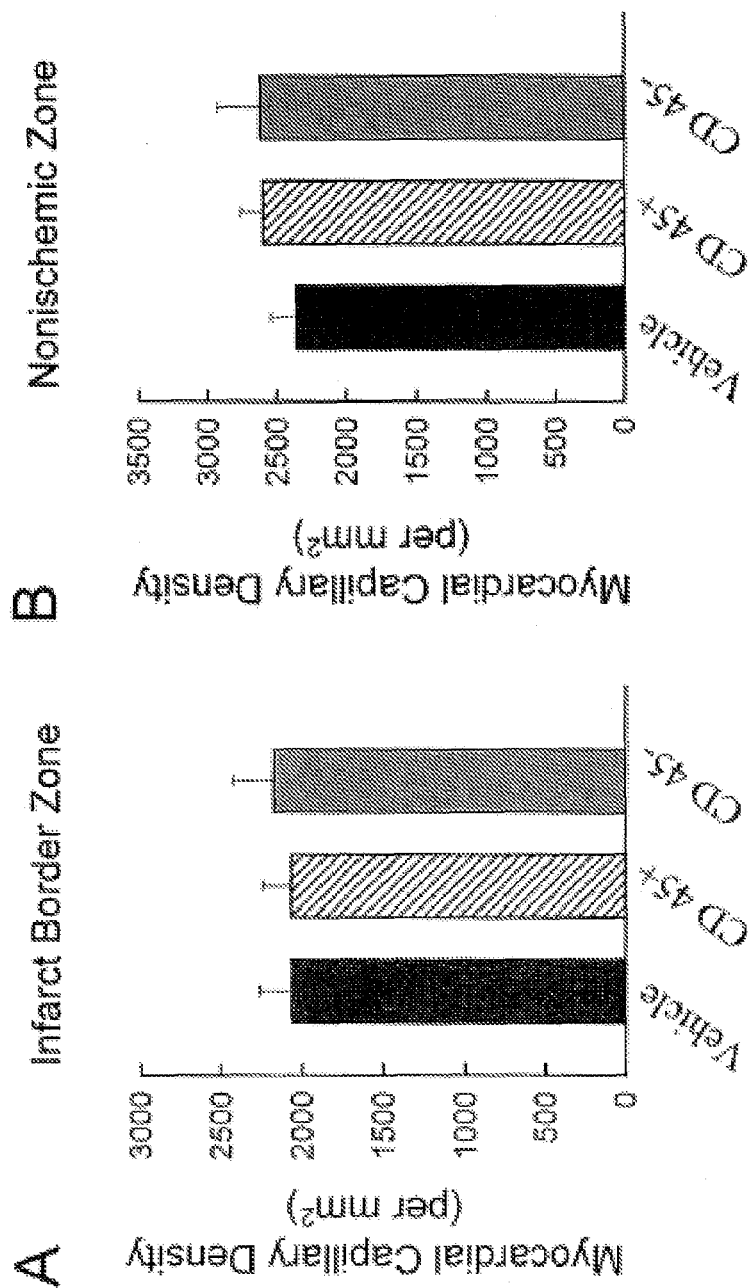
FIG. 47. Quantitative assessment of myocardial capillary density. Myocardial capillary density in the infarct borderzone (A) and in the nonischemic zone (B). There was no significant difference among the vehicle-treated, CD45+ hematopoietic stem cell-treated, and VSEL-treated hearts. Data are mean±SEM. n=11-14 mice/group.

Impact of cell therapy on capillary density, myocyte apoptosis, and myocyte cycling. Myocardial capillary density was quantitatively determined in the infarct border zone and in the nonischemic zone. In either zone, there was no significant difference among the three groups (FIG. 47). Similarly, in either zone there was no significant difference among the three groups with respect to immunoreactivity for hairpin-1 probe (for the detection of apoptosis) and Ki67 (a marker of cell cycling) (data not shown).

Discussion

BMCs represent a heterogeneous population that includes various stem/progenitor cells with diverse differentiation potential. Adult BM cells predestined to differentiate into various lineages (VSELs) might be responsible for the formation of tissue-specific cells after BMC transplantation [3-5]. In the present study we examined the ability of VSELs to improve LV function and anatomy after a reperfused MI.

The major findings of the present study can be summarized as follows: (i) myocardial transplantation of only 10,000 VSELs after a reperfused MI is sufficient to induce a demonstrable improvement in LV function and dimensions; (ii) this salubrious effect was associated with attenuation of LV hypertrophy in the noninfarcted region and presence of regenerated myocytes derived from VSELs, although the number of these myocytes was very small; (iii) in contrast, transplantation of a ten-fold greater number of Sca-1+/Lin-/CD45+ hematopoietic stem cells did not improve LV function and dimensions. These results demonstrate that even a relatively small number of BM cells with robust differentiation potential can confer cardiac reparative benefits, while a much greater number of CD45+ hematopoietic stem cells fails to do so. The observations reported here underscore the importance of proper selection of BM cells and support the concept that small quantities of VSELs present in the transplanted BM preparations may account for the beneficial effects previously observed after BMC therapy [2, 18, 19].

Small CXCR4+ cells exist within the adult BM that express markers indicative of commitment to several different lineages, including endothelial, skeletal muscle, neuronal, and cardiac lineages [3-5]. In view of the ability of VSELs to differentiate into cells with cardiomyocytic and endothelial phenotypes in vitro, the transplantation of VSELs after MI may improve cardiac function and LV remodeling. The present data supports our working hypothesis, since it demonstrates that administration of a mere 10,000 VSELs results in amelioration of LV function and attenuation of LV dilation. The magnitude of these beneficial effects was modest, possibly due to the small number of VSELs injected. The use of larger numbers of VSELs should extend these beneficial effects. There is approximately 1 VSEL for 10,000 BM mononuclear cells [5]. Thus, to inject 10,000 VSELs into one heart, we used the entire BM collected from 3-4 EGFP transgenic mice (a total of 160 EGFP transgenic mice were used for this study). Previous investigators using BMCs [20-23] injected 10-100-fold greater numbers of cells ($1 \times 10^5$ to $1 \times 10^6$ cells) into the infarcted murine heart. It is conceivable that transplantation of similar numbers of VSELs could result in greater effects than those observed in this study with 10,000 VSELs.

Because several different cell types have been reported to be beneficial, there is a perception that any cell therapy can alleviate post infarction LV remodeling. Therefore, we felt it was important to compare the effects of VSELs (which are Sca-1+, Lin-, CD45- and nonhematopoietic) not only with vehicle but also with another cell type. We chose Sca-1+/Lin-/CD45+ hematopoietic stem cells because the only difference between these two cell populations is CD45 expression; thus, Sca-1+/Lin-/CD45+ cells are perhaps the best control cells for studying the actions of VSELs. To ensure that a salubrious effect of the CD45+ cells would not be missed, and to strengthen the evidence supporting the beneficial actions of VSELs, we decided to transplant CD45+ cells at a 10-fold greater number than VSELs. (The supply of CD45+ cells is not limited by the constraints described above for VSELs.) We reasoned that if CD45+ cells have the potential to promote cardiac repair, transplantation of only 10,000 such cells may not be sufficient to detect this property. Furthermore, by comparing 100,000 CD45+ cells with 10,000 VSELs, we "biased" the experiment in favor of CD45+ cells, so that any evidence favoring the superiority of VSELs would be much stronger. Our finding that the transplantation of CD45+ cells did not favorably affect any of the measures of LV function and remodeling provides assurance that the beneficial effects observed with 10-fold lower numbers of VSELs were the result of genuine reparative properties rather than a nonspecific effect of cell therapy.

The mechanism that underlies the improvement in postinfarction remodeling after transplantation of VSELs remains unclear. Isolated new cardiomyocytes and capillaries derived from the EGFP-labeled VSELs were observed in the infarct region but their number was too small to account for the beneficial effects observed. VSELs may inhibit myocyte apoptosis and/or activate endogenous cardiac stem cells [24, 25], resulting in preservation of cardiac mass and/or new myocyte formation. Although our measurements of hairpin-1 and Ki67 positivity did not differ among the three groups at 35 d after MI, it remains possible that VSEL therapy was associated with reduction of apoptosis and/or increased cell cycling at earlier time-points. It is also possible that secretion of growth factors by VSELs might inhibit hypertrophy, which would be expected to have favorable consequences on LV function. This is supported by the attenuated cardiomyocyte hypertrophy found in VSEL-treated hearts (FIG. 37). On the other hand, the opposite is also possible, i.e., that the inhibition of hypertrophy in VSEL treated mice might have been the consequence (rather than the cause) of an improvement in LV function induced by VSELs via other mechanisms. Further studies will be necessary to test these hypotheses. Whatever the mechanism for the effects of VSELs, it seems reasonable to postulate that it would be potentiated by the transplantation of greater numbers of these cells.

The present results have implications for BMC-mediated cardiac repair. Our data indicate that CD45– nonhematopoietic VSELs are more effective than CD45+ hematopoietic stem cells, and it seems plausible that an even more substantial improvement in LV function and structure after MI would be achieved with greater numbers of VSELs. Furthermore, the present observations imply that VSELs are at least one of the specific subtype(s) of BMCs that account for the beneficial effects observed in several experimental and clinical studies of BMC transplantation [2, 18, 19, 26]. This suggests that selective administration of isolated or expanded VSELs may be more effective than unfractionated BM transplantation. Since VSELs are normally present in the adult BM [5], harvest and transplantation of these cells may be accomplished in humans.

In conclusion, we have provided proof of concept that BM-derived VSELs can be used to alleviate LV remodeling after MI. Transplantation of a relatively small number of VSELs was sufficient to improve LV function and alleviate myocyte hypertrophy. In contrast, transplantation of a 10-fold greater number of CD45+ hematopoietic stem cells was ineffective, underscoring the specificity of the actions of VSELs. Taken together, the present results support the concept that VSEL transplantation could be used therapeutically for cardiac repair after MI.

Example 33

Bone Marrow-Derived Pluripotent Very Small Embryonic-Like Stem Cells (VSELs) are Mobilized after Acute Myocardial Infarction The adult bone marrow (BM) harbors Sca-1+/Lin–/CD45– pluripotent very small embryonic-like stem cells (VSELs), which can differentiate in vitro into several lineages, including cardiac and vascular lineages. Since mobilization of stem/progenitors from the BM is a prerequisite for their participation in organ repair, we investigated whether VSELs are mobilized into the peripheral blood (PB) after acute myocardial infarction (MI). Wild-type mice (C57/BL6 strain, 6- or 15-wk-old) underwent a 30-min coronary occlusion followed by reperfusion (groups III-V, VIII-X, n=6-12/group) or al-h openchest state (sham controls, groups II and VII, n=8-12/group); mice were sacrificed 24 h, 48 h, or 7 days later and PB samples were harvested. Controls (groups I and VI, n=6/group) were sacrificed without any intervention. By flow cytometry, VSELs were barely detectable in PB under baseline conditions but their levels increased significantly at 48 h after MI, both in younger (6-wk-old) and older (15-wk-old) mice (3.33±0.37 and 7.10±0.89 cells/µl of blood, respectively). At 48 h after MI, qRT-PCR analysis revealed significantly increased levels of mRNA of markers of pluripotency (Oct-4, Nanog, Rex-1, Rif1, and Dppa1) in PB cells of 6-wk-old (but not 15-wk-old) infarcted mice compared with either controls or sham controls. Confocal microscopic analysis confirmed that mobilized VSELs expressed Oct-4 protein, while Sca-1+/Lin–/CD45+ hematopoietic stem cells did not. This is the first demonstration that Oct-4+ pluripotent stem cells (VSELs) are mobilized-from the BM into the PB after acute MI. This phenomenon may have pathophysiological and therapeutic implications for repair of infarcted myocardium Numerous studies indicate that the adult bone marrow (BM) harbors stem/progenitor cells that replenish not only the hematopoietic system, but also cells in other organs. BM-derived cells (BMCs) have been shown to participate in tissue repair following injury to several organs, including the brain, liver, lung, kidney [27-31] as well as the heart [32-37]. Cardiomyocytes derived from BMCs have been noted in the heart after myocardial infarction (MI) [32, 33, 36]. The egress of primitive cells from the BM into the blood is an essential first step for effective tissue repair by BMCs [38,39]. Although BMCs have been shown to promote tissue repair, the underlying mechanisms remain unclear. Generation of multilineage cells from BMCs has been proposed as a mechanism for BMC-mediated tissue repair, and it is plausible that pluripotent BMCs, capable of multilineage differentiation, are mobilized from the BM after tissue injury followed by homing and tissue reconstitution. The adult BM harbors several types of primitive cells, including hematopoietic stem cells (HSCs) [40] and a multitude of nonhematopoietic primitive cells, such as mesenchymal stem cells (MSCs) [41], multipotent adult progenitor cells (MAPCs) [42], the marrow isolated adult multilineage inducible (MIAMI) cells [43], tissue-committed stem cells (TCSCs) [44], and BM-derived multipotent stem cells [45]. We have identified a rare population of non-hematopoietic primitive cells in the BM that are positive for Sca-1 and negative for both lineage markers (Lin) and the panleukocyte marker CD45 (Sca-1+/Lin–/CD45–) [46].

Because these cells express a number of markers associated with a pluripotent state (SSEA-1, Oct-4, Nanog, and Rex-1) and differentiate in vitro into components of all three germ-layers, we have named these cells 'very small embryonic like stem cells' (VSELs) [46-48]. Besides markers of neural, endothelial, muscle, and pancreatic tissues, VSELs are enriched in mRNA for cardiac-specific antigens (Nkx2.5/Csx, GATA-4, MEF-2C) and can acquire a cardiomyocytic phenotype in vitro [46, 49]. We have also reported that murine BM-derived VSELs are mobilized after various forms of tissue injury [38, 50]. On the basis of the above observations, we postulated that pluripotent VSELs might be mobilized into the peripheral blood (PB) after acute MI. Mobilization of pluripotent BMCs into the PB has not been previously documented.

Accordingly, using a well-established murine model of MI [51], we investigated (i) whether VSELs are mobilized from the BM into the PB after an acute MI, and (ii) whether mobilization of VSELs is influenced by age. We used a comprehensive approach (flow cytometry, mRNA analysis by qRT-PCR, and immunocytochemistry) to determine both the absolute cell numbers as well as the kinetics of mobilization. The mobilization of VSELs (Sca-1+/Lin−/CD45−) was directly compared with that of Sca-1+/Lin−/CD45+ hematopoietic stem cells (HSCs). Our results show that the levels of Sca-1+/Lin−/CD45− VSELs increase in the PB soon after acute MI both in young and older mice, concomitant with an increase in markers of pluripotency in the PB, although the expression of these genes declines with age.

Materials and Methods

All experiments were performed in accordance with the guidelines of the Laboratory Institutional Animal Care and Use Committee (IACUC). The investigation conforms to the Guide for the Care and Use of Laboratory Animals published by the US National Institutes of Health (NIH Publication No. 85-23, revised 1996).

Experimental Protocol. Ten groups (n=6-12/group) of wild-type mice (C57BL/6 strain, Jackson Laboratory, Bar Harbor, Me.) were used. Groups I-V were 6-wk-old, whereas groups VI-X were 15-wk-old. Mice in groups III-V and VIII-X underwent coronary occlusion/reperfusion, while groups II and VII (sham controls) underwent a sham procedure (1-hour open-chest state) without coronary occlusion. Infarcted mice were sacrificed at 24 h (groups III and VIII), 48 h (groups IV and IX), or 7 d (groups V and X) after MI, while sham controls (groups II and VI) were sacrificed at 24 h after sham procedure for analysis of cell mobilization. Mice in groups I and VI were sacrificed without any intervention and served as controls.

Myocardial infarction. The experimental preparation has been described in detail [51]. Briefly, mice were anesthetized with sodium pentobarbital (50 mg/kg i.p.), intubated, and ventilated using a small rodent ventilator. Body temperature, heart rate, and arterial pH were carefully maintained within the physiological range throughout the experiments.

Using a sterile technique, the chest was opened through a midline sternotomy. An 8-0 nylon suture was passed with a tapered needle under the left anterior descending coronary artery 2 mm from the tip of the left auricle, and a nontraumatic balloon occluder was applied on the artery. Myocardial infarction was induced by inflating the balloon occluder for 30 min Successful performance of coronary occlusion and reperfusion was verified by visual inspection (i.e., by noting the development of a pale color in the distal myocardium upon inflation of the balloon and the return of a bright red color due to hyperemia after deflation) and by observing S-T segment elevation and widening of the QRS complex on the ECG during ischemia and their resolution after reperfusion [51].

Following reperfusion, the chest was closed in layers and mice were allowed to recover. To replenish perioperative fluid loss, Dextran 40 (10% v/v in 0.9% sodium chloride) was infused after surgery. Mice were euthanized at serial time-points and blood samples were collected for flow cytometry, mRNA analysis, and immunocytochemistry.

Figure 40:
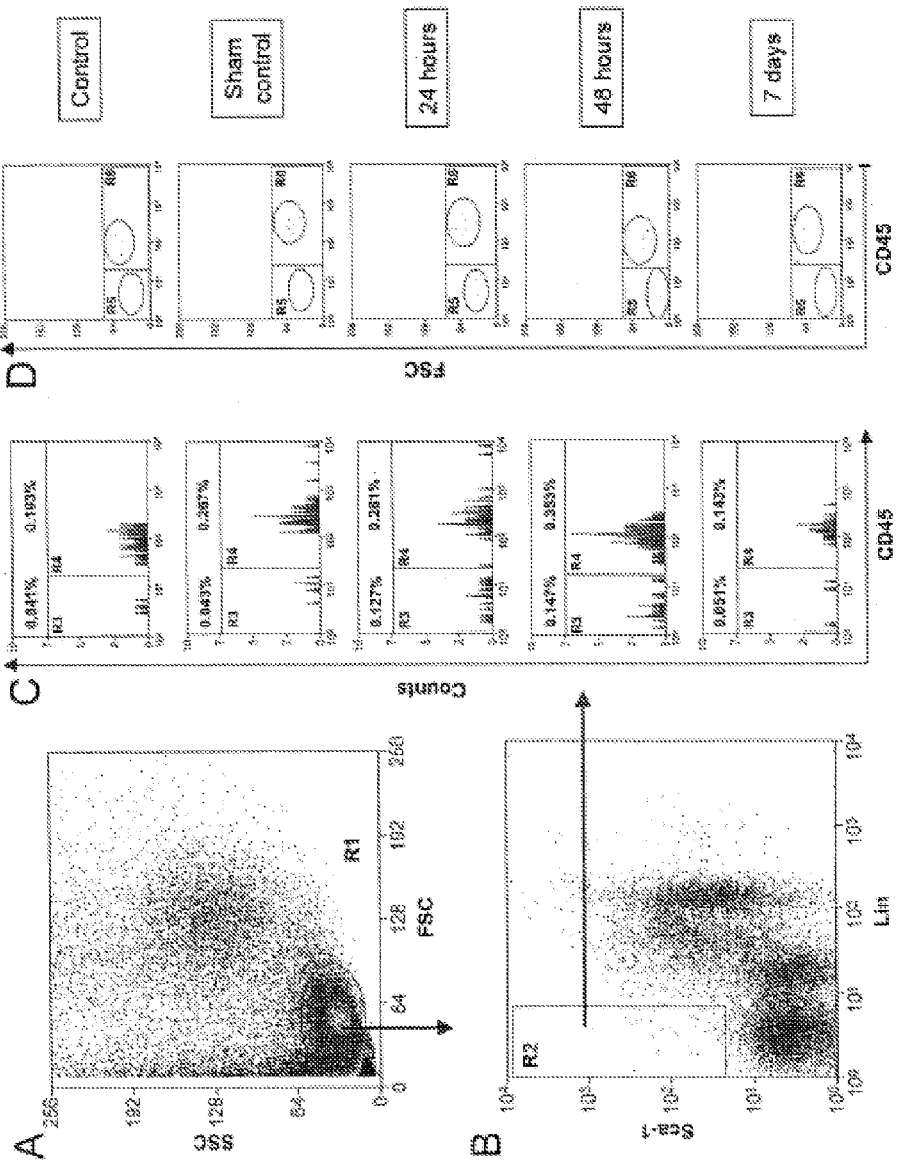
FIG. 40. Flow cytometric analysis of VSELs circulating in the peripheral blood (PB). PB samples were collected at 24 h, 48 h and 7 days after acute MI; at 24 h after sham surgery (sham control); and from untreated mice (control). The full population of PB leukocytes (PBLs) was stained for Sca-1, lineage markers, and CD45. PBLs were visualized in the dot-plot representing their forward (FSC) vs. side scatter characteristics (SSC), which are related to the size and granularity/complexity of cellular contents, respectively. Agranular, small (between 2-10 μm in size) events, which contain the VSEL population, were included in region R1 (Panel A). Cells from region R1 were further analyzed for the expression of Sca-1 and linage markers (Lin), and only Sca-1+/Linevents were included in region R2 (Panel B). Cells from region R2 were subsequently analyzed based on CD45 expression, and CD45- and CD45+ subpopulations were visualized on histograms (Panel C, regions R3 and R4, respectively). The percentages show the average content of each subpopulation in total PBLs. According to the FSC, Panel D shows the size of Sca-1+/Lin-/CD45- cells (VSELs) and Sca-1+/Lin-/CD45+ cells (HSCs) in regions R5 and R6, respectively. Red circles indicate the predominant localization of cells in each subpopulation.

Flow cytometric analysis and sorting of VSELs and HSCs from peripheral blood. The scheme for flow cytometric analysis and sorting is illustrated in FIG. 40. The full population of PB leukocytes (PBLs) was obtained after lysis of RBCs using 1× BD Pharm Lyse Buffer (BD Pharmingen, San Jose, Calif.). Cells were stained for CD45, lineage markers, and Sca-1 for 30 min in medium containing 2% fetal bovine serum (FBS). The following fluorochrome-conjugated anti-mouse antibodies were used: rat anti-CD45 (APC-Cy7; clone 30-F11), anti-CD45R/B220 (PE; clone RA3-6B2), anti-Gr-1 (PE; clone RB6-8C5), anti-TCRαβ (PE; clone H57-597), anti-TCRγδ (PE; clone GL3), anti-CD11b (PE; clone M1/70), anti-Ter119 (PE; clone TER-119) and anti-Ly-6A/E (Sca-1, biotin; clone E13-161.7, followed by staining with PE-Cy5-conjugated streptavidin) (all from BD Pharmingen). Cells were washed and re-suspended in RPMI 1640 medium with 10% FBS. The percentage of VSELs and HSCs among PBLs was analyzed by flow cytometry using MoFlo (Dako, Carpinteria, Calif.). The total leukocyte count (per unit volume of PB) was determined using the Hemavet 950, WBC hematology system (Drew Scientific, Oxford, Conn.). The absolute number of VSELs and HSCs in 1 μl of blood was computed from the respective percentage contents and the total leukocyte count. For immunocytochemistry and confocal microscopy, Sca-1+/Lin−/CD45− VSELs and Sca-1+/Lin−/CD45+ HSCs were isolated accordingly to a previously described sorting strategy (FIG. 40) [47].

Immunocytochemisty and confocal microscopy. Freshly isolated, PB-derived Sca-1+/Lin−/CD45− VSELs and Sca-1+/Lin−/CD45+ HSCs were plated for 24 h on 22-mm diameter plates coated with poly-L-lysine (Sigma). Cells were fixed with 4% paraformaldehyde solution for 20 min and permeabilized with 0.1% Triton X-100 for 5 min at room temperature (RT). Blocking with 10% donkey serum (Jackson Immunoresearch, West Grove, Pa.) was performed for 30 min at RT to avoid nonspecific binding of antibodies. Cells were incubated with primary antibodies against Oct-4 (mouse monoclonal IgG, Chemicon, 1:200) and CD45 (FITC-conjugated rat monoclonal IgGI, clone 30-F11, BD Pharmingen, 1:100) for 2 h at 37° C. Following washing, cells were incubated with TRITC-conjugated donkey anti-mouse IgG secondary antibody (Jackson Immunoresearch, 1:200) for 2 h at 37° C. Nuclei were stained with DAPI (Invitrogen) for 10 min at 37° C. Immunofluorescent photomicrographs were acquired using a LSM 510 confocal microscope (Carl Zeiss, Thornwood, N.Y.).

Assessment of expression of pluripotent genes by quantitative real-time RT-PCR (qRT-PCR). Total mRNA was isolated from the PBL fraction with the RNeasy Mini Kit (Qiagen Inc., Valencia, Calif.) and reverse-transcribed with TaqMan Reverse Transcription Reagents (Applied Biosystems, Foster City, Calif.). Quantitative assessment of mRNA expression of markers characterizing pluripotent stem cells (Oct-4, Nanog, Rex-1, Rif1, and Dppa1), hematopoietic cells (Scl), and β2-microglobulin was performed by qRT-PCR using an ABI PRISM® 7000 Sequence Detection System (Applied Biosystems, Foster City, Calif.). The primer sequences (designed with the Primer Express software) have been previously described [46]. A 25-μl reaction mixture containing 12.5 μl of SYBR Green PCR Master Mix and 10 ng of forward and reverse primers was used. The threshold cycle (Ct), i.e., the cycle number at which the amount of amplified gene of interest reached a fixed threshold, was subsequently determined Relative quantitation of mRNA expression was performed with the comparative Ct method. The relative quantitative value of target, normalized to an endogenous control (β2-microglobulin gene) and relative to a calibrator, was expressed as 2-ΔΔCt (-fold difference), where ΔCt=(Ct of target genes [Oct-4, Nanog, Rex-1, Rif1, Dppa1, Scl])−(Ct of endogenous control gene [β2-microglobulin]), and ΔΔCt=(ΔCt of samples for target gene)−(ΔCt of calibrator for the target gene). To avoid the possibility of amplifying contaminating DNA (i) all of the primers for real-time RT-PCR were designed to contain an intron sequence for specific cDNA amplification; (ii) reactions were performed with appropriate negative controls (template-free controls); (iii) a uniform amplification of the products was rechecked by analyzing the melting curves of the amplified products (dissociation graphs); and (iv) the melting temperature (Tm) was 57-60° C., and the probe Tm was at least 10° C. higher than primer Tm. Three independent experiments were performed for each set of genes.

Statistical analysis. Data are mean±SEM. The concentration of cells and the quantitative mRNA data (-fold changes in mRNA levels) for cardiac-specific transcriptions factors and those associated with a pluripotent state were analyzed with a one-way ANOVA. If the ANOVA showed an overall difference, post hoc contrasts were performed with Student's t-tests for unpaired data, and the resulting probability values were adjusted according to the Bonferroni correction. A $P<0.0025$ was considered statistically significant. All statistical analyses were performed using the SPSS (version 8.0) statistical software (SPSS Inc., Chicago, Ill.).

VSELs are mobilized into the peripheral blood after MI. The numbers of circulating VSELs (Sca-1+/Lin-/CD45-) and HSCs (Sca-1+/Lin-/CD45+) were examined at 24 h, 48 h, and 7 days after MI. At each time point, the percent content of VSELs and HSCs in PB was estimated (FIG. 8) and the absolute numbers of both cell populations per microliter of blood were computed from the respective total leukocyte counts. Combining the percentage of circulating primitive cells with the number of PB cells avoided possible confounding effects of dilution.

Figure 41:
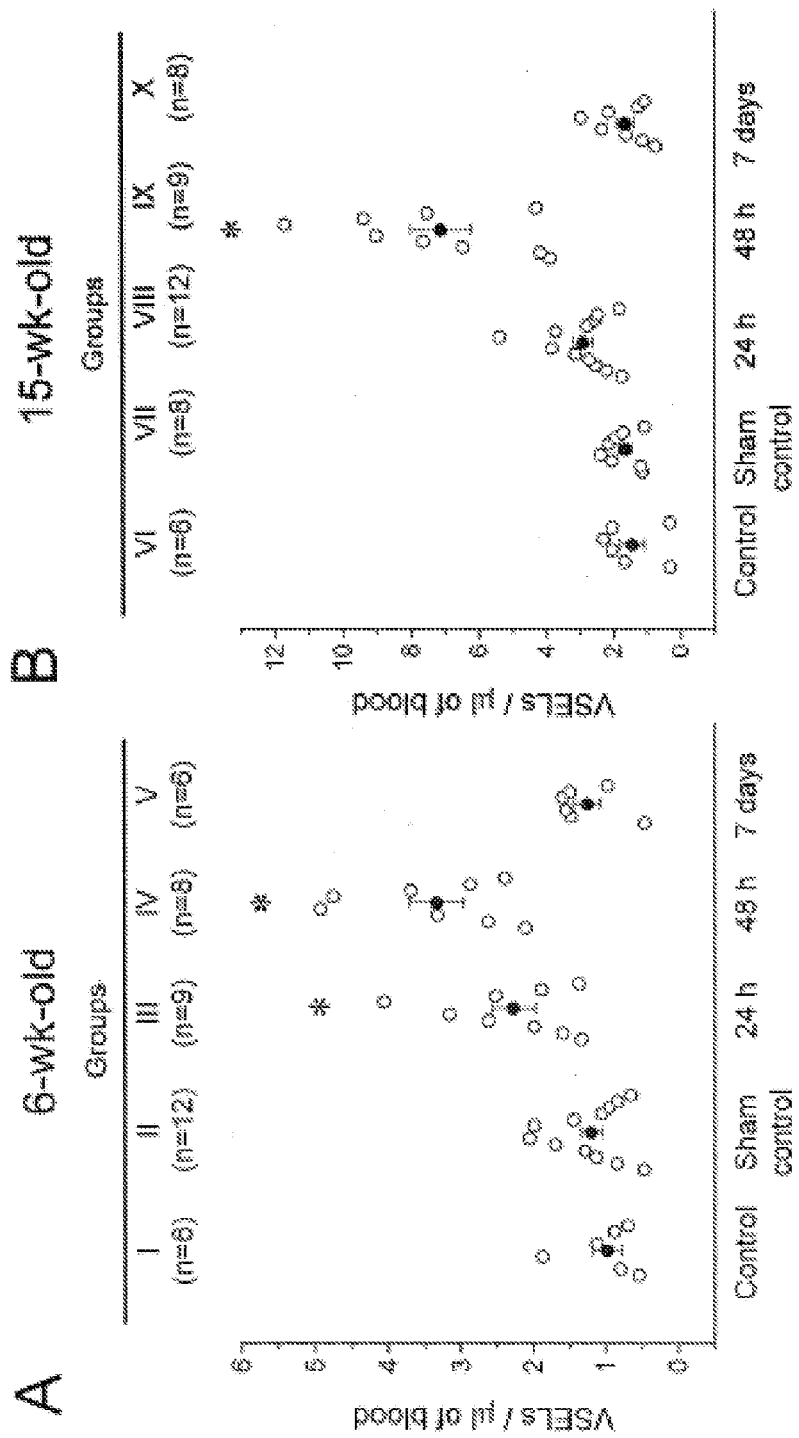
FIG. 41. Time-course of VSEL mobilization after acute MI. Shown is the absolute number of circulating Sca-1+/Lin-/CD45- VSELs per microliter of blood in untreated (control), sham-operated (sham control), and infarcted mice at 24 h, 48 h, and 7 days after MI. Panels A and B represent data obtained from 6- and 15-wk-old mice, respectively. The absolute numbers were calculated based on the percent content of VSELs among PBLs and the total leukocyte count in the peripheral blood. Data are mean±SEM. ●, mean; O, individual mice. *P<0.0025 vs. controls as well as sham controls.

In control mice, the number of circulating VSELs was very low (0.98±0.20 and 1.44±0.37 VSELs/μl of blood in 6- and 15-wk-old mice, respectively) (FIG. 41). The number of circulating VSELs in sham-operated animals at 24 h after the open-chest procedure was similar to that in respective untreated controls. (1.20±0.15 and 1.65±0.20 VSELs/μl of blood in 6- and 15-wk-old mice, respectively) (FIG. 41), indicating that opening the chest, in itself, is not sufficient to mobilize VSELs. Circulating VSELs increased significantly at 24 h after MI in 6-wk-old mice (2.28±0.30 VSELs/μl of blood [group III]; $P<0.0025$ vs. both untreated controls and sham controls) (FIG. 41). In both age groups, the number of mobilized VSELs peaked at 48 h after MI (3.33±0.37 [group IV] and 7.10±0.89 [group IX] VSELs/μl of blood in 6- and 15-wk-old mice, respectively; $P<0.0025$ vs. respective untreated and sham controls) (FIG. 41). At 7 days after MI, circulating VSELs were similar to those observed in the respective untreated controls (1.62±0.37 [group V] and 1.63±0.27 [group XI VSELs/μl of blood in 6- and 15-wk-old groups, respectively) (FIG. 41).

Figure 42:
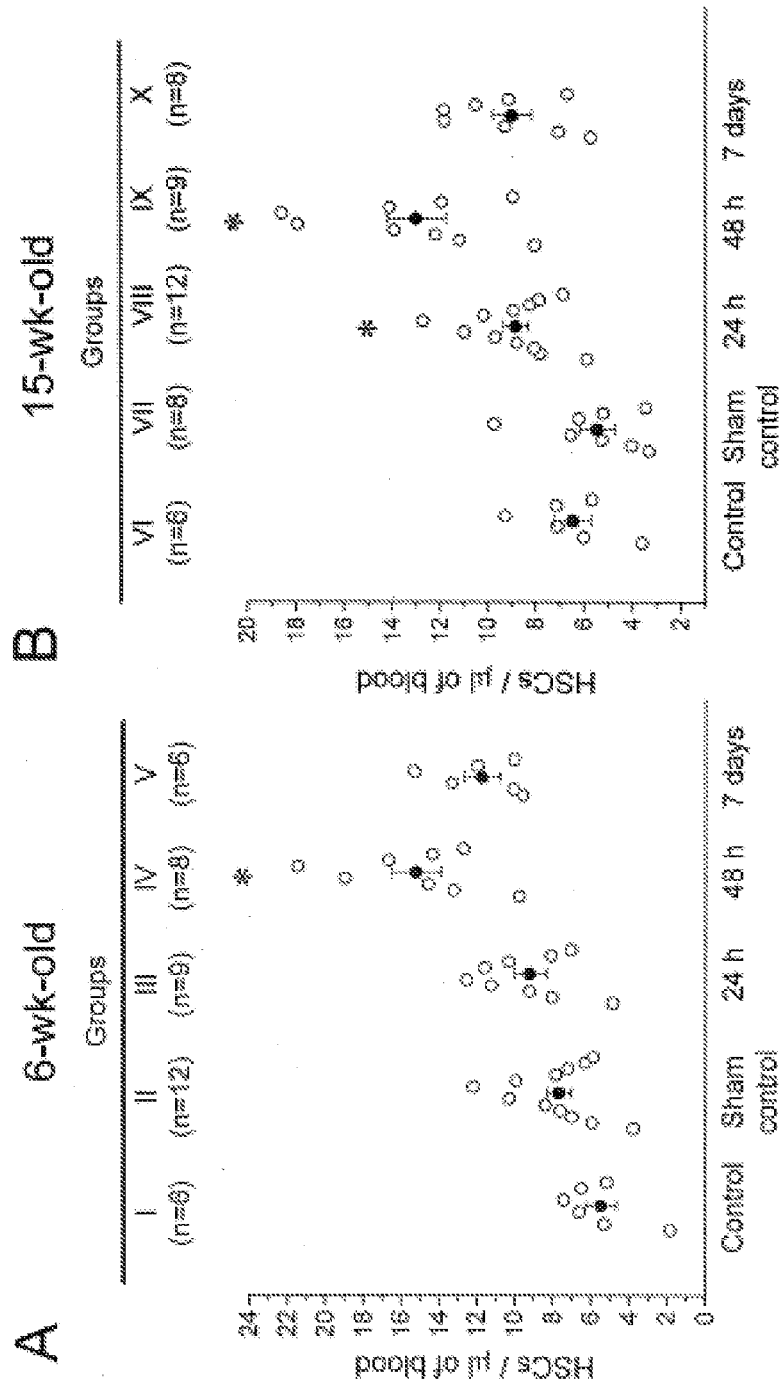
FIG. 42. Time-course of HSC mobilization after acute MI. The Figure shows the absolute numbers of circulating Sca-1+/Lin-/CD45+ HSCs per microliter of blood in untreated (control), sham-operated (sham control), and infarcted mice at 24 h, 48 h, and 7 days after MI. Panels A and B represent data obtained from 6- and 15-wk-old mice, respectively. The absolute numbers were calculated based on the percent content of HSCs among PBLs and the total leukocyte count. Data mean±SEM. ●, mean; O, individual mice. *P<0.0025 vs. controls as well as sham controls in respective age groups.

Compared with the number of VSELs, the number of circulating Sca-1+/Lin-/CD45+ HSCs in PB of control mice was greater (5.47±0.81 [group I] and 6.48±0.77 [group VI] HSCs/μl of blood in 6- and 15-wk-old mice, respectively) (FIG. 42). The number of HSCs did not change significantly at 24 h after sham surgery in either age group (7.69±0.66 [group I] and 5.46±0.74 [group VI] HSCs/μl of blood in 6- and 15-wk-old mice, respectively). However, circulating HSCs increased at 24 h after MI (9.20±0.82 [group III] and 8.82±0.53 [group VIII], in 6- and 15-wk-old mice, respectively). HSC mobilization was even greater at 48 h after MI (15.19±1.31 [group IV] and 12.96±1.12 [group IX] HSCs/μl of blood in 6- and 15-wk-old mice, respectively; $P<0.0025$ vs. respective untreated and sham controls) followed by a decline at 7 days after MI (1 1.69±0.92 [group V] and 8.99±0.82 [group XI] HSCs/μl of blood in 6- and 15-wk-old mice, respectively, $P<0.0025$ vs. sham controls (FIG. 42).

Figure 43:
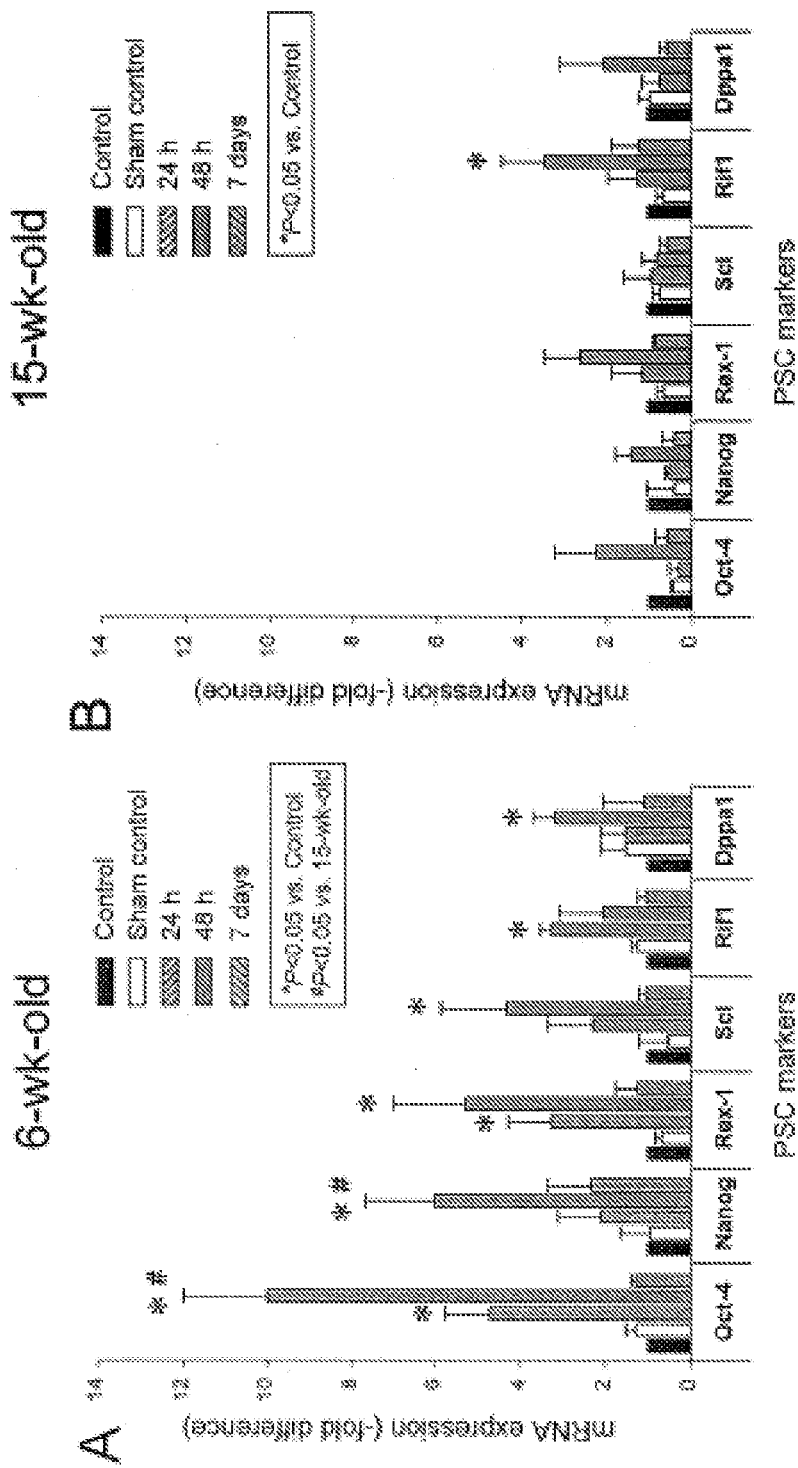
FIG. 43. mRNA levels of markers of pluripotency (Oct-4, Nanog, Rex1, Rif1, Dppa1) and of hematopoietic stem cells (Scl) in peripheral blood-derived cells from 6- and 15-wk-old mice after acute MI (Panels A and B, respectively). Cells isolated from the blood of animals in each experimental group were pooled together to obtain the average content of mRNA at each time point. qRT-PCR was performed in triplicate for all samples. The -fold increase in mRNA content was compared with controls. The average values were calculated based on three reactions. Data are presented as mean±SEM. PSC, pluripotent stem cell.

The peripheral blood is enriched in pluripotent primitive cells after acute MI. To confirm the enrichment of PB with VSELs after MI, we evaluated the expression of markers of pluripotency in PB-derived cells harvested at different timepoints after coronary occlusion/reperfusion. For this purpose, we employed qRT-PCR to detect mRNA for markers of pluripotency including Oct-4, Nanog, Rex-1, Rif1, and Dppa1. In 6-wk-old mice sacrificed at 48 h after acute MI, we found that the PB was indeed enriched in cells containing mRNA for these markers (10.01±1.98, 6.02±1.66, 5.28±1.68, 2.07±0.99 and 3.18±0.49-fold increase, respectively, in mRNA levels of Oct-4, Nanog, Rex-1, Rif1, and Dppa1 compared with untreated controls, $P<0.05$ for all comparisons, FIG. 43, panel A). In contrast, in PB cells from 15-wk-old mice the respective mRNA levels of these markers were only 2.24±0.95, 1.41±0.36, 2.61±0.84, 3.43±0.98 and 2.03±1.01-fold higher compared with untreated controls (FIG. 43, panel B), indicating that in older mice mobilized cells express considerably lower levels of genes associated with a pluripotent state. At 48 h after MI, we also observed increased mRNA levels of the marker of hematopoietic cells (Scl) in 6-wk-old mice (4.32 k1.54-fold higher compared with respective untreated controls) but not in 15-wk-old mice (0.82 k0.32-fold difference) (FIG. 43, panels A and B).

Figure 44:
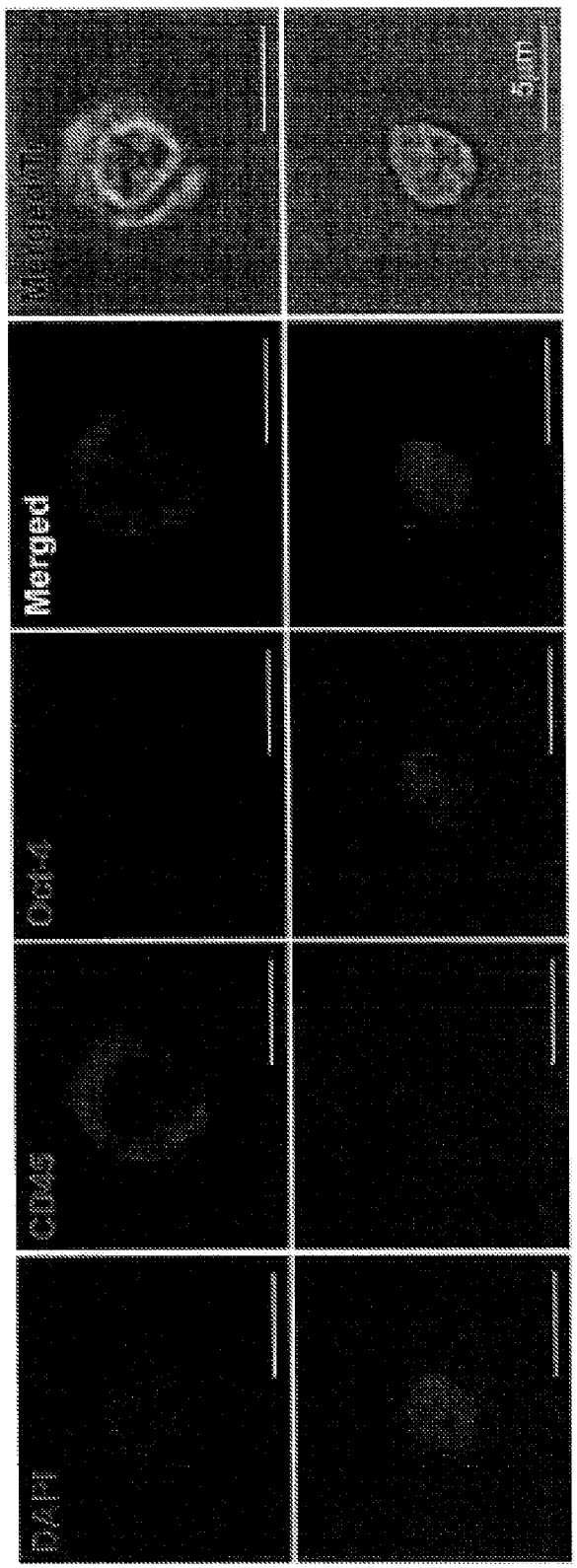
FIG. 44. Expression of Oct-4 in peripheral blood (PB)-derived VSELs. Representative confocal microscopic images of a mobilized VSEL (lower panels) and HSC (upper panels) isolated from the PB at 24 h after MI. Sca-1+/Lin-/CD45- VSELs and Sca-1+/Lin-/CD45+ HSCs were isolated by FACS followed by immunostaining. The upper panels show a Sca-1+/Lin-/CD45+ cell (HSC), which is positive for CD45 (FITC, green fluorescence), a marker of hematopoietic cells, and negative for Oct-4 (TRITC, red fluorescence). The lower panels show a Sca-1+/Lin-/CD45- cell (VSEL), which is negative for CD45 and positive for Oct-4, a marker of pluripotent cells. Nuclei were stained with DAPI (blue fluorescence). Tr, transmission image.

Mobilized VSELs isolated from the peripheral blood express OCT-4. The expression of Oct-4 (a marker of pluripotency) at the protein level in mobilized VSELs was examined by immunocytochemistry. For this purpose, both VSELs and control HSCs were isolated from the full population of PB cells by FACS. Sorted cells were stained for CD45 and Oct-4, markers for hematopoietic cells and pluripotency, respectively. Confocal microscopic analysis following immunostaining confirmed that the mobilized and sorted Sca-1+/Lin-/CD45- VSELs were very small (<5 μm in diameter), were negative for CD45, and expressed Oct-4 (FIG. 44, lower panels). In contrast, sorted Sca-1+/Lin-/CD45+ HSCs were considerably larger than VSELs, were positive for CD45, and did not express Oct-4 (FIG. 44, upper panels).

Discussion

The adult BM may harbor various primitive cells that possess the ability to repair nonhematopoietic organs. In this regard, exogenous cytokine-induced mobilization of BMCs has been shown to be beneficial after stroke as well as MI [32, 52]. Moreover, the identification of BMC-derived cells in various injured tissues, including brain, liver, kidney, lung, and heart, indicates that tissue injury can induce mobilization of BMCs from the marrow into the PB [27-32, 33, 34]. However, the mobilization of pluripotent stem cells after acute MI has never been reported.

Using complementary methods, (flow cytometry, qRT-PCR, and confocal microscopy), we report that pluripotent VSELs expressing Oct-4 are mobilized early after acute MI. We did not observe any significant difference in the levels of VSELs in the PB of untreated healthy animals vs. those subjected to an open-chest sham procedure, indicating that surgery in itself does not mobilize pluripotent cells from the BM stem cell pool. In mice subjected to MI, the levels of circulating VSELs were elevated at 24 and 48 h followed by a return to the levels observed in untreated control mice at 7 days. The observations made by flow cytometry were confirmed by qRT-PCR analysis. Previous studies have shown that various types of BMCs are mobilized after MI. These include hematopoietic stem cells [53, 54], mesenchymal stem cells [55], endothelial progenitor cells [53, 56], and other distinct subpopulations characterized by surface markers.

Circulating CD34+ progenitors [54, 57] and CD34+/CXCR4+, CD34+/c-kit+, cmet+ subpopulations [58, 59] have been observed in patients after an acute MI. Studies in animals have shown the presence of BM-derived c-kit+, CD31+ cells in the infarcted myocardium after MI [60]. The progenitor cells detected in PB of patients with acute MI express increased levels of mRNA of early cardiac (GATA-4, Nkx2.51Csx, and MEF2C) and endothelial (VE-cadherin and von Willebrand factor) markers [58]. Similar results have been obtained in mice [44]. However, the content of pluripotent cells (as reflected by expression of markers of pluripotency) in these mobilized subpopulations was not investigated in the above studies [44, 58]. In this study we documented the presence of pluripotent VSELs in blood after MI via a comprehensive approach. First, using flow cytometry, VSELs were identified in the PB by their typical phenotype (Sca-1+/Lin−/CD45−). Second, greater mRNA levels of markers of pluripotency (Oct-4, Nanog, Rex-1, Rif-I, and Dppa1) were detected by qRT-PCR. Finally, we verified by confocal microscopy the expression of Oct-4, a marker of pluripotency, at the protein level in VSELs, but not in the control population (Sca-1+/Lin−/CD45+ HSCs).

In addition to examining the time-course of VSEL mobilization after MI, we sought to determine whether the release of these cells differs between young (6-wk-old) and older (15-wk-old) mice. Using flow cytometric analysis of surface markers, we found that the kinetics of mobilization of VSELs was similar in 6- and 15-wk-old mice. However, at 48 h after MI (when mobilization peaked), the levels of mRNA for markers of pluripotency, such as Oct-4, Nanog, Rex-1, Rif1, and Dppa1, were lower in 15-wk-old mice compared with 6-wk-old mice. These data indicate that although cells with phenotypic attributes of VSELs (Sca-1+/Lin−/CD45−) were released into the PB of older animals, these cells lost markers of pluripotency with age, an observation that is consistent with previous reports regarding attrition of pluripotency and functionality of stem cells with aging [61-63]. The observation that VSELs are mobilized after MI has important implications for the repair of cardiac and other tissues. We have previously shown that VSELs express markers of pluripotency such as Oct-4, Nanog, and Rex-1 at the mRNA and protein levels [46-48]. We have also documented that under appropriate culture conditions, VSELs give rise to cellular spheres akin to embryoid bodies, expand efficiently resembling cultured embryonic stem cells, and differentiate into the components of all three germ layers in vitro [46-48]. Mobilization of these primitive cells from the BM to the PB after MI would be the first step in their involvement in cardiac repair. Therefore, the present findings of markedly increased trafficking of VSELs in the PB early after MI raises the possibility that these pluripotent cells may contribute to myocardial repair in this setting. Enhancing the mobilization of endogenous VSELs via cytokine or growth factor administration may be utilized therapeutically to promote repair after MI.

In conclusion, our results demonstrate, that pluripotent Sca-1+/lin−/CD45− VSELs are mobilized from BM after acute MI. The circulating levels of pluripotent VSELs peak early (48 h) after MI, followed by a decrease at 7 days. Consistent with these observations, the PB of infarcted animals is enriched in cells expressing markers of pluripotency (Oct-4, Nanog, Rex1, Rif-I, and Dppa1), although the expression of these genes in VSELs declines with age.

Example 34

Use of Very Small Embryonic-Like (VSEL) Stem Cells and Cardiac Stem Cells for Repair of Myocardial Infarction Bone marrow (BM)-derived cells have been shown to improve left ventricular (LV) function and attenuate adverse LV remodeling after myocardial infarction (MI). The cell type(s) responsible for these beneficial effects are identified in adult BM as a rare population of pluripotent SSEA-1+/Oct-4+/Sca-1+/Lin−/CD45− very small embryonic-like stem cells (VSELs) that differentiate into cardiac lineage in vitro. Using a murine model of MI, we found that VSELs were barely detectable in peripheral blood (PB) at baseline but increased significantly after MI, peaking at 48 h (flow cytometry), concomitant with increased levels of mRNA for markers of pluripotency (Oct-4, Nanog, Rex-1, Dppa1, and Rif1) in PB cells (RQ-PCR analysis), indicating that VSELs are mobilized into the blood shortly after MI. Importantly, direct intramyocardial injection of VSELs in mice improved LV function and attenuated LV remodeling, suggesting that these pluripotent cells could be used therapeutically for repair of MI. Another promising approach to cell therapy is the use of c-kit+ cardiac stem cells (CSCs) present in adult myocardium. We found that intracoronary administration of CSCs exerts beneficial effects both in a model of acute MI in rats and in two models of old, healed MI (rats and pigs); in all cases, CSC administration resulted in improved systolic function, reduced LV dilatation, and regeneration of myocytes and coronary vessels. These data support the therapeutic utility of CSCs for repair of both acute and old MI and provide the basis for upcoming clinical trials of CSCs.

It will be understood that various details of the described subject matter can be changed without departing from the scope of the described subject matter. Furthermore, the foregoing description is for the purpose of illustration only, and not for the purpose of limitation.

The references listed below as well as all references cited in the specification, including patents, patent applications, journal articles, and all database entries (e.g., GENBANK® Accession Nos., including any annotations presented in the GENBANK® database that are associated with the disclosed sequences), are incorporated herein by reference to the extent that they supplement, explain, provide a background for, or teach methodology, techniques, and/or compositions employed herein.

1. Bolli et al. J Am Coll Cardiol 2005; 46: 1659-1661.
2. Abdel-latif et al. Arch Int Med 2007; 167:989-997.
3. Ratajczak et al. Leukemia 2004; 18:29-40.
4. Kucia et al. Circ Res 2004; 95:1191-1199.
5. Kucia et al. Leukemia 2006; 20:857-869.
6. Guo et al. Am J Physiol 1998; 275:H I375-1387.
7. Guo et al. Proc Natl Acad Sci USA 1999; 96:11507-11512.
8. Dawn et al. Circ Res 2006; 98: 1098-1 105.
9. Li et al. J Clin Invest 1997; 100: 1991-1 999.
10. Anversa P, Olivetti G. The cardiovascular system. In: Page E, Fozzard H A, Solaro R J, eds. *The Head.* 1st ed. New York, N.Y.: Oxford University Press; 2002:75-144.
11. Anversa et al. Am J Physiol 1984; 246:H739-746.
12. Anversa et al. Circ Res 1986; 58:26-37.
13. Dawn et al. Proc Natl Acad Sci USA 2005; 102:3766-3771.
14. Orlic et al. Nature 2001; 410:701-705.
15. Wallenstein et al. Circ Res 1980; 47: 1-9.
16. Dawn et al. Basic Res Cardiol 2005; 100:494-503.

17. Kucia et al. Exp Hematol 2005; 33:613-623.
18. Strauer et al. Circulation 2002; 106:1913-1918.
19. Schachinger et al. N Engl J Med 2006; 355:1210-1221.
20. Toma et al. Circulation 2002; 105:93-98.
21. Yoon et al. J Clin Invest 2005; 115:326-338.
22. Kajstura et al. Circ Res 2005; 96:127-137.
23. Wang et al. J Mol Cell Cardiol 2006; 40:736-745.
24. Beltrami et al. Cell 2003; 114:763-776.
25. Urbanek et al. Circ Res 2005; 97:663-673.
26. Perin et al. Circulation 2004; 110:11213-218.
27. Kollet et al. J Clin Invest 2003; 112:160-9.
28. Machalinski et al. Folia Histochem Cytobiol 2006; 44:97-101.
29. De Silvestro et al. Hepatogastroenterology 2004; 51:805-10.
30. Kale et al. J Clin Invest 2003; 112:42-9.
31. Rojas et al. Am J Respir Cell Mol Biol 2005; 33: 145-52.
32. Orlic et al. Proc Natl Acadzci USA 2001; 98:10344-9.
33. Jackson et al. J Clin Invest 2001; 107:1395-402.
34. Kuramochi et al. Pediatr Res 2003; 54:319-25.
35. Kawada et al. Blood 2004; 104:3581-7.
36. Dawn et al. Circ Res 2006; 98:1098-105.
37. Dawn et al. Basic Res Cardiol 2005; 100:494-503.
38. Kucia et al. Blood Cells Mol Dis 2004; 32:52-7.
39. Ratajczak et al. Folia Histochem Cytobiol 2004; 42:139-46.
40. Morrison et al. Annu Rev Cell Dev Biol 1995; 11:35-71.
41. Pittenger et al. Science 1999; 284:143-7
42. Jiang et al. Nature 2002; 418:41-9.
43. D'Ippolito et al. J Cell Sci 2004; 117:2971-81.
44. Kucia et al. Circ Res 2004; 95:1191-9.
45. Yoon et al. J Clin Invest 2005; 115:326-38.
46. Kucia et al. Leukemia 2006; 20:857-69.
47. Kucia et al. J Physiol Pharmacol 2006; 57 SUPPI 515-18.
48. Kucia et al. Blood 2006; 108:478A (abstract).
49. Zuba-Surma et al. Circulation 2006; 114 (Suppl. 11): 11-212 (abstract).
50. Kucia et al. Leukemia 2006; 20: 18-28.
51. Guo et al. Am J Physiol 1998; 275:H1375-87.
52. Shyu et al. Circulation 2004; 110: 1847-54.
53. Massa et al. Blood 2005; 105:199-206.
54. Paczkowska et al. Eur J Haematol 2005; 75:461-7.
55. Bittira et al. Eur J Cardiothorac Surg 2003; 24:393-8.
56. Shintani et al. Circulation 2001; 103:2776-9.
57. Spevack et al. Coron Artery Dis 2006; 17:345-9.
58. Wojakowski et al. Circulation 2004~110:3213-20.
59. Wojakowski et al. Eur Heart J 2006; 27:283-9.
60. Wang et al. J Mol Cell Cardiol 2006; 41:478-87.
61. Chen et al. Exp Hematol 1999; 27:928-35.
62. Lansdorp et al. Blood Cells 1994; 20:376-80; discussion 80-1
63. Yan et al. Rejuvenation Res 2005; 8:248-53.
64. Amit et al. (2000) 227 Dev Biol 271-278.
65. Bradley et al. (1984) 309 Nature 255-258.
66. Caplan et al. (2001) 7 Trends Mol Med 259-64.
67. Castro et al. (2002) 297 Science 1299.
68. Ceradini et al. (2004) 10 Nat Med 858-864.
69. Corti et al. (2002) 277 Exp Cell Res 74-85.
70. Doetschman et al. (1985) 87 J Embryol Exp Morphol 27-45.
71. Fraichard et al. (1995) 108 J Cell Sci 3181-3188.
72. Geiger et al. 100 Blood 721-723.
73. GENBANK® Accession Nos. AAB25223; AAR16420; AF091351; AF240635; AY278951; BC031665; DQ486513; M28382; M28698; NM_002055; NM_004048; NM_004387; NM_007423; NM_007562; NM_008476; NM_008591; NM_008656; NM_008699; NM_008814; NM_009735; NM_010024; NM_010612; NM_010866; NM_011661; NM_011708; NM_013584; NM_013685; NM_016701; NM_016967; NM_016968; NM_023279; NM_024865; NM_025282; NM_027011; NM_031202; NMJ39218; NMJ44955; NMJ75238; NP_001009318; NP_002829; NP_034868; NP_035340; NP_598415; NP_612516; NP_776434; NP_999251; U85046; X02801; X15784; X52437; X83930; XP_002829; XP_223083; XP_599431.
74. Goodell et al. (1996) 183 J Exp Med 1797-1806.
75. Goodell et al. (2005) Methods Mol Biol 343-352.
76. Guo et al. (1999) 96 Proc Natl Acad Sci. USA 11507-11512. Guo et al. (2005) 23 Stem Cells 1324-1332.
77. Hao et al. (2003) 12 J Hematother Stem Cell Res 23-32.
78. Haynesworth et al. (1992) 13 Bone 81-88.
79. Holden & Vogel (2002) 296 Science 2126-2129. Ianus et al. (2003) 111 J Clin Invest 843-850. Jackson et al. (2001) 107 J Clin Invest 1395-1402.
80. Jaenisch (1988) 240 Science 1468-1474.
81. Kawada & Ogawa (2001) 98 Blood 2008-2013.
82. Kogler et al. (2004) 200 J Exp Med 123-135.
83. Korbling et al. (2002) 346 N Engl J Med 738-746. Kucia et al. (2004a) 32 Blood Cells Mol Dis 52-57.
84. Kucia et al. (2005b) 19 Leukemia 1118-1127.
85. Kucia et al. (2005c) 23 Stem Cells 879-894. Labarge & Blau (2002) 111 Cell 589-601.
86. Lee & Stoffel (2003) 111 J Clin Invest 799-801.
87. Lemischka (2002) 30 Exp Hematol 848-852.
88. Mackay et al. (1998) 4 Tissue Eng 415-28.
89. Macpherson et al. 118 J Cell Sci 2441-2450. Majka et al. (2001) 97 Blood 3075-3085.
90. Maki[pi]o et al. (1999) 103 J Clin Invest 697-705.
91. Martin & Evans (1975) in Teratomas and Differentiation (M. I. Sherman & D. Solter, Eds.), pp. 169-187, Academic Press, New York, N.Y., United States of America. McKinney-Freeman et al. (2002) 99 Proc Natl Acad Sci USA 1341-1346.
92. Nagy et al. (2003) Manipulating the Mouse Embryo. A Laboratory Manual, Third Edition, Cold Spring Harbor Laboratory Press, Cold Spring Harbor, N.Y., United States of America.
93. Orlic et al. (2003) 7 Pediatr Transplant 86-88.
94. Pennacchietti et al. (2003) 3 Cancer Cell 347-361.
95. Petersen et al. (1999) 284 Science 1168-1170.
96. Pittenger et al. (2000) 251 Curr Top Microbiol Immunol 3-11. Ratajczak et al. (2004a) 103 Blood 2071-2078.
97. Reyes & Verfaillie (2001) 938 Ann NY Acad Sci 231-235.
98. Reyes et al. (2001) 98 Blood 2615-2625.
99. Robertson (1991) 44 Biol Reprod 238-45.
100. Robertson et al. (1986) 323 Nature 445-447.
101. Sanchez-Ramos (2002) 69 Neurosci Res 880-893.
102. Schuldiner et al. (2000) 97 Proc Natl Acad Sci USA 11307-11312.
103. Schwartz et al. (2000) 109 J Clin Invest 1291-1302.
104. Shamblott et al. (1998) 95 Proc Natl Acad Sci USA 13726-13731.
105. Stamm et al. (2003) 361 Lancet 45-46.
106. Tamamura et al. (1998) 253 Biochem Biophys Res Comm 877-882.
107. Thomson et al. (1995) 92 Proc Natl Acad Sci USA 7844-7848.

108. Thomson et al. (1998) 282 Science 1145-1147
109. U.S. Pat. Nos. 5,650,550; 5,736,396; 5,750,397; 5,777,195; 5,843,780; and 6,090,622, each of which are herein incorporated by reference in their entirety.
110. Wagers et al. (2002) 297 Science 2256-2259.
111. Yamada et al. (2002) 20 Stem Cells 146-154.
112. Yoo et al. (1998) 80 J Bone Joint Surg Am 1745-57.
113. Young et al. (1998) 16 J Orthop Res 406-13.

What is claimed is:

1. A method of treating an injury to a cardiac tissue in a subject, the method comprising administering to the subject a composition comprising isolated $CD34^+/lin^-/CD45^-$ or $Sca-1^+/lin^-/CD45^-$ stem cells from bone marrow in a pharmaceutically acceptable carrier, in an amount and via a route sufficient to engraft at least a fraction of the stem cells in the cardiac tissue and differentiate therein, wherein the injury is myocardial ischemia or a myocardial infarction.

2. The method of claim 1, wherein the isolated stem cells are isolated from bone marrow or peripheral blood, wherein the stem cells isolated from peripheral blood are stems cells that have been mobilized into the peripheral blood from bone marrow.

3. The method of claim 1, wherein the stem cells comprise $Sca-1^+/lin^-/CD45^-$ and express at least one of SSEA-1, Oct-4, Rex-1, and Nanog, or comprise $CD34^+/lin^-/CD45^-$ and express at least one of SSEA-4, Oct-4, Rex-1, and Nanog.

4. The method of claim 1, wherein the stem cells comprise $CXCR4^+$ and/or $CD133^+$.

5. The method of claim 1, wherein the subject is a mammal.

6. The method of claim 5, wherein the mammal is a mouse or a human.

7. The method of claim 1, further comprising differentiating the $CD34^+/lin^-/CD45^-$ or $Sca-1^+/lin^-/CD45^-$ bone marrow stem cells in the composition to produce cardiomyocytes in the composition prior to administering the composition.

8. The method of claim 1, wherein the stem cells express one or more markers selected from the group consisting of Nsx2.5/Csx, and GATA-4.

9. The method of claim 1, wherein the stem cells comprise a stem cell for a myocardial cell.

10. The method of claim 1, wherein $CD34^+/lin^-/CD45^-$ or $Sca-1^-/lin^-/CD45^-$ stem cells are administered directly to the myocardium.

11. The method of claim 1, wherein the route of administration is intramyocardial injection.

12. The method of claim 1, wherein at least 10,000 stem cells are administered.

13. The method of claim 1, wherein the route of administration is parenteral administration.

14. The method of claim 1, wherein at least 10,000 stem cells are administered and the route of administration is parenteral administration.

15. The method of claim 14, wherein the isolated stem cells are isolated from bone marrow or peripheral blood, wherein the stem cells isolated from peripheral blood are stems cells that have been mobilized into the peripheral blood from bone marrow.

* * * * *